(12) United States Patent
Trainer

(10) Patent No.: US 7,471,393 B2
(45) Date of Patent: Dec. 30, 2008

(54) METHODS AND APPARATUS FOR DETERMINING THE SIZE AND SHAPE OF PARTICLES

(76) Inventor: Michael Trainer, 7365 Patrick Cir., Coopersburg, PA (US) 18036

(*) Notice: Subject to any disclaimer, the term of this patent is extended or adjusted under 35 U.S.C. 154(b) by 0 days.

(21) Appl. No.: 10/598,443

(22) PCT Filed: Mar. 7, 2005

(86) PCT No.: PCT/US2005/007308
§ 371 (c)(1),
(2), (4) Date: Aug. 30, 2006

(87) PCT Pub. No.: WO2005/091970
PCT Pub. Date: Oct. 6, 2005

(65) Prior Publication Data
US 2007/0165225 A1 Jul. 19, 2007

Related U.S. Application Data

(60) Provisional application No. 60/550,591, filed on Mar. 6, 2004.

(51) Int. Cl.
*G01N 15/02* (2006.01)
(52) U.S. Cl. .................................... 356/336
(58) Field of Classification Search ......... 356/336–343; 250/574
See application file for complete search history.

(56) References Cited

U.S. PATENT DOCUMENTS

| | | | | |
|---|---|---|---|---|
| 6,091,492 A | * | 7/2000 | Strickland et al. | 356/336 |
| 6,236,458 B1 | * | 5/2001 | Igushi et al. | 356/336 |
| 6,335,792 B1 | * | 1/2002 | Tsuchiya | 356/432 |
| 6,778,271 B2 | * | 8/2004 | Watson et al. | 356/336 |
| 2001/0035954 A1 | * | 11/2001 | Rahn et al. | 356/336 |
| 2007/0242269 A1 | * | 10/2007 | Trainer | 356/336 |

* cited by examiner

*Primary Examiner*—Hoa Q Pham
(74) *Attorney, Agent, or Firm*—William H. Eilberg

(57) ABSTRACT

An instrument for measuring the size distribution of a particle sample by counting and classifying particles into selected size ranges. The particle concentration is reduced to the level where the probability of measuring scattering from multiple particles at one time is reduced to an acceptable level. A light beam is focused or collimated through a sample cell, through which the particles flow. As each particle passes through the beam, it scatters, absorbs, and transmits different amounts of the light, depending upon the particle size. So both the decrease in the beam intensity, due to light removal by the particle, and increase of light, scattered by the particle, may be used to determine the particle size, to classify the particle and count it in a certain size range. If all of the particles pass through a single beam, then many small particles must be counted for each large one because typical distributions are uniform on a particle volume basis, and the number distribution is related to the volume distribution by the particle diameter cubed.

8 Claims, 83 Drawing Sheets envelope detector flow direction into page

Figure 17
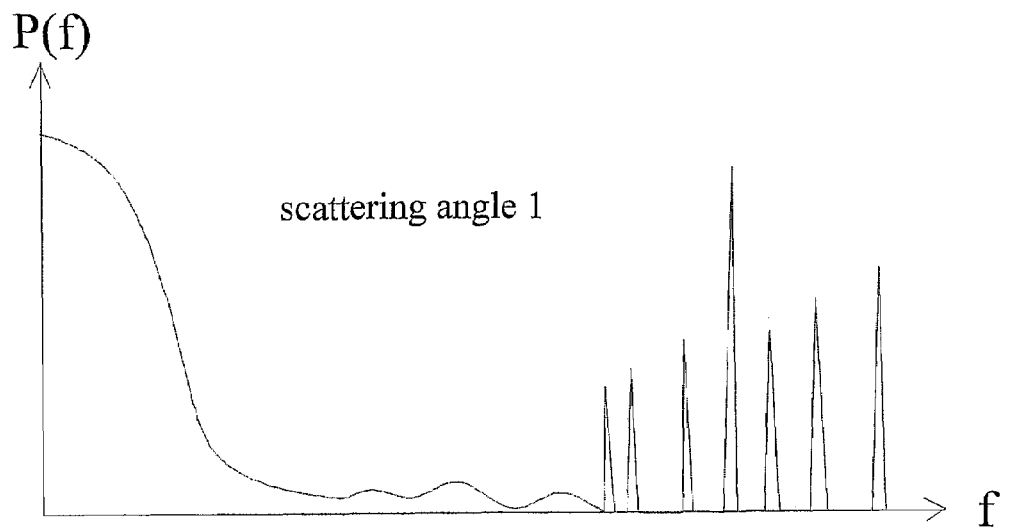
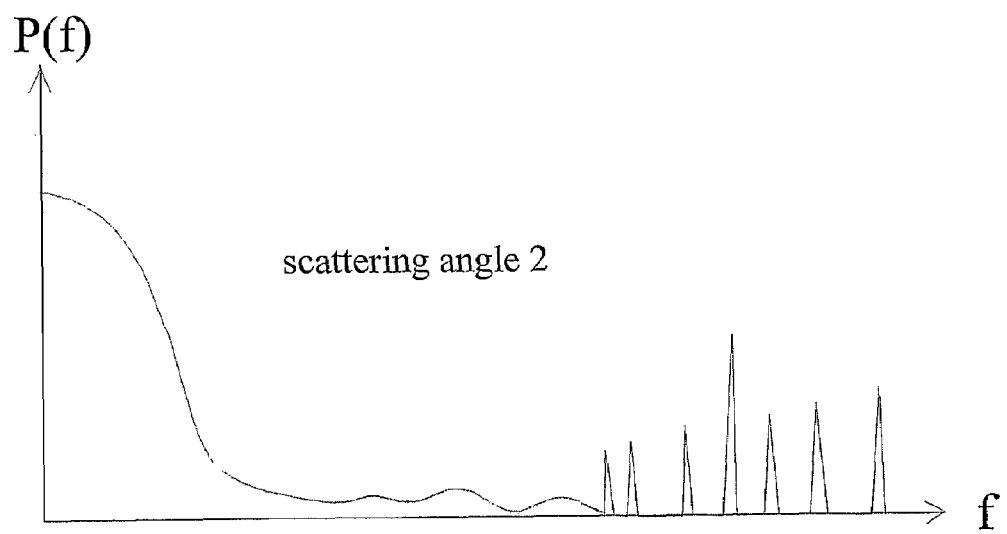

Figure 25
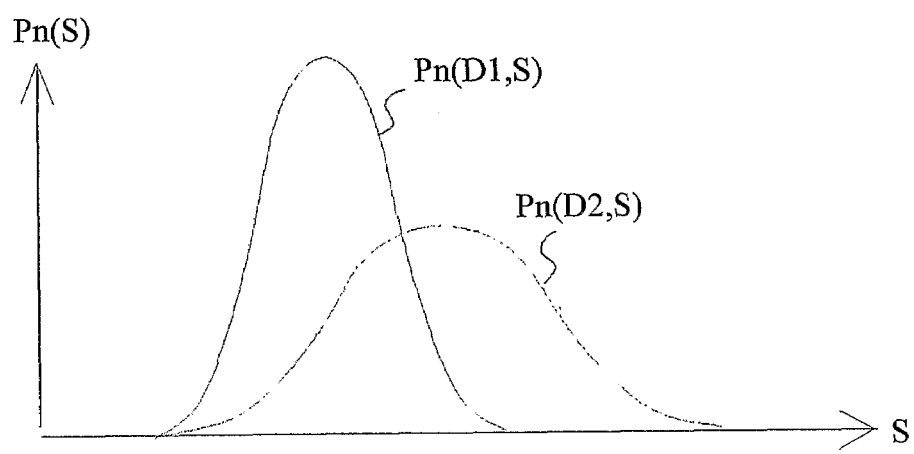
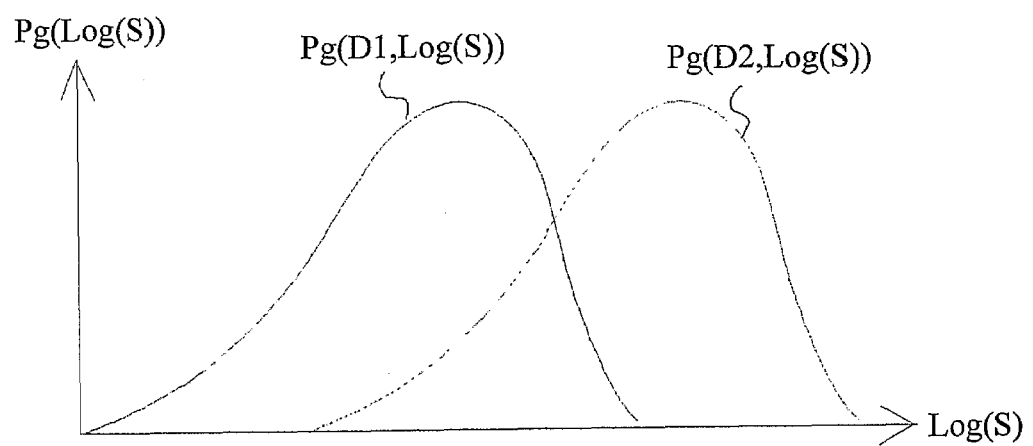

Figure 37
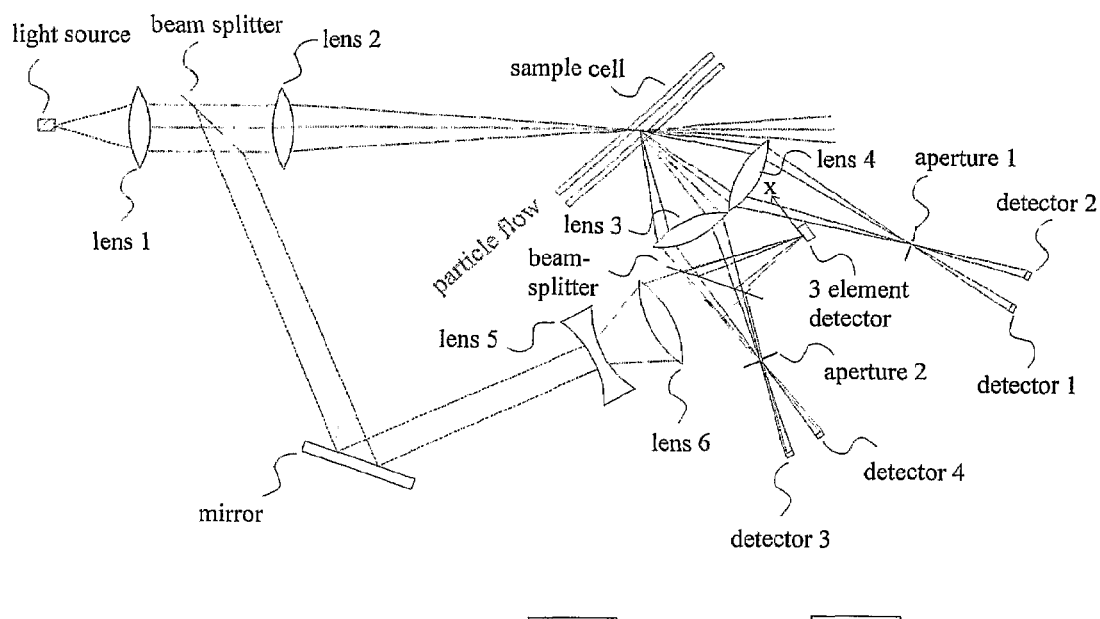
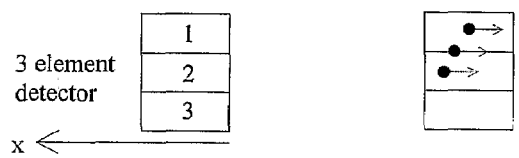

Figure 81
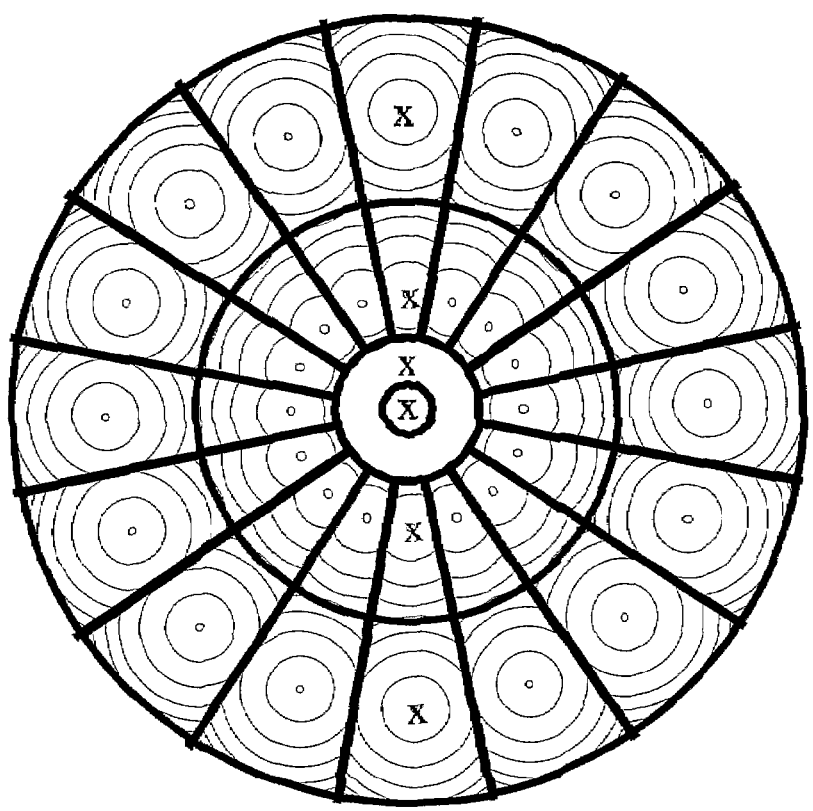
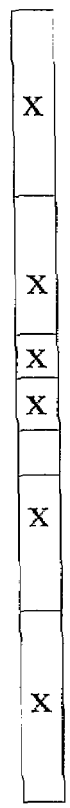
front view
side view
on edge

Figure 83
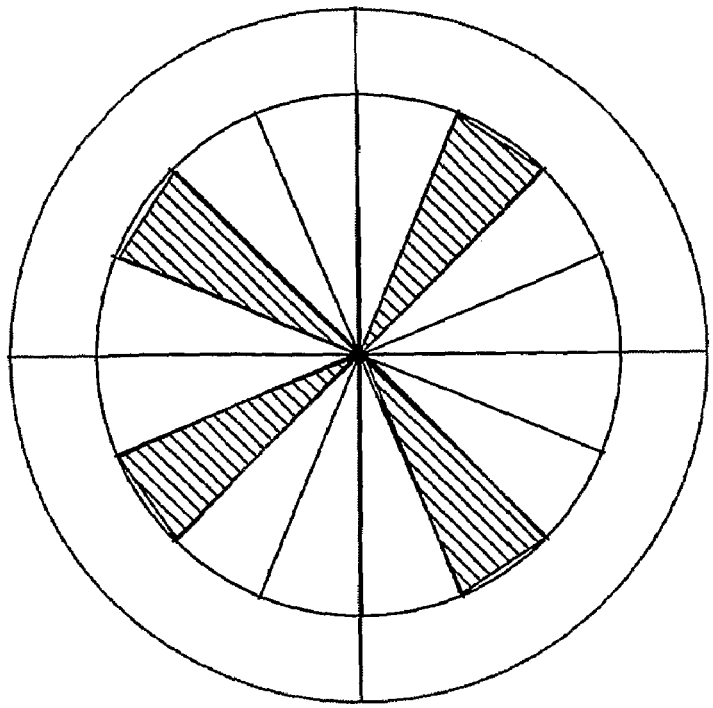
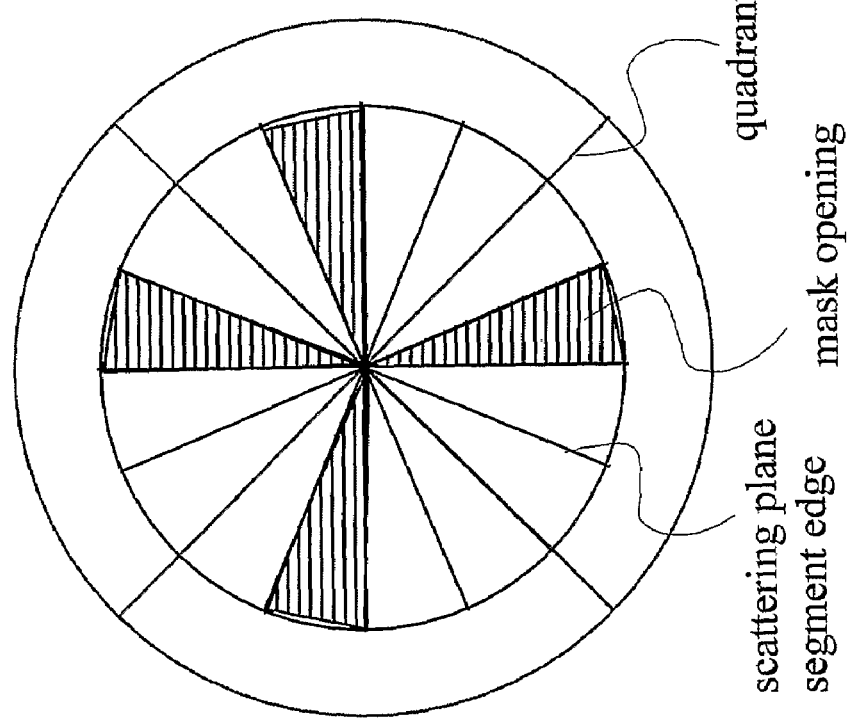

METHODS AND APPARATUS FOR DETERMINING THE SIZE AND SHAPE OF PARTICLES

CROSS-REFERENCE TO RELATED APPLICATIONS

This application claims priority of U.S. Provisional Patent Application No. 60/550,591, filed Mar. 6, 2004.

BACKGROUND OF THE INVENTION

In general, the present invention relates to systems and methods that analyze particles in a sample using laser light diffraction. More particularly, the present invention relates to systems and methods that analyze laser light diffraction patterns to determine the size of particles in a sample.

BRIEF SUMMARY OF THE INVENTION

The present invention comprises a method for improving accuracy of particle parameter distributions, the particle parameter distributions being obtained by directing light onto the particles and observing light scattered from the particles so as to observe special events, the method comprising the steps of:

a) selecting an integration time which is sufficiently short such that each special event creates a large characteristic change of integrated scatter signal parameters, when observed by a detector, b) deriving data sets corresponding to particles, by integrating signals obtained from a plurality of detectors, using the integration time selected in step (a), c) sorting the data sets obtained in step (b) into groups with similar characteristics, d) rejecting groups with undesirable characteristics, while accepting other groups for further analysis, e) calculating a particle parameter distribution from an average of said data sets, from each accepted group, to obtain a separate parameter distribution for each accepted group, and f) combining the individual particle parameter distributions from said groups to produce a final particle parameter distribution.

The invention also includes apparatus for practicing the above-described method.

In another embodiment, the invention includes a method for improving accuracy of particle parameter distributions, the particle parameter distributions being obtained by directing light onto the particles and observing light scattered from the particles so as to observe special events, the method comprising the steps of:

a) selecting a data collection period which is sufficiently short such that each special event creates a large characteristic change in a function created in step (c) below, when observed by a detector, b) deriving data sets corresponding to particles, by digital sampling of signals obtained from at least one detector, using the data collection period selected in step (a), c) creating a function of each data set, d) sorting the data sets obtained in step (b) into groups with similar characteristics for said function, e) rejecting groups with undesirable characteristics, while accepting other groups for further analysis, f) calculating a particle parameter distribution from an average of said functions of said data sets, from each accepted group, to obtain a separate parameter distribution for each accepted group, and g) combining the individual particle parameter distributions from said groups to produce a final particle parameter distribution.

The invention also includes apparatus for practicing the above-described method.

BRIEF DESCRIPTION OF THE DRAWINGS

FIG. 17 provides graphs showing power spectra of signals measured at two scattering angles for the apparatus depicted in FIG. 15.

FIG. 25 provides graphs showing the particle count probability functions in linear and logarithmic signal space, the graphs showing the creation of shift invariant functions and a convolution relationship for count distributions as a function of the logarithm of a scattering signal, according to the present invention.

FIG. 37 provides a schematic diagram of an optical system which determines the position where the particle passes through the light beam, according to the present invention.

FIG. 81 provides a front view and a side view of the array of FIG. 80, utilizing diffractive optical elements.

FIG. 83 provides diagrams showing the use of two quadrant detectors and masks to separately measure scattered light in eight different ranges of scattering planes, according to the present invention.

DETAILED DESCRIPTION OF THE INVENTION

Figure 1:
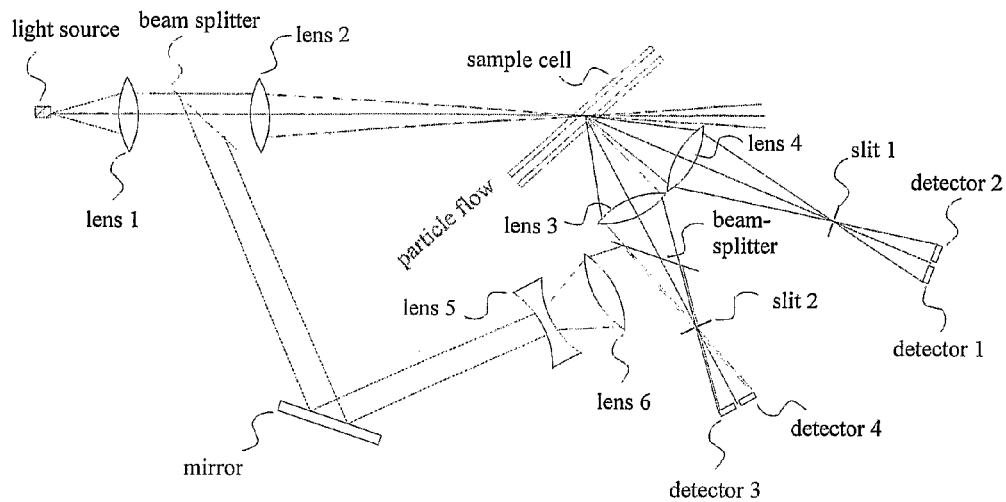
FIG. 1 provides a schematic diagram of a scattering plane view of a scattering detection system which detects scattered light from particles in a small volume, according to the present invention.

This disclosure describes an instrument for measuring the size distribution of a particle sample by counting and classifying particles into selected size ranges. The particle concentration is reduced to the level where the probability of measuring scattering from multiple particles at one time is reduced to an acceptable level. A light beam is focused or collimated through a sample cell, through which the particles flow. As each particle passes through the beam, it scatters, absorbs, and transmits different amounts of the light, depending upon the particle size. So both the decrease in the beam intensity, due to light removal by the particle, and increase of light, scattered by the particle, may be used to determine the particle size, to classify the particle and count it in a certain size range. If all of the particles pass through a single beam, then many small particles must be counted for each large one because typical distributions are uniform on a particle volume basis, and the number distribution is related to the volume distribution by the particle diameter cubed. This large range of counts and the Poisson statistics of the counting process limit the size dynamic range for a single measurement. For example, a uniform particle volume vs. size distribution between 1 and 10 microns requires that one thousand 1 micron particles be measured for each 10 micron particle. The Poisson counting statistics require 10000 particles to be counted to obtain 1% reproducibility in the count. Hence one needs to measure more than 10 million particles. At the typical rate of 10,000 particles per second, this would require more than 1000 seconds for the measurement. In order to reduce the statistical count uncertainties, large counts of small particles must be measured for each large particle. This problem may be eliminated by flowing portions of the sample flow through light beams of various diameters, so that larger beams can count large count levels of large particles while small diameter beams count smaller particles without the small particle coincidence counts of the large beam. The best results are obtained by using multiple beams of ever decreasing spot size to improve the dynamic range of the count. The count vs. size distributions from each beam are scaled to each other using overlapping size ranges between different pairs of beams in the group, and the count distributions from all of the beams are then combined.

BEST MODES OF CARRYING OUT THE INVENTION

Light scattered from the large diameter beam should be measured at low scattering angles to sense large particles. The optical pathlength of this beam in the particle sample must be large enough to pass the largest particle of interest for that beam. For small particles, the interaction volume in the beam must be reduced along all three spatial directions. The beam crossection is reduced by an aperture or by focusing the beam into the interaction volume.

The interaction volume is the intersection of the incident light beam and the field of view for the detector which measures scattered light from the particle. However, for very small particles, reduction of the optical path along the beam propagation direction is limited by the gap thickness through which the sample must flow. This could be accomplished by using a cell with various pathlengths or a cell with a wedge shaped window spacing (see FIG. 9b) to provide a range of optical pathlengths. Smaller source beams would pass through the thinner portions of the cell, reducing the intersection of the incident beam and particle dispersant volume to avoid coincidence counts. The other alternative is to restrict the field of view of the scattering collection optics so as to only detect scatterers in a very small sample volume, which reduces the probability of multiple particles in the measurement volume. So particularly in the case of very small particles, a focused laser beam intersected with the limited field of view of collection optics must be used to insure single particle counting. However, this system would require correction of larger beams for coincidence counts based upon counts in smaller beams. To avoid these count errors, this disclosure proposes the use of a small interrogation volume for small particles, using multiple scattering angles, and a 2 dimensional detector array for counting large numbers of particles above approximately 1 micron at high speeds.

Three problems associated with measuring very small particles are scattering signal dynamic range, particle composition dependence, and Mie resonances. The low angle scattered intensity per particle changes by almost 6 orders of magnitude between 0.1 and 1 micron particle diameter. Below approximately 0.4 micron, photon multiplier tubes (PMT) are needed to measure the minute scattered light signals. Also the scattered intensity can change by a factor of 10 between particles of refractive index 1.5 to 1.7. However, the shape of the scattering function (as opposed to the amplitude)

vs. scattering angle is a clear indicator of particle size, with very little refractive index sensitivity. This invention proposes measurement of multiple scattering angles to determine the size of each individual particle, with low sensitivity to particle composition and scattering intensity. Since multiple angle detection is difficult to accomplish with bulky PMT's, this invention also proposes the use of silicon photodiodes and heterodyne detection to measure low scattered signals from particles below 1 micron. However, the use of any type of detector and coherent or non-coherent detection are claimed.

Spherical particles with low absorption will produce a transmitted light component which interferes with light diffracted by the particle. This interference causes oscillations in the scattering intensity as a function of particle size. The best method of reducing these oscillations is to measure scattering from a white light or broad band source, such as an LED. The interference resonances at multiple wavelengths are out of phase with each other, washing out the resonance effects. But for small particles, one needs a high intensity source, eliminating broad band sources from consideration. The resonances primarily occur above 1.5 micron particle diameter, where the scattering crossection is sufficient for the lower intensity of broadband sources. So the overall concept may use laser sources and multiple scattering angles for particles below approximately 1 micron, and broad band sources with low angle scattering or total scattering for particle size from approximately 1 micron up to thousands of microns. We will start with the small particle detection system.

Figure 1A:
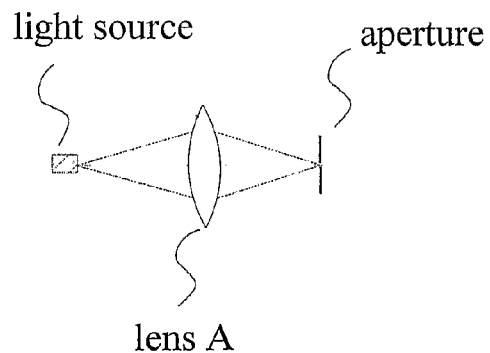
FIG. 1A provides a schematic diagram showing an aperture which controls the light intensity profile of a light source, according to the present invention.

FIG. 1 shows a configuration for measuring and counting smaller particles. A light source is projected into a sample cell, which consists of two optical windows for confining the flowing particle dispersion. The light source in FIG. 1 could also be replaced by an apertured light source as shown in FIG. 1A. This aperture, which is in an image plane of the light source, blocks unwanted stray light which surrounds the source spot. In the case of laser sources, this aperture may be used to select a section of uniform intensity from the center of the laser crossectional intensity profile. In all figures in this disclosure, either source configuration is assumed. The choice is determined by source properties and intensity uniformity requirements in the sample cell. So either the light source, or the apertured image of the light source, is collimated by lens 1 and a portion of this collimated beam is split off by a beam splitter to provide the local oscillator for heterodyne detection. While collimation between lenses 1 and 2 is not required, it provides for easy transport to the heterodyne detectors 3 and 4. Lens 2 focuses the beam into a two-window cell as a scattering light source for particles passing through the cell. The scattered light is collected by two optical systems, a high angle heterodyne system for particles below approximately 0.5 microns and a low angle non-coherent detector for 0.4 to 1.2 micron diameter particles. Each system has multiple detectors to measure scattering at multiple angles. FIG. 1 shows a representative system, where the representative approximate mean scattering angles for detectors 1, 2, 3, and 4 are 10, 20, 30, and 80 degrees, respectively. However, other angles and numbers of detectors could be used. All four scattering intensity measurements are used for each particle passing through the intersection of the field of view of each of the two systems with the focused source beam. Detectors 1 and 2 use non-coherent detection because the signal levels for the larger particles measured by these two detectors are sufficiently large to avoid the complexity of a heterodyne system. Also the Doppler frequency for particles passing through the cell at meter per second speeds are too low to accumulate many cycles within the single particle pulse envelope at these low scattering angles. The Doppler frequencies may be much larger at larger scattering angles where the heterodyne detection is needed to measure the small scattering intensities from smaller particles.

Lens 4 collects scattered light from particles in the flowing dispersant. Slit 1 is imaged by lens 4 into the cell. The intersection of the rays passing through that image and the incident source beam define the interrogation volume 1 where the particle must reside to be detected by detectors 1 and 2. Detectors 1 and 2 each intercept a different angular range of scattered light. Likewise for lens 3, slit 2 and detectors 3 and 4. The intersection of the rays by back-projection image of slit 2 and the source beam define interrogation volume 2 for the heterodyne system. The positions of slit 1 and slit 2 are adjusted so that their interrogation volumes coincide on the source beam. In order to define the smallest interaction volume, the images of the two slits should coincide with the minimum beam waist in the sample cell. These slits could also be replaced by other apertures such as pinholes. A portion the source beam, which was split off by a beamsplitter (the source beamsplitter), is reflected by a mirror to be expanded by a negative lens 5. This expanded beam is focused by lens 6 to match the wavefront of the scattered beam through lens 3. This matching beam is folded through slit 2 by a second beamsplitter (the detector beamsplitter) to mix with the scattered light on detectors 3 and 4. The total of the optical pathlengths from the source beamsplitter to the particle in the sample cell and from the particle to detectors 3 and 4, must match the total optical pathlength of the local oscillator beam from the source beamsplitter through the mirror, lenses 5 and 6, the detector beamsplitter, and slit 2 to detectors 3 and 4. The difference between these two total optical pathlengths must be less than the coherence length of the source to insure high interferometric visibility in the heterodyne signal. The scattered light is Doppler shifted by the flow velocity of the particles in the cell. By mixing this Doppler frequency shifted scattered light with unshifted light from the source on a quadratic detector (square of the combined E fields), a Doppler beat frequency is generated in the currents of detectors 3 and 4. The current oscillation amplitude is proportional to the square-root of the product of the source intensity and the scattered intensity. Hence, by increasing the amount of source light in the mixing, the detection will reach the Shot noise limit, allowing detection of particles below 0.1 micron diameter. By using a sawtooth drive function to vibrate the mirror with a vibrational component perpendicular to the mirror's surface, introducing optical phase modulation, the frequency of the heterodyne carrier can be increased to produce more signal oscillations per particle pulse. During each rise of the sawtooth function and corresponding motion of the mirror, the optical frequency of the light reflected from the mirror is shifted, providing a heterodyne beat signal on detectors 3 and 4 equal to that frequency shift. Then the mirror vibration signal could be used with a phase sensitive detection, at the frequency and phase of the beat frequency, to improve signal to noise. This could also be accomplished with other types of optical phase modulators (electro-optic and acousto-optic) or frequency shifters (acousto-optic). The reference signal for the phase sensitive detection could be provided by a separate detector which measures the mixture of light, which is reflected by the moving mirror (or frequency shifted by another device), with the unshifted light from the source.

For particles above approximately 0.4 microns, signals from all 4 detectors will have sufficient signal to noise to provide accurate particle size determination. The theoretical values for these 4 detectors vs. particle size may be placed in a lookup table. The 4 detector values from a measured unknown particle are compared against this table to find the two closest 4 detector signal groups, based upon the least squares minimization of the function:

$$(S1-S1T)^2+(S2-S2T)^2+(S3-S3T)^2+(S4-S4T)^2$$

where S1,S2,S3,S4 are signals from the 4 detectors, S1T,S2T, S3T,S4T are the theoretical values of the four signals for a particular particle size, and ^2 is the power of 2 or square of the quantity preceding the ^.

The true size is then determined by interpolation between these two best data sets based upon interpolation in 4 dimensional space. The size could also be determined by using search algorithms, which would find the particle size which minimizes the least square error while searching over the 4 dimensional space of the 4 detector signals. For particles of size below some empirically determined size (possibly around 0.4 micron), detector 1 and 2 signals could be rejected for insufficient signal to noise, and only the ratio of the signals (or other function of two signals) from shot noise limited heterodyne detectors 3 and 4 would be used to size each particle. If the low angle signals from detectors 1 and 2 are needed for small particles, they could be heterodyned with the source light using the same optical design as used for detectors 3 and 4. In any case, only signals with sufficient signal to noise should be used in the size determination, which may include only the use of detectors 1 and 2 when detector 3 and 4 signals are low. The look up table could also be replaced by an equation in all 4 detector signals, which would take the form of: particle size equals a function of the 4 detector signals. These techniques, least squares or function, could be extended to more than 4 detectors. For example, 3 detectors could be used for each system, discarding the low angle non-coherent detection when the signal to noise reaches unacceptable levels. In this case, a 6-dimensional space could be searched, interpolated, or parameterized as described above for the 4 detector system. This disclosure claims the use of any number of detectors to determine the particle size, with the angles and parameterization functions chosen to minimize size sensitivity to particle composition.

Figure 2:
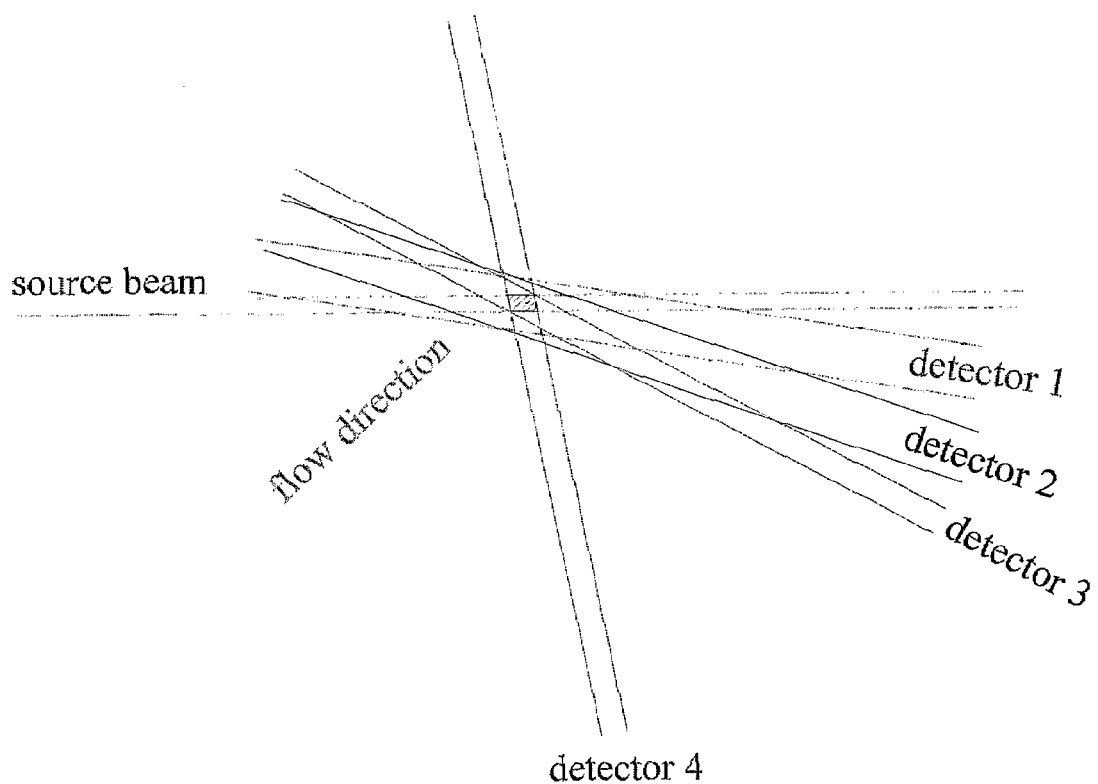
FIG. 2 provides a diagram showing the common volume between the light source and the viewing volumes of various detectors according to the present invention, the scatter volume common to all detectors being determined by detector 4.
Figure 2B:
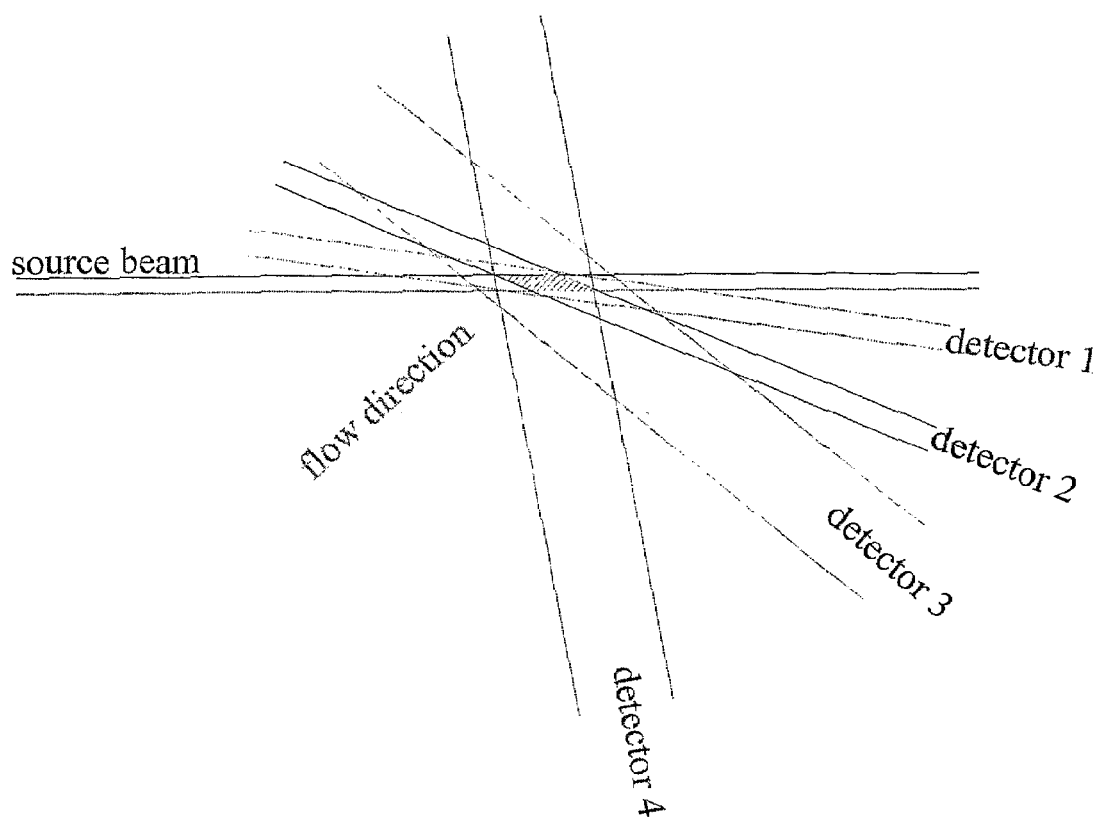
FIG. 2b provides a variation of FIG. 2, wherein the common scatter volume is determined by detector 2.

By tracing rays back from slits 1 and 2, the field of view for systems 1 and 2 are determined, as shown in FIG. 2. The traced rays and source beam converge into the interrogation volume, where they all intersect. FIG. 2 shows these rays and beam in the vicinity of this intersection volume, without detailed description of the converging nature of the beams. The intersection volume is the intersection of the source beam and the field of view of the detector. In this case, the beam from slit 1 may be wider than that from slit 2, so that the source beam and slit 2 field of view fall well within the field of view of slit 1. And the source beam falls well within the field of view of slit 2. By accepting only particle signal pulses which show coincidence with pulses from detector 4 (which has the smallest intersection with the source beam, shown by the crosshatched area), the interrogation volume is matched for all 4 detectors. The source beam could also have a rectangular crossection, with major axis aligned with the long axis of the slits. This would reduce the edge effects for particles passing near to the edges of the beam. The slit images are designed to be much longer than the major axis of the source beam, so that both slits only need to be aligned in the direction perpendicular to the source major axis. This provides for very easy alignment to assure that the intersection of images from detectors 3 and 4 and the source beam fall within the intersection of images from detectors 1 and 2. The slit position could also be adjusted along the optical axis of the detection system to bring the crossover point of both detector fields of view to be coincident with the source beam. Another configuration is shown in FIG. 2b, where slit 2 is wider than slit 1. Here detector 2 defines the smallest common volume as indicated by the cross hatched area. And so only particles which are counted by detector 2 can be counted by the other detectors. All other particles detected by the other detectors, but not detected by detector 2, are rejected because they do not produce concurrent signals in every detector. This process can be extended to more than 4 detectors. In some cases three or more detectors per optical system may be required to obtain accurate size measurement. In this case, the size could be determined by use of a look up table or search algorithm.

The data for each particle would be compared to a group of theoretical data sets. Using some selection routine, such as total RMS difference, the two nearest size successive theoretical sets which bracket either side of the measured set would be chosen. Then the measured set would be used to interpolate the particle size between the two chosen theoretical sets to determine the size. The size determination is made very quickly (unlike an iterative algorithm) so as to keep up with the large number of data sets produced by thousands of particles passing through the sample cell. In this way each particle could be individually sized and counted according to its size to produce a number-vs.-size distribution which can be converted to any other distribution form. These theoretical data sets could be generated for various particle refractive indices and particle shapes.

In general, a set of design rules may be created for the intersection of fields of view from multiple scattering detectors at various angles. Let us define a coordinate system for the incident light beam with the z axis along the direction of propagation and the x axis and y axis are both perpendicular to the z axis, with the x axis in the scattering plane and the y axis perpendicular to the scattering plane. The scattering plane is the plane which includes the source beam axis and the axis of the scattered light ray. In all cases the detector slits are oriented parallel to the y direction. Many configurations are possible, including three different configurations which are listed below:

1) The incident beam is smaller than the high scattering angle detector field crossection, which is smaller than the low scattering angle detector field crossection. Only particle pulses that are coincident with the high angle detector pulses are accepted. The incident beam may be spatially filtered in the y direction, with the filter aperture imaged into the interaction volume. This aperture will cut off the Gaussian wings of the intensity profile in the y direction, providing a more abrupt drop in intensity. Then fewer small particles, which pass through the tail of the intensity distribution, will be lost in the detection noise and both large and small particles will see the same effective interaction volume.

2) The incident beam is larger than the low scattering angle detector field crossection, which is larger than the high scattering angle detector field crossection. Only particle pulses that are coincident with the high angle detector pulses are accepted. The correlation coefficient of the pulses or the delay (determined by cross correlation) between pulses is used to insure that only pulses from particles seen by every detector are counted.

3) The incident beam width and all fields from individual detectors progress from small to large size. Then particles counted by the smallest entity will be sensed by all of the rest of the detectors. Only particles sensed by the smallest entity will be counted.

The two detector pairs, 1+2 and 3+4, could also be used independently to measure count vs. size distributions. The lower angle pair could only measure down to the size where the ratio of their angles is no longer sensitive to size and the scattering crossections are too small to maintain signal to noise. Likewise for the high angle detectors, they can only measure up to sizes where their ratio is no longer monotonic with particle size. However, absolute scattered signal levels could be used to determine the particle size outside of this size region. Since extremes of these operational ranges overlap on the size scale, the two pairs could be aligned and operated independently. The small angle detectors would miss some small particles and the high angle detectors would miss some large particles. But the two independently acquired particle size distributions could be combined using their particle size distributions in the size region where they overlap. Scale one distribution to match the other in the overlap region and then use the distribution below the overlap from the high angle detectors for below the overlap region and the distribution from the low angle detectors for the distribution above the overlap region. In the overlap region, the distribution starts with the high angle result and blends towards the low angle result as you increase particle size. Detector triplets could also be used, where the largest angle of the low angle set and the lowest angle of the high angle set overlap so as to scale the scattering measurements to each other.

In some cases, the angular range of each of the heterodyne detectors must be limited to maintain heterodyne signal visibility.

The flat window surfaces could be replaced by spherical surfaces with centers of curvature which coincide with the center of the interrogation volume. Then the focal positions of all of the beams would remain in the same location for dispersing liquids with various refractive indices. These systems can also be designed using fiber optics, by replacing beamsplitters with fiber optic couplers. Then the vibrating mirror could be replaced by a fiber optic phase modulator.

Figure 3:
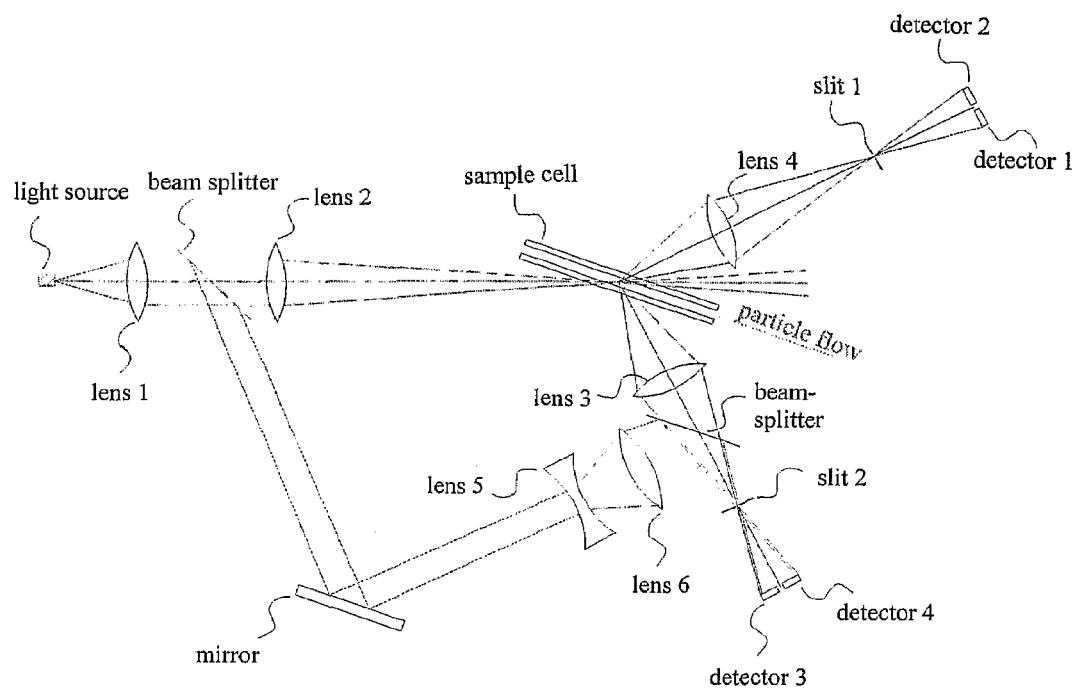
FIG. 3 provides a variation of FIG. 1, where lens 3 and lens 4 are on opposite sides of the light beam.

FIG. 3 shows an alternate optical configuration for FIG. 1, where the low angle scattering system is placed on the opposite side of the cell from the high angle system. In some cases, this configuration will facilitate the mechanical design of the support structure for the cell and optical systems.

Figure 101:
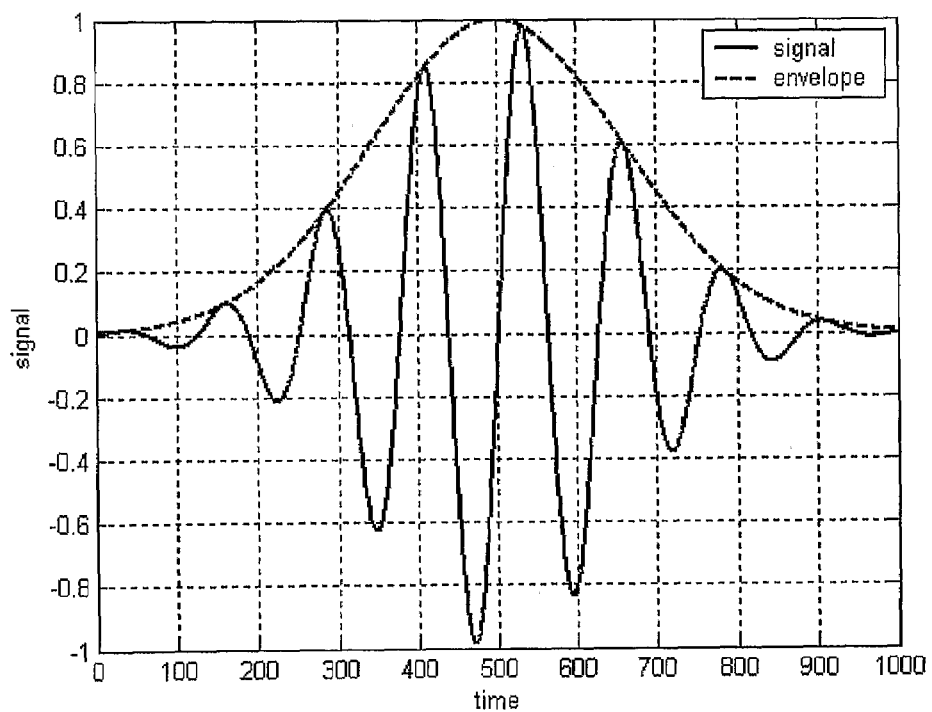
FIG. 101 provides a graph showing plots of an envelope function and heterodyne signal, which comprises a train of oscillations which are amplitude modulated by an envelope determined by the intensity profile of the incident light beam, according to the present invention.

The detector currents from the low angle system and the high angle system must be processed differently. Every particle passing through the interaction volume will produce a pulse in the detector current. Detectors 1 and 2 will show simple pulses, but detectors 3 and 4 will produce modulated pulses. The heterodyne detection measures the Doppler beat frequency as the particle passes through the beam. So each heterodyne pulse will consist of a train of oscillations which are amplitude modulated by an envelope determined by the intensity profile of the incident beam, as shown in FIG. 101 for a Gaussian beam profile. The heterodyne signal must pass through a high pass filter or bandpass filter (to remove the large local oscillator offset) and then an envelope detector (see FIG. 4) to remove the heterodyne oscillations, producing the signal envelope for further processing. This preprocessing envelope detection is used in the process steps below.

Figure 5:
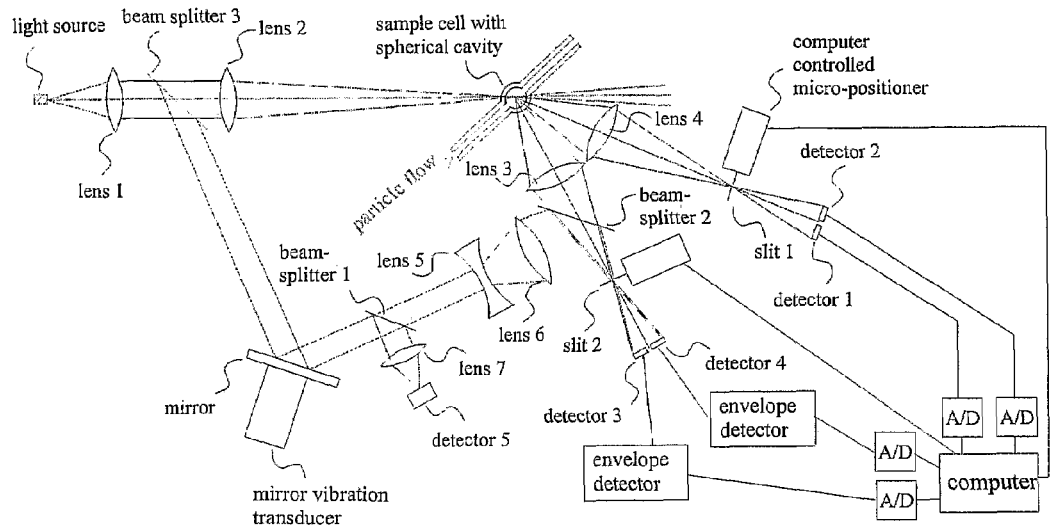
FIG. 5 provides a schematic diagram of an automated system for providing optical alignment of the system of FIG. 1.

For small particles the heterodyne signals will be buried in laser source noise. FIG. 5 shows an additional detector 5 which measures the intensity of the local oscillator laser noise. If we define a heterodyne detector current as I1 and the detector 5 laser monitor detector current as I2 we obtain the following equations which hold for each of the heterodyne detectors.

$$I1 = \mathrm{sqrt}(R*Io(t)*Is(t))*COS(F*t+A)+R*Io$$

$$I1 = \mathrm{sqrt}(R*Io(t)*S(1-R)Io)*COS(F*t+A)+R*Io$$

$$I2 = K*Io(t)$$

where:

$$COS(x) = \text{cosine of } x$$

K is a constant which includes the product of the reflectivities of the beamsplitter 1 and beamsplitter 3

R and (1−R) are the effective reflectivity and transmission of the beam splitters, respectively $$R = R2*R3*(1-R1)$$

$$(1-R) = (1-R2)*(1-R3)$$

R2 is the reflectivity of beamsplitter 2

R3 is the reflectivity of beamsplitter 3

R1 is the reflectivity of beamsplitter 1

$$\mathrm{sqrt}(x) = \text{square root of } x$$

Io(t) is the source beam intensity as function of time t

F is the heterodyne beat frequency at a heterodyne detector due to the motion of the scatterer in the sample cell. And A is an arbitrary phase angle for the particular particle.

Is(t) is the scattered light intensity from the particle:

$$Is(t) = S*(1-R)*Io(t) \text{ where } S \text{ is the scattering efficiency or scattering crossection for the particle}$$

The light source intensity will consist of a constant portion Ioc and noise n(t):

$$Io(t) = Ioc + n(t)$$

We may then rewrite equations for I1 and I2:

$$I1 = \mathrm{sqrt}(S*(1-R)*R)*(Ioc+n(t))*COS(F*t+A)+R*(Ioc+n(t))$$

$$I2 = K*(Ioc+n(t))$$

The heterodyne beat from a particle traveling with nearly constant velocity down the sample cell will cover a very narrow spectral range with high frequency F. For example, at 1 meter per second flow rate, the beat frequency would be in the megahertz range. If we use narrow band filters to only accept the narrow range of beat frequencies we obtain the narrow band components for I1 and I2:

$$I1nb = \mathrm{sqrt}(S*(1-R)*R)*Ioc*COS(F*t+A)+R*n(t)$$

$$I2nb = K*n(t)$$

where we have assumed that n(t) is much smaller than Ioc. And also n(t) is the portion of the laser noise that is within the electronic narrowband filter bandwidth (see below).

The laser noise can be removed to produce the pure heterodyne signal, Idiff, through the following relationship:

$$Idiff = I1nb - (R/K)*I2nb = \mathrm{Sqrt}(R*(1-R)*S)*Ioc*COS(F*t+A)$$

This relationship is realized by narrowband filtering of each of the I1 and I2 detector currents. One or both of these filtered signals are amplified by programmable amplifiers, whose gains and phase shifts are adjustable. The difference of the two outputs of these amplifiers is generated by a difference circuit or differential amplifier. With no particles in the beam, the gain and phase shift of at least one of the programmable amplifiers is adjusted, under computer or manual control, to minimize the output of the difference circuit (i.e. (gain for I2)*R/K=1, assuming gain for I1=1) At this gain, the source intensity noise component in the detector 3 or detector 4 beat signal, with particles present, is eliminated in the difference signal, which is fed to an analog to digital converter (A/D), through a third narrowband filter, for analysis to sense the beat signal buried in noise. This filtered difference signal could also be detected by a phase locked loop, which would lock in on the beat frequency of current from the heterodyne detector.

The particle dispersion flow rate could also be adjusted to maximize the heterodyne signal, through the electronic narrowband filter, from flowing particle scattered light.

This entire correction could also be accomplished in the computer by using a separate A/D for each filtered signal and generating the difference signal by digital computation inside the computer. The phase and gain adjustments mentioned above, without particles in the beam, could be adjusted digitally. Also these gain adjustments could also be determined from measurement of the signal offsets I1$dc$ and I2$dc$ (the average value of the signal due to the local oscillator). If the scattering component of the heterodyne signal is negligible compared to the offset caused by the local oscillator, this adjustment could be determined from measurements taken with particles in the beam. In this case, the contribution from the source intensity noise should be proportional to the offset level because the noise is the same percentage of the average level of the intensity in both I1 and I2. Then the coefficient ratio R/K in the equation for Idiff can be calculated from:

$$R/K = I1dc/I2dc$$

Where I1$dc$ and I2$dc$ are the average of the unfiltered signals I1 and I2, respectively. And the gain (or digital multiplier) of I2 is then I2$dc$/I1$dc$ (relative to a gain for signal I1=1).

If both signals were digitized separately, other correlation techniques could be used to reduce the effects of source intensity noise. Beamsplitter 2 and 3 reflections are adjusted to obtain shot noise limited heterodyne detection, with excess laser noise removed by the difference circuit.

The noise correction techniques described on the prior pages (and FIG. 5) can be applied to any heterodyning system by simply adjusting the filtering of currents I1 and I2 to pass the signal of interest, while blocking the low frequency component (Ioc) of Io(t). Excess laser noise and any other correlated noise component, which is present in both the heterodyne signal and the light source, can be removed from the signal of interest through this procedure. One application is dynamic light scattering, where the heterodyne signal is contaminated by laser source noise in the optical mixing process. The filters on I1 and I2 would be designed to pass the important portion of the Doppler broadened spectrum (using a lower frequency broad band filter or high pass filter instead of the high frequency narrow band filter) and to remove the large signal offset due to the local oscillator. Then by using the subtraction equation described below (where the narrow band filter is replaced by said broad band filter in all equations) the effects of laser noise can be removed from the Doppler spectrum, improving the particle size accuracy.

$$Idiff = I1nb - (R/K)*I2nb = Sqrt(R*(1-R)*S)*Ioc*COS(F*t+A)$$

In this case, the heterodyne signal is the sum of many COS functions with various frequencies and phases. The noise, common to both the heterodyne signal and incident light source intensity, will still be completely removed in Idiff. In the case of fiber optic heterodyning systems, the laser monitor current, I2, could be obtained at the exit of the unused output port of the fiber optic coupler which is used to transport the light to and from the particle sample, because this port carries light only from the optical source, without any scattered light.

I2 can be measured with a light detector at any point in the optical system where the light source intensity vs. time is available. This subtraction shown in the equation above could be accomplished by the analog difference circuit or by digital subtraction after digitization of both the filtered contaminated signal and the filtered source monitor as outlined previously. This procedure could also be accomplished using the unfiltered signals, but with much poorer accuracy due to the large signal offsets.

Figure 4:
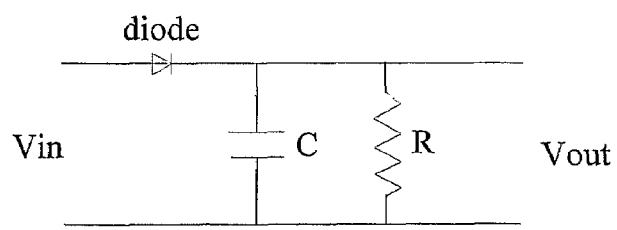
FIG. 4 provides a schematic diagram of a signal conditioning circuit which detects the envelope of a signal, as used in the present invention.
Figure 6:
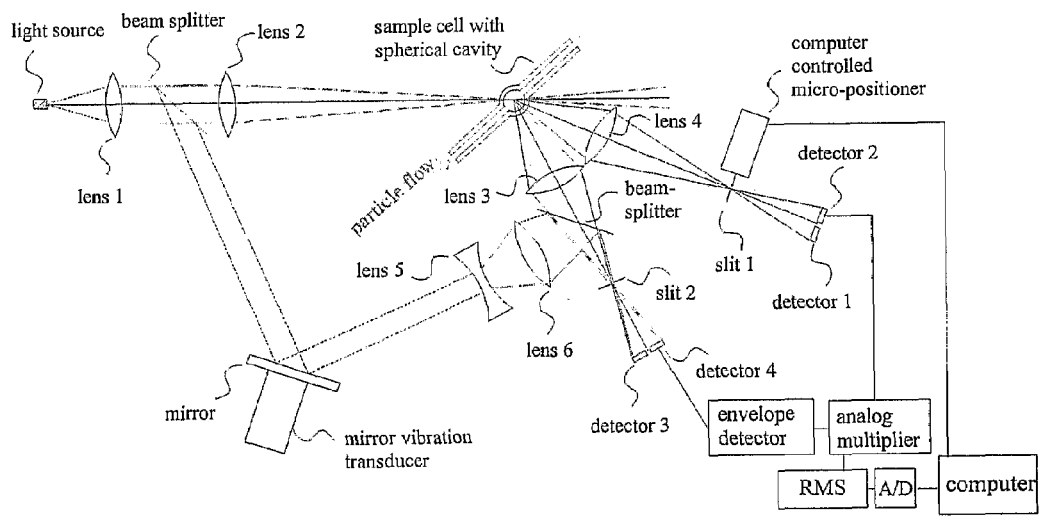
FIG. 6 provides a variation of FIG. 5, showing the use of an analog multiplier.

FIG. 6 shows the system with some additional features. The sample cell windows contain spherical surfaces with center of curvature at the interaction volume. The light source beam and detector acceptance cones pass through these spherical surfaces in order to avoid focal shift of the source and detector beams when the refractive index of the dispersing fluid is changed. The heterodyne detector currents from detectors 3 and 4 are passed through a high pass filter to remove the large local oscillator current and then (after completing the noise removal described above) they are passed through an envelope detector to remove the heterodyne oscillation due to the Doppler shifted spectrum of the scattered light from the moving particles. As mentioned earlier, this Doppler frequency may be increased by vibrating the mirror so as to add phase modulation to the local oscillator. This will provide more signal oscillations per signal pulse. After the high pass or narrowband filter, the signal will consist of a sinusoid which is amplitude modulated by the scattering pulse due to the particle's transit through the source beam (see FIG. 10I). The envelope of this modulated sinusoid is measured by an envelope detector as shown in FIG. 4. The resulting single pulse is digitized by an analog to digital converter (A/D) before analysis by a computer. This process is similar for each of detectors 3 and 4. Since lower angle scattering produces lower Doppler frequency, the lower scattering angle signals are usually measured without heterodyne detection when the signals are large. So for large signal levels, Detectors 1 and 2 do not require heterodyne detection; but a heterodyne optical system, as used for detectors 3 and 4, could be used for detectors 1 and 2 if the signal levels were small. Then the vibrating mirror phase modulator, shown in figure below, could be used to increase the heterodyning frequency. If the signals are large, the scattered light current pulses from detectors 1 and 2 can be digitized directly before computer analysis, without envelope detection. The analysis of these signals is described below.

One other aspect of this invention is a means for auto-alignment of the optics. As shown in FIG. 2, the source beam and all four fields of view, from the four detectors, must intersect at the same point to all see scattering from the same particle. Images of slits 1 and 2 define the point where the view fields from each detector pair (1+2 or 3+4) intersect. The slit apertures usually only need alignment in one direction, perpendicular to the slit, but position adjustment may also be needed along the optical axis of the detector system to place the intersection between the fields of view from detectors 1 and 2 (or 3 and 4) on the source beam. Pinhole or rectangular apertures must be aligned in two orthogonal directions which are in the plane perpendicular to the optical axis of the scattering detection optical system. Either one or both slits may be adjusted to obtain alignment. FIG. 5 shows an example where both slit positions are optimized by a computer controlled micro-positioner. For example, the digitized signals from detector 2 and detector 3 could be digitally multiplied (after the envelope detector) and the resulting product integrated or low pass filtered to produce a correlation between the two detector signals. The position slit 1 is adjusted until this correlation signal is maximum with particles flowing through the interaction volume. If needed, both slits 1 and 2 may be moved to optimize this correlation signal. In general these should be small adjustments because the spherical window surfaces will prevent large beam refractions and focal shifts due to changing particle dispersant refractive index. In systems with large beam shifts, the slits may need to be moved perpendicular and parallel to the optical axis of each optical system to maximize the correlation between the detectors. This could be accomplished with dual axis micro-positioners, which could also be used when the slits are replaced by pinholes or rectangular apertures, which require alignment in two orthogonal axes perpendicular to the optical axis of the scattering detection optical system. FIG. 2 shows larger fields of view for detectors 1 and 2 than for detectors 3 and 4. This is accomplished with slit 1 wider than slit 2 or by larger magnification for lens 4 than for lens 3 (image of the slit in the interaction volume). Hence the alignment of slit 1 is much less critical then slit 2 because image of slit 1 in the interaction volume is wider and has larger depth of focus than for slit 2. By placing computer controlled micro-positioners on slit 1 and slit 2, the system can be aligned by using the correlation between the signals. The micro-positioners move each slit perpendicular to the long axis of the slit opening and perpendicular to the optical axis of that lens. The alignment procedure is described below:

1) With low concentration of particles in the flow stream, adjust the position of slit 2 to maximize the correlation (using an analog multiplier and RMS circuit) between the signals from detectors 3 and 4. At this point the intersection of the fields of views of both detectors cross at the incident beam and the signals are maximum.

2) Then adjust the position of slit 1 until the correlation of detectors 1 and 2 with detectors 3 and 4 is a maximum. After this adjustment both detectors 1 and 2 view the intersection defined by step 1.

During particle counting and measurement, only particles seen by both detectors 3 and 4 are counted by all of the detectors, because they are a subset of the particles seen by detectors 1 and 2. By using different slit image sizes and using the smaller slit images to determine count acceptance, the system will accept only particles which are seen by all four detectors. If the slit images from detectors 3 and 4 are larger than the images from detectors 1 and 2, then detectors 1 and 2 would be adjusted before adjusting 3 and 4; and detectors 1 and 2 would select which particles are counted. The general rule is that the detector images which have the smallest intersection with the incident beam are adjusted first and they determine which particles will be counted. The slit widths are chosen to create one slit image with a small intersection volume and the other with a larger intersection volume so that when a particle is detected in the smaller volume, it is clearly within the larger volume. The smaller slit image only needs to cross the incident beam near to its image plane. Then the larger slit image only needs to cover the intersecting volume to insure that it sees all of the particles passing through the smaller slit image. Then by only counting particles detected by the smaller slit image, only particles which are seen by both detectors will be counted. If the slit images were comparable in size, very precise alignment of both slit images with each other would be required and the correlation between the detector signals would be needed to choose which particles to count. This comparable sized slit case is also claimed in this disclosure. Also the replacement of slits with rectangular apertures or pinholes is also claimed, but with the requirement for two axis alignment as indicated previously.

Figure 6B:
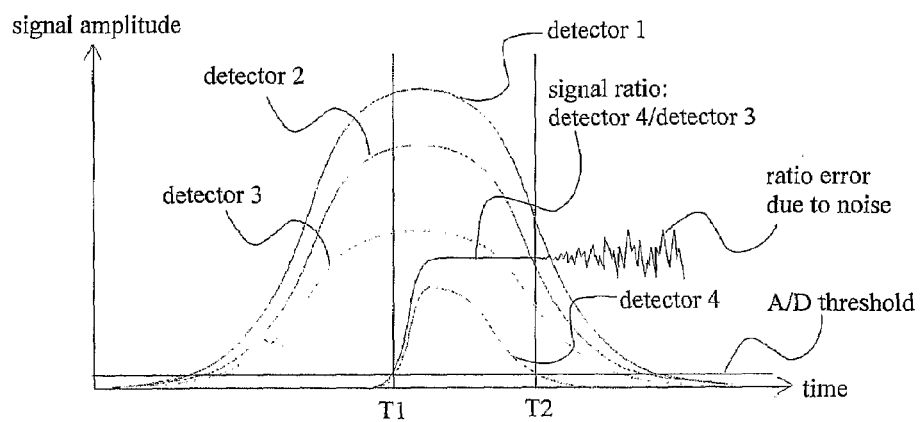
FIG. 6b provides a graph showing an example of scatter signals from a system as shown in FIG. 1.

FIG. 6b shows an example of scattered detection pulses from the four detectors. These signals are measured after a high pass filter for each of detectors 1 and 2, and after a high pass filter and envelope detector for each of detectors 3 and 4. The high pass filters could be replaced by narrow band filters. This data describes the case where the particle passes through a corner of the volume which is common to the source beam and the field of view from detector 4 (see FIG. 2). Detectors 1, 2, and 3 show similar profiles as a function of time as the particle passes through the interaction volume. However the signal from detector four is truncated at the leading edge due to the edge of the detector field of view. Over the region where the particle is well within the detector fields of view, each detector signal will maintain the same ratio with another detector signal as the detector signal amplitudes follow the particle passing through the source crossection intensity distribution. This region of stable signal ratio must be determined in order to eliminate the effects of the variation in source intensity by ratioing pairs of detector signals. Each of the four detector signals is digitized and the ratio of signal from the detector with the minimum interaction volume with one of the other detectors is calculated at each A/D (analog to digital conversion) sampling point. The A/D may be only turned on by a comparator during the period where all the detector signals are above a noise threshold, between times T1 and T2 in FIG. 6b. In this case the ratio between detectors 3 and 4 is used to determine the optimum portion the sampled data to use. The ratio of detector 4/detector 3 increases as the particle enters the field of view of detector 4. Once the particle is completely inside the field of view, the ratio between the two signals is nearly constant even though the individual signals are changing due to the source intensity distribution non-uniformity. Eventually, the signal levels drop and the signal ratio becomes very noisy. If we assume that there are 20 samples between T1 and T2, we could measure the variance of the ratio for samples 1 through 5 and then the variance of the ratio for samples 2 through 6, and so on up to samples 16 through 20. The 5 sample set with the lowest variance for the detector 3/detector 4 ratio would be chosen to determine the detector to detector ratios for all detector combinations for that particle, either by choosing the sample in the middle (sample 3) of that set or by averaging all 5 ratios to obtain an averaged ratio for the 5 samples in the set. The assumption of 20 samples and 5 samples per set is an example. This invention claims any appropriate data set size and segmentation.

The pulses shown in FIG. 6b are the result of some prior electronic filtering and envelope detection. The signals from detectors 1 and 2 will be simple pulses which may be cleaned up by a high pass filter before the A/D conversion. The signals from the heterodyne detectors 3 and 4 are the product of a pulse and a sinusoid. The pulse may consist of a megahertz sine wave, amplitude modulated by the intensity profile of the source beam over a period of about 100 microseconds, depending upon the size of the interaction volume and the particle flow velocity. This oscillatory signal sits on top of a large offset due to the local oscillator intensity. This offset and other source noise components may be removed from the heterodyne signal by high pass or narrow-band electronic filtering. The power spectrum of these pulses will reside in a 100 kilohertz band which is centered at 1 megahertz. Hence a narrow-band filter may provide optimal signal to noise for the heterodyne signals. After the filtering, the signals could be digitized directly for digital envelope detection or an analog envelope detector could be used to remove the 1 megahertz carrier, reducing the required sampling rate to only 10 to 20 samples per pulse instead of 400 samples per pulse. By using a dual phase lock-in amplifier with reference oscillator set to the heterodyne frequency (1 megahertz in this example), extremely high signal to noise could be obtained by measuring the filtered signal without the envelope detector. By using the zero degree and quadrature outputs of the dual phase lock-in amplifier, the phase sensitive signal would be recovered even though the reference and signal carriers are not in necessarily phase.

Figure 7:
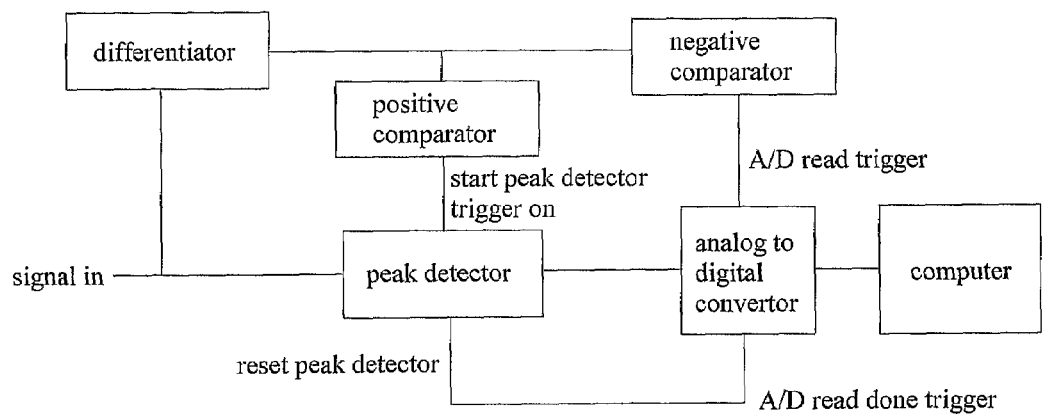
FIG. 7 provides a block diagram of a peak detection system which uses analog electronic devices to reduce the data rate requirements of the analog to digital converter, according to the present invention.

The particle counting rate can also be increased by digitizing the peak scattered signal (directly from detectors 1 and 2 and after the envelope detector from detectors 3 and 4) from each particle instead of digitizing many points across the scattering pulse and finding the peak digitally. This is accomplished by using an analog peak detector whose output is digitized in sync with the positive portion of the signal pulse derivative and reset by the negative portion of the derivative. Then only one digitization is needed for each particle, as shown in FIG. 7. The negative comparator switches on when the input signal drops below the reference setting and the positive comparator switches on when the signal is greater than the reference setting.

Figure 8:
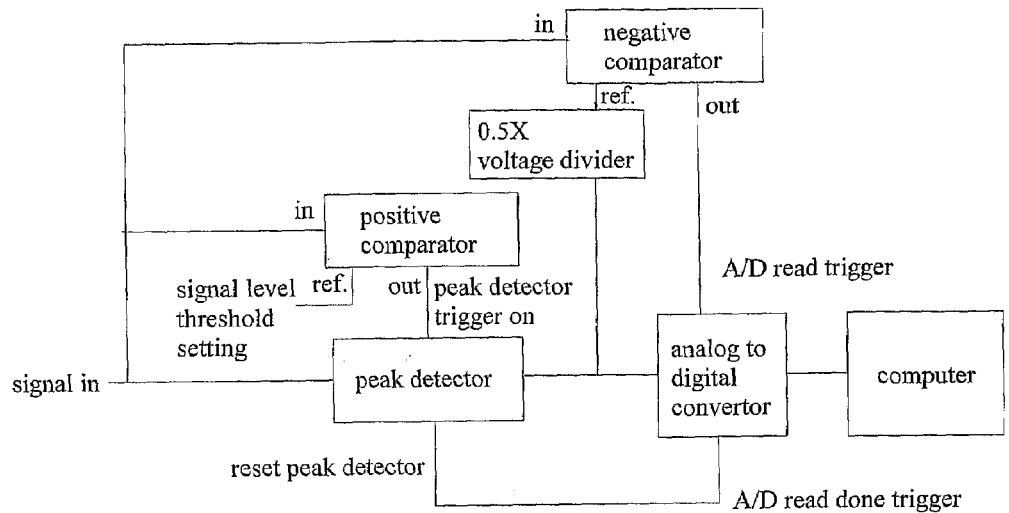
FIG. 8 provides a variation of the system shown in FIG. 7.
Figure 9:
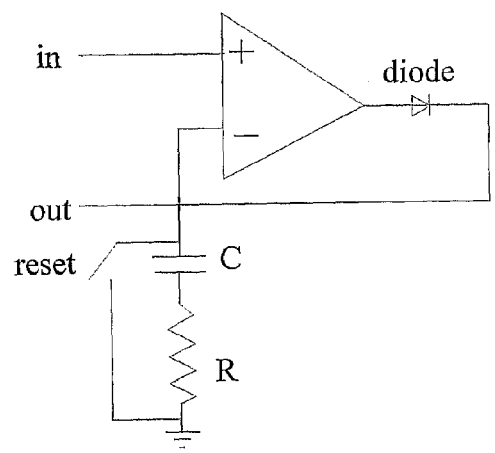
FIG. 9 provides a schematic diagram of the peak detector circuit used in the present invention.

Another variation of this concept triggers on the actual signal instead of the derivative, as shown in FIG. 8. When the signal rises above a preset threshold, the positive comparator takes the peak detector out of reset mode. As the signal rises, the output of the peak detector (see FIG. 9) follows the input signal until the signal reaches a peak. After this point, the peak detector holds the peak value with a time constant given by the RC of the peak detector circuit. The input signal drops below this as it falls down the backside of the peak. When the signal reaches some percentage of the peak value, the A/D is triggered to read and then reset the positive comparator. This percentage value is provided by a voltage divider (shown in the figure as 0.5× voltage divider, but other divider ratios would also be appropriate between approximately 0.2 to 0.8) which determines the reference level for the negative comparator. The A/D is only triggered once per signal pulse and measures the peak value of the pulse. Using this circuit, the detector with the smallest interaction volume generates the A/D trigger for all of the other detectors, so that only particles seen by all of the detectors are counted.

Figure 10:
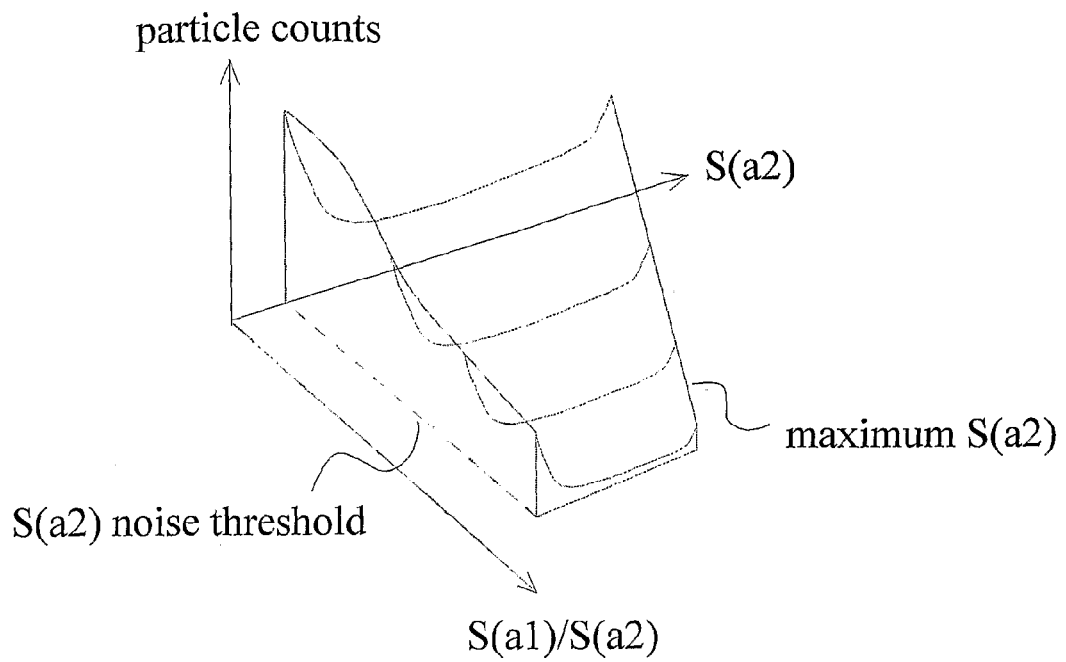
FIG. 10 provides a surface plot of a particle count distribution versus a scattering signal amplitude and a ratio of two scattering signals, according to the present invention.
Figure 10B:
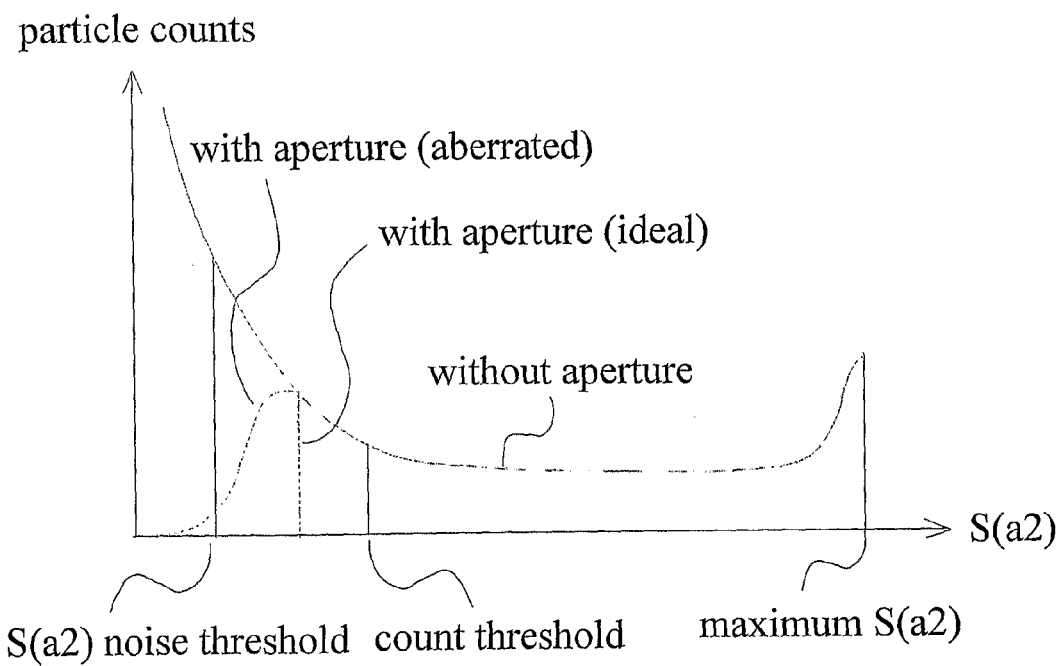
FIG. 10b shows a section of the surface plot of FIG. 10.

The detector signals are either digitized directly, peak detected with the circuit in FIG. 7 or FIG. 8, or integrated and sampled at a lower rate. The signal can be continuously integrated (up to the saturation limit of the integrator). Then the integrated signal needs to be sampled only at points of zero slope in the integrated signal, between each pulse. By subtracting the integrated values on either side of the pulse, the integral of each pulse is sampled separately without having to sample the pulse at a high sampling rate. Also each pulse could be sampled at a lower rate and then a function could be fit to these samples to determine the peak value of the pulse. This should work particularly well using Gaussian functions which model the intensity profile of the laser beam. The parameters of the best fit Gaussian solution directly provides the peak, half width, or integral of the pulse. In any case, the final signal from each pulse will be analyzed and counted. One problem associated with conventional particle counters is the incident beam intensity profile in the interaction volume. Identical particles passing through different portions of the beam will see different incident intensity and scatter light proportionally to that intensity. But the scattered intensity also depends upon the particle diameter, dropping as the sixth power of the diameter below 0.3 microns. So the effective interaction volume will depend upon particle diameter and detection noise, because particles will not be detected below this noise level. Therefore small particles will be lost in the noise when they pass through the tail of the intensity distribution. This means that larger particles have a larger effective interaction volume than smaller particles and therefore the number distribution is skewed in favor of large particles. This invention includes a method for creating a particle diameter-independent interaction volume, using signal analysis. The systems in FIGS. 1, 2, and 3 use at least 2 detectors per scatter collection system to remove the incident intensity dependence by using the ratio of two scattering angles to determine the particle size. Also for any number of detectors, ratios between any pair of detectors could be used to determine the size of particles in the size range covered by that pair. Instead of detector pairs, detector triplets or quadruplets, etc. could also be used with appropriate equations or lookup tables to determine the size of each particle independent of the incident intensity on the particle. In the case of detector pairs, both scattered signals, S(A1) and S(A2), are proportional to the scattering function, at that angle, times the incident light intensity:

$$S(a1)=K*I0*F(D,a1)$$

$$S(a2)=K*I0*F(D,a2)$$

where I0 is the incident intensity, K is an instrumental constant in this case, and F(D,A) is the scattering per particle per unit incident light intensity for a particle of diameter D, at scattering angle a. The variable "a" can refer to a single angle or a range of angles over which the signal is collected. Then a1 and a2 would refer to the a1 range of angles and a2 range of angles, respectively. For more than two detectors, there is a similar equation for each detector signal for angles a1, a2, a3, a4, etc. The scattering signals S(a) may be the pulse peak value or pulse integral of the envelope of the heterodyne signal (detectors 3 and 4) or of the direct non-coherent signals (detectors 1 and 2). So the ratio of the scattering at two angles is equal to F(D,a1)/F(D,a2), which is independent of incident intensity and relatively independent of position in the Gaussian beam profile of a laser. FIG. 10 shows a conceptual plot of number of particles vs. S(a1)/S(a2) and S(a2). A plot of number of particles vs. S(a1)/S(a2) and S(a1) could also be used. The scattering signal, for any diameter D, will show a very narrow range of S(a1)/S(a2) but a broad range of S(a2). Particles passing through the peak of the laser intensity profile will produce pulse peak amplitudes at the upper limit, maximum S(a2). The surface, describing this count distribution, is determined by fitting a surface function to, or by interpolation of, this count surface in FIG. 10. This surface function provides the parameters to determine an accurate particle count, because S(a1)/S(a2) is a strong function of particle size, but a very weak function of particle path through the beam. By setting an acceptance threshold for S(a2) at a certain percentage of this maximum value, separately at each value of S(a1)/S(a2), only particles passing through a certain volume (independent of particle size) of the beam will be accepted and counted. Because the particles, which are counted by these detectors, are all much smaller than the source beam crossection, they all have the same probability functions for describing the percentage of particles passing through each segment of the beam. Therefore, at any value of S(a1)/S(a2), the shape of the count vs. S(a2) function is nearly identical when you normalize the function to maximum S(a2). By setting a count-above threshold at a certain percentage of maximum S(a2) (but well above the noise level) at each value of S(a1)/S(a2), only particles passing through a certain portion of the interaction volume, with acceptable signal to noise, will be counted and sized, as shown in FIG. 10*b*. The noise threshold is chosen so that all particles with signals above that level will be accurately sized based upon the scattering signals.

This analysis is usually done for the detector with the smallest interaction volume, the heterodyne system in the case of FIG. 1. All four detectors are used to determine the particle diameter, but the acceptance criteria is determined by only detector 3 and 4 (S(a1)=detector 3 and S(a2)=detector 4). This analysis can also be performed, individually, on any pairs of signals, as long as the noise threshold is always the same percentage of the maximum value of signal used for the horizontal axis in FIG. 10b. These counts are accumulated into a set of size ranges, each range defines a different size channel. In many cases, each size range has a very narrow width in size and S(a1)/S(a2). The optimum channel size width is the minimum width which still contains sufficient particle counts in that channel to avoid statistical errors. Hence, the distribution of S(a2) for the range of S(a1)/S(a2) within a certain channel can determine the S(a2) acceptance limit for counts in that channel. This is accomplished by only counting particles with S(a2) above a certain percentage of the maximum S(a2) for that channel. If the theoretical scattering efficiency changes substantially across any channel, the S(a) for each count is divided by the theoretical scattering efficiency indicated by the size corresponding to the S(a1)/S(a2) for that particle. This may be especially important below 0.4 microns where the scattering efficiency drops as the inverse of the sixth power of the particle diameter.

The shape and width of the S(a2) profile is determined by how sharply the source crossectional intensity distribution drops off at the edges of the beam. If the beam profile was a step function, the effective interaction volume would be only weakly particle size dependent near the edges. This shape can be accomplished by spatially filtering the source, with the spatial filter aperture in a plane conjugate to the interaction volume. Then an image of the aperture, which is smeared by aberrations and diffraction limits, defines the sharpness of intensity drop at the edges of the beam. The intensity tails of the Gaussian beam are cut off by the aperture, which could be sized to cut off at any appropriate percentage of the peak intensity to limit the variation of scattering from a particle as it traverses the beam. The beam crossectional intensity distribution may also be shaped by use of appropriate apodization of the beam or by using diffractive beam shapers.

FIG. 10b describes this concept for data collected in one size channel. The pulse signal is collected and stored for each pulse above the count noise threshold. But only pulses which are within the range of S(a1)/S(a2) for that channel are collected into that channel. The frequency distribution of counts at each pulse level is plotted for a beam with a Gaussian intensity profile. The problem is that some particle pulses fall below the noise threshold and are not counted. The amount of missed particles depends upon the scattering efficiency of the particles. For smaller particles with lower scattering efficiency, a higher percentage of particles will be lost below the noise threshold. So the count error will be particle size dependent. The source beam can be spatially filtered to cut off the low intensity wings of the source intensity distribution. Then the count distribution would be as shown in the "with aperture (ideal)" curve and no particles would be lost in the noise. This could be accomplished by using a rectangular spatial filter that cut the wings off in the Y direction, because the particle flows in the XZ plane and the tails in this plane are actually measured in each pulse shape. However, the image of the spatial filter aperture in the interaction volume will be aberrated and diffraction limited as shown by the "with aperture (aberrated)" curve. In this case a few particles may still be lost in the noise and a count threshold must be set above this level to reject all questionable particle pulses. The maximum S(a2) value changes in each channel due to the change in scattering efficiency for the particles in that channel. As long as the count threshold is set to be the same percentage of that maximum S(a2) for each channel, all channels will lose the same percentage of particles and the distribution will be correct. Without this channel specific threshold, the smaller particle channels will lose a larger percentage of particles than the larger particle channels and the distribution will be skewed towards larger particles. This assumes that the sample is a homogeneous mixture of all the particle sizes and that the sufficient count exists in each channel to obtain an accurate estimate of the maximum S(a2).

The method described above handles the variations caused by the particle passing through various random paths in the interaction volume. This method can also correct for the variations due to random positions along the path where the digitization occurs. Therefore the peak detectors or integrators could be eliminated. The signal from the envelope detector (detectors 3+4) and direct signals from detectors 1+2 could be digitized directly at approximately 3 points per pulse. The maximum signal data point from each pulse would be added to the data list for input to the analysis described above. Any deviation from the peak value would not be a problem because the ratio of the signals determines the size and all four detectors will be low by the same percentage if they are not sampled at the peak intensity position in the interaction volume.

Also all the signals could be digitized directly after the high pass (or narrow band) filter on the detectors (detectors 3 and 4 are high pass filtered to remove local oscillator current and detectors 1 and 2 could also be high pass filtered to remove low frequency noise). Then all of the analog and digital operations (phase sensitive detection, envelope detection, etc.) could be done digitally but at the cost of reducing data collection rates. Also the source could be modulated for detectors 1 and 2 to use phase sensitive detection (lock-in amplifier) when their signals are low.

All of the optical design and algorithm techniques described in this disclosure may leave some residual size response broadening which may be particle size dependent. This instrument response broadening is determined by measuring a nearly mono-sized particle sample (such as polystyrene spheres). For example, due to noise or position dependence in the beam, a certain size particle will produce a range of S(a1)/S(a2) values as it repeatedly passes through different portions of the interaction volume. In any event, the broadening may be removed by solving the set of equations which describe the broadening phenomena. If the broadening is relatively the same for all size particles, the response broadening can be described by a convolution of the broadened number distribution response and the actual number vs. size distribution. Iterative deconvolution algorithms may be used to deconvolve the measured number vs. measured parameter distribution to obtain size resolution enhancement. This resolution enhancement will work for any ergodic stochastic process, where the broadening statistics are stable over time. This idea could be applied to (and is claimed for) any broadened counting phenomena with stable stochastic or deterministic broadening mechanisms. In particle counting measurements the amount of scatter from a particle may vary due to the random orientation and position of a particle as it passes through the exciting light beam, or by other structural and optical noise sources. The counting and classification of each of a group of identical particles will not produce a narrow peak when plotting count number vs. measured parameter. Here "measured parameter" refers to the parameter which is measured from each particle to determine its size. Examples of measured parameters are scattering optical flux amplitude, ratio of flux from two scattering angles, a function of fluxes from multiple scattering angles, or the decrease in intensity due to particle scattering and absorption, as will be described later in this disclosure. The peak of the number-vs.-measured parameter function from a group of monosized particles will be broadened in a predictable way. This broadening can be determined experimentally with a calibrated group of particles (by measuring the response from monosized particle samples) or it can be calculated theoretically based upon models for the random and deterministic broadening sources. Then the entire system can be modeled using a matrix equation, where each column in the matrix is the broadened measured parameter distribution from a certain sized particle. This broadening is reproducible as long as a large number of particles are counted for each trial. The matrix equation is described by the following relationship:

$$Nm = M*N$$

Where Nm is the vector of values of the measured (broadened) number-vs.-measured parameter distribution and N is the vector of values of the actual particle number-vs.-size distribution which would have been measured if the broadening mechanisms were not present. "*" is a matrix vector multiply. The number distribution is the number of particles counted with parameter amplitudes within certain ranges. It is a differential distribution which describes counts in different channels or bins, each bin with a different range of parameter, which may be size, scattering ratio, etc. M is a matrix of column vectors with values of the broadened number-vs.-measured parameter function for each particle size in N. For example, the nth column of M is a vector of values of the entire measured number-.vs.-measured parameter distribution obtained from a large ensemble of particles of the size which is represented by the nth element of vector N. This matrix equation can be solved for the particle number-vs.-size distribution, N, by matrix inversion of M or by iterative inversion of the matrix equation. This particle number-vs.-size distribution can be determined by using this matrix equation in many different forms. The term "measured parameter" in this paragraph can refer to many size dependent parameters including: scattering signal amplitude (pulse peak or integral, etc.), the ratio (or other appropriate mathematical relationship) between scattered signals at two or more different angles, or even particle diameter (a broadened particle size distribution determined directly from a broadened process can also be "unbroadened" by using broadened particle size distributions for each monosized sample column in matrix M). So we solve for N, given Nm and M.

If each column of M is simply a shifted version of the prior column, then the instrument response is shift invariant and the relationship is a convolution of N with the system impulse response IMP:

$$Nm = IMP**N$$

where ** is the convolution operator

For this case, deconvolution algorithms may be used to solve for N, given Nm and IMP.

Figure 9B:
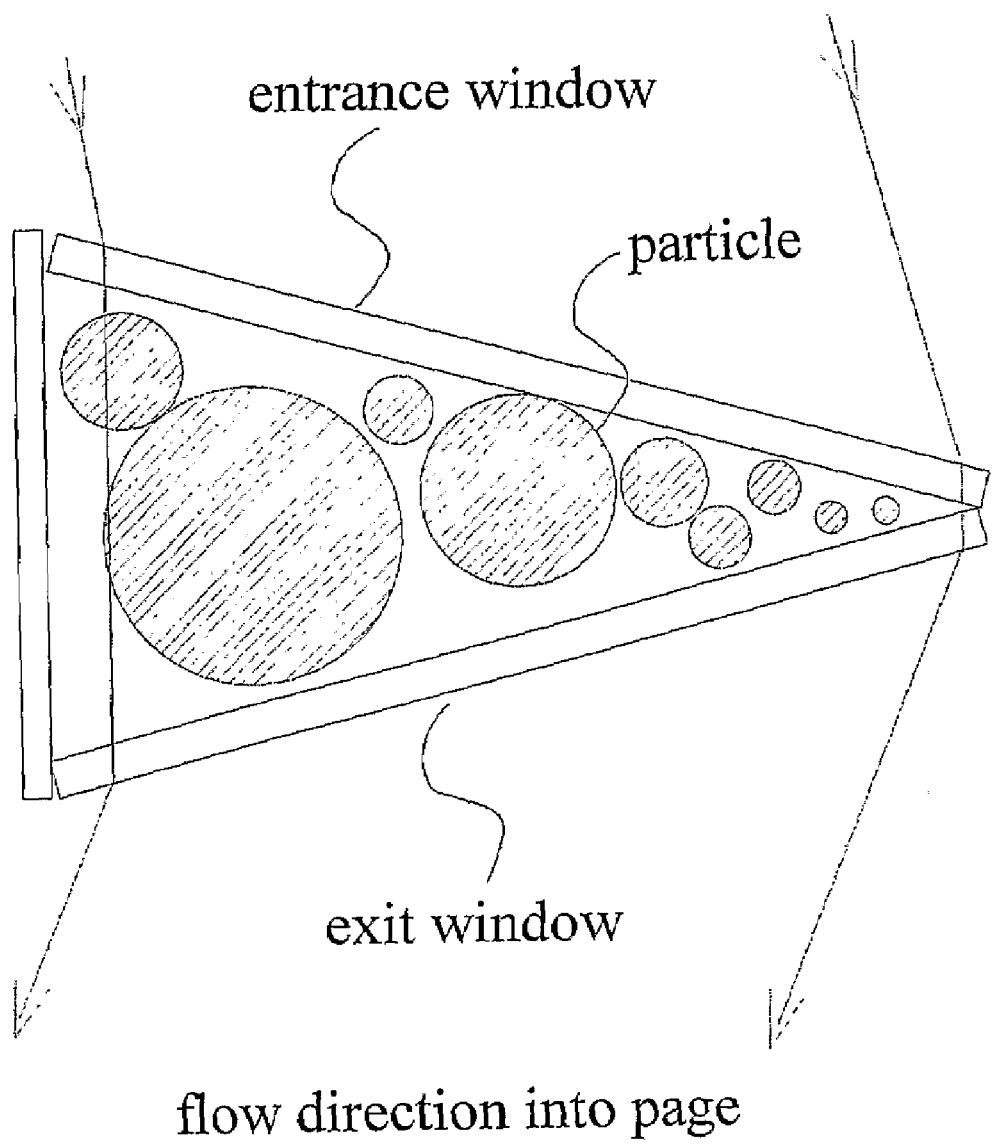
FIG. 9b provides a diagram of a wedge shaped particle dispersion sample cell, which provides a linearly increasing maximum particle size across the cell, according to the present invention.

The generalized matrix equation above may also include the effects of coincidence counting. As discussed earlier, over one million particles should be counted for a uniform volume distribution to be accurately determined in the large particle region. In order to insure low coincidence counts, the source spot size in the interaction region must be reduced to approximately 20 microns in width so that the particle concentration can be raised to count 1 million particles at flow rates of 1 meter per second in a reasonable time. For example, the worst case is slit 1 being the largest slit, because then the largest interaction volume might be approximately 20 micron×20 micron×200 micron, for example. If we require approximately 5 volumes per particle to avoid coincidence counts then the inter-particle spacing is 74 microns. 1 million particles spaced by 74 microns (on average) moving at 1 meter per second will take 74 seconds to measure. This spot size would provide good count reproducibility for the worst case of uniform volume distribution. However, a 20 micron spot and the corresponding detector fields of view may be difficult to align, requiring larger source spot size with a higher coincidence level. Even with a 20 micron spot, some coincidences will be seen at the 74 micron particle spacing. These coincidences can be corrected for by including their effects in the generalized matrix equation. If M were correcting for coincidences, a column in matrix M which corresponds to the large size end of vector N will have negative values in the region corresponding to the small size end of vector Nm, because the larger particles will block the scattered light from smaller particles which are ahead or behind that larger particle in the source beam. Also a column in matrix M which corresponds to the small size end of vector N will have a tail of positive values in the region corresponding to the large size end of vector Nm, because some smaller particles will be counted coincidentally with the larger particles and increase their measured size relative to their actual size. The effects of coincident counts can be mitigated by using a wedge shaped cell as shown in FIG. 9b. The cell consists of two windows at an angle so as to produce regions of different optical path along the cell. This cell could replace the cells in FIGS. 11 and 12. The red rays define the edges of the source beam. Then at any point along the wedge direction, only particles smaller than a certain size may pass through that portion of the cell. The size distributions gathered at different points along the wedge, from the 2 dimensional detector array in FIGS. 11 and 12, may be combined by correcting the count in the larger particle areas for coincidentally counted smaller particles by using counts in the smaller particle regions of the wedge. This correction can be accomplished by solving a matrix equation of the form shown previously.

The correction for coincidences may also be accomplished by an iterative procedure, which solves for N, given Nm, and then corrects each scattered signal for coincidences. Each scattered signal, S1 and S2, consists of light scattered (or light lost due to absorption or scattering) from all the particles in the interaction volume. Ideally, the particle concentration is low and most of the time each scattering event is from a single particle. But for the general case, multiple coincident particles can be modeled by the following equation:

$$Ai = SUMj(G(Ni,Nj)Aj)$$

where SUMj means summation over the j index. Ai is the "particle signal" for a particle of the ith size bin in the particle size distribution. Particle signals can include S1, S2, or the log of attenuation or obscuration (described later in this disclosure) due scattering and absorption of a particle. G(Ni,Nj) is a function which describes the most probable total particle signal from a combination of particles of ith and jth sizes based upon their particle numbers (or concentrations), Ni (for the ith size) and Nj (for the jth size). Since the combination of particles in the interaction volume is a random process, G(Ni, Nj) represents the sum of all combinations (given Ni and Nj), weighted by their probability functions.

In the case of signals S(a1) and S(a2), the procedure for determining the number vs. size distribution is the following:

1) Use the surface plot of FIGS. 10 and 10*b* to determine the raw number distribution Nm.
2) Solve the matrix equation Nm=M*N for the true number distribution N.
3) Recalculate S(a1) and S(a2) using the equation above and the distribution N:

$$S(a1)i = SUMj(G1(Ni,Nj)S(a1)j)$$

$$S(a2)i = SUMj(G2(Ni,Nj)S(a2)j)$$

4) Do steps 1 through 3 again
5) repeat iteration loop of step 4 until the change in number distribution N between successive loops is below some threshold.

Figure 11:
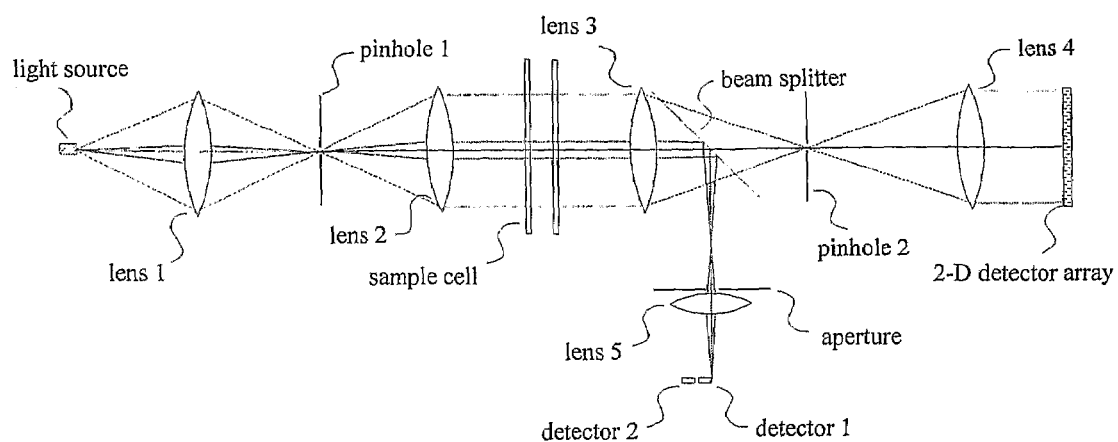
FIG. 11 provides a schematic diagram of an optical system which measures the amount of scattered light removed from the beam by each of many particles at the same time, according to the present invention.

For particles between approximately 1 and 10 microns, the ratio of scattered intensities at two angles below approximately 3 degrees scattering angle is optimal to provide highest size sensitivity and accuracy. A white light source or broad band LED should be used to reduce the Mie resonances for spherical particles. Above 10 microns, the measurement of total scatter from a white light source provides the best size sensitivity and depth of focus for a spatially filtered imaging system as shown in FIG. 11. A white light or broad band LED source is spatially filtered by lens 1 and pinhole 1 to provide a well collimated beam through lens 2. If a well collimated source beam is required to measure scattering at very low scattering angles (for large particles), a laser source might also be used. This collimated beam passes through a cell consisting of two windows, which confine the flowing particle dispersion. Lens 3 focuses this collimated beam through pinhole 2, which removes most of the scattered light from the beam. This transmitted beam is transferred to a 2 dimensional detector array through lens 4, which images the center of the sample cell onto the array. This array will see dark images of each particle on a bright background due to the light lost through scattering or absorption by the particle. A beamsplitter after lens 3 diverts a portion of the light to an aperture and lens 5. The aperture defines a narrow pencil of light through the cell and a small scattering volume, lowering the probability of coincidence counts for detectors 1 and 2, which are near to the focal plane of lens 5. The aperture is optimally placed in the optical plane which is conjugate to the center of the sample cell, through lens 3. Conjugate planes are a pair of image and object planes of an optical system. Detectors 1 and 2 are nominally placed in the optical plane which is conjugate to the optical source, through lenses 1, 2, 3 and 5. Detectors 1 and 2 measure scattered light at two angles, which are nominally below 3 degrees for larger particles but which can cover any angular range appropriate for the size range of the particle detector. Also more than two detectors could be used to increase the size range for this portion of the particle detection system. These detectors could also be annular ring detectors centered on the optical axis to reduce sensitivity to particle shape. For example, detector 1 could measure a scattering angular region around 1 degree; and detector 2 could measure around 3 degrees. By combining the particle scattering pulse signals from these detectors, by ratio or polynomial, a relatively monotonic function of particle size is created without strong Mie resonances (due to the white light source and signal ratio). Detectors 1 and 2 count and size particles in much the same way as the system in FIG. 1. The concept is to use two angles to remove the variations in scattering intensity due to particles passing through different portions of the incident beam and to reduce calculated size sensitivity to particle and dispersant composition. Particles of size between approximately 1 and 10 microns could be handled by detectors 1 and 2 of FIG. 11; and particles above approximately 5 microns are handled by the 2-dimensional detector array. The two size distributions from these two measurements are combined with blending in the overlap region between 5 and 10 microns.

The 2-dimensional detector array is imaged into the center of the sample cell with magnification corresponding to approximately 10×10 micron per array pixel in the sample cell plane. A 10 micron particle will produce a single dark pixel if it is centered on one pixel or otherwise partially darkened adjacent pixels. By summing the total light lost in these adjacent pixels, the total light absorbed or scattered outside of pinhole 2 for each single particle in the view of the array is determined. The particle concentration is limited to prevent coincidence counting in each separate 10×10 micron projection through the sample cell. At low concentrations, any group of contiguous pixels with reduced light levels will represent a single particle. And the total percentage light lost by these contiguous pixels determines the particle size. All pixels below a certain percentage of their non-obscured values are accepted as particle pixels. All contiguous particle pixels are then combined as representing one particle. This is accomplished by summing the pixel values of contiguous pixels and comparing that sum to the sum of those same pixels without the presence of a particle. This works well for smaller particles where the total scattered light is well outside of the pinhole 2 aperture, because then the total percentage drop represents the scattering and absorption extinction of the particle. For larger particles, a larger portion of the scattered light will pass through pinhole 2 and cause a deviation which will not agree with the total theoretical scattering extinction. This can either be corrected for in the theoretical model by calculating the actual percentage loss for larger particles by integrating the actual scattered light outside of the pinhole, or the particle can be sized directly by counting contiguous pixels, because for the larger particles the pixel size may be less than 0.1% of the total crossectional area of the particle. The accuracy of this calculation is improved by adding partial pixels at the edge of the particle image based upon their attenuation as a fraction of the attenuation of nearby interior pixels. Hence if a pixel in the interior of the image is attenuated by 10% and an edge pixel is attenuated by 4%, that edge pixel should count as 40% of its actual area when added to the sum of all contiguous attenuated pixels to determine the total crossectional area and size for that particle. Otherwise the theoretical loss per particle could be used.

This detector array system has an enormous particle size dynamic range. The particle will remove approximately the light captured by twice its crossectional area. So a 2 micron particle will reduce the total light flux on a 10×10 micron pixel by 8 percent. But the entire array of 1000×1000 pixels can cover a crossection of 10×10 millimeters. So the size range can cover 2 microns to 10000 microns. The size dynamic range is almost 4 orders of magnitude. The smallest particles are detected by their total light scattering and absorption. For very large particles, the angular extent of the scattering pattern may fall within the aperture of pinhole 2. Then the summed light from all the contiguous pixels may not indicate accurate size. For the larger particles, the actual imaged size is determined by counting contiguous pixels. Pixels at the outer boundary are counted as partial pixels based upon the amount of light lost as a fraction of the amount lost from pixels in the interior of the contiguous set. The light loss in each pixel is determined by storing the light value for each pixel without particles in the sample cell and subtracting the particle present values these stored values. The source intensity can also be monitored to normalize each pixel measurement for light source intensity fluctuations.

In order to avoid smeared images, the detector array must integrate the current from each pixel over a short time to reduce the distance traveled by the flow during the exposure. This may also be accomplished by pulsing the light source to reduce the exposure time. Smearing in the image can be corrected for using deconvolution techniques. But the scattering extinction measurements will be accurate as long as the contiguous pixel groups do not smear into each other. Simply add up all of contiguous pixel signals (from the smeared image of the particle) after presence of the particle to determine the particle scattering attenuation and size. If the particle image is smaller than one pixel, then the attenuation of that pixel is the scattering extinction for that particle. Essentially, you are measuring nearly the total amount of light scattered or absorbed by the particle during the exposure. Using this total lost optical flux divided by the incident intensity provides the scattering crossection for the particle, even if the particle is not resolved by the optical system or if that loss is distributed over more pixels than expected from perfect imaging of the particle. This is the power of this technique. A 10 mm by 10 mm detector array, with 10×10 micron pixels, can measure particle diameters from a few microns up to 10 mm, with thousands of particles in the source beam at one time. The 10 mm particles will be sized directly by adding up pixels and multiplying the interior pixels by 1 and the edge pixels by their fractional attenuation and adding all of the pixels up to get the total crossectional area and size. A 5 micron particle, centered on one 10×10 micron pixel, will attenuate that pixel by 50% (the total scattering extinction crossection is approximately twice the actual particle area, outside of the Mie resonance region). In both cases the particles are easily measured. You are simply adding up all of the signal differences (signal without particle—signal with particle) of contiguous changed pixels to get the total light lost due the particle. Pinhole 2 blocks all of the light scattered outside of the angular range of the pinhole 2, whose maximum scattering angle is equal to the inverse tangent of the pinhole 2 radius divided by the focal length of lens 3. So the signal difference (signal without particle—signal with particle) is the amount of light scattered by the particle at scattering angles above this maximum angle of the pinhole, including any light absorbed by the particle. The particle size is determined using scattering theory and the ratio of signal change (signal without particle—signal with particle) to the signal without a particle.

Image smearing could also be reduced by using pulsed flow. The particle sample flow would stop during the period when the light source is pulsed or when the detector array is integrating. Then a flow pulse would push the next slug of sample into the detector array field of view before the next signal collection period. The sample would be approximately stationary during the signal collection on the detector array. This pulsing could be accomplished by pressurizing the particle dispersion chamber and using a pulsed valve to leave short segments of the sample dispersion through the source beam interaction volume.

The nearly parallel window cell could also be replaced by a wedge shaped cell which would control the particle count in different size regions, as discussed above (see FIG. 9b). Non-spherical particles present another problem for single particle sizing: non-symmetrical scattering patterns. Assume that the incident light beam is propagating along the Z direction and the XY plane is perpendicular to the Z direction, with origin at the particle. The XZ plane is the center scattering plane of the group of scattering planes which are intercepted by detectors 1,2,3, and 4. Each detector subtends a certain range of scattering angles, both parallel and perpendicular to the center scattering plane. For spherical particles, the scattering pattern is symmetrical about the Z axis and the scattering function could be described in cylindrical coordinates as a function of Z and of radius R from the Z axis, at some distance Z0 from the scattering particle. However, for non-spherical particles the scattering pattern is not symmetrical about the Z axis at Z0. The 2-dimensional array in FIG. 11 measures approximately the total light lost to scattering or absorption at all scattering angles, in all scattering planes. Hence it will produce particle size estimates which are related to the total crossectional area of the particle, for both spherical and non-spherical particles, without sensitivity to particle orientation. But detectors 1, 2, 3, and 4 in FIG. 1, 3, or 11 measure the scattering only over scattering planes close to the XZ plane (or a limited range of scattering planes). If the pattern is not symmetrical, the particle size estimate will depend upon the orientation of the particle. So a group of particles with identical crossectional areas, but random orientations, would be reported over a wide range of particle crossectional area and size. This particle size distribution width could be corrected by deconvolution of the number vs. size distribution, as described by the matrix equation shown previously, where matrix M would describe the broadening of a count distribution from a group of particles, each with the same particle volume, but with all possible orientations. But the theoretical model would change with the particle shape. Another way to reduce spread is to use two sets of detector systems, one centered on the scattering plane which is +45 degrees with respect to the XZ plane and the other at −45 degrees from that plane, to sample two perpendicular particle orientations and maintain the optimum orientation for heterodyne detection. The average of the size distributions from these two systems would reduce the spread of the distribution. Another more effective method is to collect all of the scattered planes at a certain scattering angle, using the system shown in FIG. 12. A light source is focused into the sample dispersion. This focused spot is imaged onto a pinhole which removes unwanted background light. The light passed by the pinhole contains the incident light beam and the scattered light from the particles. This light is collected by lens 3 which projects the light onto two masks, using a beamsplitter. Each mask contains an annular aperture which defines the range of scattering angle accepted by the collection optics. Lens 4 collects high angle scattered light passing through mask 1 and focuses it onto detector 1. Likewise the low angle scatter is measured by mask 2, lens 5 and detector 2.

Figure 12:
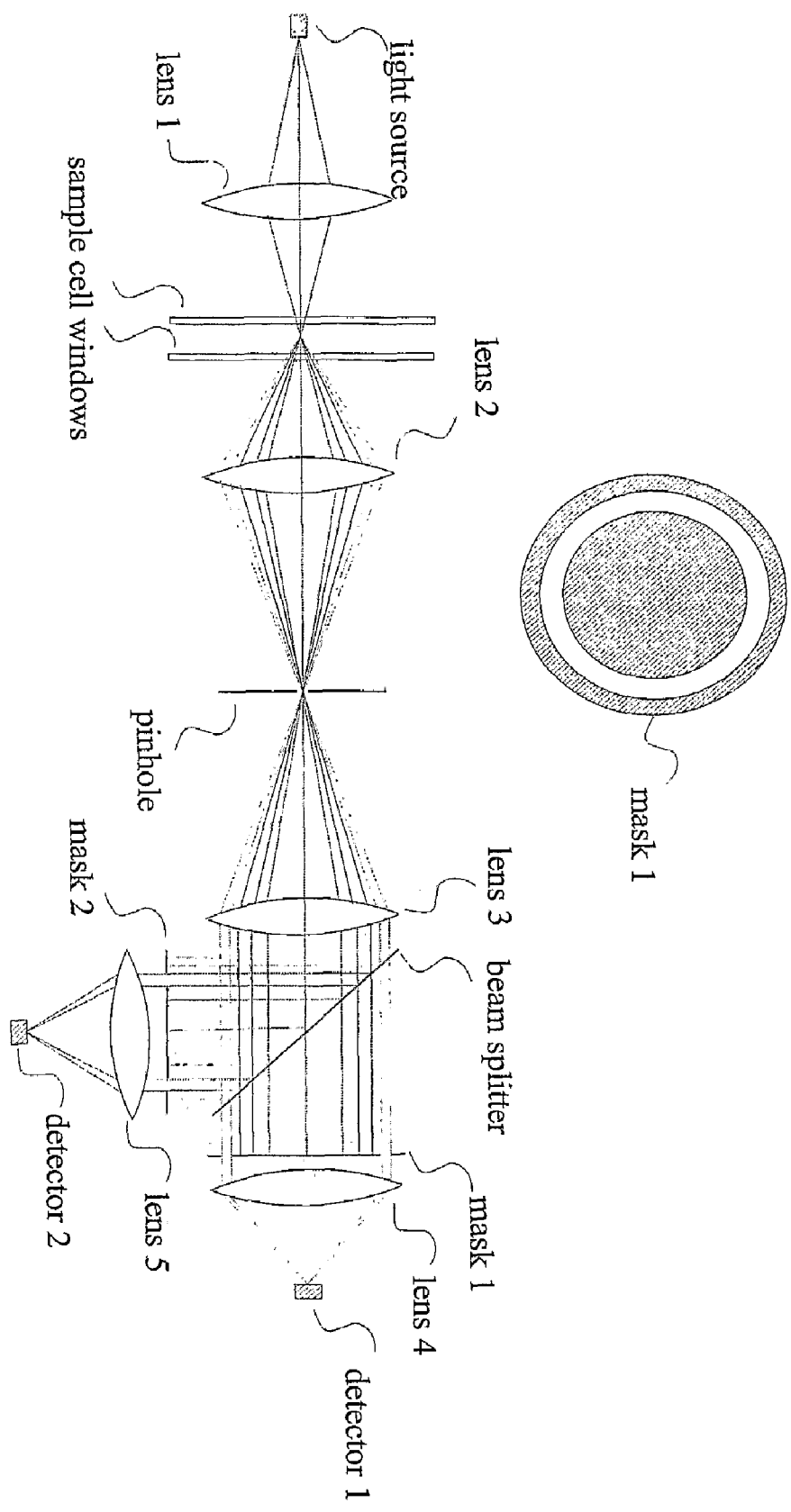
FIG. 12 provides a schematic diagram of an optical system which measures scattered light from different ranges of scattering angle, from a small volume in the particle dispersion sample cell, according to the present invention.

FIG. 12 shows the annular aperture for mask 1, defining equal scattering collection in all the scattering planes. The ratio of signals from detector 1 and 2 would precisely determine the average radius of a non-spherical particle, without size broadening of the system response due to random particle orientation. The beam splitter and dual mask concept could also be applied to the system in FIG. 11. Lens 5 and detectors 1 and 2 (all of FIG. 11) would be replaced by lens 3, the beam splitter, the dual mask system, and detectors 1 and 2 (all of FIG. 12), with the masks in the same optical plane as detectors 1 and 2. Masks 1 and 2 act as angular filters which only pass scattered light in a certain range of scattering angles. The 2-dimensional array in FIG. 11 is already insensitive to particle orientation and needs no modification.

Figure 13:
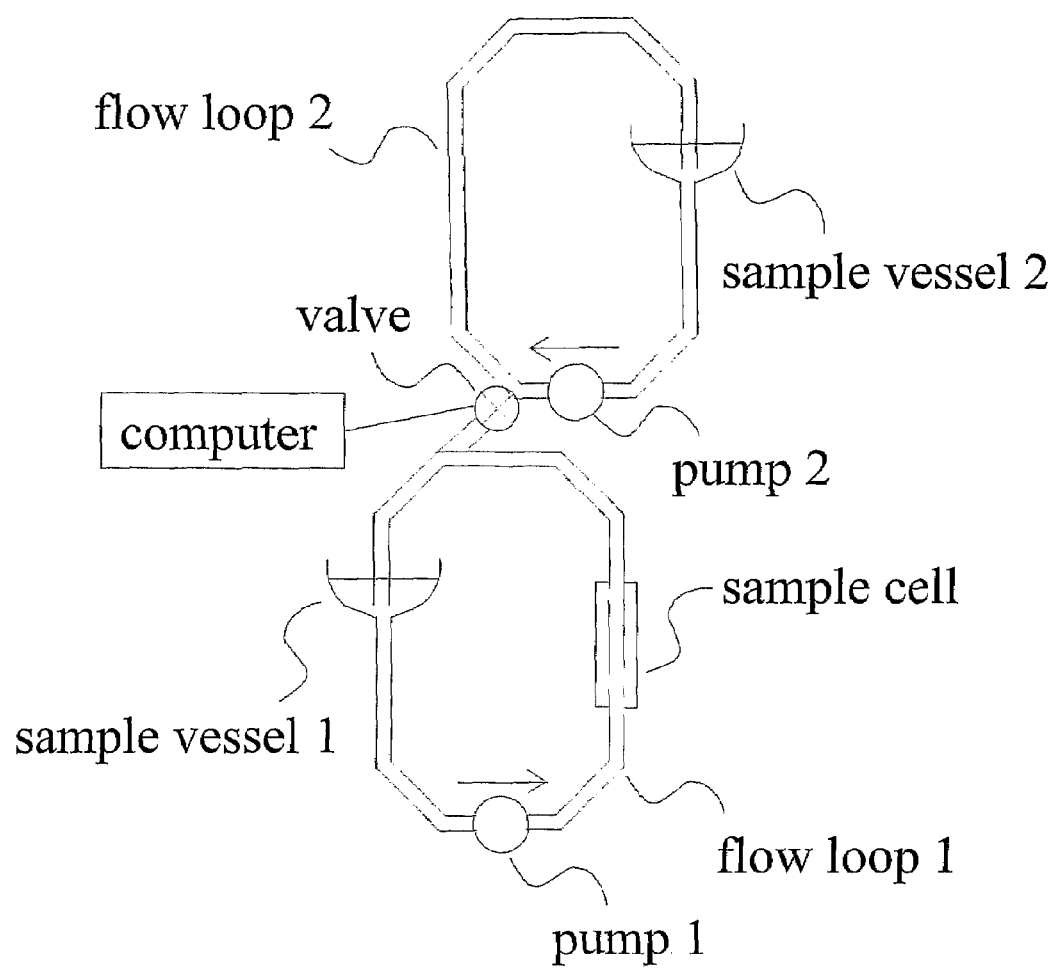
FIG. 13 provides a schematic diagram of a particle sample system which adjusts particle concentration to an optimum value, according to the present invention.

The particle concentration must be optimized to provide largest count levels while still insuring single particle counting. The concentration may be optimized by computer control of particle injection into the flow loop which contains the sample cell, as shown in FIG. 13. Concentrated sample is introduced into flow loop 2 through sample vessel 2. The sample vessel may also contain a stirring means for maintaining a homogenous dispersion in the vessel. Pump 2 pumps the dispersion around the loop to provide a homogenous dispersion in the loop and to prevent loss of larger particles through settling. A second flow system, flow loop 1, is attached to flow loop 2 through a computer controlled valve with minimal dead space. The computer opens the valve for a predetermined period to inject a small volume of concentrated dispersion into loop 1. The optical system counts the particles and determines the probability of coincidence counting based upon Poisson statistics of the counting process. The computer then calculates the amount of additional particles needed to optimize the concentration and meters out another injection of concentrated sample into loop 1, through the valve. Actually, both the concentration and pump speed for loop 1 may be controlled by computer to optimize counting statistics. When the particle concentration is low, higher pump speed will maintain a sufficient particle count rate for good count statistics. The optimum concentration may be different for different detectors and detection systems. Therefore the computer valve may adjust the concentration to various levels in succession. At each concentration level data is taken with the appropriate detector(s) or detector array for a sufficient period and flow rate to accumulate enough counts to reduce the count uncertainty (due to Poisson statistics) to an acceptable level.

Another consideration for FIG. 6b is the determination of signal baseline. The baseline for the scattered signals must be determined for each detector. Digitized values, measured before and after the scattered signal pulse, determine the signal baseline to be subtracted from the pulse signal, by interpolation of those values through the pulse region. These regions before and after each detector pulse should be chosen to be before and after the widest pulse of the group (in some rare cases, the pulse with the largest amplitude should be used if the signals are lost in noise). Then the baseline will certainly be determined from values in a region where no particle scattering has occurred in each of the detectors.

Figure 14:
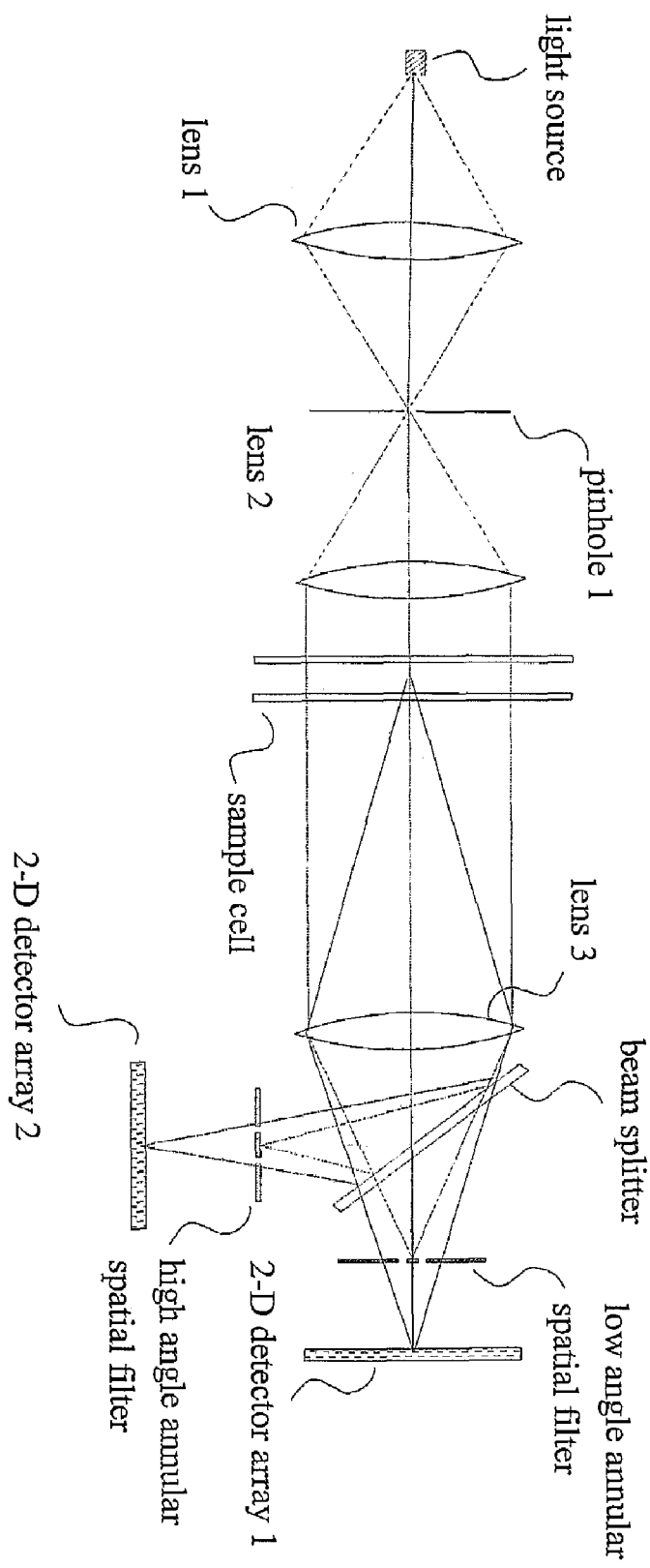
FIG. 14 provides a schematic drawing of an optical system which measures the light scattered, in multiple ranges of scattering angle, by each of many particles at the same time, according to the present invention.

The system shown in FIG. 11 can also be modified to look at only scattered light over a certain angular region, instead of the total light removed from the beam by absorption and/or scattering. FIG. 14 shows such an optical system where the light source is spatially filtered by lens 1 and pinhole 1. Lens 2 collimates and projects the source beam through the particle sample, which is imaged onto the 2 dimensional detector array by lens 3. An annular spatial mask (or spatial filter) is placed in the back focal plane of lens 3 to only pass scattered light over a certain range of scatter angle as defined by the inner and outer radii of the annular spatial mask, which is similar to mask 1 shown in FIG. 12. The very low angle scattering and incident beam are blocked by central stop of the annular aperture in the back focal plane of lens 3. Hence the detector array 1 sees an image of the particles, and the sum of the contiguous pixels associated with each particle's image is equal to the scattered light from that particle over the angular range defined by the aperture (or spatial mask) in the back focal plane of lens 3. A beam splitter splits off a portion of the light to a second annular filter (in the back focal plane of lens 3) and detector array 2. The angular ranges of the two annular filters are chosen to produce scattered values which are combined by an algorithm which determines the size of each particle. The sum of signals from contiguous pixels which view the same particle are analyzed to produce the particle size. One such algorithm would be a simple ratio of the corresponding sums (the sum of contiguous pixels from the image of each particle) from the same particle detected by both arrays. The key advantage is that when the particle size becomes too small to size accurately by dimensional measurements on the image (resolution is limited by pixel size) then the total scattered light from each particle may be used to determine the size. And if the total scattered light is sensitive to particle composition, then the ratio of the two scattering signals can be used to determine the particle size more accurately. In FIG. 14, scattered light is only present when a particle is present. In FIG. 11 the particle image creates a decrease in light, from a bright background level, on the 2-Dimensional array in the corresponding pixels, while in the system of FIG. 14 the particle image creates an increase from a dark background level. If the particle is smaller than a single pixel, then the amount of scattered light measured by that pixel will indicate the total light scattered from that particle in the angular range defined by the focal plane aperture, providing that particle's size. If more than one pixel is associated with a particle, those pixel values are summed together to obtain the scattered signal from that particle in a similar fashion as described before for FIG. 11. The only difference is that the increase in pixel signals, relative to the signal without particles, are summed to produce the total light scattered from that particle in the angular range of the annular aperture in FIG. 14. In FIG. 11, the decrease in pixel signals, relative to the signal without particles, are summed to produce the light lost due to scattering outside of pinhole 2 or absorption by that particle. Signal to background should be better for FIG. 14, but with higher sensitivity to particle composition and position in the sample cell. The depth of focus and signal to noise should be better for FIG. 11 than for FIG. 14, because the pixel values drop by the total light scattered and absorbed by the particle in FIG. 14 as opposed to the light increasing by only the amount scattered through a narrow range of scattering angles defined by the aperture. As with all other systems described in this disclosure, these ideas can be extended to more than two detector arrays or more than two scattering angles, simply by adding more annular spatial masks and detectors by using beamsplitters. Also the 2-dimensional array optics in FIG. 11 could be combined with those in FIG. 14 to provide total scatter information for determining size and to provide the unscattered intensity for each pixel to normalize the pixel scatter data of FIG. 14 detectors for the incident light intensity which may vary across the beam. In this way, each pixel in the detector array creates a small independent interaction volume with low coincidence probability. But yet contiguous pixels can be combined to measure particles of sizes approaching the dimensions of the entire detector array's image in the sample cell. The size dynamic range is enormous. FIG. 14 could also be used with a source beam which is focused into the sample cell to reduce the interaction volume and increase the beam intensity and scattered signal. In this case the center portion of the annular mask must be increased in size to block the diverging light from the source so that each detector array only sees scattered light.

The optical source used with the detector arrays in FIGS. 11 and 14 could be a pulsed broad band source such as a xenon flash lamp which produces broadband light to wash out the Mie resonances, and a short light pulse to freeze the motion of particles flowing through the cell.

Figure 15:
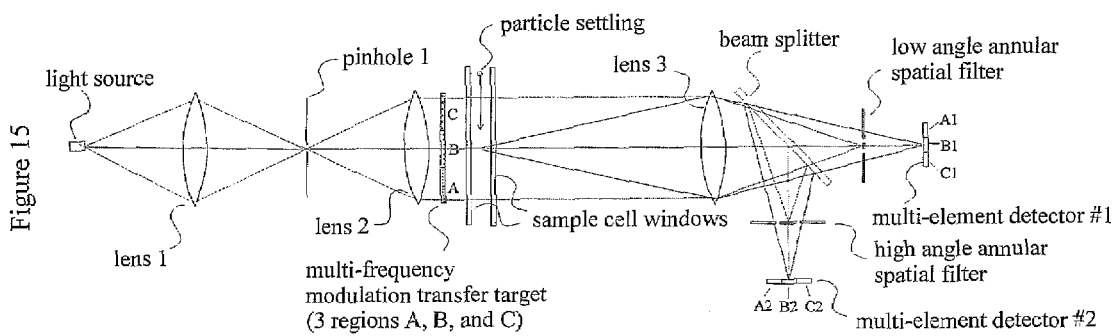
FIG. 15 provides a schematic drawing of an optical system which separates particle scatter signals based upon signal frequency and scattering angle, with a periodic mask for providing modulation of the scattering signal for particles passing through the sample cell, according to the present invention.
Figure 15B:
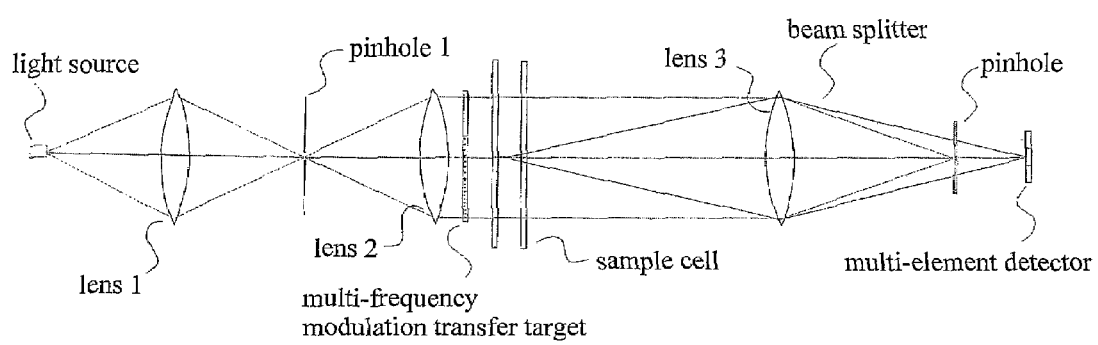
FIG. 15b provides a schematic diagram of an optical system which separates the amounts of scattered light, removed from the light beam, based upon signal frequency, according to the present invention.
Figure 16:
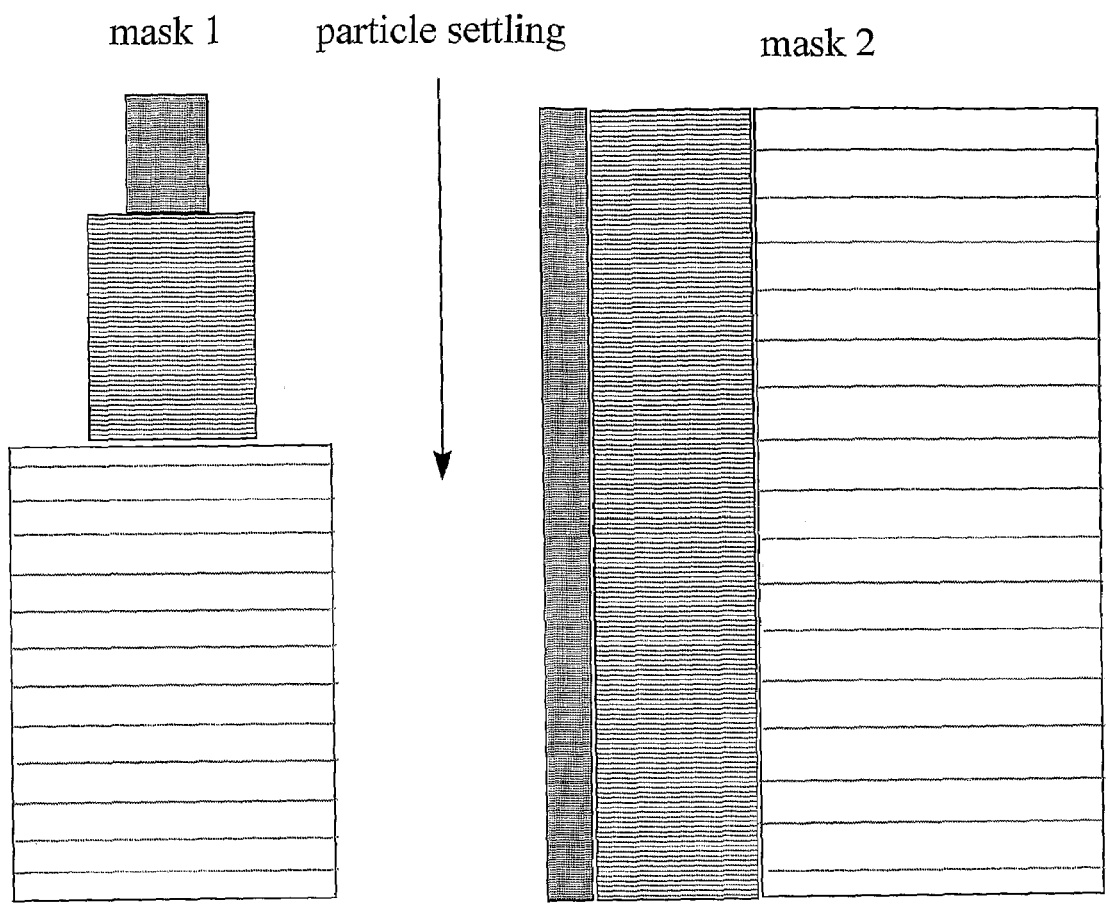
FIG. 16 depicts various masks to be utilized in the optical systems of FIG. 15 and FIG. 15b.

One problem with the techniques described above is coincidence counting. The cell path must be large to pass the largest anticipated particle (except for the wedge cell shown in FIG. 9b, where the pathlength changes across the cell). Hence for these collimated systems, many small particles may be in any sample volume seen by a single pixel. These coincidences could possibly be eliminated by measuring at various particle concentrations, but in order to count sufficient large particles to obtain reasonable count accuracy, the concentration must be raised to a level where more than one small particle is present in the sample cell volume, seen by each pixel. The scattered signals from these multiple particles can be separated, to be counted individually, by measuring their settling velocities. This is accomplished by the optical system shown in FIG. 15. A light source is collimated and spatially filtered by lenses 1 and 2 and pinhole 1. A modulation transfer target or mask with a spatially periodic transmission function is placed in the collimated beam to create a sinusoidal (or other periodic function) intensity pattern in the collimated beam. Examples of the sinusoidal (or other periodic) patterns are shown in FIG. 16. Each line in the patterns represents the peak of the sinusoidal transmission function which oscillates along the particle settling direction but is constant along the direction perpendicular to the settling. The mask consists of multiple regions with different spatial modulation frequencies. The projection of each region into the sample cell is imaged onto a separate detector by lens 3. The light from lens 3 is split into one or more directions, each having a different annular spatial mask which defines a different range of scattering angles. Each image plane for each spatial mask has multiple detectors, each of which intercept light from only one of mask regions in the sample cell. As a particle settles through the sinusoidal intensity pattern, the scattered light on the detector is modulated because the scattered light is proportional to the light intensity incident on the particle and the mask provides a spatially modulated illumination field. When a particle passes through a region where the spatial modulation wavelength is greater than the particle size, the scattered light from that particle will attain a large modulation visibility (the ratio of peak to trough values will be large). The scattered signal from the largest particles will have lowest modulation visibility in the high spatial frequency region because the particle will span over multiple cycles of the spatial modulation. Larger particles settle faster and produce higher frequency detector signals, because they have a higher terminal velocity. Therefore, a lower spatial modulation frequency can be used with larger particles to increase modulation visibility while still maintaining high signal oscillation frequency, because the scattering signal frequency is equal to the product of settling velocity and the mask spatial frequency. The size range is increased by using multiple regions with different spatial modulation frequencies, with higher frequencies for smaller slower settling particles. The area of the higher frequency portions of the mask are smaller to reduce the number of particles measured at one time by each detector, because typically there are much higher small particle counts per unit volume than for larger particles. FIG. 15b shows a similar system with a single pinhole filter. Detector signals will show the same oscillation characteristics as FIG. 15, but with a large offset due to the light transmitted by the pinhole. The power spectrum of the detector currents for the systems shown in both FIGS. 15 and 15b will be similar except that FIG. 15b will contain a large component at (and near to) zero frequency. FIG. 17 shows the power spectra from the low and high angle detector signals in FIG. 15, for the two detector elements, B1 and B2, which view the same portion, B, of the mask, but pass through different annular filters. Since each particle settles at a different velocity, each particle will produce a separate narrow peak at the same frequency in both of the power spectra of detectors B1 and B2 (from signals for scattering angle 1 and scattering angle 2, respectively). This is due to the fact that the detector signal power at any certain frequency, measured by each of the corresponding low and high angle detectors, will originate from the same particle or group of particles. Since the smaller particles will create a continuum at lower frequencies, they can be removed from the spectrum of the larger particles. The corresponding single peak values from power spectrum of current from detector B1 at frequency f1 and the power spectrum from current of detector B2 at frequency f1 for example (from each scattering angle) can be ratioed (or analyzed by other algorithms) to determine the size of the particle which created that peak in each spectra. In this way, multiple particles in the sampling volume can be counted individually. When particle size is close to the line spacing of the modulation target, the modulation of the scattered light will decrease because the signal is the convolution of the particle with the modulation target. However, the amplitude of the scattered signals at both angles will both decrease by the same percentage so that their ratio will still accurately indicate the size. Any peaks with amplitudes that are higher than that which would be expected from one particle are expected to originate from more than one particle. The expected amplitude for a single particle can be determined from the minimum value of other peaks in that frequency region for prior digitization sets. These multiple particle peaks can be either corrected for the second particle's contribution or eliminated from the particle count. If the particle density, liquid density and viscosity, are known, each individual particle size can also be determined by the frequency of the corresponding peak, by calculating the corresponding settling velocity and using the Stokes equation for settling to solve for the particle size.

The signal frequency for each particle signal pulse could also be determined individually by either the timing of zero crossings or by using a phase locked loop, avoiding the power spectrum calculation. Each particle pulse will consist of a train of oscillations which are modulated by the intensity profile through that particular mask region. The oscillation amplitude and frequency provide the scattering amplitude and settling velocity, respectively, for that particle. The size can be determined from the settling velocity, if the particle density and fluid viscosity are known, or the size can be determined from the ratio of amplitudes from two different scattering angles (or angular ranges), or the amplitude at one scattering angle (or angular range) (but with possible higher sensitivity to particle composition).

The particle density or fluid viscosity can be determined by combination of the scattering amplitudes and the signal oscillation frequency.

Figure 18:
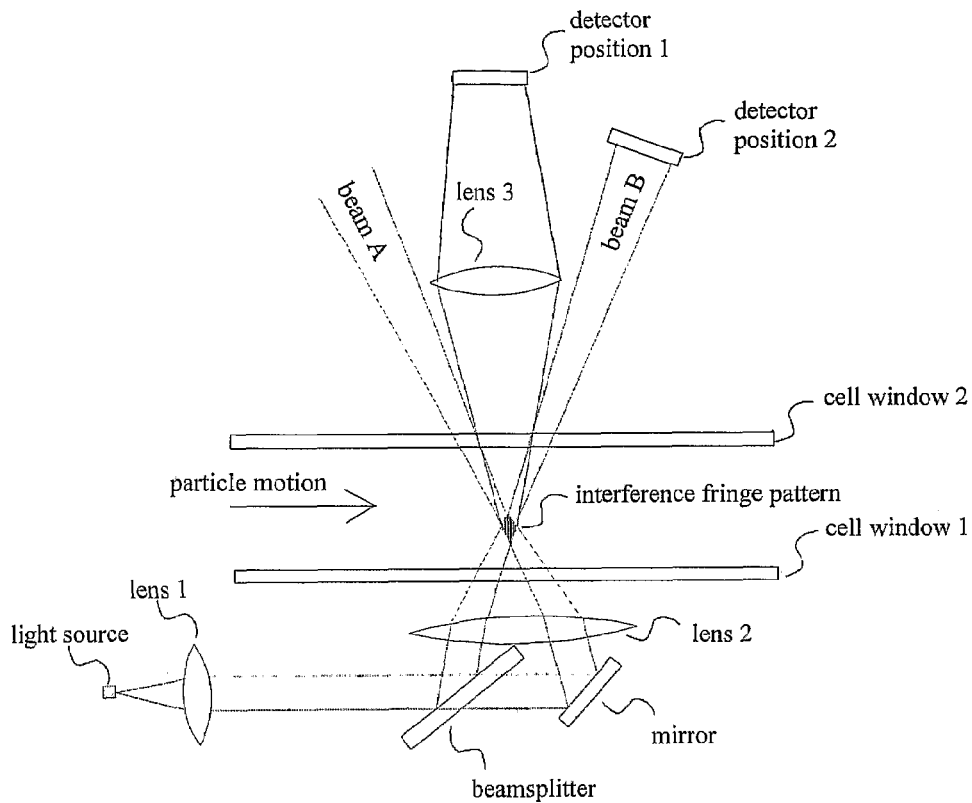
FIG. 18 provides a schematic diagram of an optical system which produces a modulated intensity profile by interference of two light beams, instead of imaging a periodic mask, according to the present invention.

FIG. 18 shows another system for measuring the settling of particles, using crossed laser beams. An interference pattern is formed at the intersection of the beams. As the particles pass through this pattern, the scattered light is modulated, producing a power spectrum as described above.

All slit apertures in this disclosure (for example, slit 1 and slit 2 in FIG. 1) can be changed to pinholes or rectangular apertures, whose images at the source beam may be or may not be smaller than the source beam. Unlike slits, the pinholes or rectangular apertures may require alignment in the both of the mutually perpendicular X and Y directions, which are both approximately perpendicular to the optical axis of the detection system.

Figure 19:
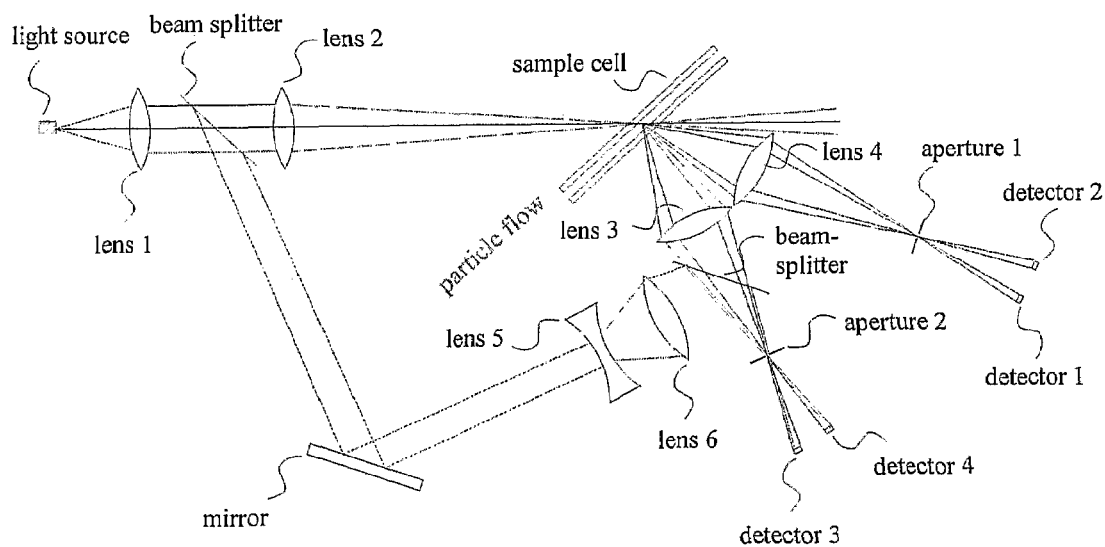
FIG. 19 provides a schematic diagram showing the use of detector size to define the angular range of each detector in FIG. 1.
Figure 20:
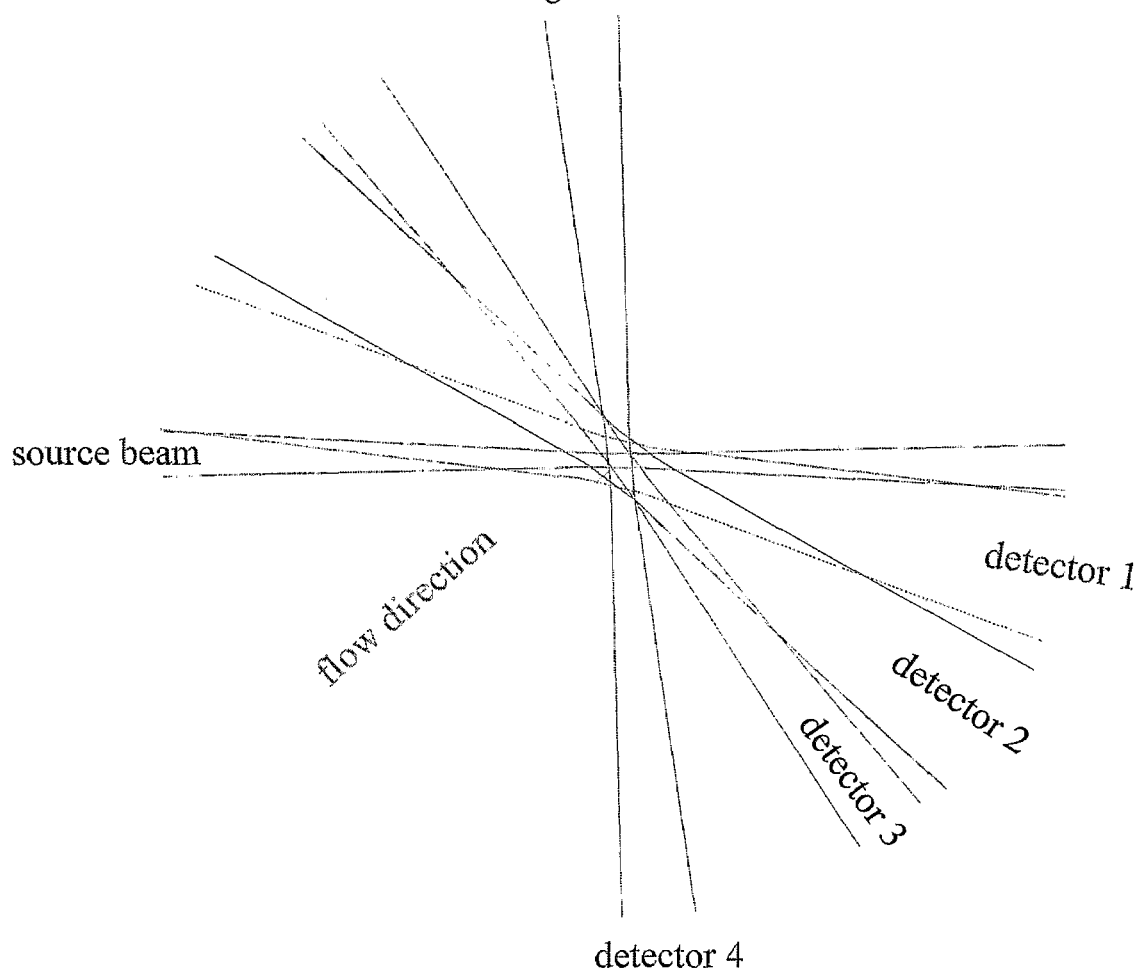
FIG. 20 provides a diagram showing more detail of the light beam focus and the focus of each detector field of view, using the concepts depicted in FIG. 2 and FIG. 2b.

FIG. 19 shows more detail of the actual beam shapes in FIG. 1 for the angular ranges specified for detectors 1 through 4. The scattering angle range for each detector is controlled by the detector size or by an aperture on front of a larger detector. FIG. 20 shows the detail of the intersection of the each detector field of view with source beam.

If the signal to noise is sufficient for non-coherent detection with any detector in FIG. 1, or in any other variation of FIG. 1 shown in this document, the local oscillator optics for that detector can be removed and non-coherent detection can be used.

The progression of crossectional size, in the interaction volume, from smallest to largest is: light source, fields of view from detectors 3 and 4, and the fields of view from detectors 1 and 2, as shown in FIG. 20. The progression could also progress from the smallest to largest as light source, field of views of detector 4, detector 3, detector 2, and detector 1, respectively. However, this would require different sized apertures for each detector. This would require a separate lens and aperture for each detector, but would insure that any particle passing through the intersection of the source beam and the detector 4 field of view, will be seen by all of the other detectors during the entire pulse period from detector 4. Then if all of the detector signal ratios are measured during a period near to the peak of the detector 4 signal (after the envelope detector), valid scattering ratios will be recorded for all of the detectors.

The particles being measured by system in FIG. 19 are all much smaller than the crossection of the source beam. Therefore particles of different sizes produce the same count-vs.-parameter distribution for the following parameters:

1) scattered light amplitude normalized to the maximum scattered light amplitude measured over all the particles of the same size at that scattering angle.
2) Pulse width at certain fraction of pulse peak level
3) delay between pulses from two different detectors
4) correlation between pulses from two different detectors Any of these parameters can be used to define a threshold for counting particles as shown in FIGS. 10 and 10b, by replacing the S(a2) axis with one of the parameters from above. If the particle count is large, the statistics of the above parameters will be stationary for all particle sizes. Then the strategy outlined for FIG. 10 can be used to properly threshold particles of all sizes in an equivalent manner, by rejecting the same percentage of particles in each size bin in the count-vs.-size distribution. The 3 dimensional surface which corresponds to the one in FIG. 10, can be interpolated or fit to a surface function in order to determine the rejection threshold. Based upon the function or interpolated values, a rejection criteria can be determined which eliminates the particles with poor signal to noise and also removes the same percentage of particles from each size range so as to maintain a true particle size distribution. The rejection threshold is chosen to maintain a sufficiently high signal-to-noise for any particles which are accepted into the total count distribution. In fact, this process will computationally define an interaction volume for the source beam and all detector fields of view, for all particle sizes being detected, where all scattering signals have sufficient signal-to-noise to produce accurate sizes based upon their amplitudes, ratios of amplitudes, or other multi-parameter functions of scattering amplitudes. This selection process is required to reduce the effects of the tails in the intensity distribution of the source and the spatial response tails at the edges of the detector fields of view, where they intersect the source beam. If these tails are sharpened (or cut off) by spatial filtering the source or by using slits, pinholes, or other apertures with low aberration optics for the detectors, the errors due to these tails are further reduced, as shown in FIG. 10b. Also diffractive optics can be used to produce a "flat top" intensity distribution from a Gaussian laser intensity profile. Then the corresponding flat top shape should be used to produce the functions in FIG. 10 and 10b. This would improve the accuracy of the particle rejection threshold and the resulting particle count distribution. In any event, there is always some parameter which is statistically well described by the millions of particles which are detected. And by eliminating particles from the count based upon this parameter, you can define a group of particles which are sorted by the same criteria at all particle sizes, thereby creating an accurate size distribution, while removing count events which have poor signal to noise.

Figure 21:
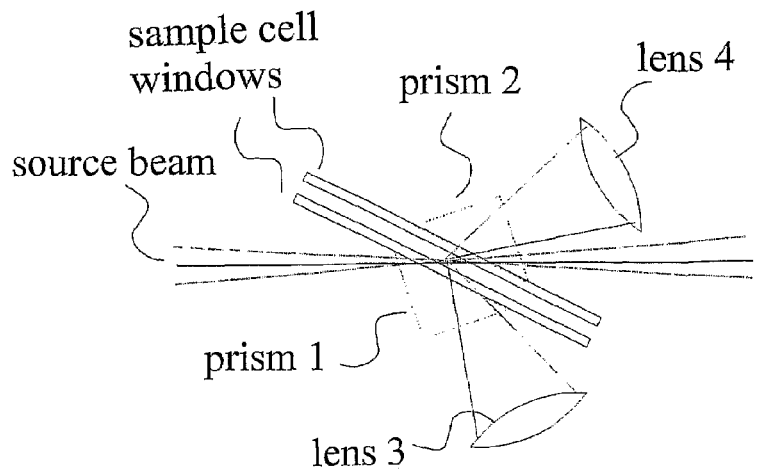
FIG. 21 provides a diagram of a particle dispersion sample cell, which utilizes prisms to reduce light reflections at sample cell window surfaces, according to the present invention.

In the sample cell with flat windows, many of the incident source beams and scattered light rays are at high angles of incidence on the sample cell windows. The interior surface of the window is in contact with a liquid which reduces the Fresnel reflection at that surface. However, the exterior surface is in air which can cause an enormous Fresnel reflection at these high incident angles. This reflection can be reduced by anti-reflection coating the exterior surface, but with high cost. A better solution is to attach prisms (see FIG. 21) to the exterior surface with index matching optical adhesive. The prism surfaces present low angles of incidence for the source beams and the scattered light. Even simple antireflection coatings on the external prism surfaces will reduce the Fresnel reflections to negligible levels. A spherical plano-convex lens, with center of curvature near to the center of the cell could also be used instead of each prism, with plano side attached to the window.

Another configuration for the sample cell is a cylindrical tube. The particle dispersion would flow through the tube and the scattering plane would be nearly perpendicular to the tube axis and flow direction. In this case, the beam focus and detector fields of view would remain coincident in the scattering plane for various dispersant refractive indices and only inexpensive antireflection coatings are needed. However, since the flow is perpendicular to the scattering plane, the heterodyne oscillations cannot be produced by the particle motion. The optical phase modulation mirror in the local oscillator arm (called "mirror") in FIGS. 1 and 19 (and other figures) could be oscillated to provide a heterodyne signal on detectors 3 and 4 as described before. This could also be accomplished with other types of optical phase modulators (electro-optic and acousto-optic) or frequency shifters (acousto-optic).

Any of the measurement techniques described can be used individually or in combination to cover various particle size ranges. Examples of possible combinations are listed below:

For particle diameter 0.05-0.5 microns use FIG. 19 with detectors 3 and 4 at 30 and 80 degrees, respectively.

Use heterodyne detection (if needed). Take ratio of the detector signals.

For particle diameter 0.4-1.2 microns use FIG. 19 with detectors 1 and 2 at 10 and 20 degrees, respectively.

Use heterodyne detection (if needed). Take ratio of the detector signals.

All 4 signals can also be used together for the range 0.05 to 1.2 microns, using a 4 parameter function or lookup tables.

Use the detector with the smallest interaction volume to trigger data collection. These angles are only representative of general ranges. For example, instead of 10, 20, 30, 80 degree angles, any group of angles with one widely spaced pair below approximately 30 degrees and another widely spaced pair above approximately 30 degrees would work. Each detector sees an angular range centered about the average angle specified above. But each detector angular range could be somewhat less than the angular spacing between members of a detector pair. In some cases, without optical phase modulation, the angular ranges of each heterodyne detector should be limited to maintain heterodyne interferometric visibility. The particle size distribution, below 2 microns, from this system is combined with the size distribution above 1 micron as determined from various other systems described in this disclosure, including the following systems:

For particle diameter 1-10 microns use detectors 1 and 2, in FIG. 11 or 14, at approximately 1 degree and 3 degrees, respectively. Use white light or LED source. Use ratio of detector signals to determine individual particle size.

For particle diameter greater than 1 microns, use the 2 dimensional array in FIG. 11 with a pulsed white light source (such as a pulsed xenon source) to freeze the motion of the flowing particles. The two dimensional array could also be used alone to measure greater than 1 micron, without detectors 1 and 2. The system in FIG. 14 could also measure particles greater than 1 micron in diameter, with one (absolute) or both (ratio) detector arrays.

Another configuration is to use the scattering flux ratio of scattering at 4 degrees and 1 degree, in white light, for 0.5 to 3.5 microns. And use absolute flux at 1 degree (white light, same system) for 3 to 15 microns. And use the 2 dimensional array in FIG. 11 or 14 for particles above 10 microns. As noted above, each array in FIG. 14 can separately be used to size particles by measuring the absolute scattered light from each particle, or light lost due to the particle, over one angular range. However, the system size response will be more composition (particle and dispersant refractive indices) dependent using data from a single array than the ratio of the corresponding measurements from both arrays.

In all of these systems, the white light source can be replaced by a laser. However, the particle size response will become more sensitive to particle and dispersant composition. And also the response vs. size may not be monotonic due to interference effects between the particle scattered light and light transmitted by the particle (Mie resonances), producing large size errors. If lasers or LEDs are required for collimation or cost requirements, scattering measurements can be made at more than one wavelength, using multiple sources, to reduce the composition dependence. Particle size of each object would be determined from all of these multi-wavelength measurements by using a multi-parameter function (size=function of multiple parameters), by interpolation in a lookup table as described above, or by a search algorithm. And in all cases the angles are nominal. Many different combinations of average angles, and ranges of angles about those average angles, can be used. Each combination has a different useable particle size range based upon size sensitivity, composition sensitivity, and monotonicity. All of these different possible combinations are claimed in this description. Also note that the ratio of $S(a1)/S(a2)$ in FIG. 10 can be replaced by any parameter or function of parameters which have nearly exclusive sensitivity to particle size, with low sensitivity to incident intensity on the particle. This may include functions of scattering measurements at more than 2 angles.

These cases are only examples of system combinations which could be combined to provide a larger particle size range. Many other combinations are possible and claimed by this inventor.

One problem associated with measuring large particles is settling. The system flow should be maintained at a sufficiently high level such that the larger particles remain entrained in the dispersant. This is required so that the scattered light measurements represent the original size distribution of the sample. For dense large particles, impracticable flow speeds may be required. This problem may be avoided by measuring all of the particles in one single pass, so that the total sample is counted even though the larger particles may pass through the light beam as a group (due to their higher settling velocities) before the smaller particles.

Figure 22:
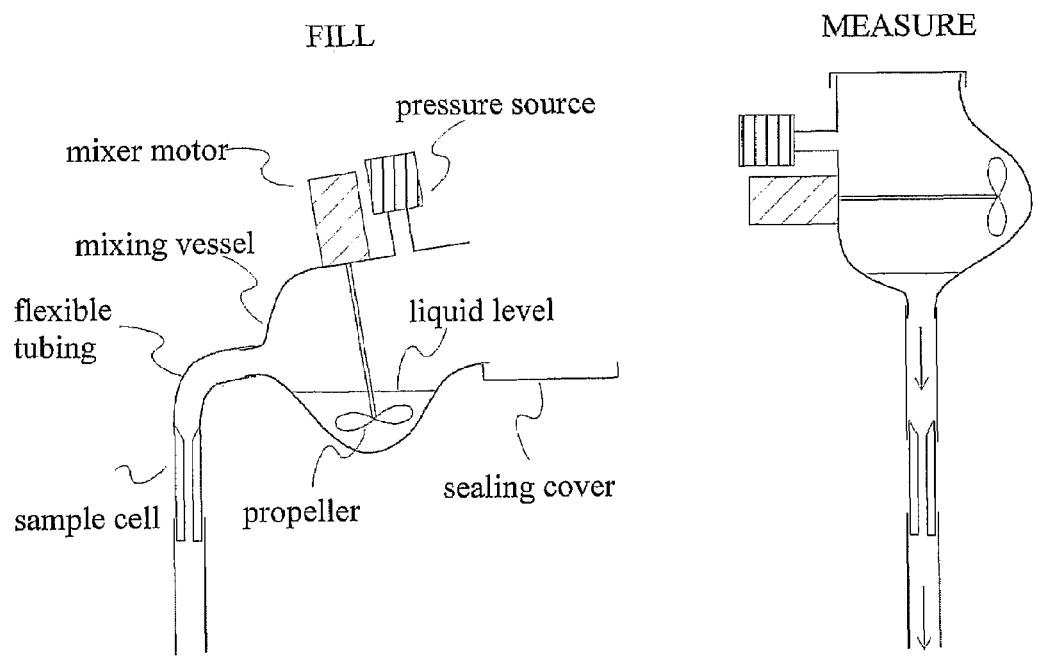
FIG. 22 provides a diagram, partly in schematic form, showing an apparatus for mixing the particle dispersion and passing all of said dispersion through a sample cell in a single pass, according to the present invention.

A small open tank is placed above the sample cell region, connected to the cell through a tube. The tube contains a valve which can be shut during introduction of the particle sample into the tank to prevent the sample from passing through the cell until the appropriate time. The liquid in the tank is continuously stirred during the introduction of sample to maximize the homogeneity in the tank. A light beam may be passed through the mixing vessel via two windows to measure scattered light or extinction to assist in determining the optimum amount of sample to add to obtain the largest counts without a high coincidence count level. The optical detectors are turned on and the valve is opened to allow the particle mixture to pass through the cell with gravitational force. This can also be accomplished by a valve below the sample cell or by tilting the tank up to allow the mixture to flow over a lip and down through the cell, as shown in FIG. 22. The light beam could be wider than the width of the flow stream through the cell so that all of the particles passing through the cell are counted. Single particle counting is assured by only introducing a sufficiently small amount of sample into the tank. Since all of the larger particles are counted in one pass, the count distribution is independent of the sample inhomogeneity. After the entire sample has passed through the cell, the conventional flow system for ensemble scattering measurements is then turned on to circulate the sample through the cell. This flow rate must only be sufficient to suspend the particles which were too small, or too numerous, to be counted during the single pass. During this flow period, settling of the larger particles which have been counted does not matter because their count distribution (from the single pass) will be combined with the count-vs.-size distribution of the smaller particles (obtained during flow) to produce a single volume distribution over the entire size range, using the size distribution blending and combination methods described previously.

The system in FIG. 22 could also be used alone to provide significant cost savings by eliminating the pump and associated hardware. FIG. 22 shows the concept for dispersing and measuring the particles in a single pass through the optical system. The particles and dispersant are mixed continuously in a mixing vessel which is connected to the optical system through a flexible tube. The mixing vessel is tilted while being filled, so that no sample enters the optical system. Then once the dispersion is well mixed, the mixing chamber is sealed with a gas tight cover and the mixing vessel is moved into an upright position to allow the dispersion to either fall through the sample cell under gravity (without gas tight cover) or to be pushed through the cell using gas pressure. If gas pressure is not used, the flexible tube could be eliminated and the mixing vessel could pour into a funnel on top of the sample cell.

The systems based upon FIG. 19 and similar systems, where scattered light at multiple-angles are measured from a single particle, will have a lower particle size limit due to the lower scattering intensity of small particles and insensitivity of the scattering ratio to particle size. If the particle refractive index and dispersant refractive index are known, various scattering theories can be used to calculate the scattering signal ratios and absolute scattering signals vs. particle size to provide the look up table or function to calculate the size of each particle from these signals. Since these refractive index values are not always available, the scattering model (the effective refractive indices) may need to be determined empirically from scattering data measured in a region where the scattering ratio is independent of refractive index, but where the absolute scattering amplitudes are dependent upon refractive index. In this region the signal ratio will determine the particle size. And then the absolute scattering signals (relative to the incident source intensity) and this size value can be used to determine the refractive indices by using global search algorithms to search for the refractive indices which give the best fit to the particle size and absolute signal values. This process assumes that the entire particle ensemble is homogeneous in individual particle composition (however, a method is proposed for dealing with inhomogeneous samples in FIG. 27b). This method can be used for any particle which shows a ratio in the size sensitive region of the response, can be used to determine the effective refractive index of the particle by using the ratio and the absolute values of the scattering signals, because these are unique for particle and dispersant refractive index. The optical model for this effective refractive index could then be used to extend the size response range of any set of detectors to a size range outside of the ratio determined size region (where the scattering signal ratio is sensitive to size and the ratio cannot be used). This process can extend the size to both smaller and larger particles by using the absolute scattering intensity in regions where the scattering signal ratio no longer works. Theoretically, very small particles are Rayleigh scatterers, where the shape of the angular scattering distribution is not size dependent. However for very small particles, the peak of the scattering intensity distribution scales as the $6^{th}$ power of the particle diameter and the heterodyne signal scales as the $3^{rd}$ power of the diameter. So as the particle size decreases, the ratio of the intensity at two angles becomes constant, but the actual intensities continue to drop as the particle size decreases. So when the intensity ratio approaches this constant, the particle size algorithm should use absolute scattering intensity to determine the size. The absolute scattered intensity is proportional to a constant (which is a function of scattering angle, particle and dispersant refractive indices, and light wavelength) divided by particle diameter to the $6^{th}$ power ($3^{rd}$ power for the heterodyne signal). This constant is determined from the absolute scattered intensities of particles, in the distribution, whose intensity ratios still provide accurate particle size. Also the functional form for the absolute intensities can be calculated using various scattering theories (Mie theory for example). This process can also be used to extend the useful range to larger particles. As the particle becomes larger, the scattering signal ratio from the detector pair will become more dependent upon the refractive index of the particle. The absolute intensity data from particles, in the region where the ratio is independent of particle composition, can be used to determine the effective composition of the particles and determine which theoretical scattering model to use for absolute scattering intensity from particles outside of that size region. Then the larger particles are measured using this model and the absolute values from each scattering detector, instead of the ratio of scattering signals. Absolute intensity data from particles, in the region where the ratio is independent of particle composition is preferred, but absolute scatter data from multiple scattering angular ranges in any size region can be used to determine the particle and dispersant refractive indices by using the global search algorithm described above. The scattering values depend more strongly on the ratio of particle refractive index to dispersant refractive index, than their absolute values. So in many cases, only the refractive index ratio must be determined by this search algorithm.

One other remaining problem with absolute scattering intensity measurements is the sensitivity of pulse intensity to the position where the particle passes through the beam. Measuring the distribution of pulse amplitudes from a nearly mono-sized calibration particle dispersion (with a low coefficient of variation for the size distribution) provides the response of the counter for a group of particles of nearly identical size. This count distribution, which is the same for any particle whose size is much smaller than the light beam crossection, provides the impulse response for a deconvolution procedure like the one described previously. The scattering pulses can be selected based upon their pulse length by only choosing pulses with intensity normalized lengths above some threshold or by using the various pulse selection criteria listed below. This selection process will help to narrow the impulse response and improve the accuracy of the deconvolution. This process is also improved by controlling the intensity profile to be nearly "flat top" as described previously.

The scattered signal from any particle is proportional to the intensity of the light incident on the particle. Hence as the particle passes through different portions of the incident light beam, each scattered signal will vary, but the ratio of any two signals (at two different scattering angles) will theoretically be constant as long as the field of view of each detector can see the particle at the same time. This can be insured by eliminating the signals from long intensity tails, of the Gaussian intensity profile of the laser beam, which may not be seen by all detectors. This is accomplished by placing an aperture, which cuts off the tails (which may be Gaussian) of the incident light intensity distribution, in an image plane which is conjugate to the interaction volume. This aperture will produce a tail-less illumination distribution in the interaction volume, providing a narrower size range response to monosized particle samples (the impulse response). In the case of an elliptical Gaussian from a laser diode, the aperture size could be chosen to cut the distribution at approximately the 50% points in both the x and y directions (which are perpendicular to the propagation direction). Such an aperture would cause higher angle diffractive lobes in the far field of the interaction volume, which could cause large scatter background for low scattering angle detectors. Since this aperture should only be used for measurements at high scattering angles where the background scatter can be avoided, the low angle detector set and high angle detector set may need to view separate light beams. The apertured beam size should be much larger than the particles which are being measured in that beam. Hence, to cover a large size range, apertured beams of various sizes could be implemented. The particle size distributions from these independent systems (different source beams or different detector groups) could be combined to produce one continuous distribution. These apertures could also have soft edges to apodize the beam, using known methods to flatten the beam intensity profile while controlling the scattering by the aperture. This could also be accomplished by using diffractive optics for producing flat top distributions from Gaussian beam profiles as mentioned earlier. Also apertures can be oriented to only cut into the beam in the appropriate direction such that the diffracted light from that beam obstruction will be in the plane other than the scattering plane of the detectors. This is accomplished by orienting the aperture edges so that they are not perpendicular to the scattering plane. The aperture edges which cut into the beam at higher levels of the intensity profile should be nearly parallel to the scattering plane to avoid high scattering background.

The apertured beams will help to reduce the size width of the system response to a mono-sized particle ensemble, because the intensity variation of the portion of the beam which is passed by the aperture is reduced. Other analysis methods are also effective to reduce the mono-sized response width for absolute scattering and scattering ratio measurements. Methods which accept only scattering signal pulses, or portion of pulses, which meet certain criteria can be very effective in narrowing the size width of the system response to mono-sized particles. Some examples of these acceptance criteria are listed below. Any of these criteria can be used to determine which peaks or which portion of the peaks to be used for either using the scattering signal ratios or absolute values to determine the particle size.

1. Choose only the time portion of both pulses where the pulse from the detector which sees the smaller interaction volume, or has the shorter duration, is above some threshold. The threshold could be chosen to be just above the noise level or at some higher level to eliminate any possibility of measuring one signal while the second signal is not present. Then either take the ratio of the signals (or ratio the peaks of the signals with peak detector) over that time portion or the ratio of the integrals of the signals over that time portion. The absolute integrals or peak values during this time portion could also be used to determine size, as described before.
2. Only accept pulses where the separation (or time delay between peaks or rising edges) between pulses from the multiple detectors is below some limit
3. Only accept pulses where the width of a normalized pulse or width of a pulse at some threshold level is above some limit
4. Only accept the portion of the pulses where the running product S1.*S2 (a vector containing the products of S1 and S2 for every point during the pulses) of the two signals is above some limit. Then either take the ratio of the signals over that portion or the ratio of the integrals of the signals over that portion.
5. Only use the portion of pulses where sum(S1.*S2)/(sum (S1)*sum(S2)) is greater than some limit (sum(x)=summation of the data points in vector x)
6. Use only the portion of the pulses where (S1.*S2)/(S1+S2) is greater than some limit
7. integrate each pulse and normalize each integral to the pulse length or sample length
8. Use only the portion of the pulses where the value of S1*S2 is be greater than some fraction of the peak value of the running product S1.*S2
9. Integrate both signals S1 and S2 only while the signal from the smaller interaction volume is above a threshold or while any of the above criteria are met.
10. fit a function to the selected portion (based upon various criteria described above) of each pulse. The fitting function form can be measured from the signal of a particle passing through the center of the beam or can be based upon the beam intensity profile
11. When both S1 and S2 have risen above some threshold, start integrating (or sample the integrators from) both signals. If the integrators for S1 and S2 are integrating continually (with resets whenever they approach saturation) then these integrators could be sampled at various times and the differences would be used to determine the integrals in between two sample times. Otherwise the integrators could be started and stopped over the period of interest. These sampled integrals are IT10 and IT20 for S1 and S2 respectively, when each of them rises above the threshold. When the first signal to drop falls back down below the threshold, sample the integrator on each of S1 and S2 (integrals IT1a and IT2a). When the second signal (signal number *) to drop falls below the threshold, sample the integral IT*b for that signal. Use the ratio of the integral differences, (IT1a-IT10)/(IT2a-IT20), during the period when both signals are above the threshold to determine size. Accept and count only pulses where a second ratio (IT*a-IT*0)/(IT*b-IT*0) is above some limit. This second ratio indicates the fraction of the longer pulse which occurs during the shorter pulse. As the particle passes through the light beam further away from the center of the interaction volume, this ratio will decrease. Only particles which pass through the beam close to the center of the interaction volume will be chosen by only accepting pulses where the shorter pulse length is a large fraction of the longer pulse length. These pulse lengths could also be determined by measuring the difference in the length of time between the above trigger points for each pulse. Pulses with a shorter difference in time length are accepted into the count by ratioing their integrals during the period when both of them are above the threshold.

Figure 23A:
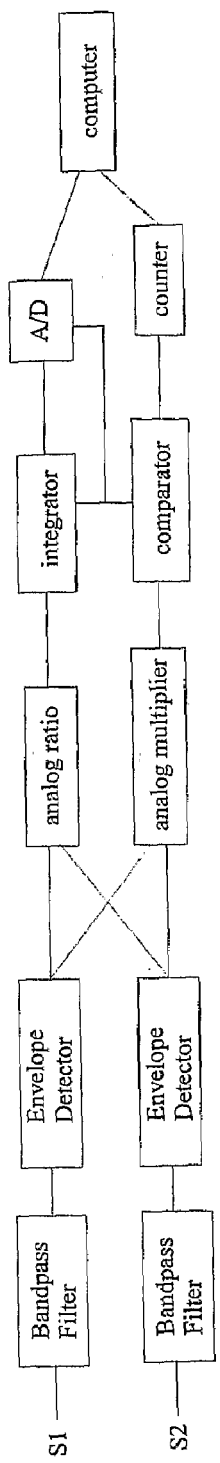
FIG. 23a and FIG. 23B provide block diagrams of systems of analog electronic modules which implement selection criteria used to determine which signal peaks, or portions of the signal peaks, to be utilized in the particle count data, according to the present invention.
Figure 23B:
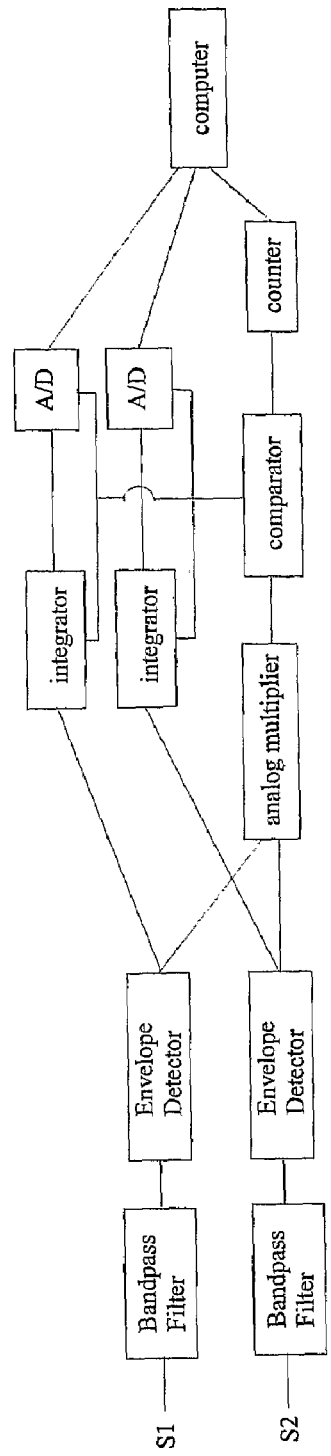

These criteria can be easily implemented by digitizing S1 and S2 and then doing the above comparisons digitally. However, full waveform digitization and digital analysis of 1 million particles may require too much time. FIGS. 23a and 23b show configurations for implementing some of these criteria using analog circuits. The signal digitization and computational load is greatly reduced by using analog equivalents to preprocess data before digitization. This concept is particularly effective when the thresholding or comparative functions, of the criteria described above, are replaced by analog equivalents; but the actual signal analysis used for size determination is done digitally to avoid the poorer linearity and accuracy of the analog equivalents. An example of this is shown in FIG. 23b, where both integrator outputs (one integration per signal pulse) are separately digitized by the A/D converters to do the amplitude or signal ratio calculations digitally instead of using analog ratio circuits; but the criteria related functions, analog multiply and comparator, are done analog to reduce the digitization load. This overall concept of using analog circuitry specifically for only the criteria related functions to reduce the digitization load is claimed by this disclosure, along with applications to other systems.

All of these variations will not be perfect. Many of them rely upon approximations which can lead to variation in calculated size for a particle that passes through different portions of the beam. The important advantage is that the broadening of the mono-sized particle response is the same for all size particles which are much smaller than the source beam. Therefore this broadened response, which is calculated by measuring the count distribution from a mono-sized distribution or by theoretical modeling, can be used as the impulse response to deconvolve the count distribution of any size distribution.

The intensity ratio is sensitive to size and mildly sensitive to particle and dispersant refractive index. Size accuracy is improved by using Mie theory, for the actual refractive index values, to calculate the scattering ratio vs. particle diameter function. However, sometimes these refractive indices are not easily determined. Three scattering angles could be measured to generate a function which has reduced sensitivity to refractive index.

$$D = A1*(S2/S1) + A2*(S2/S1)^2 + A3*(S2/S1)^3 + B1*(S3/S1) + B2*(S3/S1)^2 + B3*(S3/S1)^3 + C1$$

D=particle diameter

A1, A2, A3, B1, B2, B3 are constants

S1=scattering signal at the first scattering angle (over the first scattering angle range)

S2=scattering signal at the second scattering angle (over the second scattering angle range)

S3=scattering signal at the third scattering angle (over the third scattering angle range)

Solve the set of equations:

$$Di = A1*(S2/S1)ij + A2*((S2/S1)ij)^2 + A3*((S2/S1)ij)^3 + B1*(S3/S1)ij + B2*((S3/S1)ij)^2 + B3*((S3/S1)ij)^3 + C1$$

where i=diameter index
j=index of refraction index
and

S1ij=theoretical scattering signal over scattering angular range #1, for particle diameter D=Di and the jth index of refraction S2$ij$=theoretical scattering signal over scattering angular range #2, for particle diameter D=Di and the jth index of refraction ( . . . )ij indicates that all the variables inside the parentheses have index ij.

A set of simultaneous equations are created for various diameters Di using signal ratios calculated from the appropriate scattering theory (Mie theory or non-spherical scattering theory) for various particle and dispersant refractive indices. These equations are then solved for the constants A1, A2, A3, B1, B2, B3, C1. Of course this process can be extended to more than 3 angles and for polynomial order greater than 3.

Particles which are two small for single particle counting may be measured by stopping the flow and using the heterodyne signal of the scattered light to measure the size distribution from the Brownian motion of the particles. The particle size distribution is determined by inverting either the power spectrum or the auto-correlation function of the Doppler broadened scattered light from the moving particles. The particle size distribution from Brownian motion can also be used to determine the effective particle/dispersant refractive index (scattering model) by measuring the hydrodynamic size of a particle along with the scattering signal amplitudes. The scattering model can be determined from the scattering intensity at each angle, and the true size for a representative single particle or a group of particles. The true size can be determined from the power spectrum or autocorrelation function of the heterodyne signal via Brownian motion, from the ratio of intensities of light scattered at two angles in the size region where the ratio is an accurate indicator of size, or by other size measurement techniques. This scattering model could then be used for computations of particle size in a counting process, which does not use Brownian motion.

Other methods of generating the heterodyne local oscillator are also claimed in this disclosure for systems like in FIG. 19. For example a small reflecting sphere or scattering object could be placed in the interaction volume to scatter light into the heterodyne detectors along with the light scattered by the moving particle. Since this sphere or object is stationary, the optical phase difference between the scattered light from the moving particle and light scattered (or reflected) from the sphere or object would increase as the particle passed through the beam, creating an oscillating beat scatter signal on the detectors, at high frequencies. Then the local oscillator beam, which passes through lens 6, could be eliminated.

Figure 24:
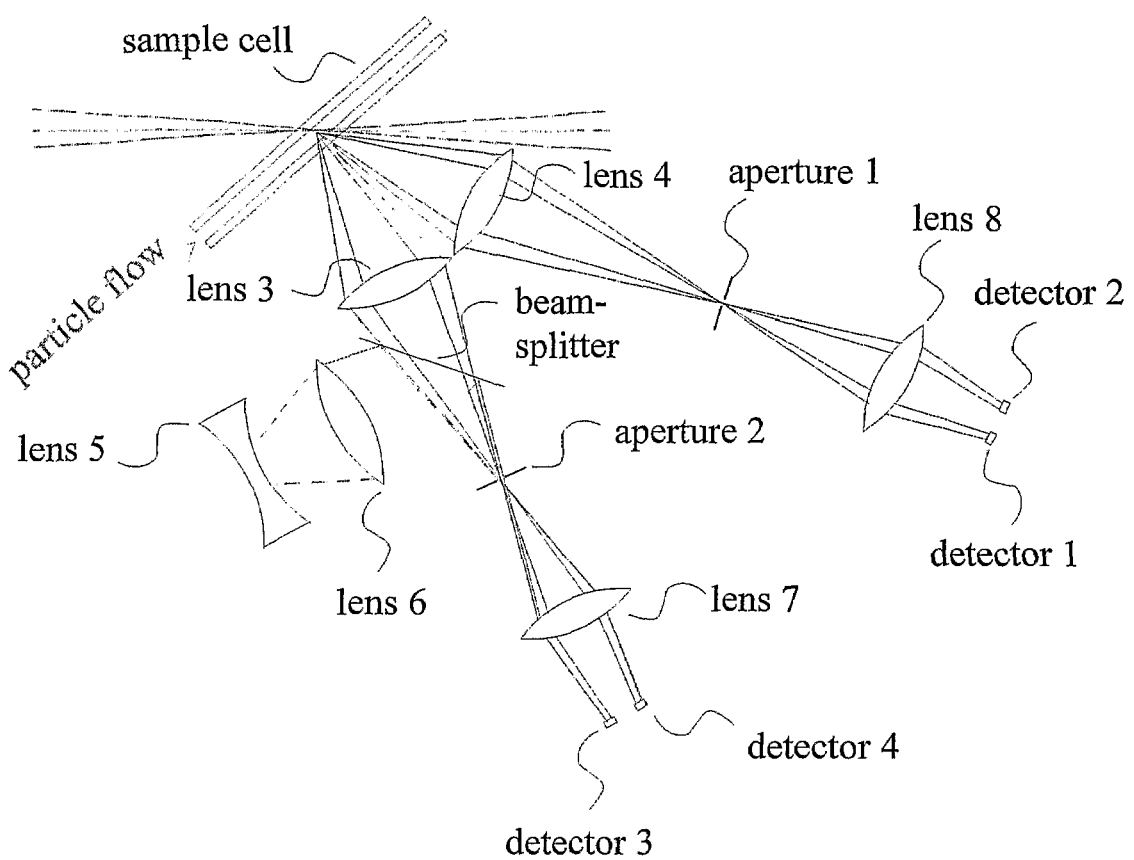
FIG. 24 provides a schematic diagram showing the use of additional lenses to reduce the sensitivity of scattering angle to particle position, according to the present invention.

In FIG. 19, the effective scattering angles seen by each detector can depend upon the position of the particle in the beam. The addition of lenses 7 and 8, as shown in FIG. 24 (which only shows the detection portion of FIG. 19), will lower the scatter angle sensitivity to particle position. Each of these lenses place the detectors in a plane which is conjugate to the back focal plane of either lens 3 or lens 4. Essentially the back focal plane of lens 3 is imaged by lens 7 onto detectors 3 and 4; and the back focal plane of lens 4 is imaged by lens 8 onto detectors 1 and 2. Also the detectors could be placed in the back focal planes of lens 7 and lens 8, where each point in the focal plane corresponds to the same scattering angle from any point in the interaction volume. This configuration nearly eliminates dependence of detector scattering angles on the position of particles in the beam.

By powering the source at various intensity levels, the scattered light from particles which span a large range of scattering intensities can be measured with one analog to digital converter. Even though the dynamic range of the scattered light may be larger than the range of the A/D, particles in different size ranges can be digitized at different source intensity levels. The resulting signals can be normalized to their corresponding source intensity and then used to determine the size of each particle.

In FIG. 11, the 2-Dimensional detector array could also be moved farther away from lens 4 to the plane which is nearly optically conjugate to the center of the sample cell. This may provide better imaging resolution of the particles on the array.

Also it is recognized that many of the ideas in this disclosure have application outside of particle counting applications. Any other applications for these ideas are also claimed. In particular, the ideas put forth in FIGS. 21 and 22 would also have application in ensemble particle sizing systems.

Many drawings of optical systems in this disclosure show small sources with high divergence which are spatially filtered by a lens and pinhole and then collimated by a second lens. In all cases, a low divergence laser beam could replace this collimated source, as long as the spectral properties of the laser are appropriate for smoothing of Mie resonances if needed.

Another issue is interferometric visibility in the heterodyne signals described before. Misalignment of beamsplitter or lenses 5 or 6 in FIG. 24 can lower the visibility of the heterodyne signals. Since this loss may be different on different detectors, the ratio of two signals may not be preserved. However, the ratio of the visibilities for two detectors will be the same for all particles. Therefore a correction for the effects of low visibility, for both absolute signals and signal ratios, can be determined by measuring scattered signals from one or more nearly mono-sized particles of known size and comparing the results with theoretical values to determine the effective visibility for each channel or visibility ratio for pairs of channels. This is most easily accomplished by measuring larger particles with scattering signals of very high signal to noise and looking at the actual heterodyne signals to determine the interferometric visibility for each detector. This could be determined by blocking the local oscillator light and measuring the scattered signal pulse with and without the local oscillator to calculate the theoretical heterodyne signal from the measurement of the local oscillator power and the scattered pulse amplitude. Also simply comparing the ratio of two scattering heterodyne signals to the theoretical value for that particle size would also provide a correction factor for the ratio, directly.

For particles which are much smaller than the size of the laser spot, the scattered signal for particles passing through various portions of the laser spot will be distributed over a range of peak amplitudes. For a group of monosized particles, the probability that a peak amplitude will be between value S-deltaS/2 and S+deltaS/2 is Pn(S)deltaS, where Pn(S) is the probability density function for scattering amplitude in linear S space. "deltaQ" means the difference in Q between the end points of the interval in Q, where Q may be S or Log(S) for example. For a group of monosized particles of a second size (diameter D2 in FIG. 25), the scattering amplitudes, S, for particles that have passed through the same region of laser beam, as particles of the first size diameter D1, are changed by a multiplier R and the probability density amplitude is changed by a multiplier of 1/R, as shown in first graph of FIG. 25 for two particle diameters, D1 and D2 and the following equation:

$Pn(S) \text{delta}S = Pn(RS)\text{delta}S/R$

If we switch to logarithmic space for S, we find that the probability density becomes shift invariant to a change in particle size (Pg(Log(S)) only shifts along the Log(s) axes as R or particle size changes.

Using delta$S=R*$deltaLog($S$)

$Pg(\text{Log}(S))\text{deltaLog}(S) = Pg(\text{Log}(R) + \text{Log}(S))$ deltaLog($S$)

Where Pg(Log(S)) is the probability density function in Log(S) space. This shift invariance means that the differential count-vs.-Log(S) distribution, Cg, in logarithmic space is a convolution of the probability function Pg shown in FIG. 25, with the number-vs.-size Ng, where all are functions of Log(S).

Cg=Ng⊖Pg in convolution form where Pg is the response (impulse response) from a monosized particle ensemble Cg=Ng*Pgm in matrix form, where each column in matrix Pgm is the probability function for the size corresponding to the element of Ng which multiplies it. This equation can also be used when Pg is not a convolution form.

These equations can be inverted to solve for Ng, given Cg and Pg, by using deconvolution techniques or matrix equation solutions. Pg is determined theoretically from the laser beam intensity profile or empirically from the Cg measured for one or more monosized particle samples. If Pg has some sensitivity to particle size, the matrix equation is preferable.

Figure 26:
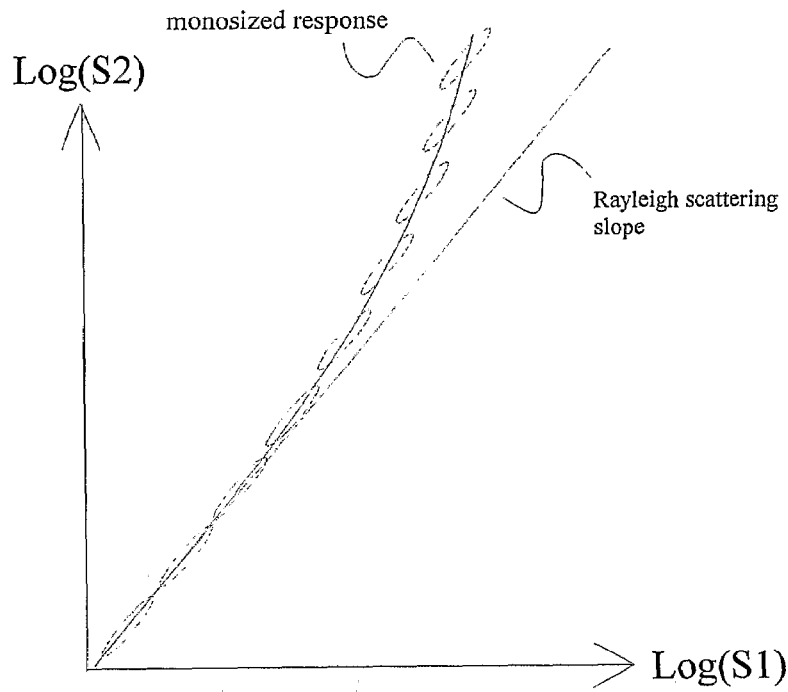
FIG. 26 provides a graph showing an example of scatter signal response in two dimensions, where each dimension is a function of the logarithm of the scatter signal, according to the present invention.

These relationships also hold for the above functions, when they are functions of more than one variable. For example, consider the case where Cg is a function of scattering values S1 and S2 from two scattering detectors at different scattering angles. Then Cg(Log(S1),Log(S2))deltaLog(S1)deltaLog(S2) is the number of events counted with log signals between Log(S1)−delta(Log(S1))/2 and Log(S1)+delta(Log(S1))/2, and between Log(S2)−delta(Log(S2))/2 and Log(S2)+delta(Log(S2))/2. Then Cg(Log(S1),Log(S2)) could be plotted as a surface on the (Log(S1),Log(S2)) plane as shown in FIG. 26. This surface is determined from the event density of the "scatter plot" or "dot plot" of all of the particles on the Log(S1),Log(S2) plane (each particle is represented by its values of Log(S1) on the X axis and Log(S2) on the Y axis on the scatter plot). So an event is the dot or point in Log(S1),Log(S2) space (or S1,S2 space) which represents a counted object. The distribution functions Pg and Cg are calculated from the number of events for each small area in this space. A group of monosized particles will theoretically produce a group of points in S1,S2 space which follow the function Log(S2)=Log(S1)+Log(R). Hence the data points will line up along a line of slope=1 and with an offset of Log(R). The distribution of points along the length of the line for the particle group is determined by range of S1 and S2 for that group due to the intensity distribution of the source beam. If particles pass through the beam at random locations, the distribution of data points along the line will follow the intensity distribution along each of the S1 and S2 axes. R, which is the ratio between S2 and S1, changes with particle size. As the particle size decreases below the wavelength of the source, R becomes a constant for all sizes, as determined from Rayleigh scattering theory. However, real measurements do not follow theory exactly due to structural imperfections in the optical system. These imperfections will cause broadening of the line. This broadening is illustrated by an elliptical shape (however the actual shape may not be elliptical) in FIG. 26. Each ellipse represents the perimeter around a group of counted data points on the S1,S2 plane from particles all of one size.

Notice, if the only cause of response broadening is due to the intensity distribution of the source spot, then the ellipses in FIG. 26 will become nearly circles, because both signals will come from similar intensity distributions.

Figure 27:
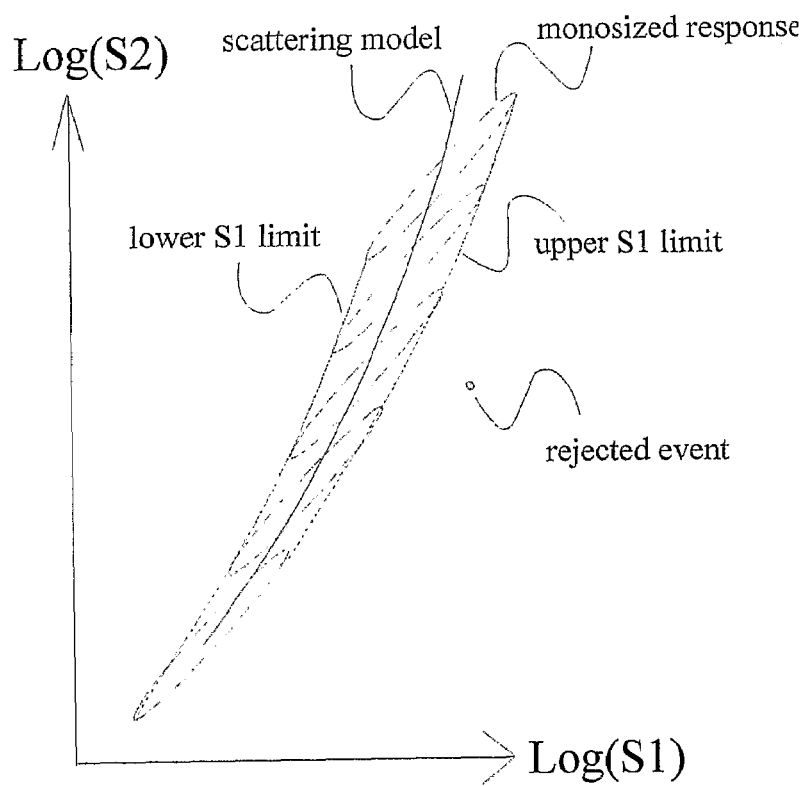
FIG. 27 shows details of the graph of FIG. 26, illustrating limits in the two dimensional space for separation of particles from non-particle events.
Figure 28:
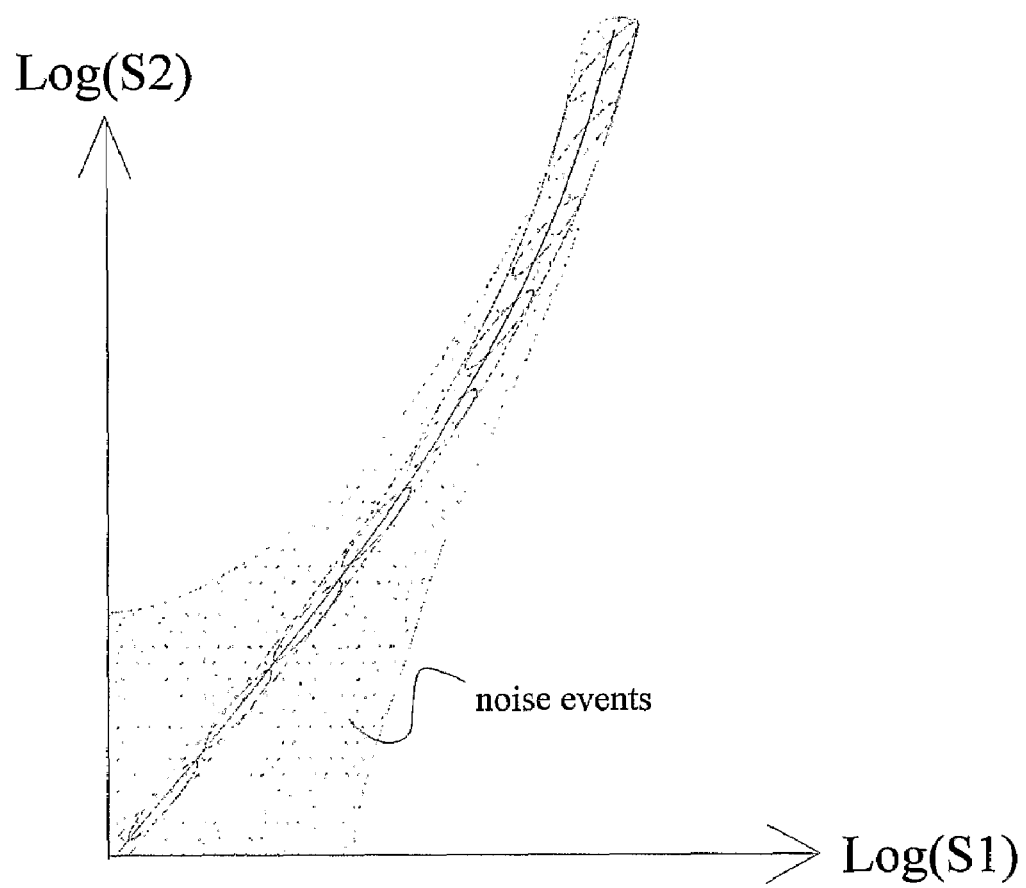
FIG. 28 provides a graph showing noise events which are rejected from the count distribution, according to the present invention.

A group of monosized particles will produce a differential count distribution in S1,S2 or Log(S1),Log(S2) space. In each case, a differential count distribution from a polysized sample will be the sum of the monosized distributions, each weighted by the percentage of particles of that size in the total distribution. Hence the particle number-vs.-size distribution can be determined by inverting this total differential count distribution, as a function of S1 and S2, or Log(S1) and Log(S2), using algorithms which may include those already developed for image restoration. In Log(S1),Log(S2) space the monosized response functions will be similar in shape over a large size range, because the functions are approximately shift invariant to size over the Log(S1),Log(S2) space. In this logarithmic space, deconvolution can be used to invert the count distribution in either one or more dimensions. The signal pulse from each event may pass through an analysis or sorting as described before, to sharpen the monosized response for higher size resolution. These pre-processed pulses are counted vs. a parameter (S1, S2, etc) such as peak value, total area, total correlated signal, etc., using the methods outlined previously. Each counted event is placed into the S1,S2 or Log(S1),Log(S2) space, where S1 and S2 may be the pulse peak value, pulse area, or any of the other size related parameters which can be calculated from the scattering signals. Then this space is broken up into very small regions, and the events in each region are summed to give sampled values of the differential count-vs.-parameter distribution in the 2 dimensional space. The known monosized response (in the 2 dimensional space), which may be size dependent, is used to invert this differential distribution to produce the particle number vs. size distribution. This monosized response may be calculated from scattering theory and the optical design parameters, or it may be measured empirically by recording the differential event count distribution in the space from monosized particle groups of known sizes. The known monosized response defines a region in the space, where scattering from single particles can produce counts as shown in FIG. 27. Events which are outside of this region, can be rejected as non-particle events (i.e. non-single particle events or noise), which may be due to multiple particles in the interaction volume or noise. This is particularly important for small sized particles with low scattering signals, where detection noise can cause many non-particle counted events as shown in FIG. 28. These noise events can also be included into the monosized response functions. For example, when a group of monosized particles are measured to produce an empirical monosized response function, many noise events will be measured. These noise events can be included in the monosized response function so that they are removed as part of the inversion process, when that function is used as one of response set in the inversion algorithm. The complete monosized response function set can be generated from scattering data from only a few well chosen monosized particle groups. The intervening response functions are interpolated from the trend of the theoretical scattering/optical system model. The empirical data from monosized samples may only be needed to locate the theoretical model in the space. The power of this process is that both the absolute signal data, which is needed to size particles in the Rayleigh scattering regime, and the scattering signal ratio information are combined into one space, where non-particle events are easily identified. This process can be applied to data taken in any number of dimensions, from one scattering angle to any number of scattering angles. Also any dimension of this process can be represented by a scattering signal related parameter (peak, integral, etc.) or combination of scattering signals (ratio of S2/S1, correlation between S2/S1, etc.). Higher number of dimensions provides better discrimination against non-particle events, but with added cost of more detectors and computer processing time. For example, more than two detectors could be placed behind each of slit 1 or slit 2 (aperture 1 or aperture 2), in the previous figures, to provide additional dimensions to the problem. For 3 detectors you could plot each event on the S3/S1, S2/S1 plane. Then the effects of source spot intensity variations would be reduced and the impulse responses (the ellipses shown previously) would become very localized, perhaps eliminating the need for deconvolution. All four detectors from these figures (detectors 1, 2, 3, 4) could also be combined into one four dimensional space as described in this section or into two 2-dimensional spaces, which are first solved separately and then the results are combined into one final size distribution by blending methods described previously.

If all of the particles in a particular sample are in a size region where the signal ratio is not sensitive to particle size, such as the Rayleigh size regime, the scattering model could be determined empirically from dynamic scattering measurements. If the particle flow is stopped, the heterodyning detection system can measure the Doppler spectral broadening due to Brownian motion (dynamic light scattering). The particle size distribution from this measurement may be used directly, or the optical scattering model may be determined from the dynamic scattering size distribution to invert the absolute scattering signal amplitudes from the count-vs.-scattering signal distribution. In this way, the low size resolution distribution from dynamic light scattering will provide scattering model selection for the higher size resolution counting method. This technique can be used over the entire size range of the dynamic light scattering to select the scattering model for counting particles inside or outside of the size range of dynamic light scattering. The scattering model may also be determined by inverting the count distribution in S1,S2 or Log(S1),Log(S2) space. This inversion will create a line function in the space. The shape of this line function in the size transition from Rayleigh scattering (where the ratio between S1 and S2 is constant) to larger particles will indicate the scattering model and refractive index of the particles.

Figure 27B:
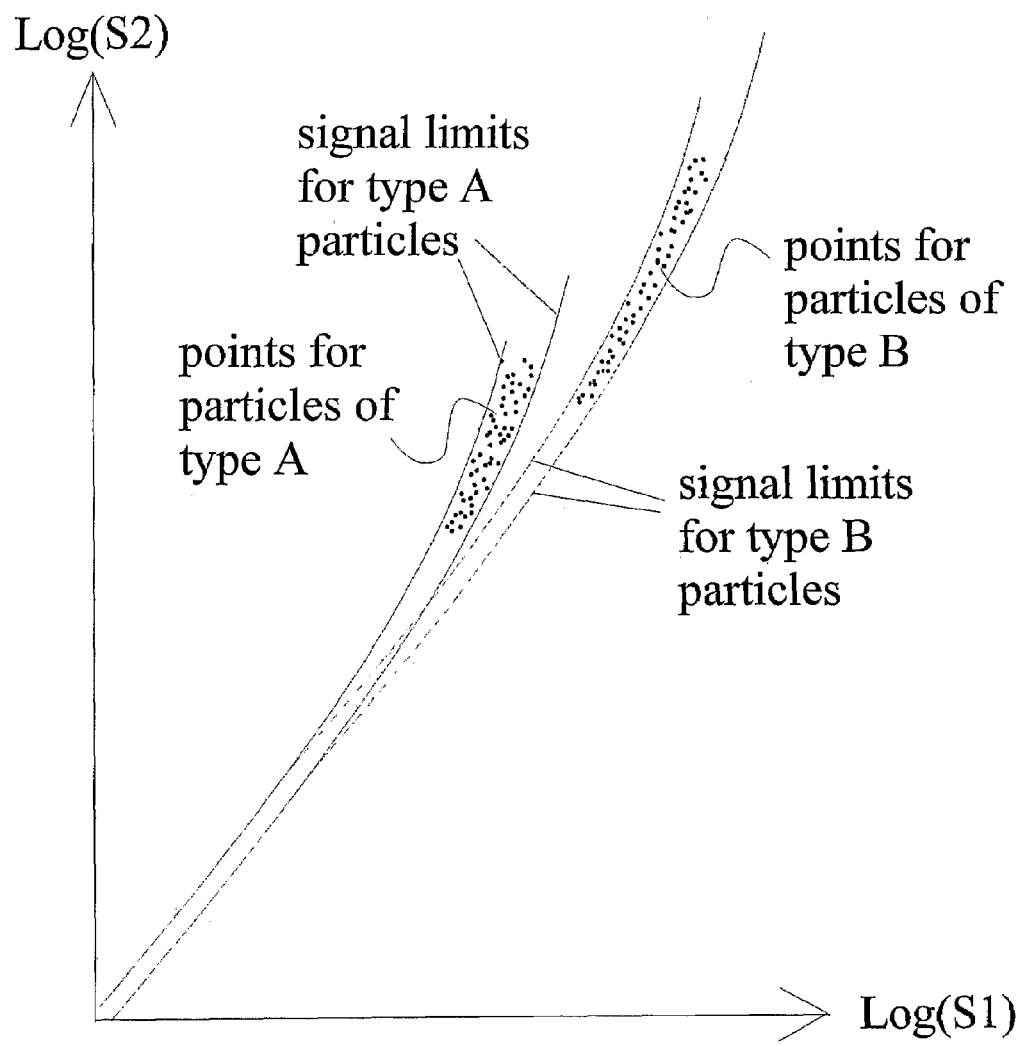
FIG. 27B provides a graph showing the scatter signal responses in two dimensions for particles of two different types, according to the present invention.

This multi-parameter analysis also provides for separation of mixtures of particles of different compositions such as polymer particles mixed with metal particles or polymer particles mixed with air bubbles. Hence, the count of air bubbles could be eliminated from the count distribution. FIG. 27B shows the methodology. Particles of different composition will have different response profiles in the multi-dimensional space. And the count events will be grouped to follow different profiles for each particle composition. So the data points (events) for particles of different composition will occupy different response profiles as shown in FIG. 27B. Individual particle size distributions and particle concentrations, for each particle type, could be determined from analysis of this data using the techniques described in this disclosure, individually for each response profile. Hence, a different particle refractive index and optical scattering model would be determined and used to calculate the size distributions for particles in each composition group, separately. These techniques could also be extended to larger numbers of dimensions by measuring more signals.

This process could also be used by replacing signals, in these multiple parameter plots, with ratios of signals. Any of these multiple angle configurations may be extended to many more angles simply by adding more scatter detectors which view the same interaction volume. For example, consider 4 such detector signals, S1, S2, S3, S4. Each of these signals could be pulse peak, pulse area, or correlated peak, etc. The ratios S4/S1, S3/S1, and S2/S1 are plotted in 3-dimensional space, one point for each particle counted. These ratios could also be S4/S2, S3/S2, S2/S1, etc. The point here is that the Mie resonances cause the scattering signals at various angles to oscillate together vs. particle size. For any size range, there is always a region of scattering angles where the ratio of scatter from two different ranges of angle are nearly independent of Mie resonances and particle composition. The path of these ratios in 2-dimensional space (e.g. S3/S1,S2/S1) or 3-dimensional space (e.g. S4/S1,S3/S1,S2/S1), are only weakly dependent on particle composition. The strongest particle composition dependence is for spherical particles in the size region of the Mie resonances. When thousands of particles are measured, their points will follow a multi-dimensional curve or line, in this multi-dimensional space, which indicates the sphericity or composition of the particles. This multi-dimensional line is formed by the highest concentration of points in this multidimensional space. Only points which are within a certain distance of this line are accepted as true particles. The outliers represent particles which passed through the edge of the source beam or whose signals are contaminated by noise. Also non-single particle events, such as noise pulses or multiple particles, would also be rejected because their combination of coordinates in this space would not agree with the possible coordinates of a particle. The signal ratios could also be replaced by the signal values to take advantage of absolute signal information, which is particularly advantageous in the Rayleigh region where signal ratios are weakly dependent on particle size, but absolute signal levels are strongly dependent on particle size. For particles of size above the Rayleigh region, the signal ratios may be preferred because the spread of particle events around the multi-dimensional line is very small for signal ratios which remove the dependence upon the particle position in the beam, removing a portion of the monosized response broadening shown in FIGS. 27 and 28. Both of the techniques, described here and in the description of FIGS. 27 and 28, will be needed to cover the entire size range, because the signal ratios are not strongly size dependent in the Rayleigh region (for particles below 0.1 micron in visible light). Another option would be to use a multi-dimensional space where some dimensions were signal ratios and other dimensions where absolute signals. Then the monosized response would only be strongly broadened in the absolute signal dimensions. For small particles, the absolute signal dimension would be processed with deconvolution and noise event rejection as shown in FIGS. 27 and 28; and for larger particles, signal ratio dimensions would be used to determine size with outlier rejection and minimal deconvolution. The entire path of the line constructed by the particle events determines the optical scattering model. This is particularly important for the Rayleigh region where the particle refractive index must be determined to calculate the dependence of absolute scattering amplitude on particle size. In any case, there will be a line or curve, in multi-dimensional space, which follows the path defined by the highest concentration of counted events. This line will define the optical scattering model and the particle shape or composition, if the user cannot provide that information. Size accuracy may be improved by using any apriori information about the particles to determine the scattering model from theoretical models. For example, the path of the multi-dimensional line could be calculated from scattering theory, given the particle refractive index and shape, but sometimes this information is not well known. If the particle composition or shape is unknown, then this empirically determined line in multidimensional space is compared to the theoretical lines for particles of various compositions and shapes. The theoretical line, which most closely matches the measured line from the unknown particle dispersion, is assumed to represent the composition and shape of the unknown particles.

The accuracy of the process described above improves as more scattering angles are measured. For example, the measured values of the scattered light for each of three scattering angles could be measured for each particle. These data points are then analyzed in a three dimensional scatter or dot plot. A line could be generated in 3 dimensional space by determining the path where the maximum concentration of particles (or dots in the plot) reside. In any one axis, this line may be multi-valued vs. particle diameter, especially in the region of Mie resonances. However, the line will not be multi-valued in 3 dimensional space. The spread of points about this line will be determined by the intensity distribution of the source beam in the interaction region. This group of points could be deconvolved in 3 dimensional space to produce a more sharply defined set of points, with less spread from the line, providing better size resolution along the line. But a better solution is to measure 4 scattering values at 4 different scattering angles for each particle. And then take ratio of each of any 3 values with the fourth value (or any other value) to remove the effect of intensity variation for particles which pass through different portions of the beam. Produce a scatter plot of these 3 ratios in three dimensions, where each point in 3 dimensional space is placed in Xm, Ym, and Zm values corresponding to the three ratios for each particle. Since the intensity distribution broadening is reduced, most of the points will tightly follow a line in three dimensional space. Outliers which are not close to the line passing through the highest concentration of data points may be eliminated as not being real single particles. The remaining data points (Xm,Ym,Zm) are then compared to different theoretical models to determine the composition and/or shape of the particles. The 3 dimensional function which describes the theoretical scattering is Zt where Zt is a function of Xt and Yt:

$$Zt=Zt(Xt,Yt)$$

Let (Xm,Ym,Zm) be the set of data points measured from the counted particles. Where the values in the X,Y,Z coordinates represent either absolute scattering signals S1, S2, S3 or signal ratios S4/S1, S3/S1, S2/S1 (or any other combination of ratios). Then define an error function Et for a certain theoretical model as:

$$Et(Xm,Ym)=(Yt(Xm)-Ym)^2 \text{ for Xm in the region Xmy}$$
where Yt(Xm) is single-valued $$Et(Xm,Zm)=(Zt(Xm)-Zm)^2 \text{ for Xm in the region Zmy}$$
where Zt(Xm) is single-valued Where Yt(Xm) is the theoretical value of Yt at Xm and Zt(Xm) is the theoretical value of Zt at Xm. Then find the theoretical model which produces the minimum sum of Esum over all values of Xm in the data set.

$$Esum=SUM(Et(Xm,Ym))/Ny+SUM(Et(Xm,Zm))/Nz$$

Where Ny is the number of points in region Xmy and Nz is the number of points in Xmz. And SUM is the sum of Et over its valid region of Xmy or Zmy. Esum is calculated for various theoretical scattering models, for spherical and non-spherical particles, and the model with the lowest Esum is chosen as the model for the sample. The sum of Esum values from multiple particle samples can also be compared for different theoretical models. The model with the lowest sum of Esum values is used to analyze all of those samples of that type. This calculation may be computationally intensive, but it only needs to be done once for each type of sample. Once the optimal theoretical model is determined for each particle sample type, the appropriate stored model can be retrieved whenever that sample type is measured. The chosen theoretical model will provide the particle diameter as a function of Xm, Ym, and Zm for each detected object.

Signal ratios show reduced sensitivity to the position of the particle in the source beam because each scattering signal is proportional to the optical irradiance on the particle. Usually to obtain optimal signal to noise, a laser source will be used to provide high irradiance but with lower irradiance uniformity due to the Gaussian intensity profile. The broadening in the monosized response, as shown in FIGS. 27 and 28 for example, may be reduced by insuring that only particles which pass near to the peak of the beam intensity profile are counted. Many methods have been described above to accomplish this selection process. Other methods could include the use of small capillaries or sheath flow to force all of the particles to go through the center of the source beam. But these methods are sometimes prone to particle clogging. In sheath flow, the particle dispersion is restricted to flow through a narrow jet, which is surrounded by a flow sheath of clean dispersant. If the particle concentration is low, the particles in this narrow stream will pass through the laser in single file and in locations close to the center of the beam. This method could be used with the ideas in this disclosure, but the wide range of particle sizes would require many different sized jets to handle the entire size range with the constant danger of clogging. The methods described in this disclosure can be used within a flow system of much larger dimensions, because the optical system only views and counts particles within a small interaction volume of that much larger volume. Particles which pass through that volume and which are outside of the size range for that measurement system will produce data points in the multidimensional space which are far from the multi-dimensional line of the optical model. They may be rejected based upon this criteria or simply based upon the length of the scattering pulse. The small particles are counted and sized by the higher angle system. The larger particles are sized by the 2-dimensional array or lower angle scattering systems. These independent particle size distributions are then combined to produce one size distribution over the full size range of the instrument.

Figure 29:
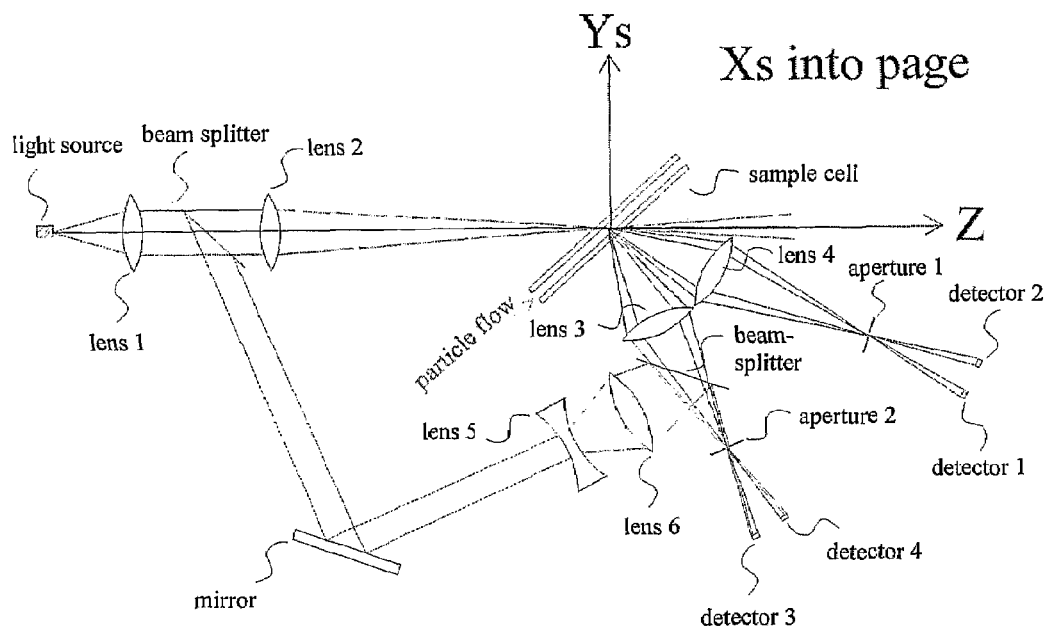
FIG. 29 provides a schematic diagram of an optical system, used in the present invention, the system measuring scattered light in each of two scattering planes, the diagram showing the optics of one scattering plane.
Figure 30:
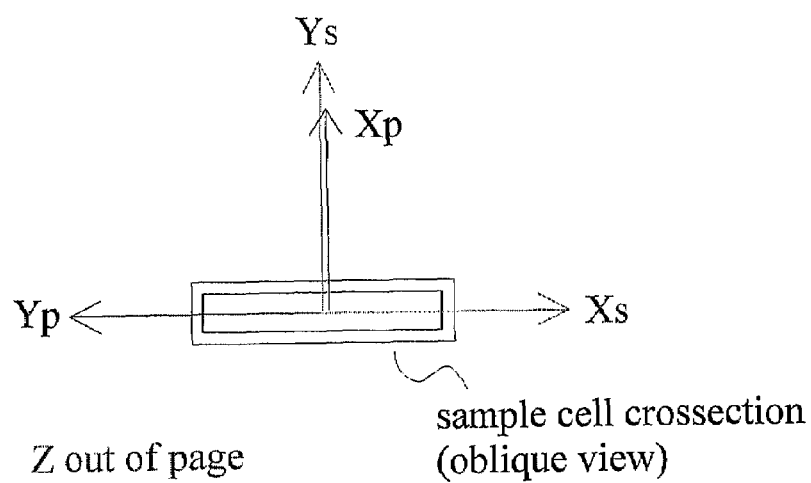
FIG. 30 provides a diagram showing the orientation of the two scattering planes for the system shown in FIG. 29.
Figure 31:
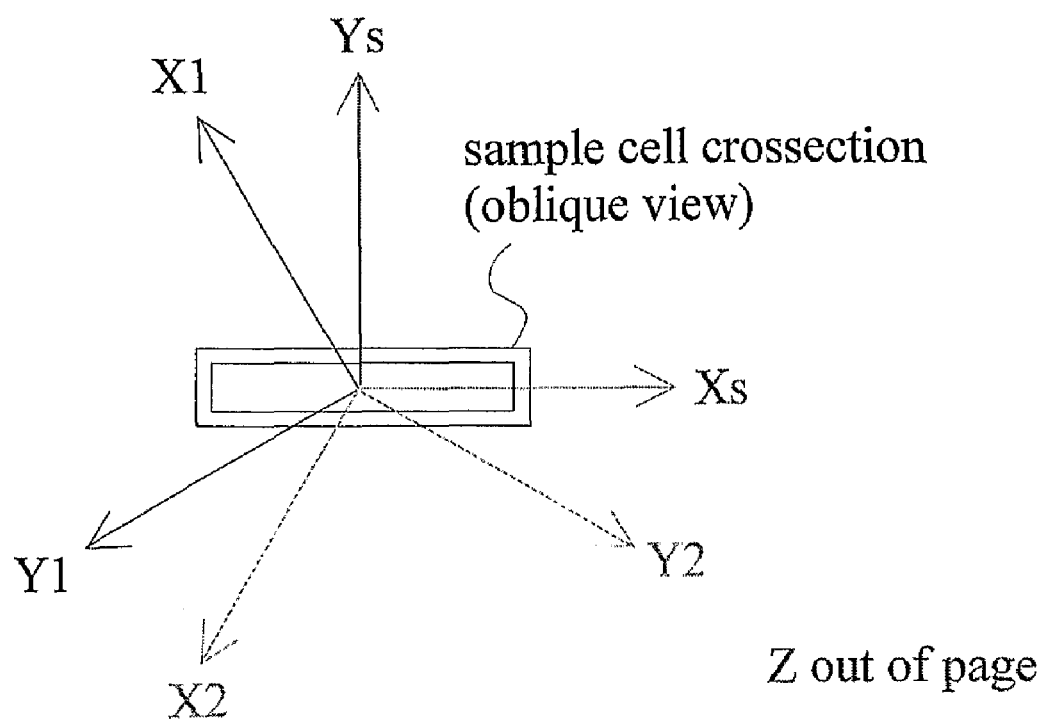
FIG. 31 provides a diagram showing the scattering plane orientations for an optical system, similar to that shown in FIG. 29, with three scattering planes.

The measurement of particle shape has become more important in many processes. Usually the shape can be described by length and width dimensions of the particle. If the length and width of each particle were measured, a scatter plot of the counted particles may be plotted on the length and width space to provide useful information to particle manufacturers and users, and this type scatter plot is claimed in this invention. If the particles are oriented in a flow stream, the angular scattering could be measured in two nearly orthogonal scattering planes, one parallel and one perpendicular to the flow direction. Each of these scatter detection systems would measure the corresponding dimension of the particle in the scattering plane for that detection system. If the flow of particle dispersion flows through a restriction, so as to create an accelerating flow field, elongated particles will orient themselves in the flow direction. FIG. 29 shows one of these scatter detection systems where the scattering plane is parallel to Ys and measures the projected particle dimension in the Ys direction, which is parallel to the projection of the flow direction of the particles in the Ys/Xs plane. A second scattering detection system could be placed in a scattering plane which includes the Z axis and Yp as shown in FIG. 30. This detection system would measure the particle dimension in the plane perpendicular to the flow. Each particle is counted with two dimensions, one parallel to and the other perpendicular to the flow, as measured concurrently by these two detection systems. In some cases, the particles cannot be oriented in the flow and they pass through the beam in random orientations. The detection configuration in FIG. 31 shows three scattering systems. Each system is in a scattering plane which is approximately 120 degrees from the next one. If the particle shapes are assumed to be of a certain type: rectangular, ellipsoid, etc., three size measurements in various scattering planes can be used to solve for the length, width, (or major and minor axis, etc.) and orientation of each particle. These planes can be separated by any angles, but 120 degrees would be optimal to properly condition the 3 simultaneous equations formed from these three size measurements.

Figure 32:
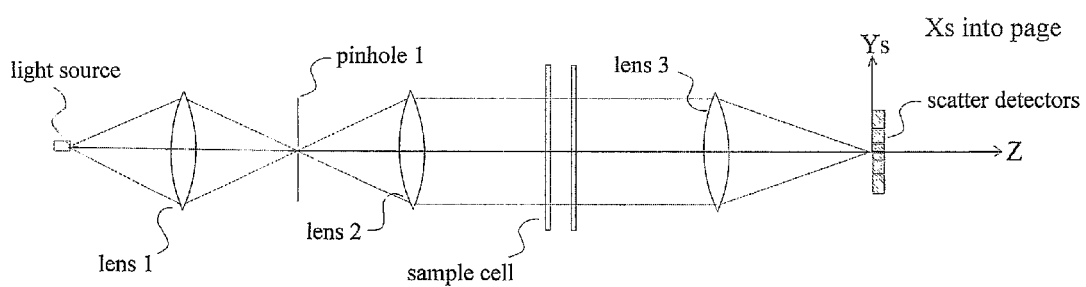
FIG. 32 provides a schematic diagram of an optical system which measures scattered light in multiple scattering planes by utilizing multiple detector elements, according to the present invention.
Figure 33:
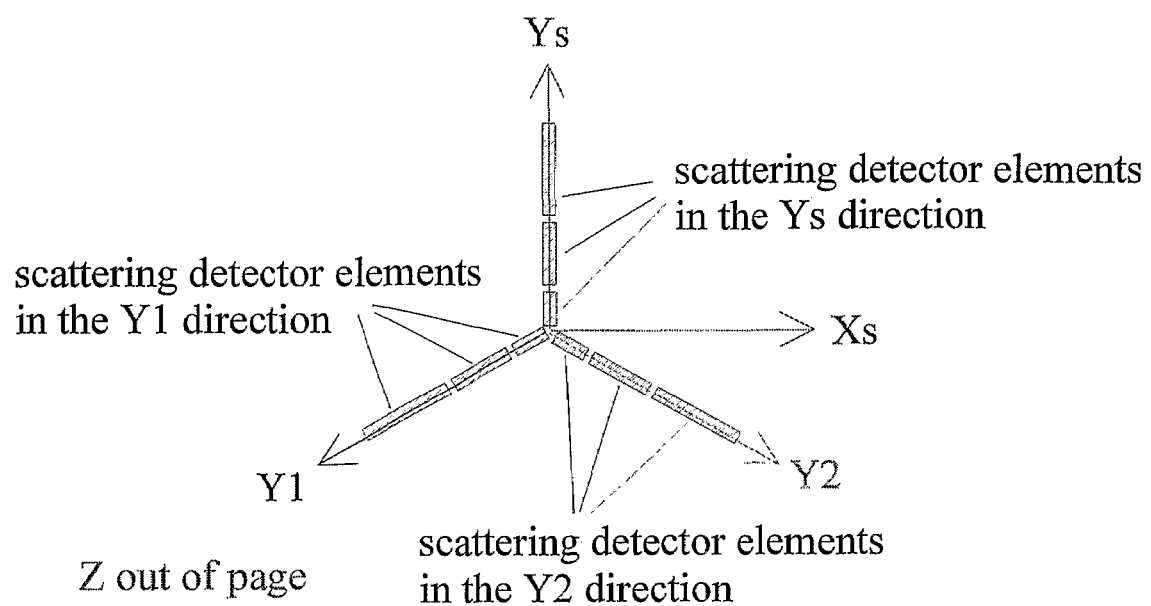
FIG. 33 provides a diagram showing an example of detector element structure for the system of FIG. 32.
Figure 34:
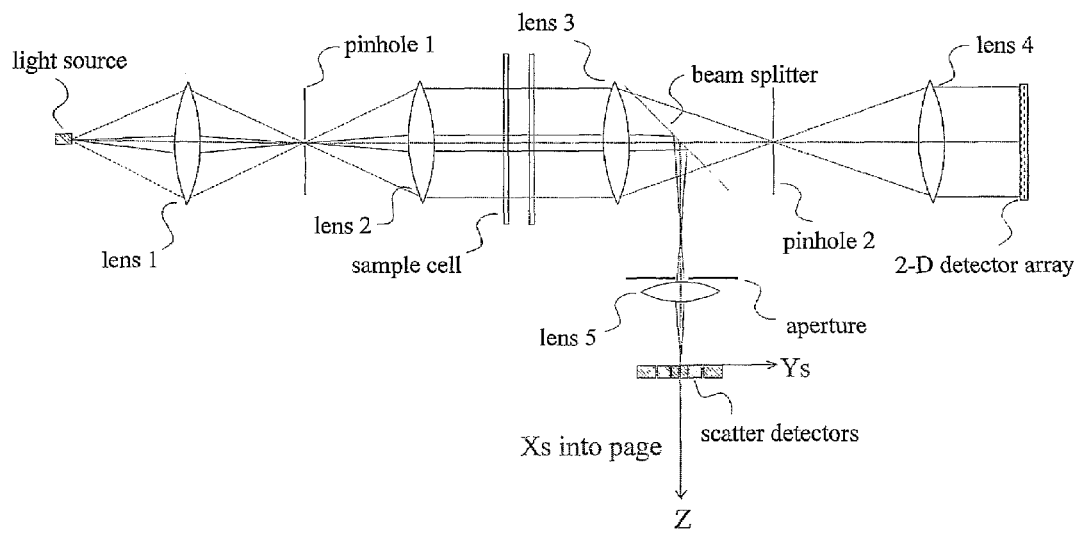
FIG. 34 provides a schematic diagram of a combination of the multiple-element detector systems, such as shown in FIG. 32 or FIG. 33, with the optical system of FIG. 11.

When measuring larger particles, which require smaller scattering angles, the scatter collection lens may be centered on the Z axis, with scattering detectors in the back focal plane of the collection lens, as shown in FIG. 32. As shown before, lens 1, pinhole 1, and lens 2 are not needed if a spatially clean collimated beam, such as a clean laser beam, is incident on the particle dispersion in the sample cell. Lens 3 collects scattered light from the particles and focuses it onto a group of detectors in the back focal plane. As before, the length and width of each randomly oriented particle is determined by 3 independent size measurements or, in the case where the size measurements are not independent, you must solve a set of simultaneous equations as described below. If the particles are oriented in the flow, only the Ys direction (parallel to the flow) and a set of detectors in the direction perpendicular to Ys are needed. As before, these two directions can be at any angle, but parallel and perpendicular to the flow are optimal. In the random orientation case, each measurement is made by a separate arm of the detector set in the three directions Ys, Y1, and Y2. These directions can be separated by any angles, but 120 degrees (see FIG. 33) would be optimal to properly condition the 3 simultaneous equations formed from these three size measurements. The scatter detector signals in each direction (or scattering plane) are combined by ratio of signals or other algorithms to determine the effective size in that direction. Then three simultaneous equations are formed from these size measurements to solve for the width, length, and orientation of each particle. FIG. 34 shows how this detector configuration is used in the system from FIG. 11. And as indicated above, the scatter in various scattering angular ranges can be measured each scattering plane by a separate optical system, as shown in FIG. 29 for example, in each scattering plane. The scattering plane is the plane which includes the center axis of the source beam and the center axes of the scattered light beams which are captured by the detectors.

The accuracy of the methods outlined above is improved by solving another type of problem. The sizes calculated from angular scattering data in each of two or more directions are not usually independent. In order to accurately determine the shape parameters of a particle, the simultaneous equations must be formed in all of the scattering signals. The form of the equations is shown below:

$$Si=Fi(W,L,O)$$

Where Si is the scattering signal from the ith detector. In the case of three directions (or scattering planes) and three detectors per direction, we have 9 total detectors and i=1, 2, . . . , 9)

W is the "width" parameter and L is the "length" parameter of the particle. In the case of a rectangular shape model, W is width and L is length. In the case of an ellipsoidal model, W is the minor axis and L is the major axis, etc. O is the orientation of the particle which could be the angle of the particle's major axis relative to Ys, for example. The functions Fi are calculated from non-spherical scattering algorithms and the form of Fi changes for different particle shapes (rectangles, ellipsoids, etc.). These equations, Si=Fi, form a set of simultaneous equations which are solved for W, L and O for each particle. If the Fi functions do not have a closed form, iterative methods may be employed where the Jacobian or Hessian are determined by numerical, rather than symbolic, derivatives. Also the closed form functions for Fi could be provided by fitting functions to Fi(W,L,O) calculated from the non-spherical scattering algorithms.

If we had two detection angles per each of three scattering planes, we would have 6 equations with 3 unknowns. With three detectors per scattering plane the size range may be extended and we will have 9 equations with 3 unknowns. For particles with more complicated shapes, such as polygonal, more scattering planes may be required to determine the particle shape parameters. In any case, a shape model is assumed for the particles and the set of equations Si=Fi are created for that model where Fi is a function of the unknown size parameters and Si is the scattered signal on detector i. This method can be applied to any of the shape measuring configurations shown before. This technique can also be applied to ensemble size measuring systems when the particles all have the same orientation as in accelerating flow. This invention claims scattering measurements from any number of angular ranges, in any number of scattering planes.

Figure 35:
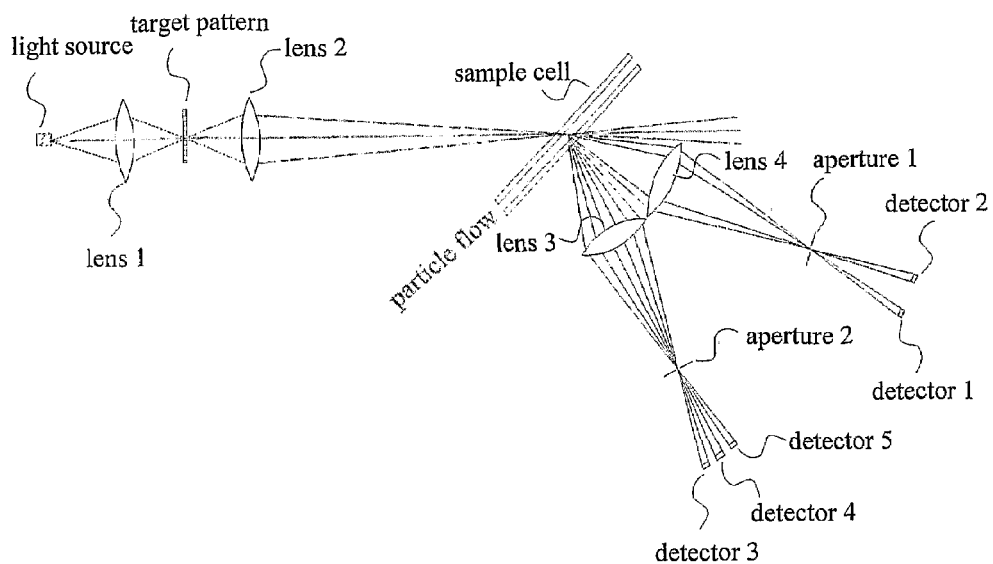
FIG. 35 provides a schematic diagram of a variation of the system shown in FIG. 1, where the signal oscillation is provided by a mask or target pattern, without interferometric mixing of source and scattered light.

Low scattering signals from small particles may be difficult to detect. FIG. 35 shows another variation where the source beam is passed through a patterned target which is conjugate to the interaction volume. The image of the target occurs in the interaction volume which is defined by aperture 1 or aperture 2. This target could consist of a sinusoidal transmission pattern or a Barker code pattern. As the particles pass through the image of this pattern, the scattered light is modulated by the modulated source intensity distribution in the interaction volume and so the scattered signal-vs.-time distribution is equivalent to the spatial intensity distribution. For a sinusoidal pattern, a phase sensitive detector with zero degree and quadrature outputs could be used to detect the sinusoidal signal of arbitrary phase. For a given particle velocity, the scattered signal could be filtered by a bandpass filter which is centered on the frequency equal to the particle velocity divided by the spatial wavelength of the sinusoidal intensity distribution in the interaction volume. The phase sensitive detector reference signal would also match this frequency. Better signal to noise may be achieved with other types of patterns. A Barker code target pattern will produce a single peak with very small side lobes when the scattering signal is correlated with a matching Barker code signal using a SAW or CCD correlator. When two scattering signals are multiplied and integrated, the zero delay (tau) value of the correlation function is obtained. This value will have the lowest fluctuation when the two signals have strong correlation as when both signals are from the same particle, instead of uncorrelated noise. The integrated product of the two signals will show less noise than the separated integrated signals. So the product of signals from two different angular ranges or the integral of this product over the particle pulse period will provide a signal parameter which is less sensitive to noise and which can be substituted for Si in any of the analyses described above. FIG. 35 also illustrates an additional scattering detector on aperture 2 for detection of three scattering angles. This can also be extended to a larger number of detectors.

Figure 36:
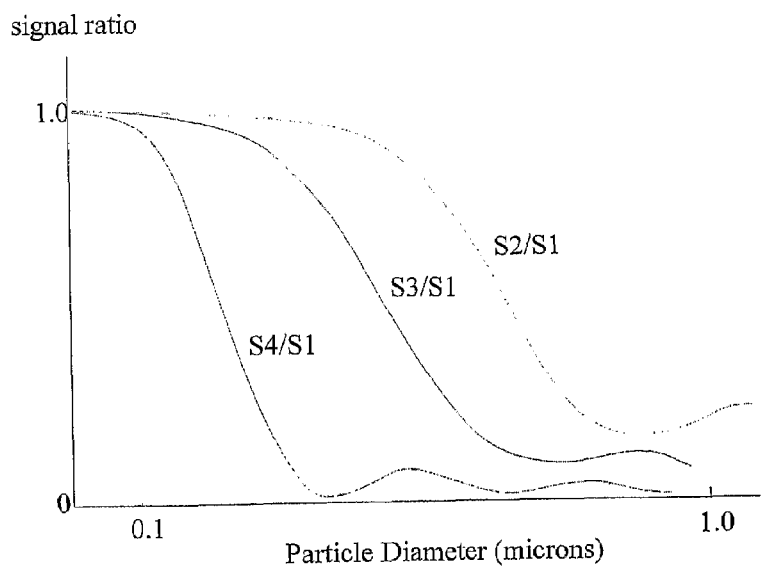
FIG. 36 provides a graph containing plots of examples of three ratios, between four scatter measurements, as a function of particle diameter, according to the present invention.

As shown before, ratios of scattering signals can be analyzed as a multi-dimensional function. Another method is to look at the individual signal ratios vs. particle diameter as shown in FIG. 36 for the case of three signal ratios. Any real particle event should produce a point on each curve which align vertically at the same diameter. Each curve indicates the particle size, but the most accurate size is determined from the curve where its point is in a region of high slope and monotonicity. For any particle, the 3 measured ratios would determine the approximate particle size region and allow selection of the one ratio which is in the region of highest slope vs. particle size and is also not in a multi-valued region (caused by Mie resonances). This selected ratio would then be used to determine the precise particle size for that particle.

The ratio of scattering signals from different scattering angles reduces the dependence of the particle size determination on the particle path through the light beam. Particles with signals below some threshold are eliminated from the count to prevent counting objects with low signal to noise. The accuracy of counts in each size bin will depend upon how uniform this elimination criteria is over the entire size range. Many methods have been described in this disclosure for reducing this problem. These methods are improved by having a source beam with a "flat top" intensity distribution and very sharply defined edges. This flat top intensity distribution can be provided by placing an aperture in an optical plane which is conjugate to the interaction volume or by using diffractive optic or absorption mask beam shapers. Another technique which will accurately define an interaction volume is shown in FIG. 37. No selection criteria is required for the direction which is parallel to the particle flow direction, because in this direction each particle passes through a similar intensity distribution and digitized signal values may be analyzed to find maximum or the integral for each particle signal. The primary criteria for eliminating particles from the count is based upon the position of the particle along the axis which is perpendicular to particle flow direction. The position of the particle along the direction perpendicular to the particle flow and the scattering plane (y direction) can be determined by using a 3 element detector which is in an optical plane which is conjugate to the interaction volume as shown in FIG. 37. This figure shows the position and orientation of the 3 element detector in the optical system and an enlarged view of the detector elements showing the path of various particles passing through the interaction volume as seen by the detector elements. The beamsplitter, following lens 3, splits off some scattered light to the 3 element detector. By measuring the signal ratio between elements 1 and 2 or elements 3 and 2, the y position of the each particle is determined and only particles within a certain y distance from the center of the light beam are accepted. This signal ratio criteria is extremely accurate and uniform among all particle sizes so that proper mass balance is maintained over the entire size range. The ratio is also insensitive to how well the particle is optically resolved because the fraction the particle image on each the two detectors spanning the image is not strongly dependent on the size or sharpness of the image, but is strongly dependent on the y position of the particle. FIG. 37 shows the 3 element detector in a heterodyne arrangement, with a portion of the source light being mixed with the scattered light. However, this idea is also applicable to non-heterodyne configurations by just removing the beamsplitter between lens 1 and lens 2.

Figure 38:
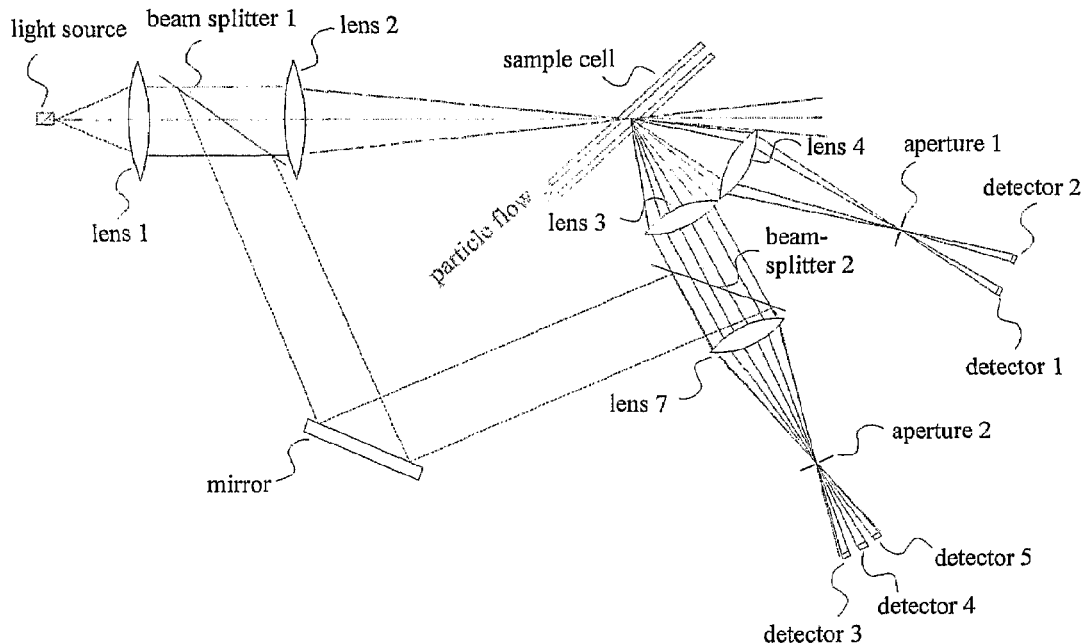
FIG. 38 provides a schematic diagram of an alternative to FIG. 1, where all beams are nearly collimated in the regions of the beamsplitters.

Many figures (FIG. 19 for example) show the heterodyne system with a negative and positive lens pair (lenses 5 and 6) which provide a local oscillator beam which matches the wavefront of scattered light from the particles. FIG. 38 shows an alternative design where all beams are nearly collimated in the regions of the beamsplitters. This configuration may be easier to align and focus. Lens 1 collimates the source light which is sampled by beamsplitter 1 and directed to beamsplitter 2 by the mirror. Lens 3 collimates the light scattered by the particle and this light is combined with the source light by beamsplitter 2 and focused through aperture 2 by lens 7. As before, aperture 2 is conjugate to the particle interaction volume and defines the interaction volume, in the sample cell, which is viewed by the detectors 3, 4 and 5. Usually, the focal length of lens 2 is long to provide a source beam of low divergence and the focal length of lens 3 is short to span a large range of scattering angles. If the light source is a laser diode, without anamorphic optics, the major axis of the intensity distribution ellipse at the interaction volume should be in the plane of the particle flow and scattering plane to provide a long train of heterodyne oscillations for signal detection and to provide the lowest beam divergence in the scattering plane. A circular source beam may require anamorphic optics to create an elliptical beam in the interaction volume to provide the advantages mentioned above. However, the advantages of the ideas described in this disclosure can be applied to a source beam with any intensity distribution.

The matching of light wavefronts between the source beam and scattered light at the heterodyne detectors is important to maintain optimum interferometric visibility and maximum modulation of the heterodyne signal on each detector. Since perfect wavefront matching is not achievable, the interferometric visibility must be determined for each detector to correct the signals for deviation from theoretical heterodyne modulation amplitude. The visibility is determined by measuring particles of known size and comparing the heterodyne signals to the signals expected from theory. To first order, the interferometric visibility should be independent of particle size for particles much smaller than the source beam in the interaction volume. The visibility could be measured for particles of various sizes to measure any second order effects which would create visibility dependence on particle size. If only signal ratios are used for determining size determination, only the ratios of interferometric visibility need to be calibrated by measuring scattering from particles of known size.

The number of cycles in the heterodyne modulated pulse is determined by the length of the trajectory of the particle through the source beam. The frequency of the heterodyne modulation is determined by the velocity of the particle through the beam. In general the power spectrum of the signal will consist of the spectrum of the pulse (which may be 10 KHz wide) centered on the heterodyne frequency (which may be 1 MHz). Both of these frequencies are proportional to the particle velocity. Actually the best frequency region for the signal will be determined by the power spectral density of the detector system noise and/or the gain-bandwidth product of the detector electronics. For this reason, in some cases the particle flow velocity should be lowered to shift the signal spectrum to lower frequencies. The particle concentration is then adjusted to minimize the time required to count a sufficient number of particles to reduce Poisson statistic errors. This is easily accomplished for small particles which usually have higher count per unit volume and require lower noise to maintain high signal to noise.

In cases where optical heterodyne detection is not used, the signal to noise may be improved by phase sensitive detection of the scattered light. Modulation of the optical source may provide for phase sensitive detection of the scattering signal. The source is modulated at a frequency which is much larger than the bandwidth of the signal. For example, consider a source modulated at 1 megahertz with a scattering pulse length of 0.1 millisecond. Then the Fourier spectrum of scattered signal pulse would cover a region of approximately 10 KHz width centered at 1 megahertz. If this signal is multiplied by the source drive signal at 1 megahertz, the product of these two signals will contain a high frequency component at approximately 2 megahertz and a difference frequency component which spans 0 to approximately 10 KHz. In order to eliminate the most noise but preserve the signal, this product signal could be filtered to transmit only the frequencies contained in the scattering pulse, without modulation (perhaps between 5000 and 15000 Hz). This filtered signal product will have higher signal to noise than the raw signal of scattered pulses. This signal product can be provided by an analog multiplier or by digital multiplication after both of these signals (the scattering signal and the source drive signal) are digitized. This product is more easily realized with a photon multiplier tube (PMT) whose gain can be modulated by modulating the anode voltage of the PMT. Since the PMT gain is a nonlinear function of the anode voltage, an arbitrary function generator may be used to create PMT gain modulation which follows the modulation of the source. The voltage amplitude will be a nonlinear function of the source modulation amplitude, such that the gain modulation amplitude is a linear function of the source modulation amplitude. An arbitrary function generator can generate such a nonlinear modulation which is phase locked to the source modulator.

As described at the beginning of this disclosure, multiple sized beams can also be used to control the effects of seeing more than one particle in the viewing volume at one time. The key is to choose the proper scattering configuration to provide a very strong decrease of scattering signal with decreasing particle size. Then the scattering signals from smaller particles do not effect the pulses from larger ones. For example, by measuring scattered light at very small scattering angles, the scattered light will drop off as the fourth power of the diameter in the Fraunhofer régime and as the sixth power of diameter in the Rayleigh régime. In addition, for typically uniform particle volume vs. size distributions, there are many more smaller particles than larger ones. The Poisson statistics of the counting process will reduce the signal fluctuations for the smaller particles because individual particles pulses will overlap each other producing a uniform baseline for the larger particles which pass through as individual pulses. This baseline can be subtracted from the larger particle pulse signals to produce accurate large particle pulses. A typical optical configuration is shown in FIG. 41.

Figure 41:
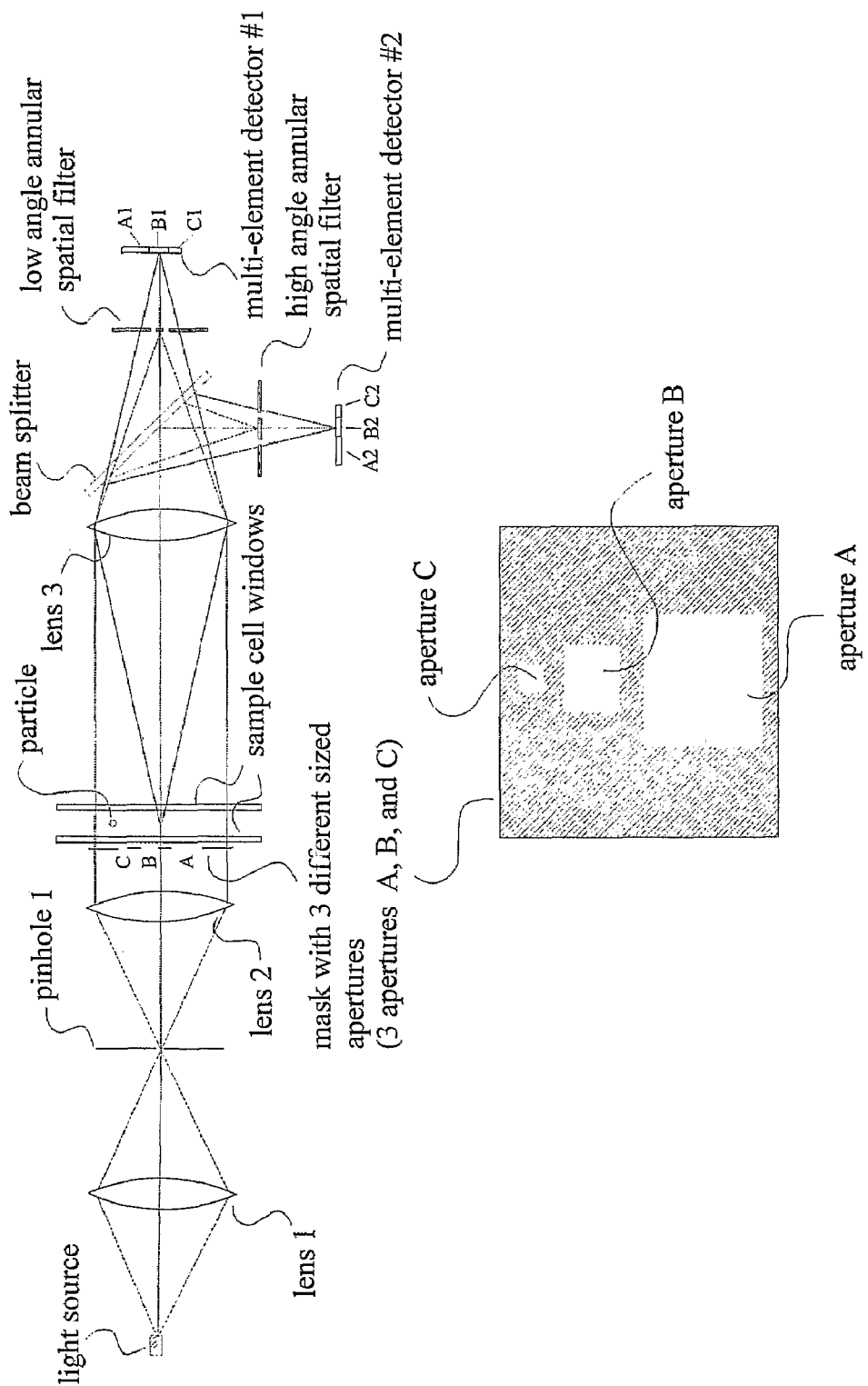
FIG. 41 provides a schematic diagram of an optical system which utilizes mask openings to define interaction volumes of various sizes, according to the present invention.

FIG. 41 shows such an optical system where the light source is spatially filtered by lens 1 and pinhole 1. Lens 2 collimates and projects the source beam through the particle sample and an aperture mask, which is imaged onto the detector array by lens 3. Lens 2 could also focus the beam into the sample cell to increase light intensity. An annular spatial mask is placed in the back focal plane of lens 3 to only pass scattered light over a certain range of scatter angle as defined by the inner and outer radii of the annular filter, which is similar to mask 1 shown in FIG. 12. The very low angle scattering and incident beam are blocked by central stop of the annular aperture in the back focal plane of lens 3. Hence the detector array 1 sees an image of mask apertures and each detector element measures the scattered light only from particles in it's corresponding mask aperture over the angular range defined by the aperture (or spatial mask) in the back focal plane of lens 3. Each detector element is equal to or slightly larger than the image of the corresponding mask aperture at the detector plane, as long as each detector only sees the light from only it's corresponding mask aperture. A beam splitter splits off a portion of the light to a second annular filter (in the back focal plane of lens 3) and detector array 2. The angular ranges of the two annular filters are chosen to produce scattered values which are combined by an algorithm which determines the size of each particle. One such algorithm would be a simple ratio of the corresponding pulses from both arrays. And if the total scattered light is sensitive to particle composition, then the ratio of the two scattering signals can be used to determine the particle size more accurately. As with all other systems described in this disclosure, these ideas can be extended to more than two detector arrays or more than two scattering angles, simply by adding more annular spatial masks and detectors by using beamsplitters. And the signals can be processed and analyzed, using the methods described previously.

Figure 71:
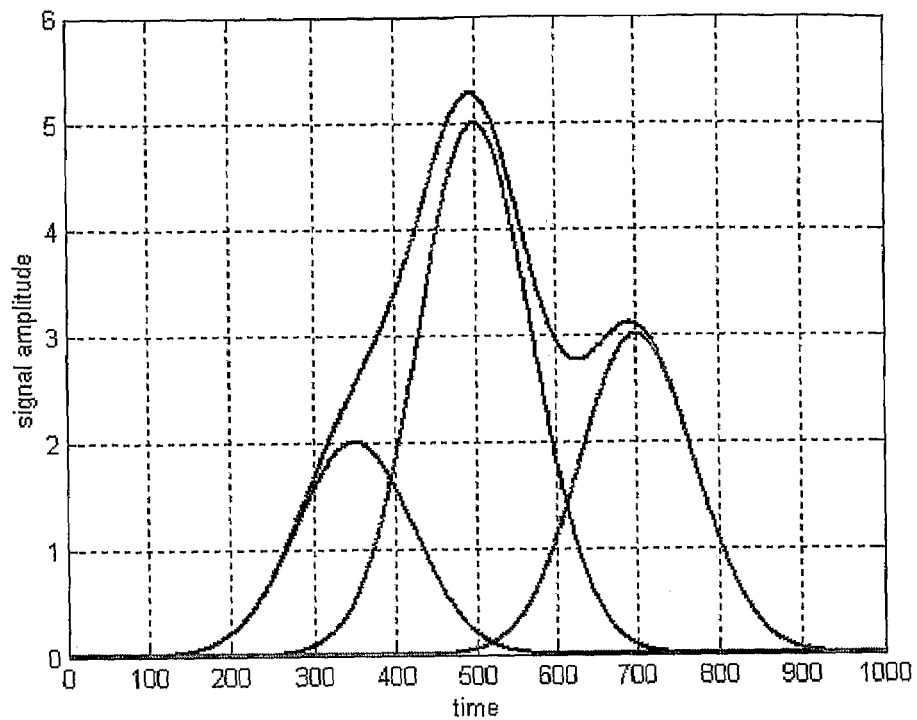
FIG. 71 provides a graph of three overlapping signal pulses and the sum of those three signals as measured by a detector, according to the present invention.
Figure 72:
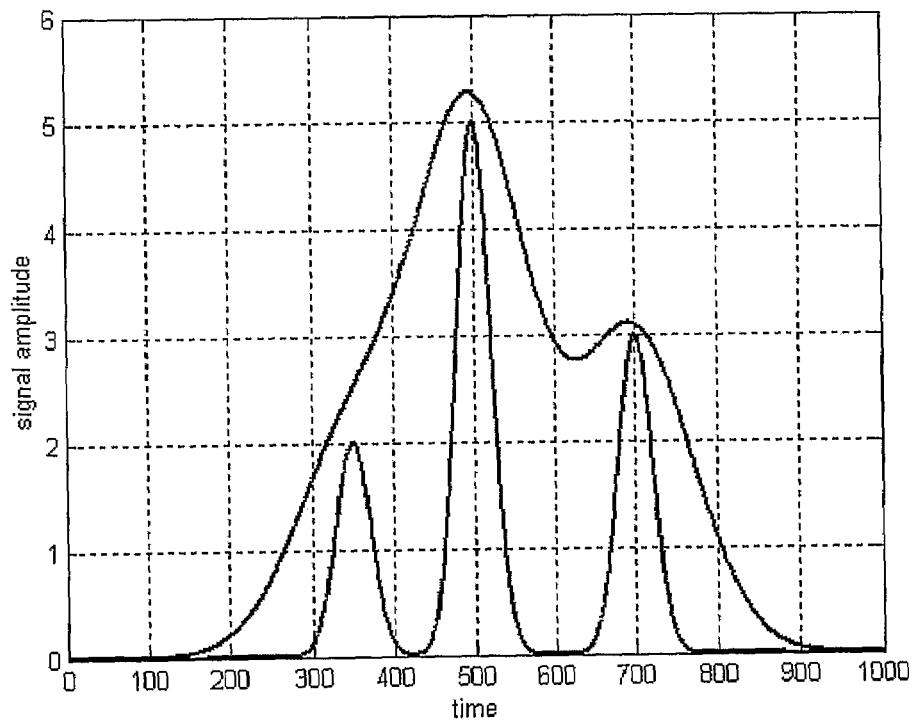
FIG. 72 provides a graph of the sum of those three signals of FIG. 71, and the signal which results from deconvolution of said sum of three signals.
Figure 73:
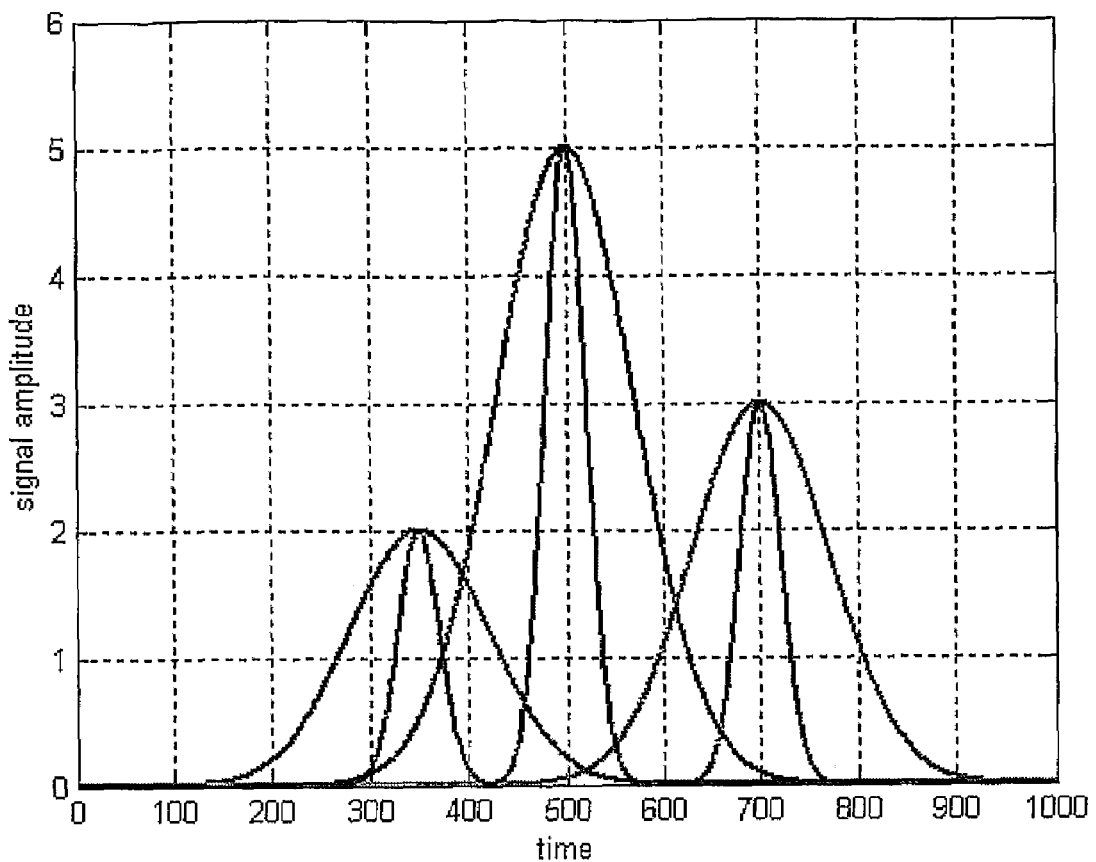
FIG. 73 provides a graph showing the original set of three overlapping signal pulses and the signal, which results from deconvolution of said sum of three signals, according to the present invention.

This configuration allows each detector element to see scatter from only a certain aperture in the mask and over a certain scattering angle range determined by it's spatial mask. If the spatial mask defines a range of low scattering angles, the total scatter for the detectors viewing through that spatial mask will show a strong decrease with decreasing particle size. The signal will decrease at least at a rate of the fourth power of the particle diameter or up to greater than the sixth power of the diameter. Assuming the weakest case of fourth power, we can obtain a drop by a factor of 16 in signal for a factor of 2 change in diameter. This means that you need to control the particle concentration such that no multiple particles are measured for the smallest particle size measured in each aperture. The largest particle size which has significant probability of multiple particles in the aperture at one time should produce scattering signals which are small compared to the scattering from lower size measurement limit set for that aperture. However, this particle concentration constraint is relaxed if multiple pulses are deconvolved within a signal segment, as shown in FIGS. 71, 72 and 73.

One annular filter aperture could also be replaced by a pinhole, which only passes the light from the source (the red rays). Then the signals on each detector element would decrease as a particle passes through it's corresponding aperture at the sample cell. This signal drop pulse amplitude would directly indicate the particle size, or it could be used in conjunction with the other annular signals. No limits on the number of apertures in the sample cell mask or of annular filter/detector sets are assumed. More annular filter/detector sets can be added by using more beamsplitters.

Figure 42:
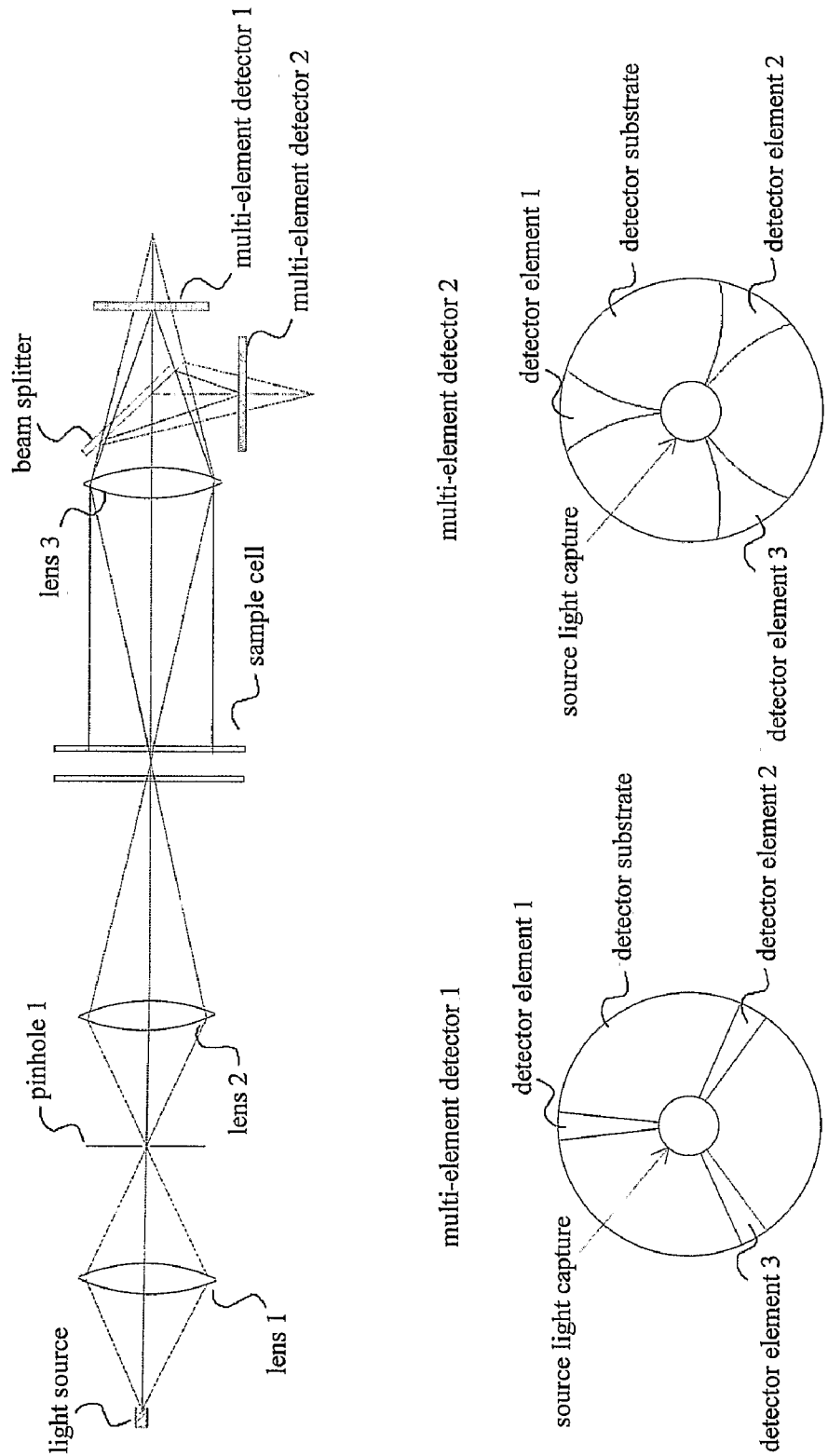
FIG. 42 provides a schematic diagram of an optical system which utilizes detector elements with different angular weighting functions, according to the present invention.

FIG. 42 shows another configuration for determining particle size and shape. The light source light is focused through pinhole 1 by lens 1 and then focused into the sample cell by lens 2. The beam divergence and spot size in the sample cell are determined by the range of scattering angles to be measured and the size range of the particles. Essentially the spot size increases and the divergence decreases for larger particles. The scattered light is collected by lens 3, which focuses it onto many multi-element detector assemblies, which are in the back focal plane of lens 3. Each multi-element detector has multiple detector elements which measure a certain range of scattering angles along various scattering planes. FIG. 42 shows an example with three scattering planes separated by approximately 120 degrees between adjacent planes. However, any number of scattering planes with any angular separation is claimed in this disclosure. Each multi-element detector contains a central region which either captures of passes the source light so that it does not contaminate the measurement of the scattered light. The beam divergence will determine the size of the source light capture region on the multi-element detectors.

Each detector element has a shape which determines how much of the scattered light at each scattering angle is collected by the detector element. For example detector 1 has wedge shaped detectors which weights scattering angles progressively. Detector 2 has a higher order weighting, the larger scattering angles are gradually weighted more in the total signal for each detector element. These detector element shapes can take on many forms: rectangular, wedged, and higher order. Any shape will work as long as the progression of collection width of the detector is different between the two multi-element assemblies so that when the particle pulse signals from the corresponding detector elements of the two multi-element detectors are ratioed, you obtain a ratio which is particle size dependent. The progression of the weighting function can also be defined by placing a variable absorbing plate, over each detector element, which varies absorption vs. radius r from the center of the detector assembly. This absorption plate can provide a weighting similar to that obtained by varying the width of the detector element vs. r. And since these size measurements are made in different scattering planes, multiple dimensions of each particle are determined separately. In general each detector element produces a signal Sab, where "a" is the multi-element detector assembly number and "b" is the element number within that assembly. Then we can define Sab as:

$Sab = \int wa(r) f(r,d) \partial r$ for the bth element in the ath assembly

Here d is the dimension of the particle in the direction of the corresponding scattering plane. The scattered intensity at radius r from the center of the detector assembly (corresponding to zero scattering angle) for dimension of d is f(r,d). And wa(r) is the angular width (or weighting function) of the detector element at radius r in assembly "a", in other words the angle which would be subtended by rotating the r vector from one side of the element to the other side at radius r. For the simple 3 element assemblies shown in FIG. 42, we obtain 6 measured values:

S11, S12, S13 for assembly 1

S21, S22, S23 for assembly 2

The signal on each detector element will consist of pulses as each particle passes through the beam. The Sab values above can be the peak value of the pulse or the integral of the pulse or other signal values mentioned in this disclosure. For example, one possible case would be:

Angular width for assembly 1 $w1(r) = Ar$

Angular width for assembly 1 $w2(r) = Br*r$

For this case S1/S21, S12/S22, and S13/S23 are almost linear functions of the particle dimension in the direction of the corresponding scattering plane. These 3 dimensions can also be determined from an algorithm which uses all 6 S values by solving simultaneous equations which include the interdependencies of these values on each other, as described previously. In any event, the actual dimensions of the particle can be determined by assumption of a certain particle form such as rectangular, ellipsoidal, hexagonal, etc. More detector elements in each assembly will produce more accurate dimensions for randomly oriented particles. The true power of this technique is that the shape of each particle can be determined over a large size range by measuring only a few signals. Each element of each detector assembly could be broken up into sub-segments along the "r" direction to provide better size information by measuring the angular scattering distribution in each of the scattering planes. However, this may reduce the particle count rate because more digitizations and data analysis may be required per particle.

These S values can also be analyzed using methods shown in FIGS. 26 through 28, by creating two dimensional plots of absolute measurements of S1* vs. S2*(S11 vs. S21, S12 vs. S22, and S13 vs. S23). Also a virtual 6 dimensional plot of all 6 values can be created (but not plotted). Then the same methods can be used to eliminate particles which do not meet criteria for having passed through the central portion of the beam or which are caused by noise pulses (the absolute S values are not consistent with the size determined from the S ratios)

The actual particle size system may consist of systems, each which is similar to the one shown in FIG. 42. Each system would have a different source beam divergence and spot size in the sample cell to accommodate different size ranges. The count distributions from the systems are then concatenated (or blended as shown previously) into one total distribution over the entire size range of the product. For example, for rectangular or ellipsoidal particles, the width and length dimensions of each particle could be plotted on a "scatter" plot to display the information in a useful format.

For smaller particles, the source beam will be more focused (higher divergence and smaller spot size in the sample cell region) into the sample cell. This will help to define a smaller interaction volume for the smaller particles which usually have higher number concentration than the larger particles.

Figure 43:
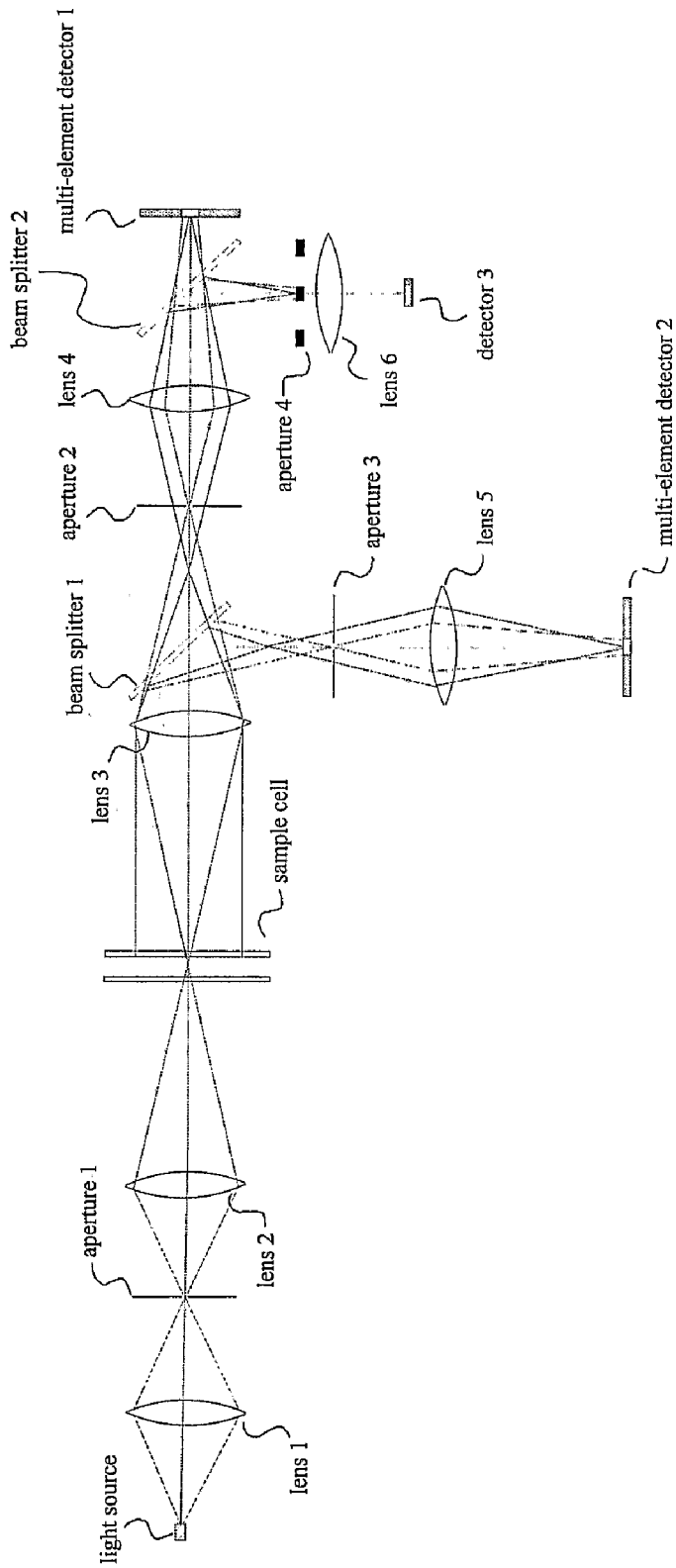
FIG. 43 provides a schematic diagram of an optical system with multi-element detectors which only receive scattered light from a small volume of particle dispersion, according to the present invention.

FIG. 43 shows another version of this concept where the interaction volume for particle scattering is controlled by appropriately positioned apertures and by correlation measurements between signals from different scattering angles. The system is similar to that shown in FIG. 42. But in this case additional apertures and lenses are added in the detection system. Aperture 2 and aperture 3 are placed in optical planes which are conjugate to the source focused spot in the sample cell. These apertures are sized and oriented to only allow the image of the focused spot to pass on to the multi-element detector. The source beam in aperture 1 may have significant intensity variation so as to produce a large variation in scatter signals when particles pass through different portions of the source spot in the sample cell. In this case, the size of apertures 2 and 3 may be reduced such that their images, at the sample cell, only pass the uniform portion of the source beam intensity profile in the sample cell. These apertures and lens 3 limit the volume, in the sample cell, from which scattered light can be detected by the multi-element detectors. Lenses 4 and 5 image the back focal plane of lens 3 on to the multi-element detector so that the detector sees the angular scattering distribution from the particles. The multi-element detectors 1 and 2 can also measure scattered light in the back focal plane of lens 4 and lens 5, respectively. Detector 3 collects all of the light that is scattered in a range of scattering angles which are defined by the annular aperture 4. This detector provides a equivalent diameter based on equivalent spherical particle crossectional area, without shape dependence. In some cases the size as determined by the total scatter thorough aperture 4 will be more accurate than the particle dimensions from the multi-element detectors. For example, detector 3 could be used to determine the particle area and the multi-element detectors could determine the aspect ratio of the particle using the ratio of the determined dimensions. Using the area and the aspect ratio, the actual dimensions could be determined. This may be more accurate than simply determining the dimensions separately using the multi-element detectors for particles whose major or minor axis may not line up with a scattering plane and which require the solution of simultaneous equations to determine the particle shape.

Figure 44:
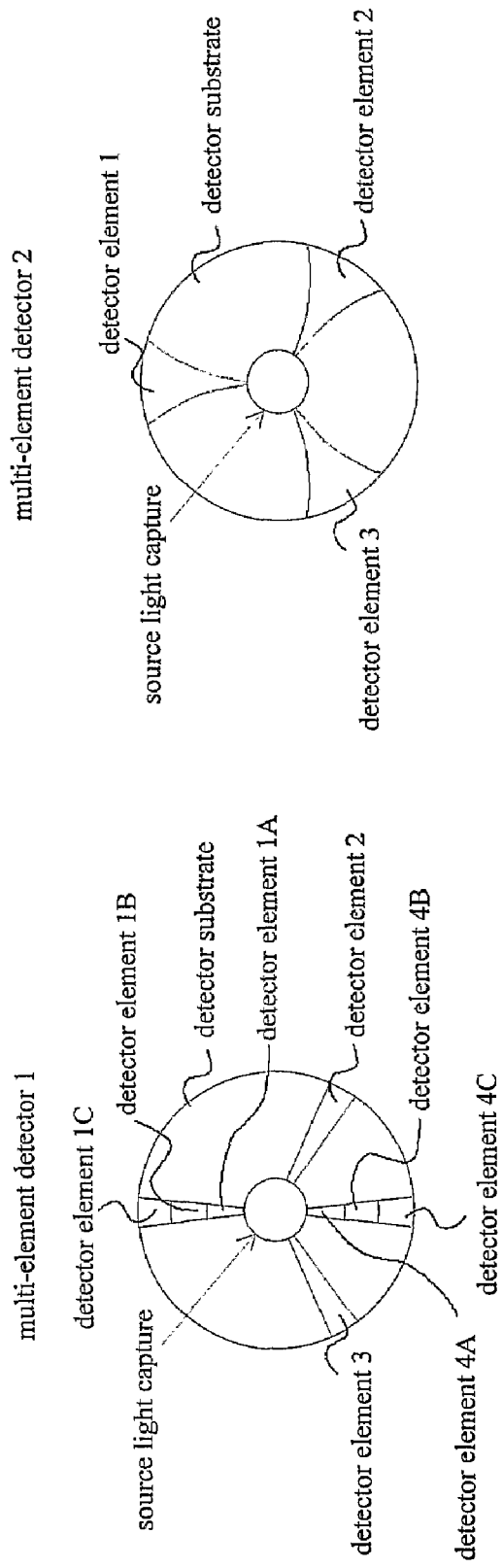
FIG. 44 provides a diagram showing an example of multi-element detectors with different angular weighting functions and additional detector elements for detecting the position of each particle relative to best focus of the light beam, according to the present invention.
Figure 45:
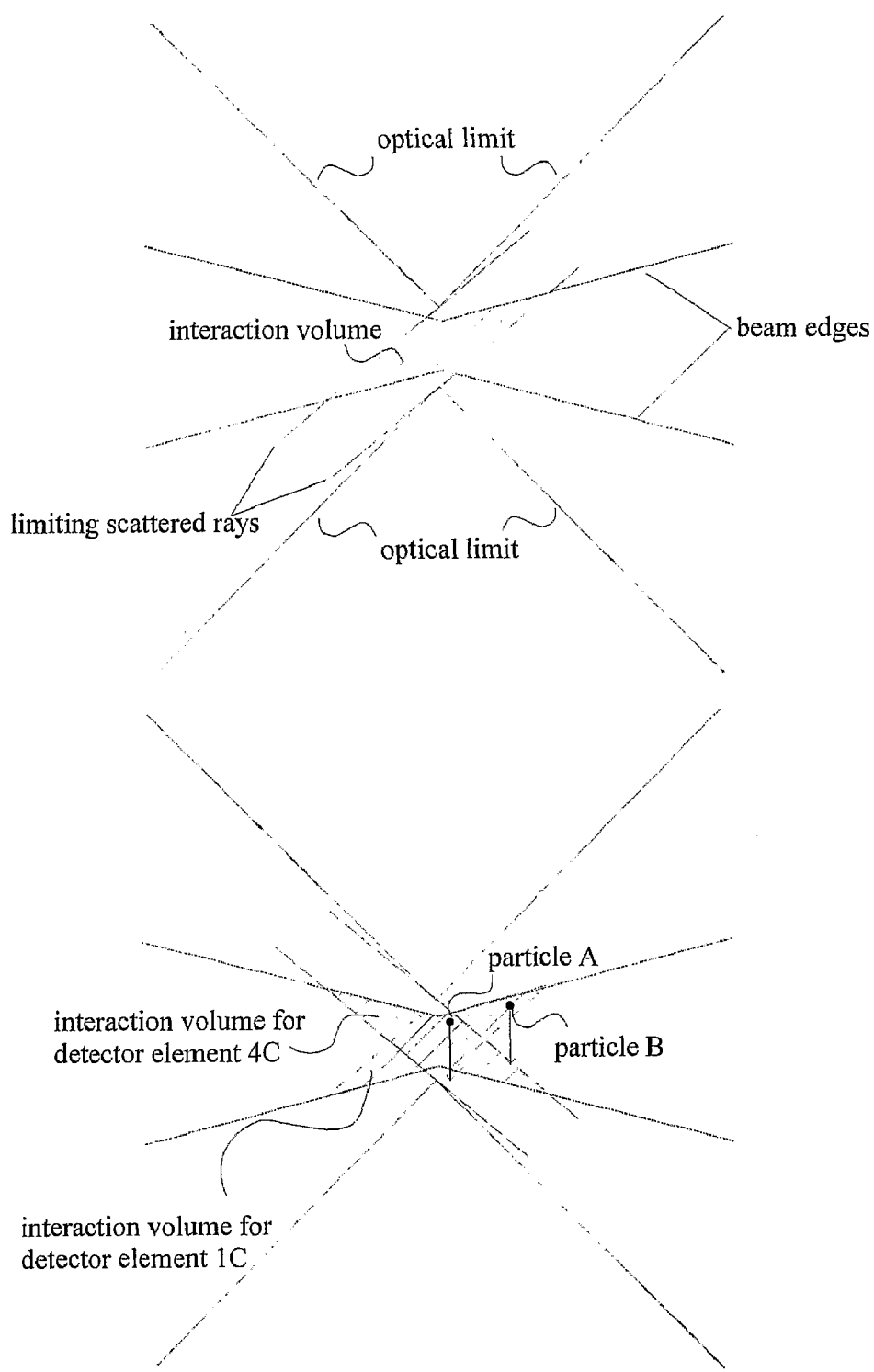
FIG. 45 provides a diagram showing the interaction volume and scattering volumes associated with the concept of FIG. 44.
Figure 46:
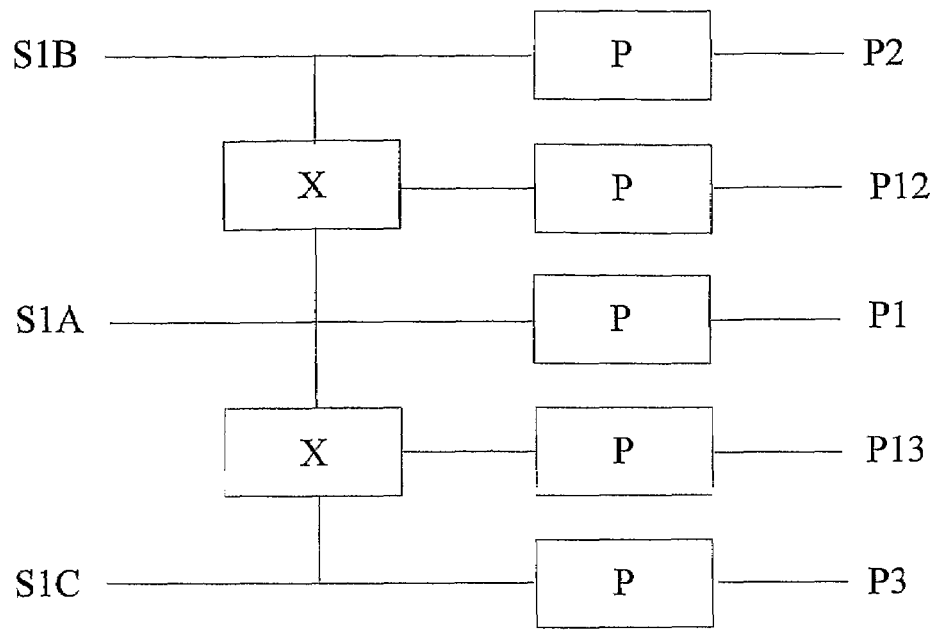
FIG. 46 provides a block diagram showing analog electronics for determining pulse correlation by multiplying scatter signals, used in the present invention.

Another feature of this design is the ability to use correlation or pulse alignment to determine which particle pulses are accurately measured and which pulses may be vignetted in the optical system. FIG. 45 shows a crossection of the source beam focus in the sample cell. The outline of the beam is shown in red and the outline of the optical limits for scattered rays is shown in black. These optical limits are defined by the angular size of the detector elements and the size of aperture 2 or aperture 3. Two extreme scattered rays are drawn in blue for scattered light at a particular scattering angle. The intersection (crosshatched area) of volume between those scattered rays and the source beam is the interaction volume in which a detector can detect scattered light at that scattering angle. For example, consider the highest angle detector elements, 1C and 4C (see FIG. 44) which are both in a scattering plane which is parallel to flow direction of the particles. The bottom portion of FIG. 45 shows an approximation to the interaction volumes for each of these detector elements. Notice that as particle A passes through these interaction volumes, both scattering signals from 1C and 4C will be highly correlated, they will rise and fall together with a large amount of overlap in time. However, particle B, which is farther from best focus, will show very poor correlation between these two detectors. In fact the pulses will be completely separated in time. This pulse separation between 1C and 4C can be used to determine where the particle has passed through the interaction volume; and particles that are too far from best focus can be eliminated from the particle count. This correlation or pulse separation can be measured between any two detector elements, within a group (i.e. 1A and 1C) or between groups (i.e. 1C and 4C). Typically the scattering plane for detector groups 1 and 4 would be parallel to the particle flow to obtain maximum delay. The correlation or pulse separation can be determined from the digitized signals using algorithms. However, this may require very high speed analog to digital converters and enormous computational load to obtain a high particle count and size accuracy. Another solution is to use analog electronics to measure the correlation or the pulse separation as shown in FIG. 46, where the P boxes are processing electronics which measure the pulse peak (peak detector) or pulse integral. The X box is an analog multiplier. And S1A, S1B, and S1C are the analog signals from detector elements 1A, 1B, and 1C, respectively. The following equations will provide an estimate to the correlation between the pulses:

$R12=P12/(P1*P2)$ $R13=P13/(P1*P3)$

When R12 or R13 are small, the pulses have poor correlation and they should be eliminated from the count.

Figure 47:
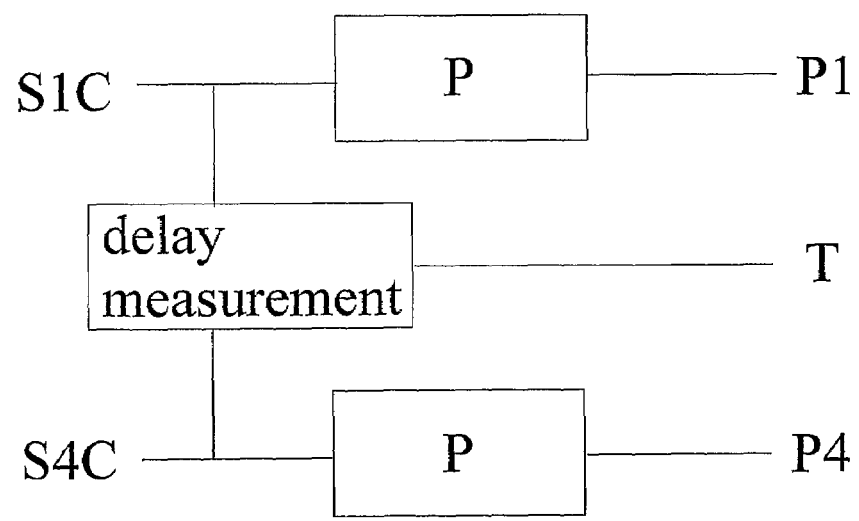
FIG. 47 provides a block diagram of a system for measurement of time delay between two scatter signal pulses, according to the present invention.

The delay between any two pulses from separate detector elements can also be used to select valid pulses for counting. As the particle passes through the beam farther from best focus of the source beam, the delay between the pulses will increase. Some threshold can be defined for the delay. All pulse pairs with delays greater than the threshold are not included in the count. One example is shown in FIG. 47, where the delay between pulses from detector elements 1C and 4C (see FIG. 44) is measured to reject particles which pass through the beam too far from the source beam best focus.

Another criteria for pulse rejection is pulse width. As shown in FIG. 45, particle B will produce a shorter pulse than particle A, because the detector element will only see scattered light from the particle while it is in the interaction volume (the crosshatched area) for that particular detector element. The pulses could be digitized and the pulse width would then be computed as the width at some percentage of the pulse peak height to avoid errors caused by measuring pulses of different heights. Any of these techniques discussed above can be implemented using digitization of the detector element signals and computation of parameters of interest from that digitized data or using analog modules which directly produce the parameter of interest (pulse delay, pulse width, correlation, etc.). While the analog modules may have poorer accuracy, they can be much faster than digitization and computation, allowing a larger particle count and better count accuracy.

Figure 48:
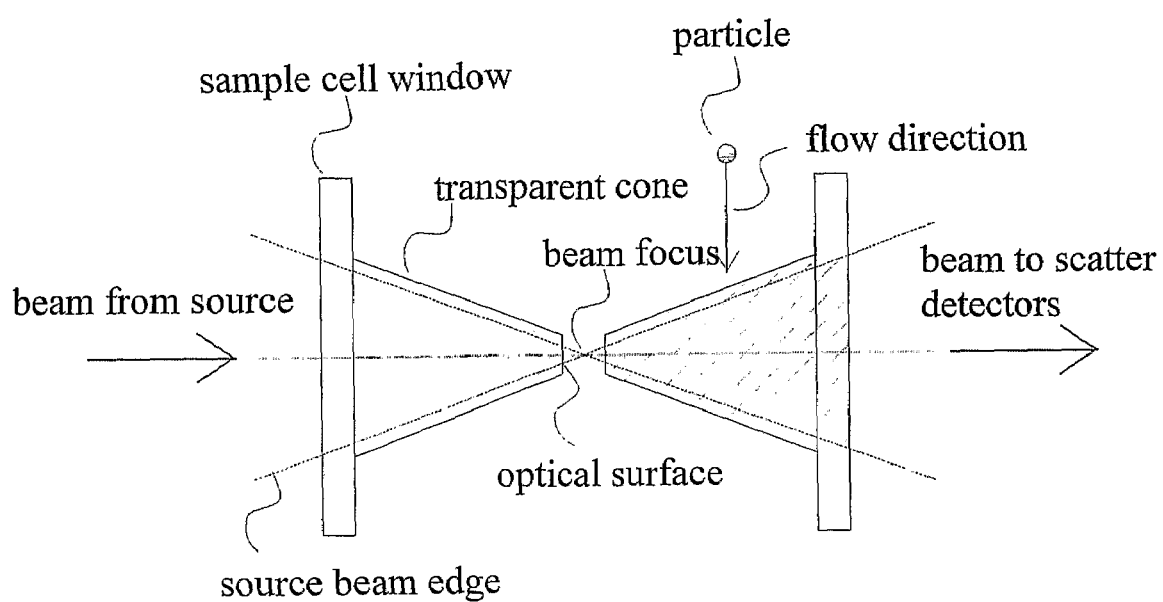
FIG. 48 provides a diagram showing an apparatus for removing particles from regions, of the light beam and scattered light rays, which are far from the interaction volume, according to the present invention.

The pulse rejection criteria described above is used to reduce the number of coincidence counts by using apertures to limit the volume which is seen by the detectors. The interaction volume can also be limited by providing a short path where the particles have access to the beam as shown in FIG. 48. Two transparent cones are bonded to the inner walls of the sample cell windows using index matching adhesive. The tips of each cone is cut off and polished to either a flat or a concave optical surface. The optical windows and transparent cones could also be replaced with solid cell walls with holes which are aligned to hollow truncated cones with optical windows on the truncated tip of each cone. This way the light travels through air, except for a thin layer of particle dispersion between the two windowed cone tips. The gap between the cone tip surfaces provides the only volume where the flowing particles can pass through the source beam and scatter light to the detectors. A dispersion with a large range of particle sizes will not clog this gap because the larger particles will flow around the gap and the particle concentration is very low. The cone tip surfaces can be tilted slightly so that the spacing between them is smaller on the side where the particles enter the gap and larger where they leave the gap. In this way, particles larger than the minimum width of gap, but smaller than the maximum gap width, are prevented from jamming inside the gap.

The beam focus may shift with different dispersant refractive indices due to refraction at the flat surface on the end of each cone. This shift in focus and angular refraction can be corrected for in software by calculating the actual refracted rays which intercept the ends of each detector element to define the scattering angular range of that element for the dispersant refractive. This correction is not needed for concave surfaces, on each cone tip, whose centers of curvature are coincident with the best focal plane of the source between the two tips. Then all of the beam rays and scattered rays pass through the concave surface nearly normal to the surface with very little refraction and low sensitivity to dispersant refractive index.

Another problem that can be solved by particle counting is the problem of background drift in ensemble scattering systems which measure large particles at low scattering angles. An ensemble scattering system measures the angular distribution of scattered light from a group of particles instead of a single particle at one time. This angular scattering distribution is inverted by an algorithm to produce the particle size distribution. The optical system measures scattered light in certain angular ranges which are defined by a set of detector elements (see FIG. 53). Each detector element is usually connected to it's own separate electronic integrator, which is connected to a multiplexing circuit which sequentially samples each of the integrators which may integrate while many particles pass through the beam (see a portion of FIG. 54). So particle pulses cannot be measured in the ensemble system.

The detector elements which measure the low angle scatter usually see a very large scattering background when particles are not in the sample cell. This background is due to debris on optical surfaces or poor laser beam quality. Mechanical drift of the optics can cause this background light to vary with time. Usually the detector array is scanned with only clean dispersant in the sample cell to produce background scatter signals which are then subtracted from the scatter signals from the actual particle dispersion. So first the detector integrators are scanned without any particles in the sample cell and then particles are added to the dispersion and the detector integrators are scanned a second time. The background scan data is subtracted from this second scan for each detector element in the array. However, if the background drifts between the two scans, a true particle scattering distribution will not be produced by the difference between these two scans. A third scan could be made after the second scan to use for interpolation of the background during the second scan, but this would require the sample cell to be flushed out with clean dispersant after the particles are present.

A much better solution is to connect each of the detector elements, for the lowest angles of scatter, to individual analog to digital converters or peak detectors as shown before in this disclosure (see FIG. 54). Then these signals could be analyzed by many of the counting methods which are described in this disclosure. This would essentially produce an assemble/counting hybrid instrument which would produce counting distributions for the large particles at low scattering angles and deconvolved particle size distributions from the long time integrated detector elements at higher scattering angles for the smaller particles. These distributions can be converted to a common format (such as particle volume vs. size or particle count vs. size) and combined into one distribution. The advantage is that the frequency range for the particle pulses is so much higher than the frequencies of the background drift. And so these pulses can be measured accurately by subtracting the local signal baseline on either side of each pulse. At very low scattering angles, the scattering signal drops off by at least the fourth power of particle diameter. Therefore larger particle pulses will stand out from the signals from many smaller particles which may be in the beam at any instant of time. Also the number concentration of larger particle will be low and provide for true single particle counting.

As mentioned before in this disclosure, the particle shape can be determined by measuring the angular distribution of scattered light in multiple scattering planes, including any number of scattering planes. The particle shape and size is more accurately determined by measuring the angular scattering distribution in a large number of scattering planes, requiring many detector elements in the arrays shown in FIGS. 33 and 44. As the number of detector elements becomes large, the use of less expensive 2-dimensional detector arrays, such as CCD arrays, becomes more attractive to take advantage of the economies of scale for production of commercial CCD cameras. However, the use of these 2-dimensional detector arrays presents some problems, which are not associated with custom detector arrays with optimally designed elements as shown previously. These arrays usually have poor dynamic range, poor sensitivity, poor A/D resolution, slow digitization rates, and high levels of crosstalk between pixels (blooming for example). Methods for mitigation of these problems are described below.

The detector array could be scanned at a frame rate, where during the period between successive frame downloads (and digitizations) each pixel will integrate the scattered light flux on its surface during an entire passage of only one particle through the source beam. Each pixel current is electronically integrated for a certain period and then its accumulated charge is digitized and stored; and then this cycle is repeated many times. During each integration period the pixel detector current from scattered light from any particle which passes through the beam will be integrated during the particle's total passage through the light source beam. Therefore the angular scattering distribution for that particle will be recorded over a large number of scattering planes by all of the detector elements in the array. This 2-dimensional scattering distribution could be analyzed as described previously, using a large number of simultaneous equations and more shape parameters, by assuming a certain model for the particle shape (ellipsoidal, rectangular, hexagonal, etc.). As shown before, the particle shape and random orientation can be determined from these equations. Also, conventional image processing algorithms for shape and orientation can be used on the digitized scattering pattern to find the orientation (major and minor axes, etc.) and dimensions of the scatter pattern. The particle size and shape can be determined from these dimensions. Also the particle size and shape can be determined from the inverse 2-dimensional Fourier transform of the scattering distribution for particles in the Fraunhofer size range, but with a large computation time for each particle. The inverse Fourier transform of the scattering distribution, which is measured by the 2 dimensional detector array, will produce an image, of the particle, from which various dimensions can be determined directly.

For example, consider an absorbing rectangular particle of width and length dimensions A and B, with both dimensions in the Fraunhofer size range and minor and major axes along the X and Y directions. The irradiance in the scattering pattern on the 2-dimensional detector array will be given by:

$$I(a,b)=Io*(SINC(\pi a)*SINC(\pi b))^2$$

Where $SINC(x)=SIN(x)/x$

Io is the irradiance in the forward direction at zero scattering angle relative to the incident light beam direction $$a=A*\sin(anga)/w1$$

$$b=B*\sin(angb)/w1$$

where:

w1=wavelength of the optical source anga=the scattering angle relative to the incident source beam direction in the scattering plane parallel to the A dimension of the particle angb=the scattering angle relative to the incident source beam direction in the scattering plane parallel to the B dimension of the particle The corresponding x and y coordinates on the 2 dimensional detector array will be:

$$x=F*\tan(anga) \text{ and } y=F*\tan(angb)$$

Figure 49:
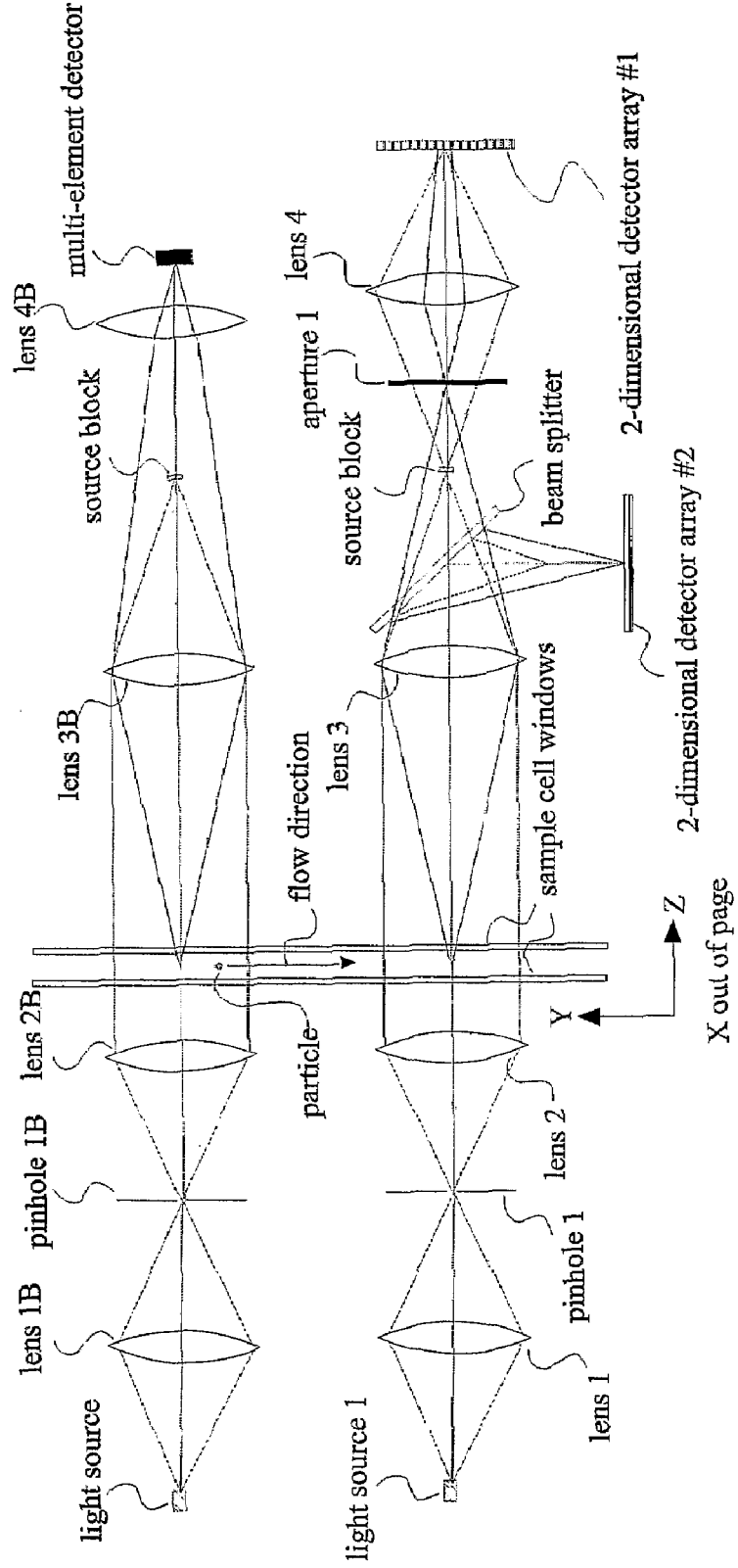
FIG. 49 provides a schematic diagram of an optical system which measures the 2-dimensional scattering distribution and image of each particle, wherein an upstream optical system adjusts this optical system for the characteristics of each particle, according to the present invention.

The scattering pattern crossections in the major and minor axes consist of two SINC functions with first zeros located at:

$$xo=F*\tan(\arcsin(w1/A))$$

$$yo=F*\tan(\arcsin(w1/B))$$

where F is the focal length of the lens 3 in FIG. 32 or F=M*F3 in FIG. 49 where F3 is the focal length of lens 3 in FIG. 49 and M is the magnification of lens 4 between the back focal plane of lens 3 (source block) and the detector array, which is in an image plane of said back focal plane. By inspection of these equations, the dimension of the scattering distribution is inversely proportional to the particle dimension along the direction parallel to direction of the dimension measurement. So for a rectangular particle, use known image processing methods to determine the major and minor axes of the scattering pattern and then measure the width and length of the pattern at the first zeros (xo and yo) in the scattering distribution in the directions of the major and minor axes. Then the particle dimensions are given by:

$$A=w1/(\sin(\arctan(xo/F))$$

$$B=w1/(\sin(\arctan(yo/F))$$

These equations describe the process for determining particle shape for a randomly oriented rectangular particle where we have assumed that the particle is much smaller than the uniform intensity portion of the source beam. Other parameters (such as the point in the scatter distribution which is 50% down from the peak) which describe the width and length of the scattering pattern can be used instead of xo and yo, but with different equations for A and B. In general, the corresponding particle dimensions can be determined from these parameters, using appropriate scattering models which describe the scattering pattern based upon the effects of particle size, shape, particle composition and the fact that the scattering pattern was integrated while the particle passed through a light source spot of varying intensity and phase. This analysis for rectangular particles is one example for rectangular particles. The model for each particle shape (polygon, ellipsoid, cube, etc.) must be computed from scattering theory for nonspherical particles using algorithms such as T-matrix method.

Figure 50:
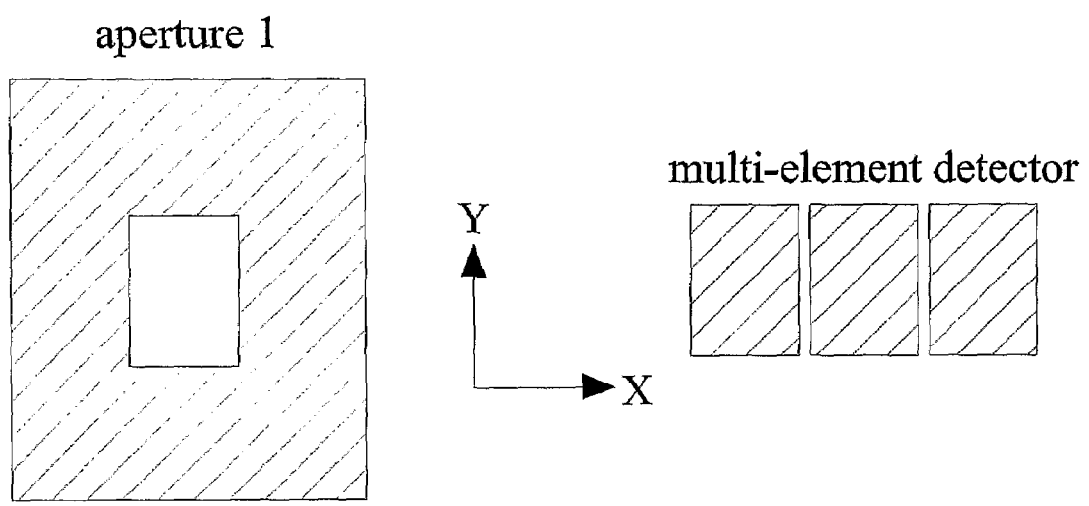
FIG. 50 provides a diagram of a rectangular aperture for defining an interaction volume and a multi-element detector for determining the position where the particle passes through the light beam, according to the present invention.

The hardware concept is shown in FIG. 49. This system is very similar to those shown previously in this disclosure in FIG. 32. Pinhole 1 removes high angle background from the light source and lens 2 collimates the source for passage through the sample cell through which the particle dispersion flows. The light source, lenses 1 and 2, and pinhole 1 could be replaced by a nearly collimated light beam such as a laser beam. Two optical systems view the particles. The 2-dimensional array #1 measures the scattering distribution from each particle and 2-dimensional array #2 measures the image of each particle. Array #1 is used to measure the dimensions of a smaller particle and array #2 measures the larger particles where the array pixel size can provide sufficient size resolution as a percentage of particle dimension for accurate dimension measurement. The scattering pattern from the particle is formed in the back focal plane of lens 3 and this scatter pattern is imaged onto array #1 by lens 4. A small block is placed in the back focal plane of lens 3 to block the unscattered focused light from the light source so that it will not reach array #1. The source light would saturate some pixels on that array and these pixels may bloom or crosstalk into adjacent pixels where very low level scattered light is being measured. The source block could also be replaced by an annular spatial mask (as shown previously) to measure scatter only over a certain range of scattering angles. Aperture 1 (also see FIG. 50) is placed in an image plane of the sample cell to define a restricted region of the beam where particles will be counted. This region is confined to where the intensity profile of the source beam has sufficient uniformity. If this region of confinement is not required and access to the surface of the CCD is available (windowless CCD array) then lens 4 and aperture 1 could be removed and the CCD array could be placed in the back focal plane of lens 3, directly behind the source block. The beam diameter and lens diameters are not drawn to scale. They are drawn to display the details of beam divergence and conjugate planes. Lenses 2B, 3 and 3B might actually be much larger than the beam diameter to collect scatter over a large range of scattering angles.

A second similar optical system (system B which contains lenses 1B, 2B, 3B, 4B etc.) is placed upstream of the particle flow from the system (the main system which contains lenses 1, 2, 3, 4, etc.) described above (see FIG. 49). This system B reduces many of the problems associated with CCD arrays which are mentioned above. System B measures the scattered light from each particle before it passes through the main system described above. This scattered light level determines the particle size and predicts the signal levels which will be seen from that particle when it passes though the main system. These predicted levels provide the ability for the system to either adjust the intensity of light source 1 or the gain of array #1 to nearly fill the range of the analog to digital converter which digitizes the scattering pattern data from array #1 and to improve signal to noise. The analog to digital converter and array pixel dynamic signal range is not sufficient to measure scattered light levels from particles over a large range of sizes. For example, the lowest scatter angle signal will change over 8 orders of magnitude for particles between 1 and 100 microns. However, the dynamic range of most CCD arrays is between 200 and 1000. Therefore, by adjusting the source intensity so that the maximum pixel value on array #1 will be just below saturation for each particle, the optimum signal to noise will be obtained. The time of the pulse from the upper system B will predict when each particle will pass through the main system, using the flow velocity of the dispersion through the cell. So the array only needs to integrate during the particle's passage through the source beam. This minimizes the integration time and shot noise of array #1. This timing could also be used to pulse the laser when the particle is in the center of the source beam for imaging by array #2 to freeze the particle motion during the exposure. Also the predicted size from system B could be used to choose only particles in a selected size range for shape measurement. Or some smaller particles could be passed without dimensional measurement to increase the statistical count of larger particles relative to the smaller particles to improve the counting statistics for the larger particles which are usually at lower number concentration than the smaller particles. But the size distribution could then be corrected by the total count distribution from the upper system B, while the particle shape count distribution is determined from the fewer particles counted by the main system. The size of the scattering pattern could also be predicted by system B so that an appropriate sub-array of array #1 would be digitized and analyzed to save digitization time. The size prediction can also determine which array (#1 #2 or both) will be digitized to determine the particle dimensions. The upstream system B particle counts could also be used to determine coincidence counting while the particle concentration is being adjusted. Many of these techniques are used to reduce the digitization load on the analog to digital converter, if required.

Lens 4B acts as a field lens to collect scattered light and place the scatter detector in the image plane of the sample cell. This detector could be a single element detector which simply measures the all of the scattered light over a large range of scattering angles. However, this single detector measurement could be complicated by the variation of light intensity across the source beam. The use of a three detector multi-element detector (see FIG. 50) could be used in this image plane of the sample cell. Then only particles which produce signal primarily on the center detector (of the three detector set) would be accepted for counting. This particle selection could be based upon the ratios between the signal from the center detector element with the corresponding signal from either of the outer elements, as described previously in FIG. 37. The particle will be counted only if these two ratios are both above some threshold. If a large single detector is used instead of the multi-element detector, lens 4B could be removed and the detector could be placed directly behind the source block if it is large enough to collect all of the scattered flux. Otherwise a lens should be used to collect the scattered light and focus it onto the detector.

If the upstream system B is not used, the CCD array scans of each scatter pattern should be made over multiple long periods (many individual particles counted per period with one array scan per particle) where the light source intensity or detector pixel gain is chosen to be different during each period. In this way particles in different size and scattering efficiency ranges will be counted at the appropriate source irradiance or detector pixel gain to provide optimal signal to noise. So during each period, some particles may saturate the detectors and other particles may not be measured due to low scattering signals. Only particles whose scattering efficiency can produce signals within the dynamic range of the array for that chosen light source level or gain will be measured during that period. So by using a different source level or gain during each period, different size ranges are measured separately, but with optimal signal to noise for each size range. The counting distributions from each period are then combined to create the entire size and shape distribution. This method will require longer total measurement time to accumulate sufficient particle counts to obtain good accuracy because some particles will be passed without counting. The use of system B to predict the optimal light source level or pixel gain provides the optimum result and highest counts per second.

The main system counting capability, as shown in FIG. 49, could be added to any diffraction ensemble system by using the scatter collection lens (lens 3 in FIG. 53) in the ensemble system to act as lens 3 in the counting system in FIG. 49. The light path after the ensemble system scatter collection lens (the lens forming the scatter pattern) would be partially diverted, by a beamsplitter, to a detection system as shown in FIG. 49 after lens 3. This detection system could be any appropriate variation of the detection system (with or without array#2 and its beamsplitter as shown in FIG. 49 for example). Also if source region confinement (as discussed above) is not required and access to the surface of the CCD is available (windowless CCD array) then lens 4 and aperture 1 could be removed and the CCD array could be placed in the back focal plane of lens 3, behind the source block. System B could also be added to the ensemble scattering system, but with significant added expense.

Figure 51:
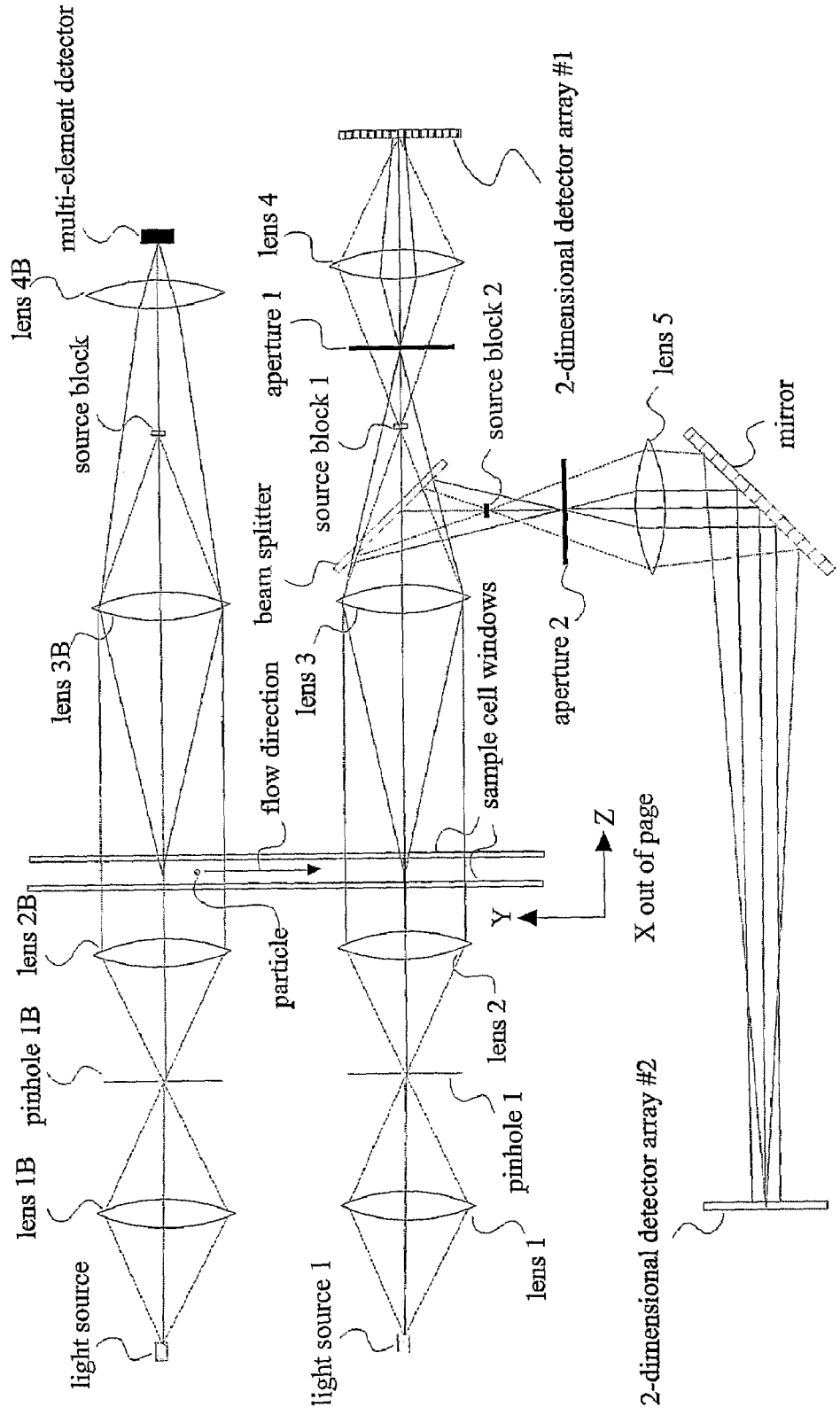
FIG. 51 provides a schematic diagram of an optical system which uses multiple detector arrays, with different scattering angle scales, to extend the particle size range, according to the present invention.

Linear CCD arrays do not have sufficient dynamic spatial range to accurately measure scatter pattern profiles from particles over a large range of particle size. For example, for a million pixel array, the dimensions are 1000 by 1000 pixels. If at least 10 pixel values are needed to be measured across the scatter profile to determine the dimension in each direction, then 1000 pixels will only cover 2 orders of magnitude in size. This size range can be increased to 4 orders of magnitude by using two arrays with different angular scales. FIG. 51 shows a system similar to that shown in FIG. 49, but with an additional scatter detection array (2-dimensional array #2). Arrays #1 and #2 are in the back focal planes of lens 4 and lens 5, respectively. Lens 5 has a much longer focal length than lens 4, so that each pixel in array #1 covers a proportionately larger scattering angle interval. As each particle passes through system B, the particle size is estimated to determine which array (#1 of #2) should be scanned and digitized. Array #1 should be used for small particles which scatter over large angles and Array #2 should be used for larger particles. The use of two arrays with different angular scales provides much higher particle count rates. For example, for 2 orders of size magnitude with a single array, 1 million pixels must be digitized (1000 by 1000 with minimum of 10 pixels for the largest particle). However, if two smaller 100 by 100 pixel arrays were used for array #1 and array #2 and the focal length for lens #5 was 10 times longer than the focal length of lens #5. Then these two 10,000 pixel arrays could cover 2 orders of magnitude in size, equivalent to that of the single 1 million pixel array; but only a maximum of 10,000 pixels must be digitized for each particle by using the size estimate from system B to determine which array to digitize. This design provides a factor of 100 increase in the particle count rate. This rate could be further increased by only digitizing the minimum subarray needed to measure each particle, based upon the size prediction provided by system B. Also, FIG. 51 shows the use of separate apertures (aperture #1 and aperture #2) which have different size openings. A smaller opening is used for the smaller particle detector array to reduce the scatter volume and reduce the probability of coincidence counting.

Figure 49B:
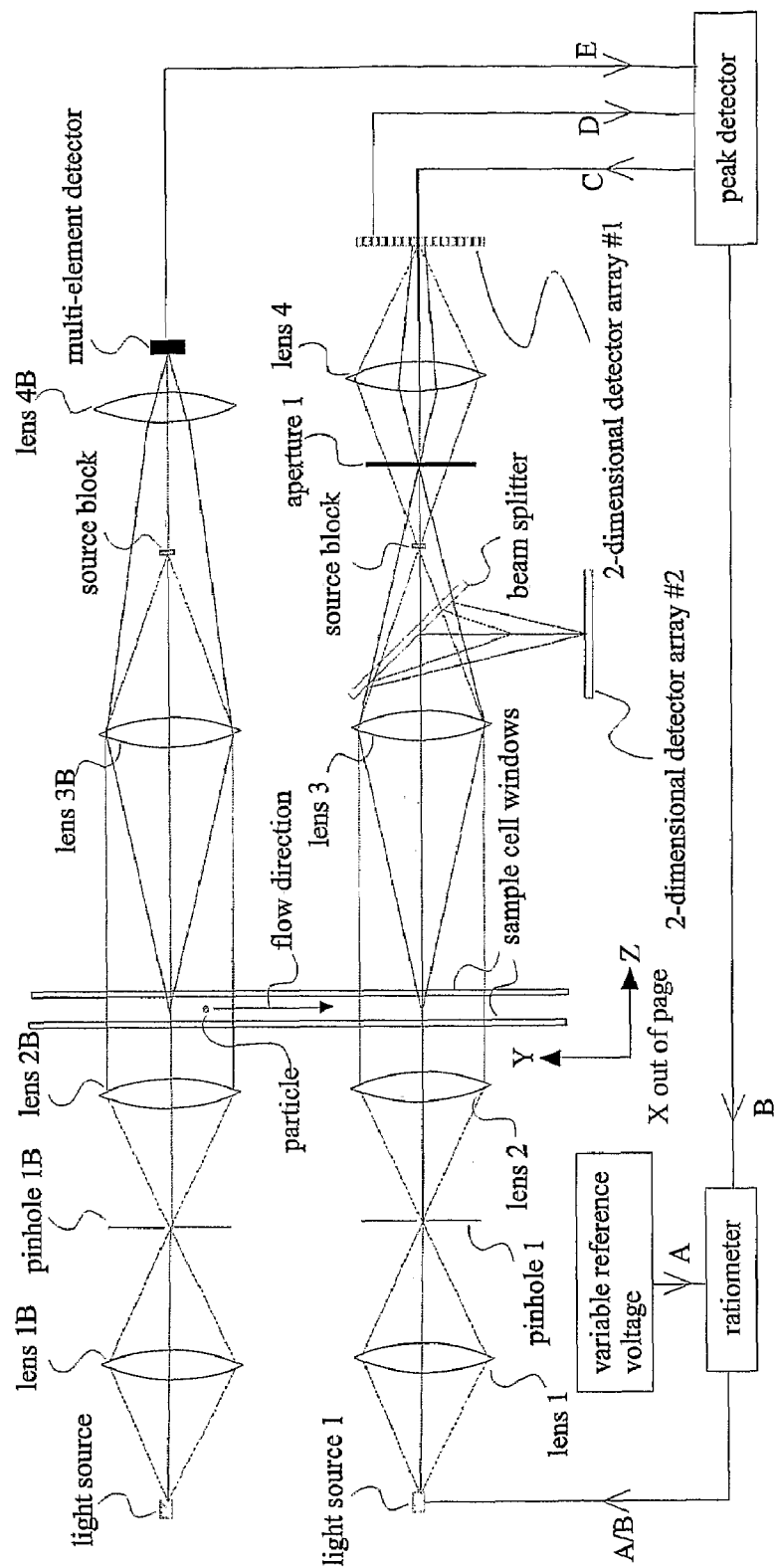
FIG. 49B provides a schematic diagram of an optical system which measures the 2-dimensional scattering distribution and image of each particle, with an analog version of laser power control by an upstream optical system, according to the present invention.

FIG. 49B shows an analog version of the laser power control by system B. The peak detector receives the total signal, through port E, from the detector elements of the multi-element detector behind lens B. This detector could also be a single element detector if particle position detection is not used to define a small interaction volume, as described previously. When the peak detector breaks a threshold, it starts (by port C) the integration of the detector arrays in the main system after an appropriate delay, accounting for the distance between the systems and the flow velocity. When the integration is finished, the array (through port D) resets the peak detector to start to look for the next particle. The peak value held by the peak detector is input (input B) to an analog ratiometer with an adjustable reference voltage input A, which can be set to adjust the laser power, and hence the scatter signal, to nearly fill the analog to digital converter of the detector array in the main system. In this way, the light source intensity is rapidly changed to always nearly fill the range of the A/D converter for particles over a large range of size and scattered light signal. The value A/B could also be used to set the gain on the detector arrays, but this will probably not have sufficient speed. This entire process could also be replaced by its digital equivalents, but with much slower response and lower count rate.

One note must be made about diagrams in this disclosure. The size of the scatter collection lens, (i.e. lens 3 in FIGS. 49 and 50) is not shown in proper size relationship to the source beam in order to show more detail of the source beam and different focal planes in the design. This is true for all scatter collection lenses shown in this disclosure. In all cases we assume that the scatter collection lens is of sufficient diameter to collect scattered light from the particles over all of the scattering angles being measured. In some cases this may require the lens diameter to be much larger than the diameter of the source beam.

Figure 53:
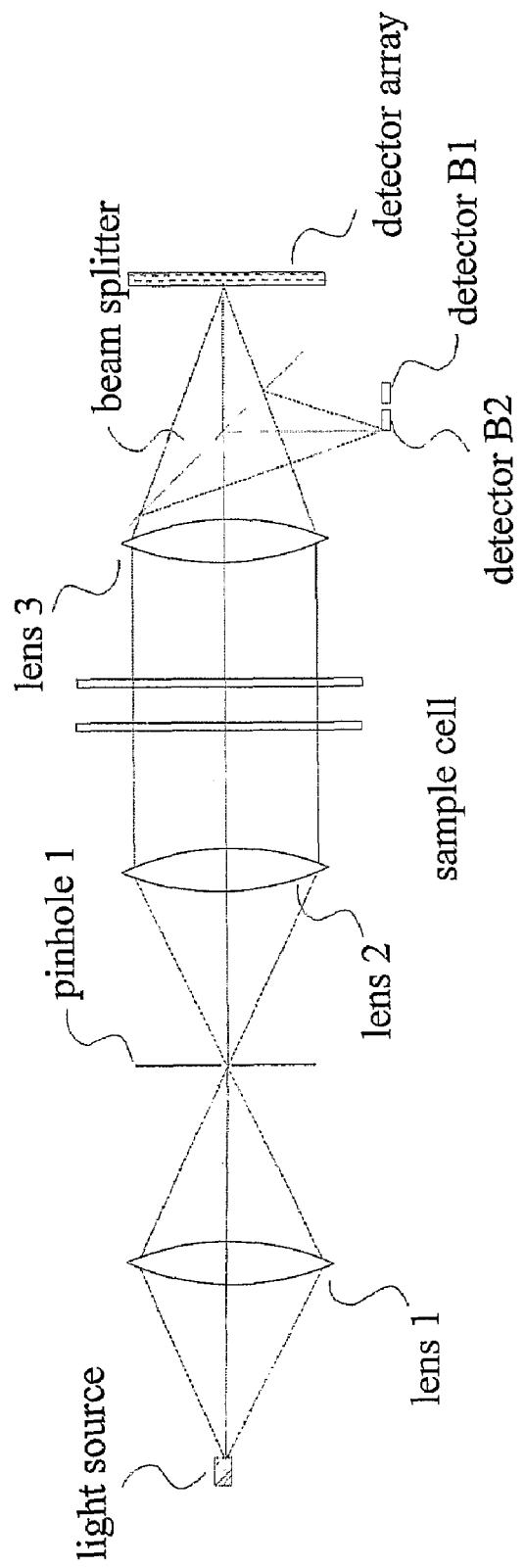
FIG. 53 provides a schematic diagram of an optical system which measures the angular distribution of scattered light with detector arrays in the back focal plane of the scatter light collection lens, according to the present invention.
Figure 54:
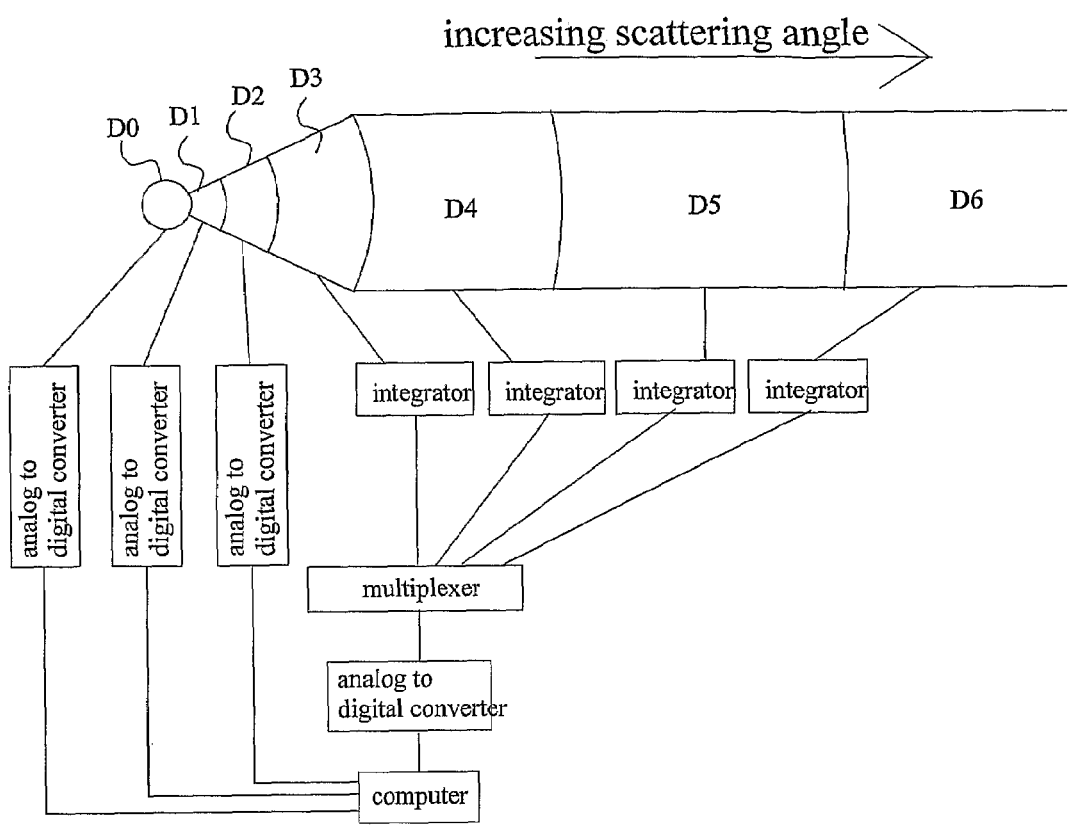
FIG. 54 provides a block diagram showing an example of a detector array and electronics for measuring scatter signals from individual particles and a particle ensemble, according to the present invention.

This disclosure also describes concepts for combining three different particle size measurement modalities: particle counting, ensemble scattering measurements, and dynamic light scattering. In this case, particle counting is used for the largest particles (>100 microns) which have the largest scattering signals and lowest particle concentration and least coincidence counts. The angular scatter distribution from a particle ensemble is used to determine particle size in the mid-sized range (0.5 to 100 microns). And dynamic light scattering is used to measure particles below 0.5 micron diameter. These defined size range break points, 0.5 and 100 microns, are approximate. These methods will work over a large range of particle size break points because the useful size ranges of these three techniques have substantial overlap:

Single beam large particle counting (depends on the source beam size) 10 to 3000 microns Particle ensemble 0.1 to 1000 microns Dynamic light scattering 0.001 to 2 microns One problem that can be solved by particle counting is the problem of background drift in ensemble scattering systems which measure large particles at low scattering angles. An ensemble scattering system measures the angular distribution of scattered light from a group of particles instead of a single particle at one time. FIG. 53 shows an ensemble scattering system (except for detectors B1 and B2 which illustrate additional detectors) which illuminates the particles with a nearly collimated light beam and collects light scattered from many particles in the dispersion which flow through the sample cell. The light source is focused through pinhole 1, which removes high angle defects in the beam intensity profile. Lens 2 collimates the beam through the sample cell. Lens 3 collects scattered light from the particles in the sample cell and focuses that light onto a detector array in the back focal plane of lens 3. An example of the detector array design is shown in FIG. 54. The optical system measures scattered light in certain angular ranges which are defined by the set of detector elements. The elements can have different shapes, but in general the scattering angle range for each element is determined by the radius from the optical axis in the back focal plane of lens 3. In some cases, the detector array will have a central detector, D0, which captures the light from the source beam. Detectors D1, D2, etc. collect various angular ranges of scattered light. Each detector element is connected to its own separate electronic integrator, which is connected to a multiplexing circuit and analog to digital converter (ADC) as shown in FIG. 54 for detectors D3, D4, D5, and D6. This multiplexer sequentially samples each of the integrators which may integrate while many particles pass through the beam. So particle pulses cannot be measured in the ensemble system. All detector elements are connected to the multiplexer through integrators in a particle ensemble measuring system. FIG. 54 shows the modification, for detector elements D0, D1 and D2, proposed by this invention.

The detector elements which measure the low angle scatter (for example D1 and D2) usually see a very large scattering background without particles in the sample cell. This background is due to debris on optical surfaces or poor laser beam quality. Mechanical drift of the optics can cause this background light to vary with time. Usually the detector array is scanned with only clean dispersant in the sample cell to produce background scatter readings which are then subtracted from the subsequent readings of the actual particle dispersion. So first the detector integrators are integrated and scanned without any particles in the sample cell and then particles are added to the dispersion and the detector integrators are integrated and scanned a second time. The first background scan data is subtracted from this second scan for each detector element in the array. However, if the actual background drifts between the two scans, a true particle scattering distribution will not be produced by the difference between these two scans.

A much better solution is to connect each of the detector elements, for the lowest angle scatter, to individual analog to digital converters, or peak detectors as disclosed before by this inventor. Then these signals could be analyzed by many of the counting methods which were disclosed by this inventor. This would essentially produce an ensemble/counting hybrid instrument which would produce counting distributions for the large particles at low scattering angles and deconvolved particle size distributions from the long time integrated detector elements (ensemble measurement) at higher scattering angles for the smaller particles. These distributions can be converted to a common format (such as particle volume vs. size or particle count vs. size) and combined into one distribution. The advantage is that the frequency range for the particle pulses is much higher than the frequencies of the background drift. And so these pulses can be measured accurately by subtracting the local signal baseline (under the pulse), determined from interpolation of the signals on the leading and trailing edge of each pulse, using the digitized signal samples. At very low scattering angles, the scattering signal drops off by at least the fourth power of particle diameter. Therefore larger particle pulses will stand out from the signals from many smaller particles which may be in the beam at any instant of time. Also the number concentration of larger particle will be low and provide for true single particle counting.

Figure 55:
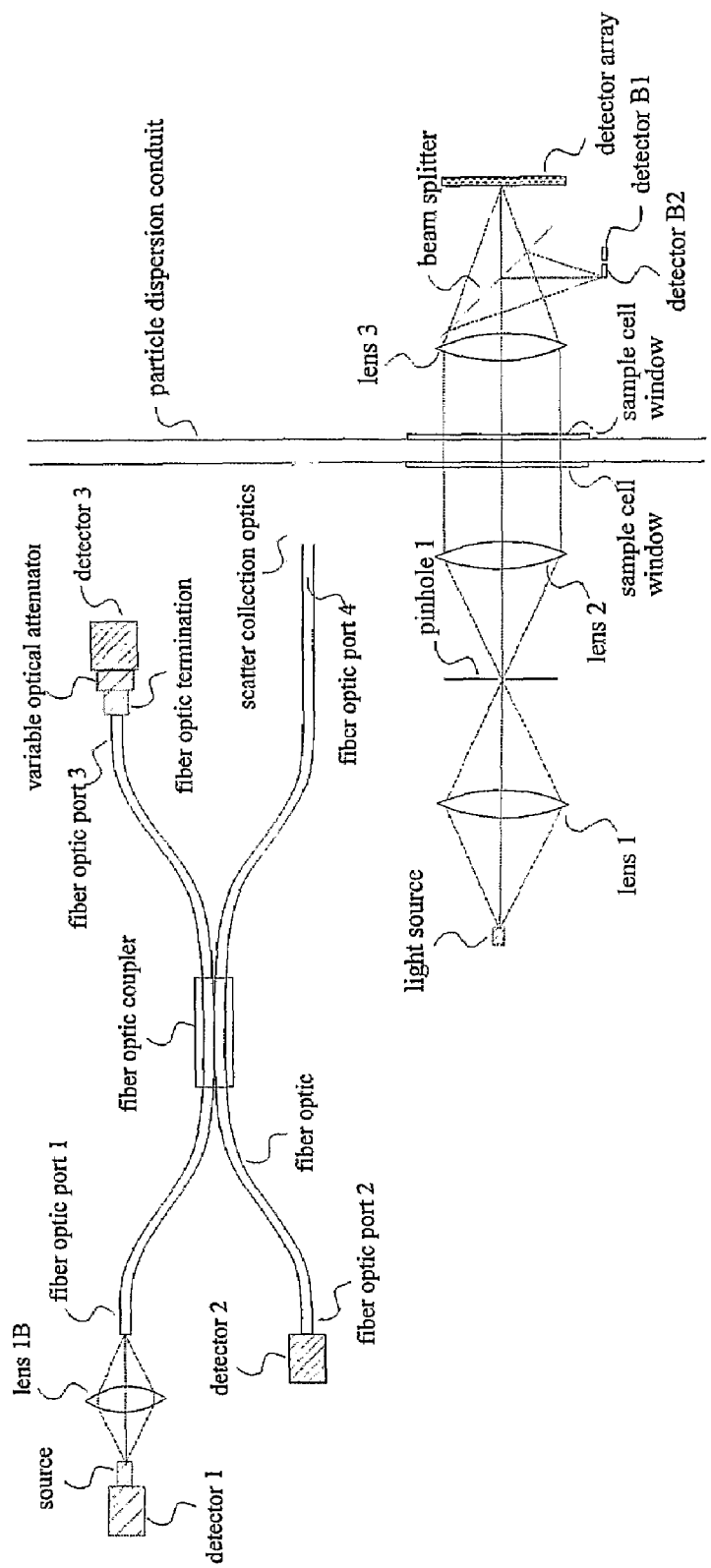
FIG. 55 provides a schematic diagram of an optical system which combines dynamic light scattering and angular light scattering measurements, according to the present invention.

The smallest particles are measured using dynamic light scattering as shown in FIG. 55. A fiber optic dynamic light scattering system, as described previously by the inventor, is inserted into the tubing through which the particle dispersion flows. The counting and ensemble scattering measurements are made with dispersion flowing through the system. This flow would be turned off during the collection of dynamic light scattering signals to avoid Doppler shifts in the scattering spectrum due to particle motion.

Figure 52:
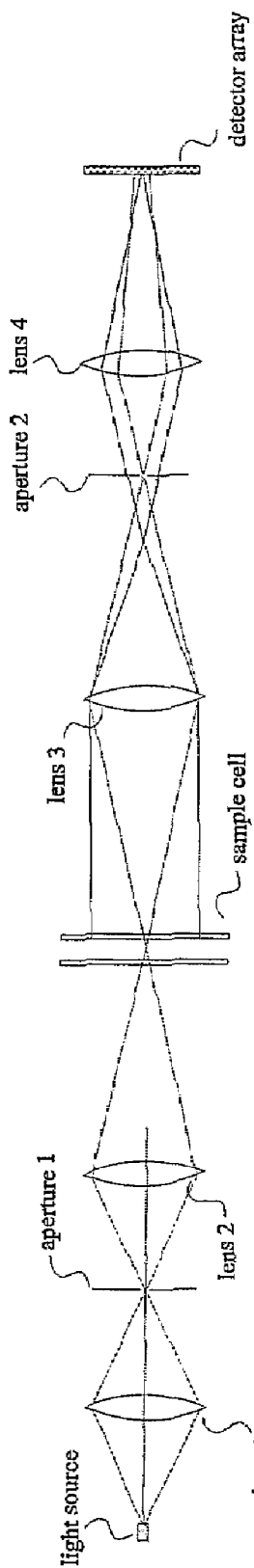
FIG. 52 provides a schematic diagram showing multiple planes, in an optical system, where an aperture would eliminate scattered light from particles passing through portions of the light beam with poor intensity uniformity, according to the present invention.
Figure 56:
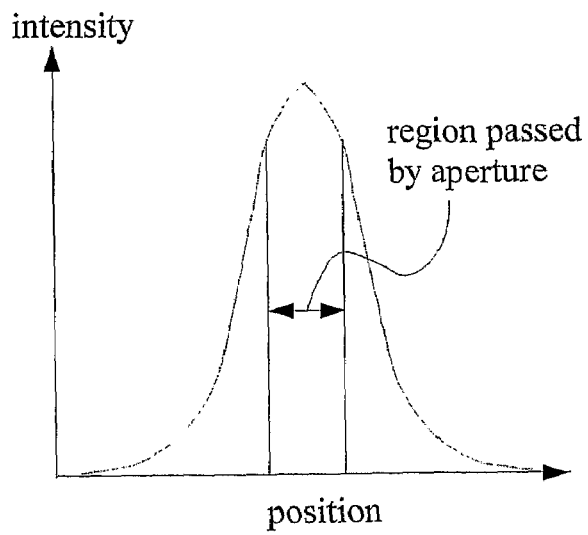
FIG. 56 provides a graph showing the intensity distribution across the width of an optical beam and the portion of the beam which is passed by an aperture, according to the present invention.
Figure 57:
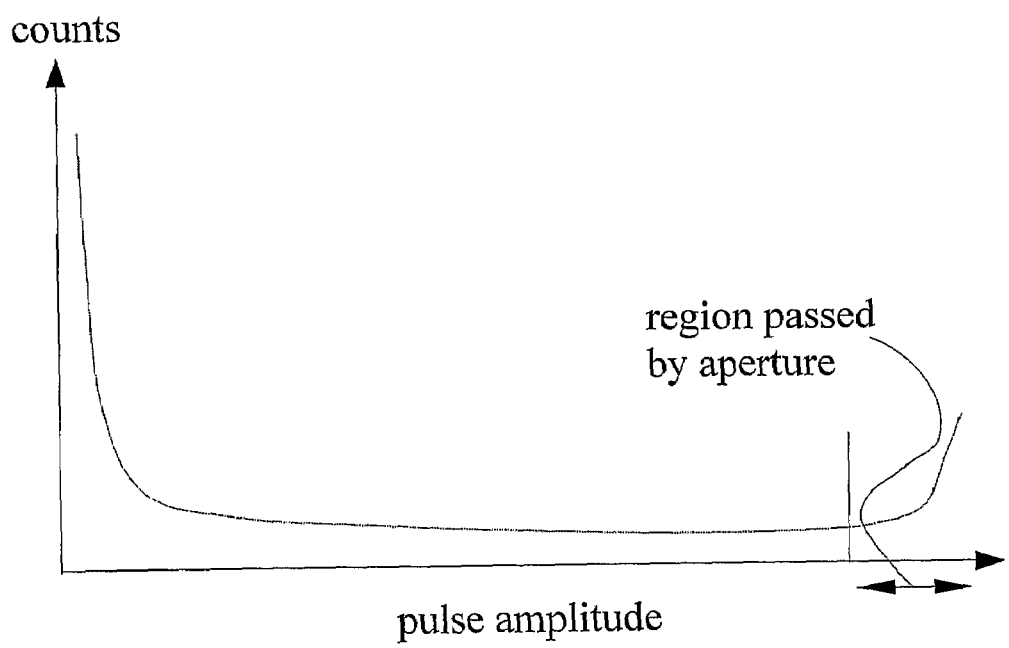
FIG. 57 provides a graph showing a count distribution, indicating the portion of the count distribution which is removed by an aperture, according to the present invention.

The particle counting uses the lowest angle zones (D1, D2, etc.) and the beam measuring zone (D0) of the detector array (an example of a detector array is shown in FIG. 54). Each of these detector elements are connected to a separate ADC to measure the scattering pulse in D1, D2, etc. and the signal drop on detector D0 as each particle passes through the interaction volume where the beam illuminates and from which the scattering detectors can receive scattered light from the particles. One problem is that the amount of scattered light is nearly proportional to the illumination intensity of the source on the particle. Therefore as particles pass through different regions in the beam they may produce different pulse heights. FIG. 56 shows a Gaussian intensity distribution which might be characteristic of the cross-section of a laser beam. Since the probability of particle passing through this beam at any position is approximately the same, we can generate the count vs. pulse amplitude distribution in FIG. 57, which shows the count distribution for large number of identical particles (also shown in FIGS. 10 and 10b). Notice that most of the particles pass through the low intensity portions of the intensity distribution and many particles also pass through the uniform intensity region which is close to the peak of the intensity distribution, with a region of lower count level in between. This broad count response to a group of mono-sized particles will prevent accurate determination of complicated particle size distributions, because the pulse heights may be ambiguous for various sized particles. For example, a large particle passing through the lower intensity region can produce a pulse which is very similar to that from a smaller particle passing through the higher intensity region. The region of the intensity distribution which can produce scattered light into the detectors must be truncated by apertures in the source optics (aperture 1 in FIG. 52) or in the detection optics (aperture 2 in FIG. 52). Either of these apertures can create a "region passed by aperture" as indicated in FIGS. 56 and 57. By using either or both apertures, only the upper region of the count vs. pulse amplitude distribution will be seen for many particles of a single particle size. This truncation by aperture can be used in any of the systems described in this document to reduce the broadening of the particle count peaks due to intensity variations of the source. Any residual broadening is then removed by algorithms such as deconvolution.

Figure 58A:
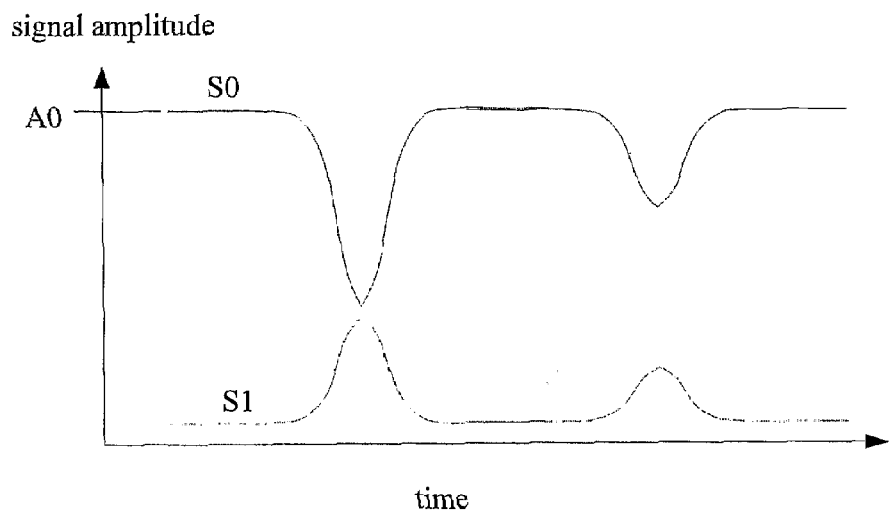
FIG. 58A provides a graph showing two scatter signals, the first signal (S0) showing attenuation of the light beam due to particle scatter, and the second signal (S1) showing a signal from a detector receiving scattered light from a particle, according to the present invention.
Figure 58B:
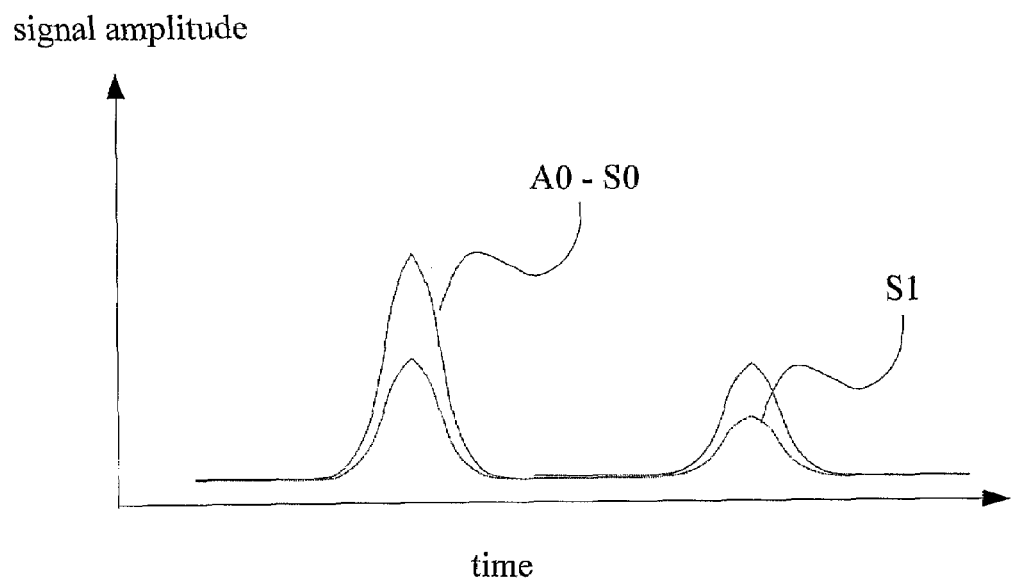
FIG. 58B provides a graph showing two signals produced after the first signal in FIG. 58A is modified to produce a signal which increases with the scattered light.
Figure 59:
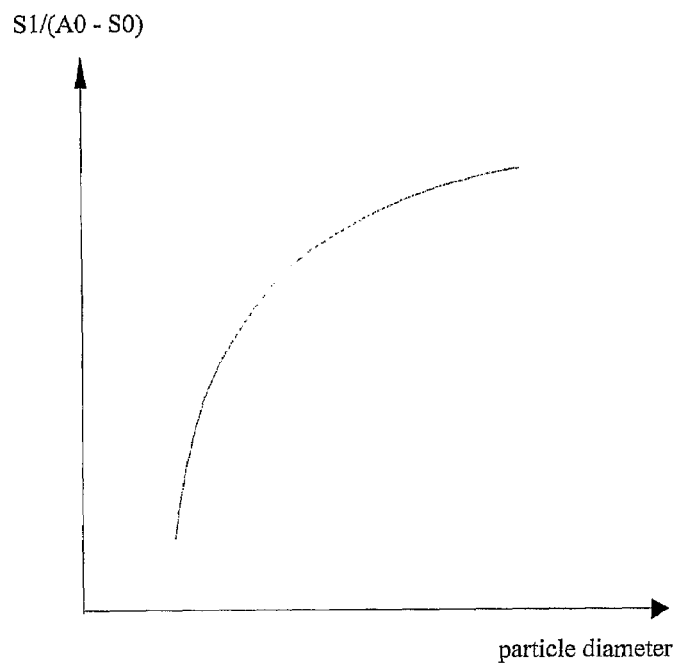
FIG. 59 provides a graph showing the ratio of values from FIG. 58B as a function of particle diameter.

Another method for eliminating this intensity distribution effect is to use ratios of detector signals. This works particularly well when many of the detectors have scatter signals. However, for very large particles, only scattering detector D1 will see a high scatter signal with high signal to noise. So for very large particles, the apertures described previously may be required to use the absolute scatter from D1. Another solution is to use the ratio of the drop in D0 (signal S0) and the increase in D1 (signal S1) due to scatter as shown in FIG. 58A. As a particle passes through the beam D0 will decrease by approximately the total scattered light and D1 will increase by only the amount of light scattered into the angular range defined by that detector. The drop in D0 can be determined by subtracting the minimum of drop in S0 from the baseline A0 to produce a positive pulse A0-S0 as shown in FIG. 58B. As shown in FIG. 59, the ratio of either the integral or the peak value of the corresponding pulses from these two signals can be used to determine the size of the counted particle for the largest size particles which have insufficient scatter signal in D2 to produce a ratio between S1 and S2. As long as D2 has sufficient scatter signal and D2 captures a portion of the primary lobe of the angular scatter distribution, the ratio between S1 and S2 will produce more accurate indication of size, than a ratio between S0 and S1. The primary lobe of the scattering distribution is the portion of the distribution from zero scattering angle up to the scattering angle where the size information becomes more ambiguous and particle composition dependent. Usually this happens when the scatter function first drops below 20% of the zero angle (maximum) value of the function. For a certain range of smaller particles, the ratio between S1 and S3 (if D3 were connected to an A/D as D2) may have higher sensitivity to particle size than the ratio of S1 to S2. For smaller particle diameters, ratios to larger angle scatter signals will provide better sensitivity. A0-S0, S1, etc. could be also analyzed using the other methods described in this document.

Figure 60:
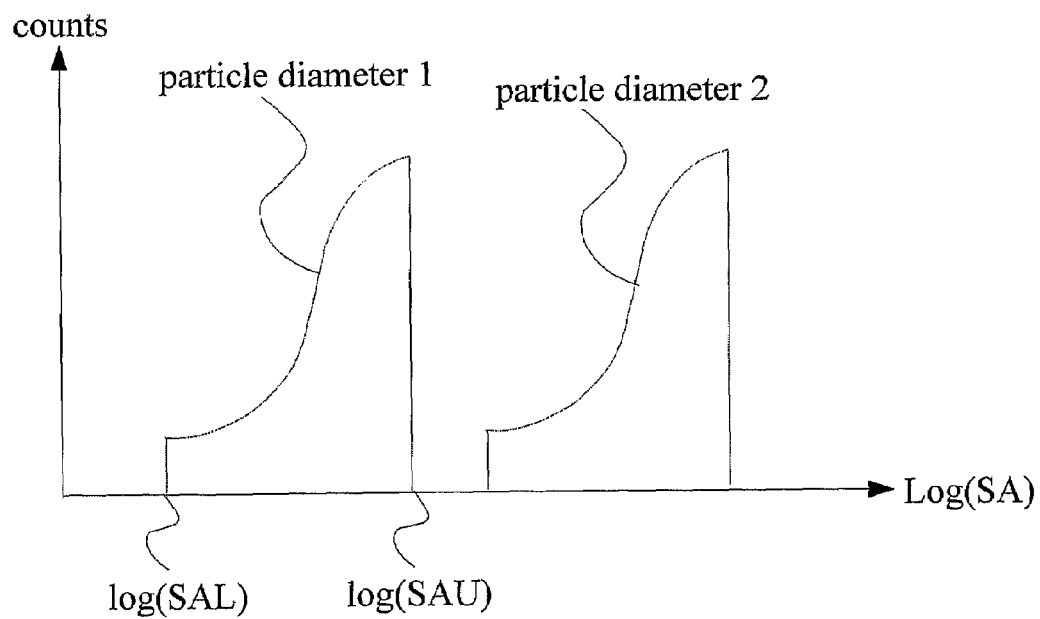
FIG. 60 provides a graph showing count distribution as a function of a logarithm of scatter signal, or scatter parameter, for two different particle sizes, the functional shapes demonstrating the shift-invariant impulse response, according to the present invention.
Figure 61:
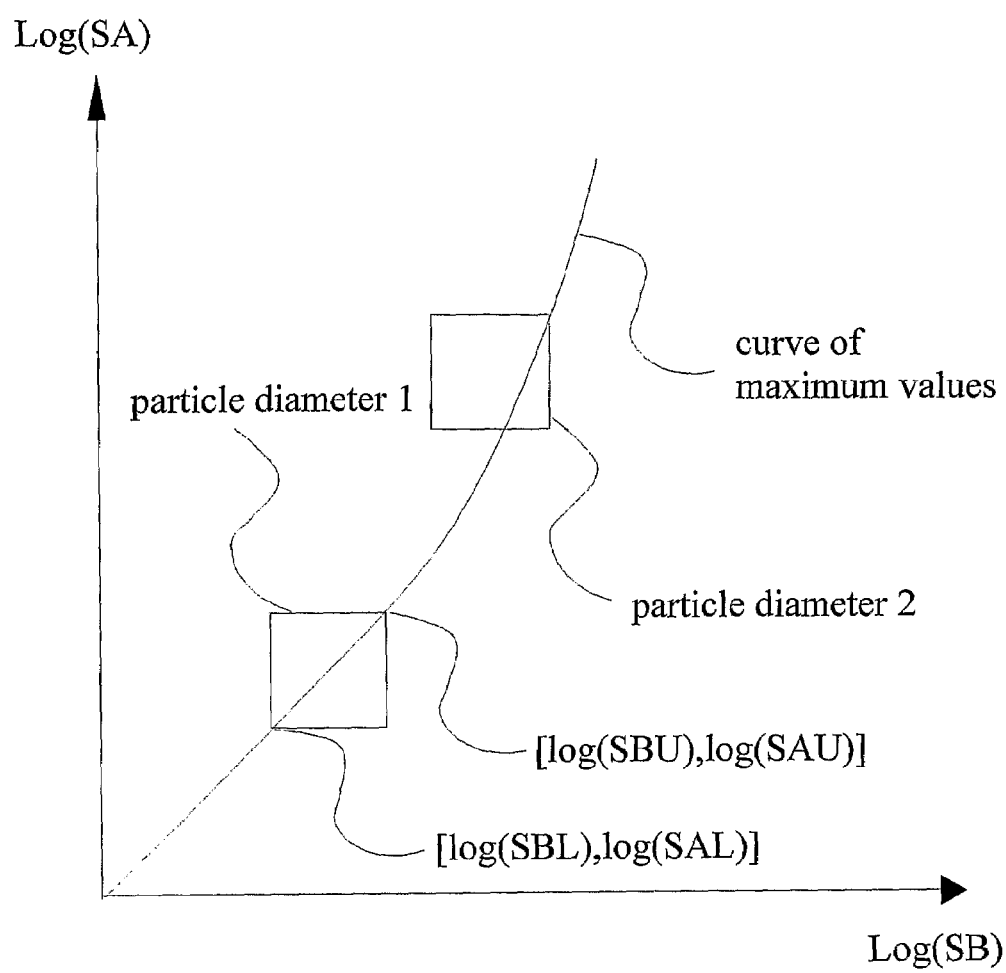
FIG. 61 provides a graph showing the response region limits for a two-dimensional scatter plot, of counted events, as a function of the logarithms of two scattering signal values, wherein the functional shapes demonstrate the two-dimensional shift-invariant impulse response for particles of two different diameters, according to the present invention.

The signal ratio technique is needed when the "region passed by aperture" in FIGS. 56 and 57 is too large such that mono-sized particles produce pulse peaks over a large amplitude range. For example, if no aperture were used, then mono-sized particles will produce the entire count distribution shown in FIG. 57, with ambiguity between small particles passing through the center of the Gaussian intensity distribution and large particles passing through the tail of the distribution. In cases where the "region passed by aperture" is too large, the use of signal ratios (as described previously) is required to reduce the effect of the intensity variation (because the intensity variation drops out of the ratio, approximately). If the source intensity distribution can be made more uniform by use of an aperture (aperture 1 of FIG. 52) or by use of a non-coherent source, or if the viewing aperture (aperture 2 in FIG. 52) of the detector only views a restricted region where the source intensity is more uniform, then scattering amplitude can be used directly to determine size as shown in FIGS. 60 and 61.

This may have some advantages when only one detector has sufficient signal so that two signals are not available to create a ratio. Also the absolute signal amplitude information, which is lost in the ratio calculation, can be useful in determining the particle composition and in eliminating pulses which are due to noise, as will be described in FIG. 61. FIG. 57 shows a count vs. pulse amplitude response with a "region passed by aperture". This count distribution in the "region passed by aperture" is plotted on a logarithmic scale of S (or pulse peak or integral) for two different particle sizes, in FIG. 60. Each function has an upper and lower limit in log(S). Notice that, in logarithmic S space, the two functions are shift invariant to particle diameter. The upper limit is due to particles which pass through the peak of the source intensity distribution and the lower limit is from the edge of the truncated source intensity profile. So that the count vs. log(S), $Ns(\log(S))$, distribution from particles of the count vs. particle diameter distribution $Nd(d)$ is the convolution between the shift invariant function in FIG. 60, $H(\log(S))$, and the count vs. particle size distribution, $Nd(d)$:

$$Ns(\log(S)) = Nd(d) \Theta H(\log(S))$$

This equation is easily inverted by using iterative deconvolution to determine $Nd(d)$ by using $H(\log(S))$ to deconvolve $Ns(\log(S))$. In some cases, for example when S=A0-S0, the form of this equation may not be a convolution and a more generalized matrix equation must be solved.

$$Ns(\log(S)) = H(\log(S)) * Nd(d)$$

Where H is the matrix and $Nd(d)$ is a vector of the actual counts per unit size interval. Each column of matrix H is the measured count vs. log(S) response to a particle of size corresponding to the element in $Nd(d)$ which multiplies times it in the matrix multiply '*'. This matrix equation can be solved for $Nd(d)$, given $Ns(\log(S))$ and $H(\log(S))$. This equation will also hold for the case where the functions of log(S) are replaced by other functions of S.

Figure 39:
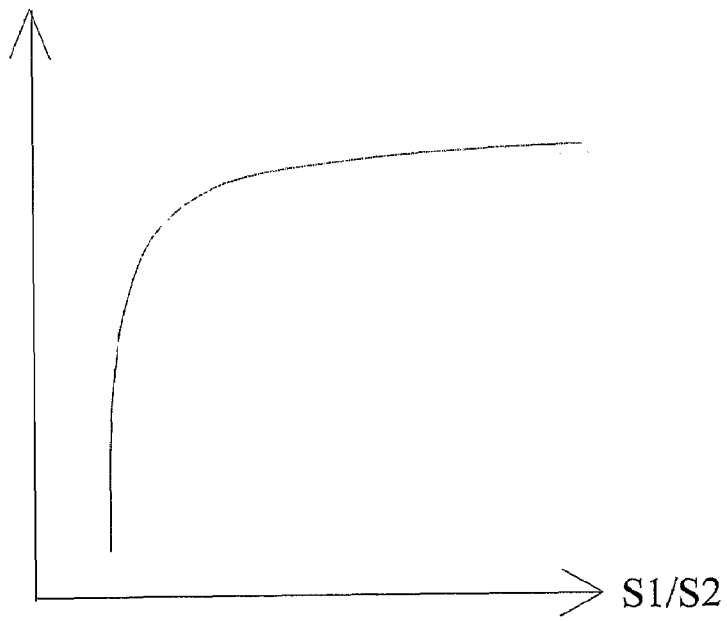
FIG. 39 provides a graph showing a functional relationship between the logarithm of a scattering signal value and the ratio of signal values, measured in two ranges of scattering angle, for various particle diameters, according to the present invention.
Figure 62:
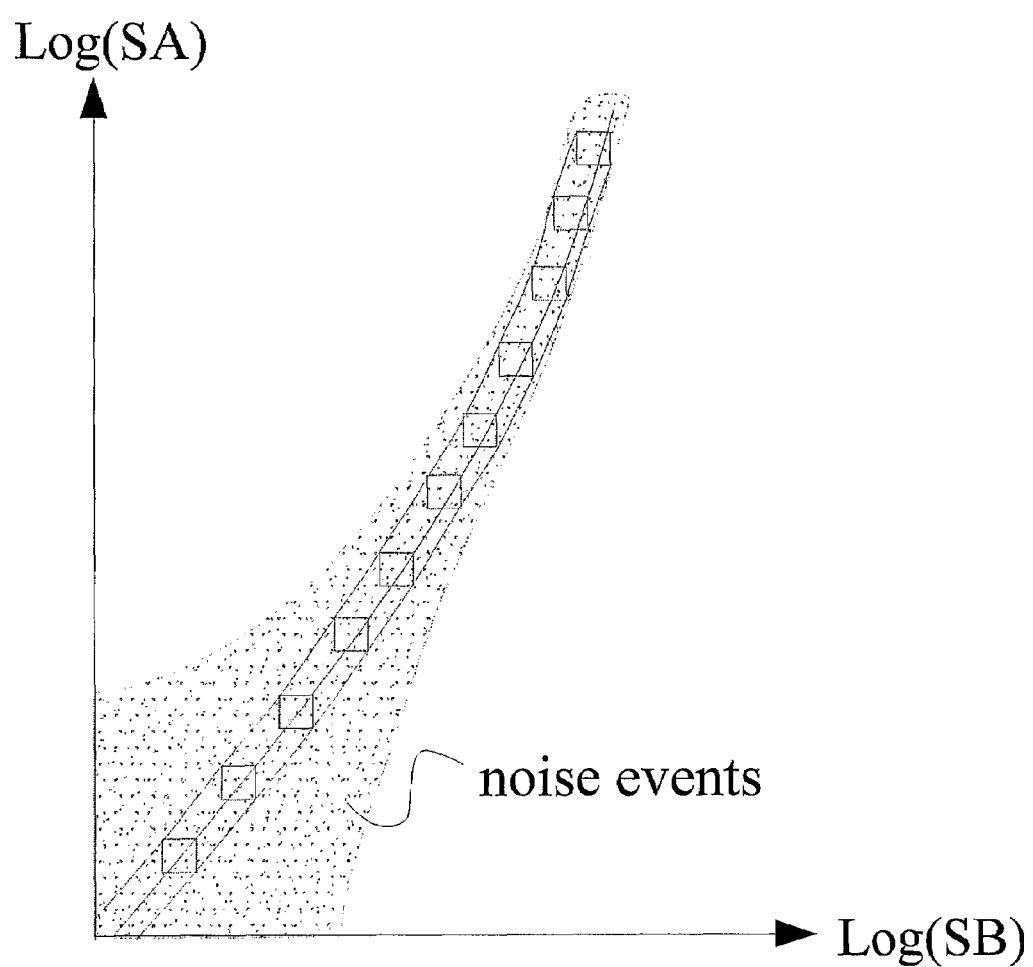
FIG. 62 provides a graph showing a scatter plot of signal events, as described in FIG. 61, wherein particle scatter impulse response region limits and noise events are indicated.

FIG. 61 shows a scatter plot of the counted data points in the two dimensional space, where the two dimensions are the logarithm of pulse amplitude or pulse integral for two different signals A or B. For example SA and SB could be S1 and S2, or A0-S0 and S1. Two squares are shown which encompass the approximate region where counts from particles could occur for each of two particle diameters. SAU and SAL refer to the upper and lower limits of the signal, respectively, as shown in FIG. 60. The lower limit, SAL, is determined by the cutoff of the aperture on the source intensity profile. The upper limit, SAU, is the maximum signal value when the particle passes through the peak of the source intensity profile. In the two dimensional space, shown in FIG. 61, points are shown where the particle passes through the intensity peak, [log(SBU),log(SAU)], and where the particle passes through the edge of the intensity profile, [log(SBL),log(SAL)], where the intensity is lowest. As particle size changes, this square region will move along a curve which describes the scatter for particles of a certain composition, as shown in FIG. 62. The moving square will define a region, between the two blue lines which pass through the edges of the square. Real particles can only produce points within this region. Points outside this region can be rejected as noise points or artifact signals. This two dimensional count profile can be deconvolved using 2-dimensional image deconvolution techniques (as described previously), because each square defines the outline of the two dimensional impulse response in Log(S) space. The two dimensional count profile is the concentration (counted points per unit area of log(SA) and log(SB) plot 2-dimensional space) of counted points at each coordinate in the log(SA) and log(SB) space. This count concentration could be plotted as the Z dimension of a 3-dimensional plot where the X and Y dimensions are log(SA) and log(SB), respectively. The two dimensional impulse function plotted in the Z dimension of this 3-dimensional space is determined from the product of functions as shown in FIG. 60, one along each of the log(SA) and log(SB) axes of FIGS. 61 and 62. The 2-dimensional plot of Log(S1) vs. S1/S2 could also provide the particle size solution, as shown in FIG. 39. All of the techniques for multi-dimensional analysis, described previously, apply to this case. In this case, the 2 dimensional space would deconvolved in the Log(S1) direction only, where the function broadening due to source intensity variation occurs. Very little broadening will occur in the S1/S2 function due to the ratio correction. These multi-dimensional views and the previously described methods apply to all combinations of signals (S1, S2, etc.), Log(signals) (Log(S1), Log(S2), etc), Ratios of signals (S2/S1, S3/S1, etc), and/or any combinations of these (S1/S2 and Log(S1), etc.). Where the signals S1, S2, etc. are functions of the measured scatter signal (such as peak value, integral, value at a certain time during the pulse, product of two scatter signals, etc.)

Figure 63:
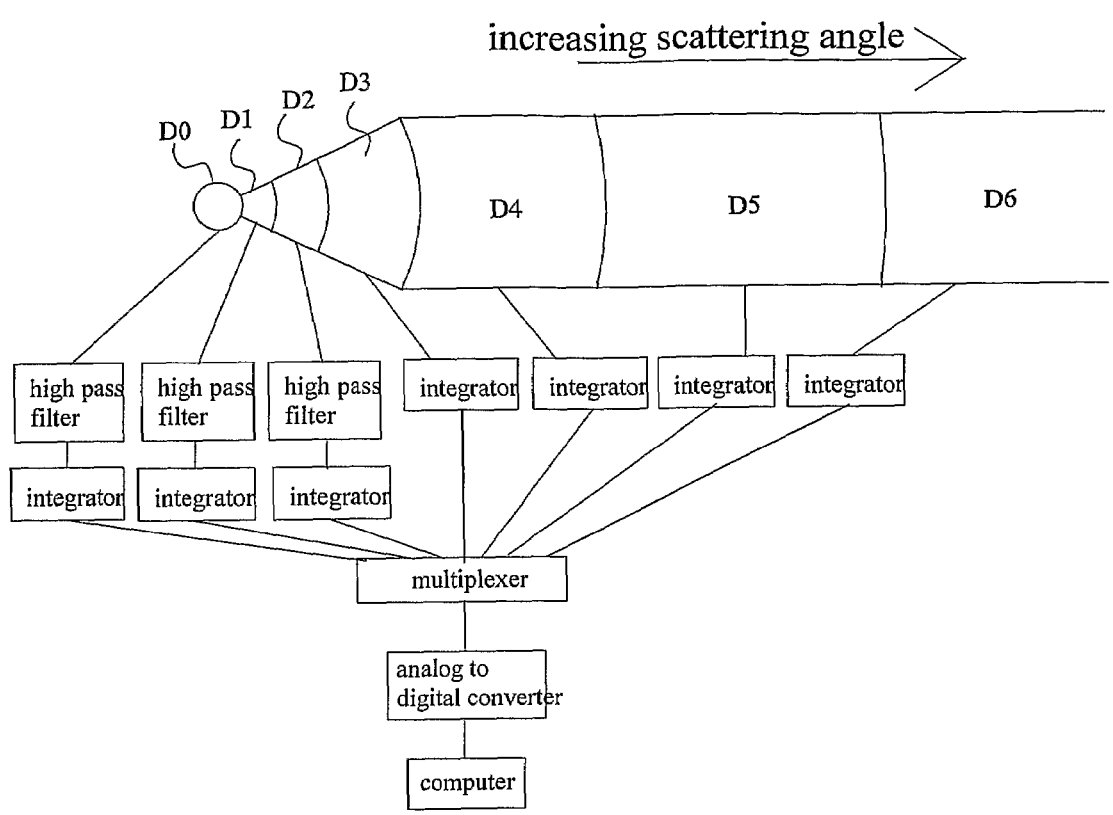
FIG. 63 provides a block diagram of a detector array and electronics for measuring scatter signals from individual particles and a particle ensemble, by utilizing high pass filters, according to the present invention.

The previous concept for ensemble particle systems uses particle counting to eliminate the particle size errors caused by background drift in the angular scattering signals, because the frequency content of the counted pulses is much higher than the background drift, and so the pulses can be detected by methods described previously by this inventor, without being effected by background drift. The local baseline is easily subtracted from each pulse because the background drift is negligible during the period of the pulse. However, this advantage can also be used with the integrators as shown in FIG. 63. The slowly varying baseline can be removed by high pass analog electronic filters with a cutoff frequency between the lowest frequency of the particle scatter pulse spectrum and the highest frequency of the background drift spectrum. The input to each of the integrators which follow each high pass filter are the particle scatter pulses, without background which is attenuated by the filter. These pulses can be integrated and multiplexed into the same analog to digital converter as the higher scattering angle signals, which do not need the highpass filtering to remove the baseline drift. These integrators integrate over an extended period where many particles pass through the beam. In the case of smaller particles, there may be many particles in the beam at any instant in time. However, since the scatter signal from larger particles is much larger than that for smaller particles and with many smaller particles in the beam, these smaller particle signals will have very low fluctuations relative to the discrete pulses from the larger particles. So this high pass filtering will select the larger particles where the scatter signal fluctuations are large. This measurement could also be made with an RMS (root mean squared) module which only detects the higher frequency portion of the scatter signal for the lower angle detectors. All of these integrated signals, from low and high angle scatter detectors, are then inverted by techniques such as deconvolution. The detector signals could also be digitized directly; and the filtering and integration steps could be done digitally. However, the optical scatter model for the deconvolution must include the loss of the small particle contribution to these filtered signals, because as the number of particles in the beam increases, the higher frequency components will be attenuated due to overlap of pulses. Given this attenuation process and the fact that signals at the lowest scattering angles scale as the fourth power of particle diameter, the smaller particle signals should not be significant in these filtered low angle signals. The correction to the model is very minor; essentially the small particle contribution to these filtered detector signals can be assumed to be small in the scattering model.

These methods do not assume any particular number of lower angle zones. For example, D0, D1, D2, and D3 could be handled with the techniques above. Essentially, any detectors with background drift problems should be handled with these methods.

Normally all of the ADC scans of the multiplexer output are summed together and this sum is then inverted to produce the particle size distribution. But due to the large difference in scattering efficiency between large and small particles, smaller particles can be lost in the scatter signal of larger ones in this sum. This problem can be mitigated by shortening the integration time for each multiplexer scan and ADC cycle to be shorter than the period between pulses from the large particles. Then each multiplexer scan and subsequent digitization can be stored in memory and compared to each other for scattering angle distribution. ADC scans of similar angular distribution shape are summed together and inverted separately to produce multiple particle size distributions. Then these resulting particle size distributions are summed together, each weighted by the amount of total integration time of its summed ADC scans. In this way, scans which contain larger particles will be summed together and inverted to produce the large particle size portion of the size distribution and scans which contain only smaller particles will be summed together and inverted to produce the small particle size portion of the size distribution, without errors caused by the presence of higher angle scatter from larger particles.

Another method to measure larger particles is to place a sinusoidal target in an image plane of the sample cell on front of a scatter detector as described previously by this inventor. The dispersant flow could be turned off and particle settling velocity measured by the modulation frequency of the scatter signal from individual particles settling through the source beam.

The hydrodynamic diameter of each particle can then be determined from the particle density, and dispersant density and viscosity.

Finally the three size distributions from dynamic light scattering, ensemble scattering and counting are combined to produce one single distribution over entire size range of the instrument by scaling each size distribution to the adjacent distribution, using overlapping portions of the distribution. Then segments of each distribution can be concatenated together to produce the complete size distribution, with blending between adjacent distributions in a portion of each overlap region. This method works well but it does not make most effective use of the information contained in the data from the three sizing methods. Each inversion process for each of the three techniques would benefit from size information produced by other techniques which produce size information in its size range. This problem may be better solved by inverting all three data sets together so that each of the three methods can benefit from information generated by the others at each step during the iterative inversion process. For example, the logarithmic power spectrum (dynamic light scattering), logarithmic angular scattering distribution and logarithmic count distribution could be concatenated into a single data vector and deconvolved using an impulse response of likewise concatenated theoretical data. However, in order to produce a single shift invariant function, the scale of the counting data must be changed to produce a scale which is linear with particle size. For example, the pulse heights on an angular detector array will scale nearly as a power function of particle size, but the power spectrum and ensemble angular scattering distributions shift along the log frequency and log angle axes linearly with particle size. So a function of the pulse heights must be used from the count data to provide a count function which shifts by the same amount (linear with particle size) as the dynamic light scattering and ensemble distributions. This function may vary depending upon the particle size range, but for low scattering angles the pulse height would scale as the fourth power of the particle diameter, so that the log of the quarter power of the pulse heights should be concatenated into the data vector. This technique will work even though the concatenated vectors are measured verses different parameters (logarithm of frequency for dynamic light scattering, logarithm of scattering angle for ensemble scattering, and logarithm of pulse height or integral for counting), simply because each function will shift by the same amount, in its own space, with change in particle diameter. And so the concatenation of the three vectors will produce a single shift invariant function which can be inverted by powerful deconvolution techniques to determine the particle size distribution. This technique can also be used with any two of the measurement methods (for example: ensemble scattering and dynamic light scattering) to provide particle size over smaller size ranges than the three measurement process. This problem can also be formulated as a matrix equation, where the function variables can be Log(x) or x (where x is the variable frequency (dynamic light scattering), scattering angle (ensemble angular scattering) or S (the counting parameter)). Again these functions can be concatenated into vectors and a matrix of theoretical concatenated vectors. And this single matrix equation, which contains the dynamic light scatter, the ensemble scatter and the count data, can be solved for the differential particle volume vs. size distribution, Vd.

$$Fm=Ht*Vd$$

Where Fm is the vector of measured values which consist of three concatenated data sets (dynamic, angular, and counting). Ht is the theoretical matrix, whose columns are the theoretical vectors which each represent the theoretical Fm of the size corresponding to the value Vd which multiplies that column. This matrix equation can be solved for Vd, given Fm and Ht.

If the convolution form holds, then the equation becomes:

$$Fm=Him \Theta Vd$$

Where Him is the Fm response at a single particle size and $\Theta$ is the convolution operator. This equation can be solved for Vd, given Fm and Him.

Another way to accomplish this is to constrain the inversion process for each technique (dynamic light scattering, ensemble scattering and counting), to agree with size distribution results from the other two techniques in size regions where those other techniques are more accurate. This can be accomplished by concatenating the constrained portion of the distribution, Vc, onto the portion (Vk) which is being solved for by the inversion process during each iteration of the inversion. The concatenated portion is scaled relative to the solved portion (AVc), at each iteration, by a parameter A which is also solved for in the inversion process during the previous iteration. This can be done with different types of inversion methods (global search, Newton's method, Levenburg-Marquart, etc.) where the scaling parameter A is solved for as one additional unknown, along with the unknown values of the particle size distribution. This technique will work for any processes where data is inverted and multiple techniques are combined to produce a single result.

$Fn=Hnm*Vn$ (matrix equation describing the scattering model)

$Vn=Vk|AVc$ (concatenation of vectors Vk and AVc, n number of total values in Vn)

Solve for k values of Vk and constant A $Vn=Fn/Hnm$ (solution of the matrix equation by iterative techniques (not a literal division))

$k \leq n+1$

Figure 64:
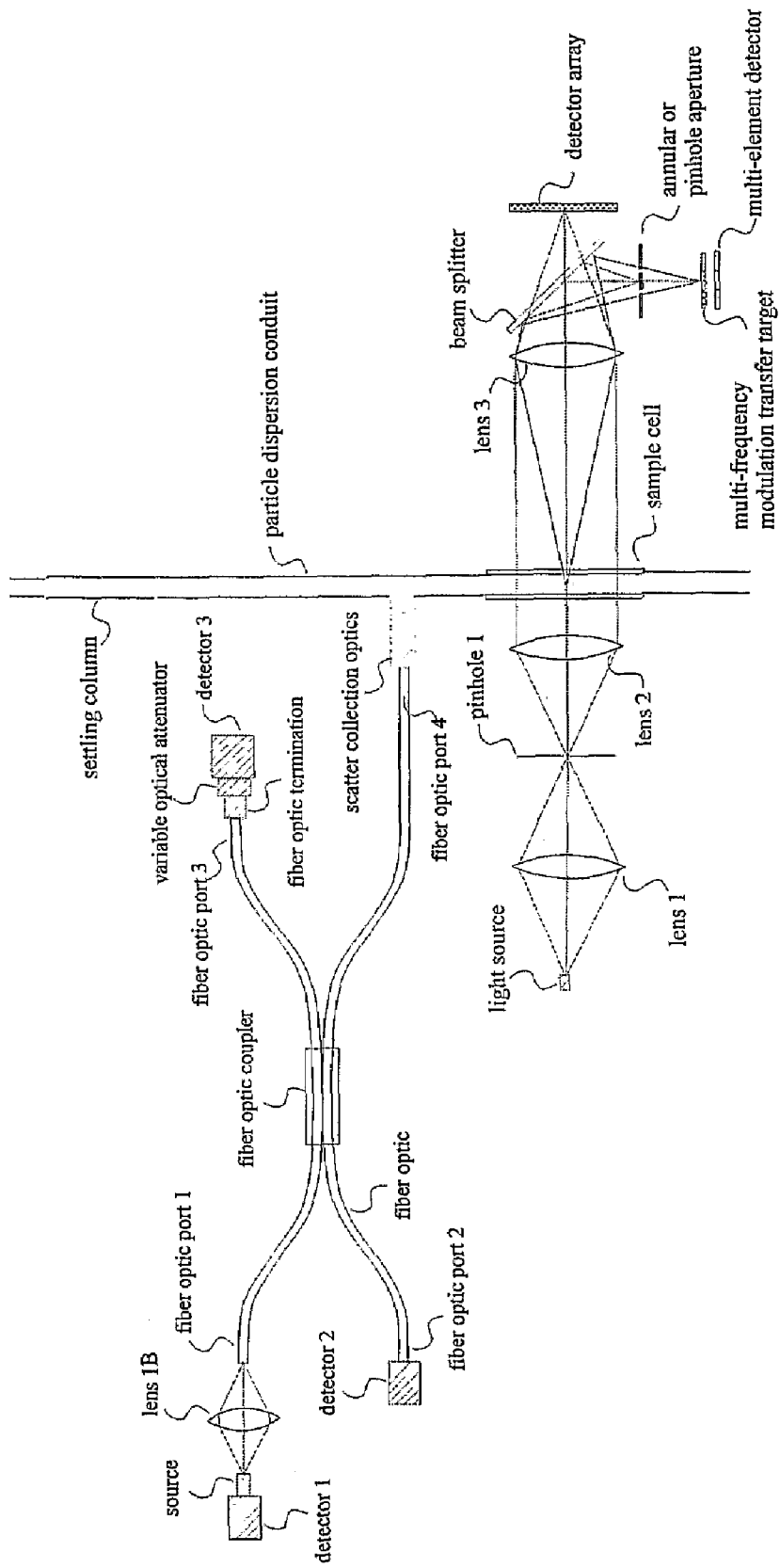
FIG. 64 provides a schematic diagram of an optical system which combines particle settling, ensemble angular scattering, and dynamic light scattering, according to the present invention.
Figure 66:
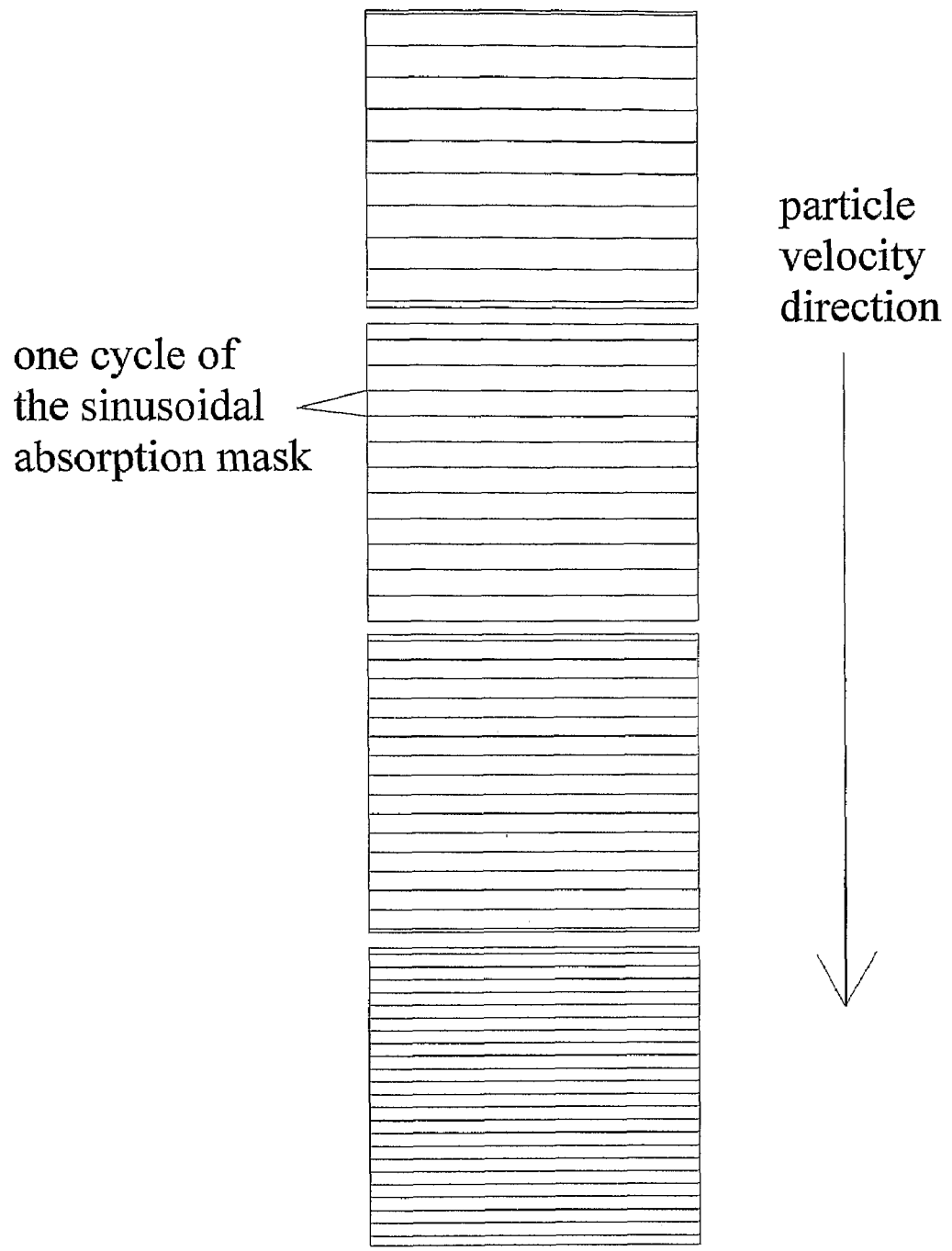
FIG. 66 provides a diagram of a periodic mask for producing an oscillating scatter signal, according to the present invention.

Another hybrid combination is particle settling, ensemble scattering, and dynamic light scattering as shown in FIG. 64. As before, dynamic light scattering probes a portion of the particle dispersion flow stream, with the flow turned off. The ensemble scattering system uses a detector array to measure the angular scattering distribution from groups of particles in the sample cell as the dispersion flows through the cell. A particle settling measurement is used for the largest particles which have the highest settling velocities. The settling is measured by sensing the power spectrum of the scattered light as viewed through a set of sinusoidal or periodic masks, which are also referred to as a multi-frequency modulation transfer target. Some examples of these masks are shown in FIGS. 16 and 66. The mask can be placed between lens 2 and lens 3 or on front of a group of detectors as shown in FIG. 64. The detector is placed in the back focal plane of lens 3, as shown previously by the inventor, to collect scattered light in separate ranges of scattering angle. A portion of the scattered light is split off by a beam splitter to an aperture in the focal plane of lens 3. This aperture can be an annular opening, which passes a certain range of scattering angles (signal rises as particle passes through a bright fringe), or a pinhole centered to pass only the focused spot of the source (signal drops as particle passes through a bright fringe) in the back focal plane of lens 3. Where the fringe is defined in the sample cell plane as an image of each highly transmitting line in the multi-frequency target. The light passing through the aperture, also passes through a periodic mask, as described previously, which is in a plane conjugate to the sample cell. This mask contains multiple regions, each with a different spatial frequency for the periodic absorption or reflection pattern. Behind each region in the mask is a separate detector which collects the light which only passes through that region. As particles pass through a region, the scattered light (for the annular aperture) or the attenuation (for the pinhole passing the source) of the beam are modulated by the motion of the particle's image across the absorption cycles of the mask. The particle dispersion flow pump is turned off and the particles are allowed to settle through the sample cell. The frequency of signal modulation for any particle is proportional to its settling velocity, which indicates the hydrodynamic size of the particle, given the particle and dispersant densities and the dispersant viscosity. The signal can be digitized and analyzed on an individual particle basis to count and size individual particles by measuring the settling velocity of each particle. In this case zero crossing measurement or Fourier transform of the signal segments for each particle could be used. In the case where many particles are in the beam at each instant, the power spectrum of the signal could be measured over an extended time. This power spectrum would then be inverted to produce the particle size distribution using a matrix model as described previously. As identical particles pass though different focal planes (planes perpendicular to the optic axis) in the sample cell, the power spectrum will change because the sharpness of the image of the mask will be reduced as the particle moves farther from the image plane. Also if the source beam is focused into the sample cell, as shown previously, then the source intensity and the scatter signal will drop as the particle passes farther from the best focus plane of the source. These effects can be included in the counting system model which is inverted to produce the particle size. The H function (or H matrix) described previously will contain columns which describe the count vs. signal frequency from a group of identical particles, of the size corresponding to that matrix column, passing through every point in the sample cell. For the ensemble scattering system model, the H function (or H matrix) will contain columns which describe the integrated scatter signal vs. angle from a group of identical particles, of the size corresponding to that matrix column, passing through every point in the sample cell.

The following list describes the various options for using scattered light to measure size. In each case, the following matrix equation must be solved to determine V from measurement of F:

$$F=H*V$$

This equation can be solved by many different methods. However, because this equation is usually ill-conditioned, the use of constraints on the values of V is recommended, using apriori knowledge. For example, constraining the particle count or particle volume vs. size distributions to be positive is very effective. In some cases, as shown previously by this inventor, changing the abscissa scale (for example from linear to logarithmic) of F can produce a convolution relationship between F and V, which can be inverted by very powerful deconvolution techniques.

$$F = H\Theta V$$

Particle Counting

1) Angular scatter or attenuation due to scatter:

V=particle count per size interval vs. size

F=count per signal amplitude interval vs. signal amplitude where signal amplitude is either pulse peak value, integral of the pulse, or other function of these values H=matrix where each column is the F function for the particle size corresponding to that column Response broadening mechanisms in the H matrix:

source intensity variation in x and y directions where particles can pass (mitigated by aperturing of intensity distribution at an image plane of the sample cell or using diffractive or absorptive optic beam shapers and apodizers)

source intensity variation in z direction (mitigated by double pulse sensing and detector aperture at image plane of sample cell)

Advantages: high resolution and aerosol capability

Disadvantages: counting statistic errors for low count

2) Settling (Hydrodynamic Size)

V=particle count per size interval vs. size

F=count per signal frequency interval vs. signal frequency where signal frequency is the frequency of the scatter signal segment for the counted particle H=matrix where each column is the F function for the particle size corresponding to that column Response broadening mechanisms in the H matrix:

Finite length of modulated signal segment from each particle

Brownian motion

Variation of signal frequency along z direction

Advantages: high size resolution, excellent detection of small particles mixed with large particles, excellent measurement of low tails in the size distribution Disadvantages: counting statistic errors for low count; and possible difficulty measuring large particles in aerosols due to very high settling velocities Ensemble scattering 1) Angular scatter or attenuation due to scatter V=particle volume per size interval vs. size F=scattered light flux per scattering angle interval vs. scattering angle H=matrix where each column is the F function for the particle size corresponding to that column Response broadening mechanisms in the H matrix:

The broad angular range of scatter from a single particle

Advantages: excellent size reproducibility

Disadvantages: low size resolution, poor detection of small particles mixed with large particles, poor measurement of low tails in the size distribution.

2) Settling (Hydrodynamic Particle Size)

V=particle volume per size interval vs. size

F=scattered light detector current power per frequency interval vs. frequency

H=matrix where each column is the F function for the particle size corresponding to that column Response broadening mechanisms in the H matrix:

Finite length of modulated signal segment from each particle

Brownian motion

Variation of signal frequency along z direction

Figure 67:
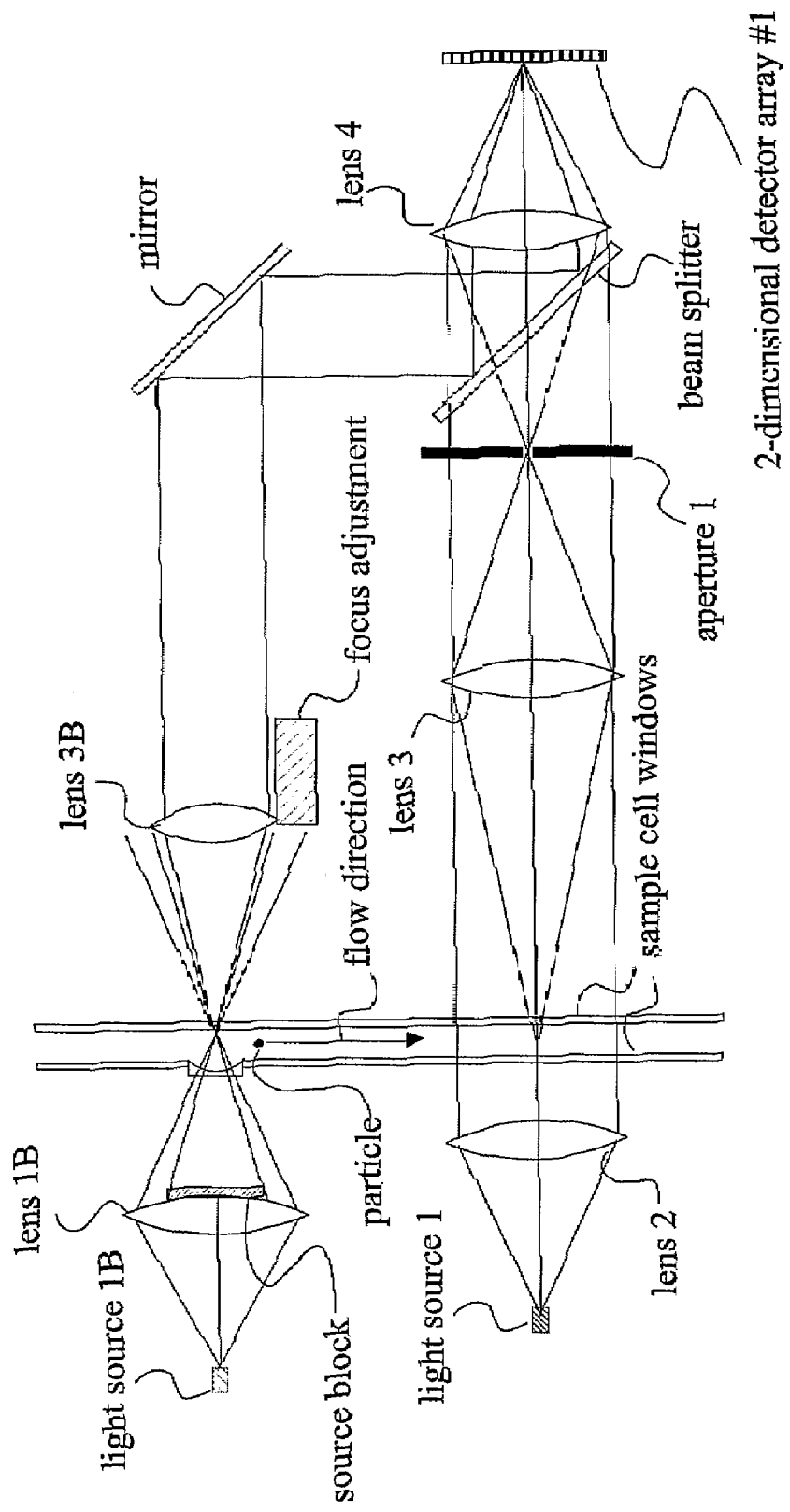
FIG. 67 provides a schematic diagram of an optical system which multiplexes a detector array between two light sources, where one source is utilized for measuring the light beam attenuation due to light scattered by particles, according to the present invention.

Advantages: high size resolution, excellent detection of small particles mixed with large particles, excellent measurement of low tails in the size distribution Disadvantages: difficulty measuring large particles in aerosols due to very high settling velocities Another system for counting and sizing particles, using imaging, is shown in FIG. 67. There are two optical systems, using light source 1 and light source 1B. The source 1 system measures larger particles by direct imaging of the particles, flowing through the sample cell, onto 2-dimensional detector array #1. The source 1B system produces a cone shaped illuminating beam, using the source block on lens 1B, which defines an illuminated focus volume in the particle dispersion. This focal volume is imaged by lens 3B though the mirror and beamsplitter onto the same 2-dimensional detector array #1. The focal volume is placed close to the sample cell window which is closest to the 2-dimensional array. Before and after the focal point of the source 1B in the cell, the illumination beam is a hollow cone, which provides an un-illuminated volume through which lens 3B can view the focal point of source 1B in the sample cell. The 2-dimensional array is multiplexed between the two systems by sequentially turning on either source 1 or source 1B. Each source is pulsed so as to only illuminate the flowing particles during a travel distance which is less than the required imaging resolution. Alternately, the flow can be stopped during the exposure to eliminate any smearing of the image.

Figure 68:
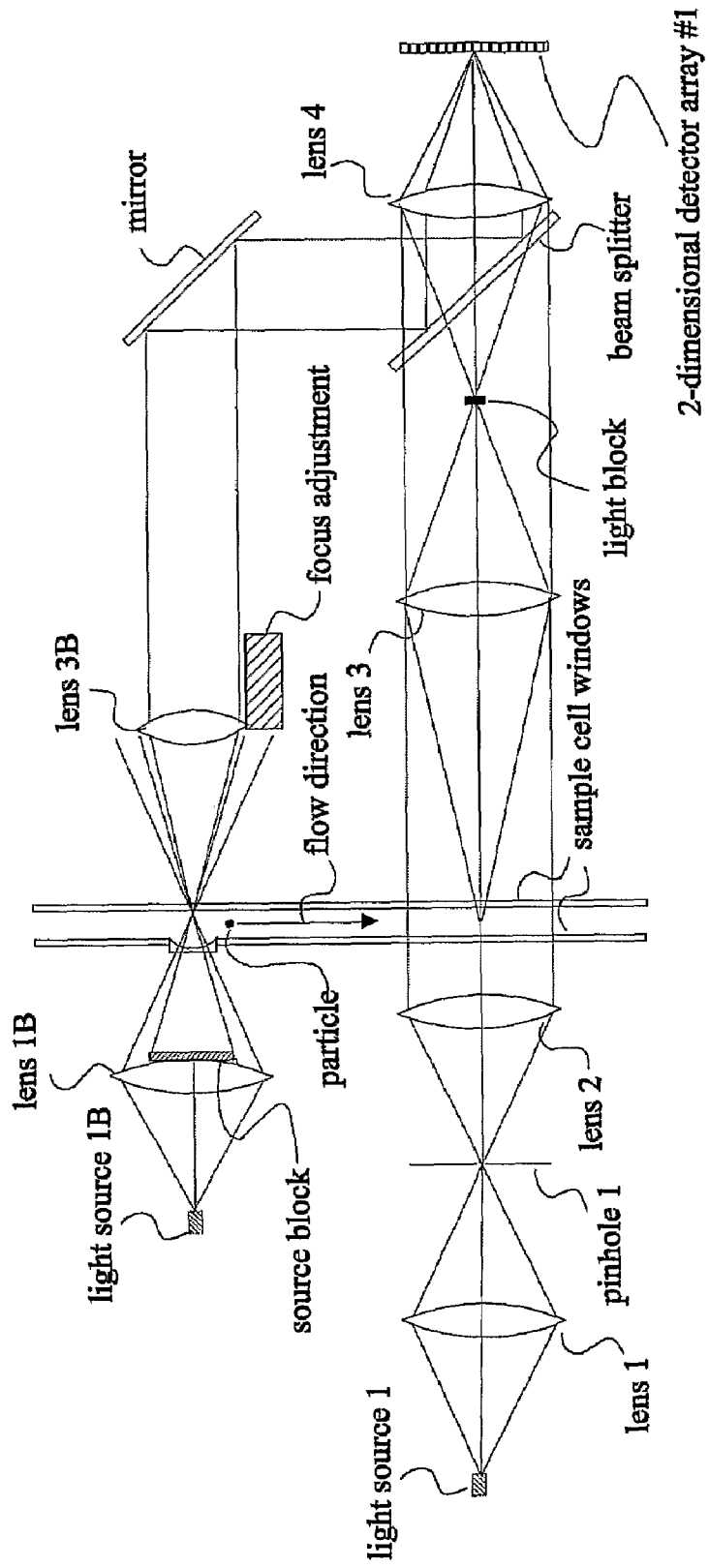
FIG. 68 provides a schematic diagram of an optical system which multiplexes a detector array between two light sources, where one source is utilized for measuring the light scattered by particles, according to the present invention.

The source 1 system can take many forms. In FIG. 67, aperture 1 blocks the scattered light and passes the un-scattered light (approximately) so that particles will appear as dark on a bright background. In FIG. 68, aperture 1 blocks the un-scattered light and passes the scattered light (approximately) so that particles will appear as bright on a dark background. In FIG. 68, pinhole 1 is used to remove any higher angle components of light source 1 which could create background light which can pass around the light block. In either case, contiguous detector array pixel values, which are above some threshold in FIG. 68 or below some threshold in FIG. 67, can be combined to determine the total light extinction of the particle (in FIG. 67) or the light scattered in the acceptance angle of lens 3 in FIG. 68. These values can be used to determine the size of particles throughout the size range, even for a particle whose image size is less than the size of single pixel, as described previously in this document. However, for very small particles, many particle coincidence counts may occur in the source 1 system and the signal to noise may drop below acceptable levels. So the smaller particles are measured by the source 1B system, which focuses the source to a higher irradiance in the sample cell and defines a much smaller interaction volume than the other system. The source block on lens 1B creates a hollow cone of light, which is focused close to inner sample cell window wall which is closest to the detector array. This is shown in more detail in FIG. 69. Lens 3B collects scattered light from the particles, with a field of view which falls inside of the hollow cone of light. Therefore, only particles in the source focal volume will contribute to the scattered light and the image formed on the detector array. Since the focus is close to the inner wall, few particles will block or rescatter light which is scattered by particles in the focal volume. However, this method will produce good results for any location of the lens 1B focus, as long as lens 3B is focused to the same location. Also particles in the extended illuminated portions of the hollow cone cannot contribute scatter to lens 3B due to the limited acceptance cone of this lens. The optical magnification is chosen such that the 2-dimensional array only sees the focal volume, without seeing any light from the hollow light cones on the input or exit of the focal volume. The scattered light, accepted by lens 3B, is reflected by a mirror and a beamsplitter, through lens 4, to the detector array. The lenses 3, 3B, and 4 are designed to work at infinite conjugates, however lens 4 could be removed and lens 3 and lens 3B could be adjusted to create images of the particles directly onto the detector array at finite conjugates. In both Figures, the size of very large particles can be measured directly by the size of digitized image to avoid errors in the magnitude of the scattered light from these large objects which only scatter at very small scattering angles, where the background light is high.

Figure 69:
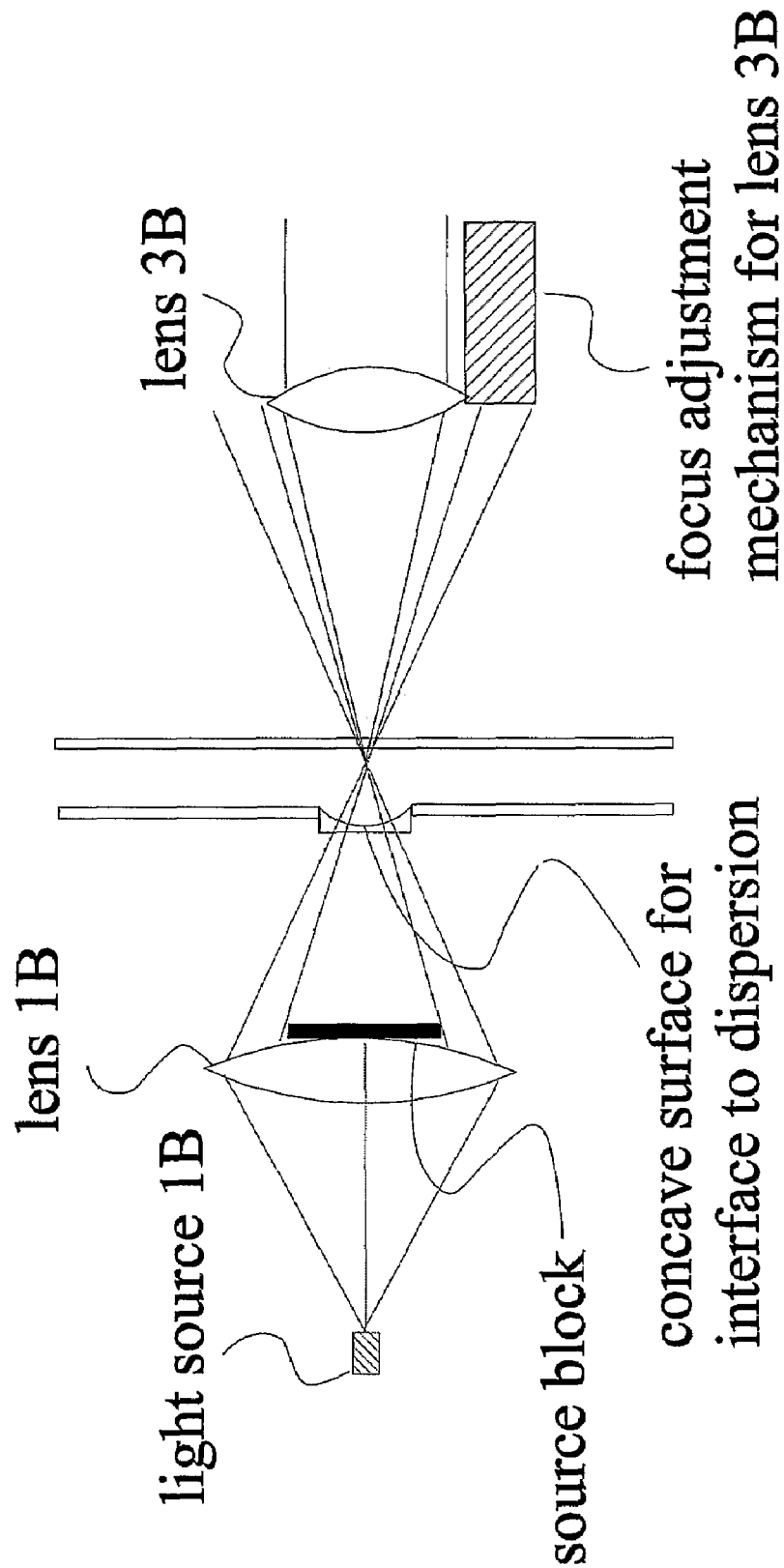
FIG. 69 provides a schematic diagram of an optical system schematic diagram, which shows more details of FIG. 67 and FIG. 68.

As shown in FIG. 69, the Source 1B system also uses a concave inner surface whose center of curvature is approximately coincident with the focal volume. This design produces a focal volume which does not shift with change in the refractive index of the dispersing fluid in the sample cell. A concave surface could also be used on the opposing window to control the focal shift of lens 3B due to refractive index change of the dispersant, to maintain sharp focus of the scattered light in the particle image on the detector array. Again, the center of curvature would be coincident with the focal volume. However, FIG. 69 shows another alternative which may be more flexible and provide better focus precision. Lens 3B is attached to a focus mechanism which can move the lens to various focal positions. This mechanism could be any appropriate mechanical means, including motor or piezoelectric drivers. The position of lens 3B, along the optical axis, is changed under computer control to maximize particle edge sharpness in the image on the detector array. This sharpness could be determined by many criteria which include the spatial derivative of the image. In the case where the depth of field of lens 3B is shorter than the depth of the focal volume of lens 1B, this focus adjustment can be used to only select particles which are in sharp focus, by measuring the edge sharpness of each particle in the field of view, at three different focal positions. Only particles, whose edge sharpness is maximum in the middle focal position, are sized and counted. In this way, only particles which are accurately sized are counted. The maximum edge sharpness for each particle may vary among different particles which may have soft edges. So by measuring the edge sharpness in three different planes, the particles which are located in the middle plane can be selected by choosing only the ones whose sharpness is maximum in that plane. The edge sharpness could be determined by the spatial derivative of the intensity profile at the edge of each particle. This could also be calculated from the maximum of the spatial derivative of the entire particle, because this usually occurs at the particle's edge. The derivative could also be calculated from a smoothed version of the image, if image noise is a problem. This comparison can be done while the particles are stationary or by using 3 successive source pulses with a detector array scan during each pulse.

Figure 70:
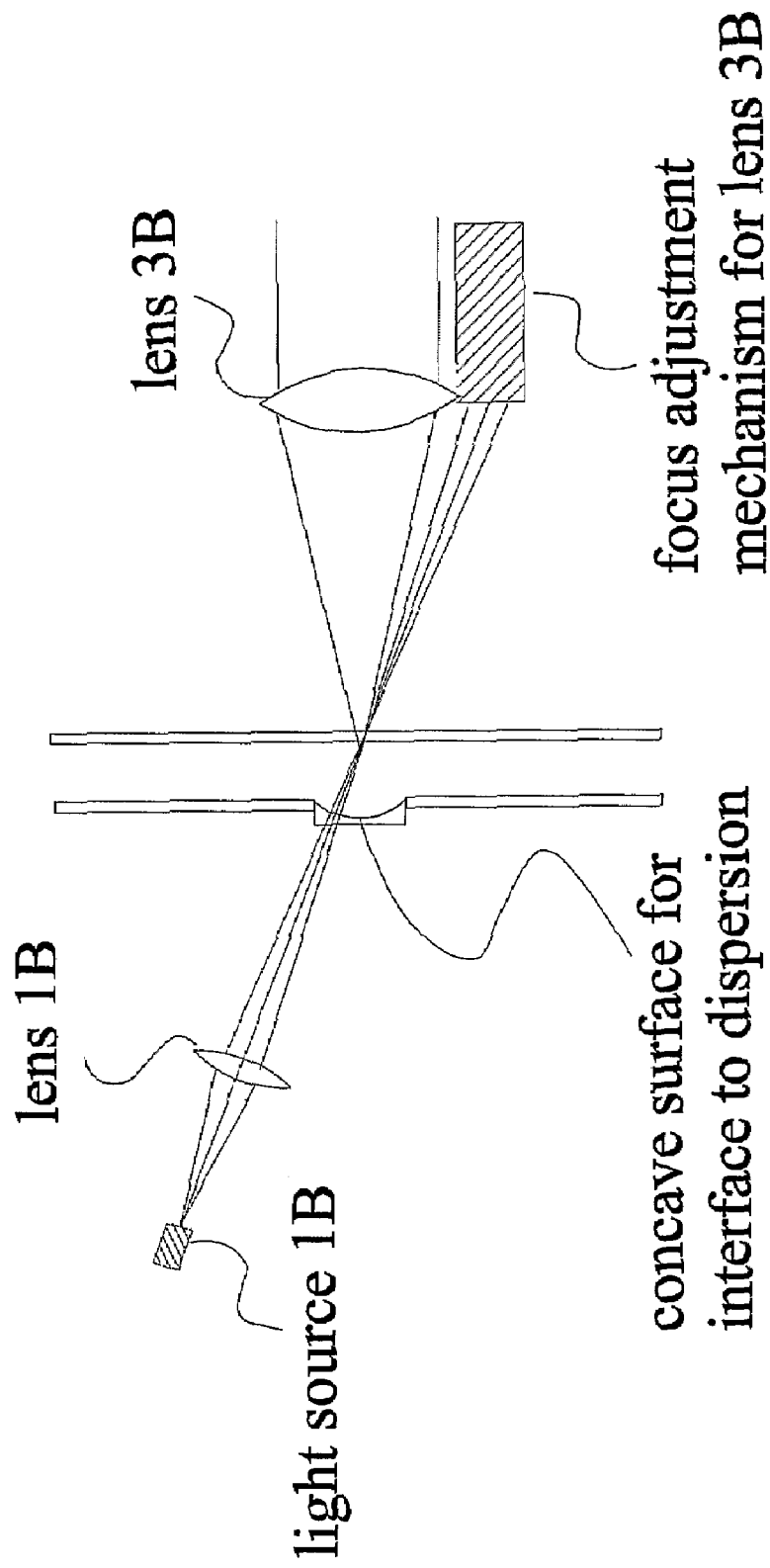
FIG. 70 provides a schematic diagram of an optical system schematic diagram, depicting a variation of the optical system in FIG. 69.

Also, the hollow cone source in FIG. 69 could be replaced by a single focused light beam, which is focused through the focal volume and projected at an angle to the optical axis of lens 3B, such that it is not captured by lens 3B, as shown in FIG. 70. The scattering interaction volume is the intersection of the viewing focus of lens 3B and the source focus of lens 1B. The 2-dimensional detector array sees the image of the particles at the focus of lens 1B, using only light scattered from the particles. In this way, the 2-dimensional array only sees particles in a very small interaction volume. All of the other focusing mechanisms and options mentioned previously for FIG. 69, also apply for FIG. 70.

Another problem associated with counting techniques is the coincidence counting error. In some cases, pulses from individual particles will overlap as shown in FIG. 71, which shows three pulses and the signal which represents the sum of those three pulses. In most cases, these pulses all have the same shape, but with different pulse amplitudes. For example, any particle passing through a Gaussian laser beam will produce a pulse with a Gaussian shape. The only difference between different pulses from different particles is the amplitude of the pulse and the position of the pulse in time. Therefore, the sum of the pulses is simply the convolution of a single pulse with three delta functions, each delta function centered at one of the different pulse positions. The general equation for this sum of pulses is:

$$S(t) = H(t) \Theta \Sigma(A_i * \partial(t - t_i))$$

Where:

$\Sigma$=sum over variable i t=time

S(t)=the total signal from the overlapping pulses $\partial(t)$=the delta function ti=the time at the center of the ith pulse Ai=the amplitude of the ith pulse $\Theta$ is the convolution operator H(t)=the function describing a single particle pulse shape So the original pulses can be recovered from S(t) by inverting the above equation, using H(t) as the impulse response in a Fourier transform deconvolution or in iterative deconvolution algorithms. As shown by FIG. 71, the individual pulse heights and areas cannot be determined from the sum of the pulses S(t). However, through deconvolution the pulses can be separated as shown in FIG. 72, which shows S(t) and the total deconvolved signal resulting after some degree of deconvolution of S(t). Due to signal noise in S(t), S(t) cannot be deconvolved down to separate delta functions, the deconvolution will usually stop at some point before artifacts are created, leaving separated pulses of finite width. However, these pulse heights will be proportional to the actual heights of the original separated pulses. So that by using a single scale factor on the deconvolved signal, all of the individual pulse heights will agree with those of the original separated pulses. FIG. 73 shows this scaled deconvolved result along with the original separated pulses to show that the separated pulse heights are recovered by the decovolution process. This technique can be applied to any time signals which have overlapping pulses of the same shape, such as found in particle counting. For most laser beams, H(t) will be a Gaussian. However, in some cases, where the laser beam has been apodized or truncated to reduce the large intensity variation, H(t) will take on the functional form describing the signal vs. time profile of a single particle passing through that beam, which may be flat-topped Gaussian, rectangular, etc.

Figure 74:
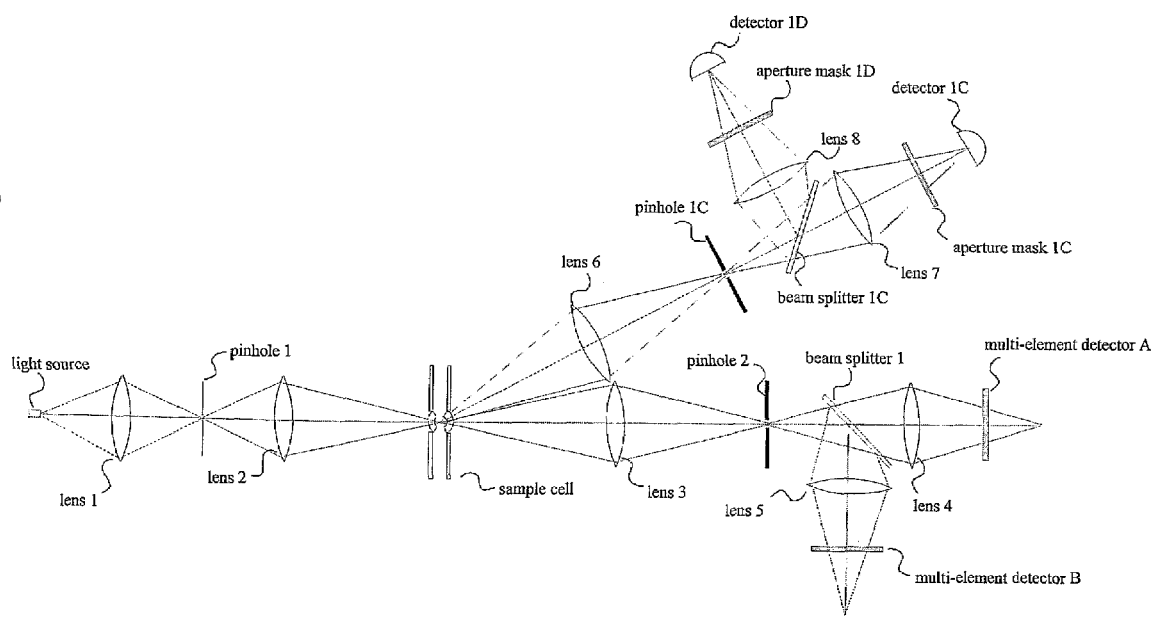
FIG. 74 provides a schematic diagram of a scatter plane of an optical system, which is repeated in multiple scattering planes to determine the shape of a particle, according to the present invention.
Figure 75:
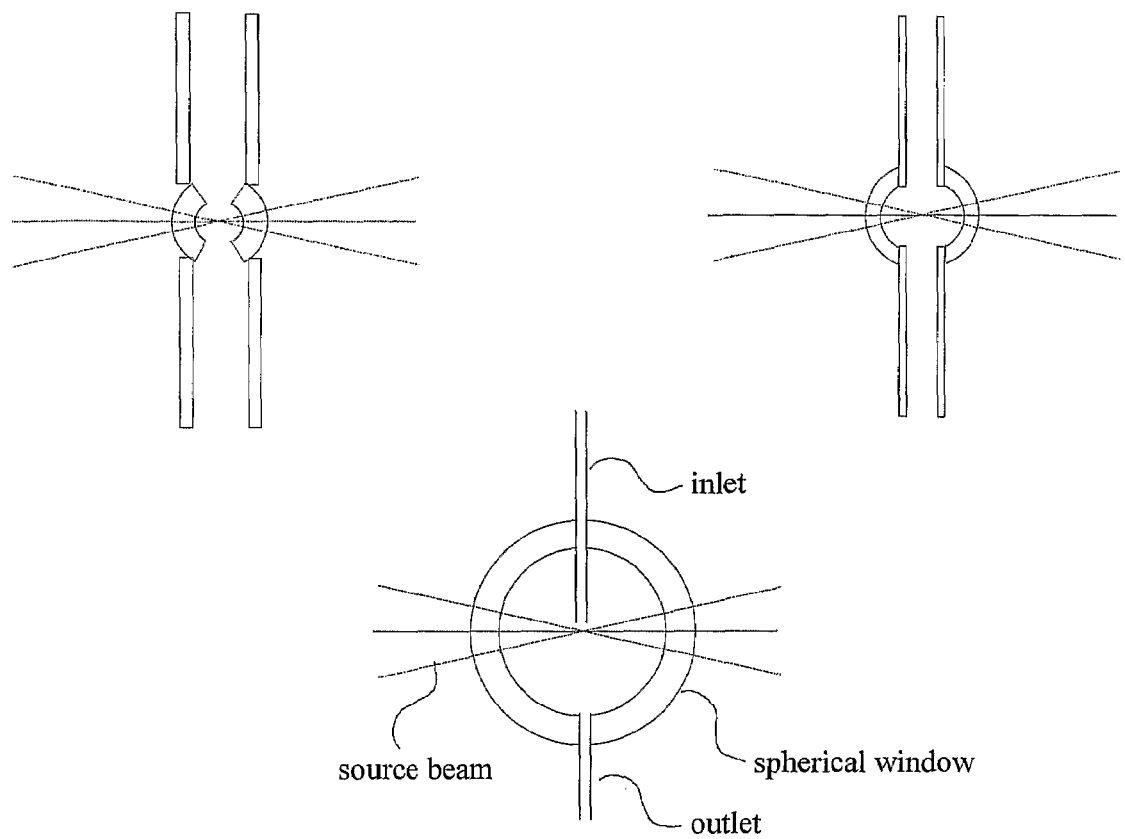
FIG. 75 provides diagrams of three variations of particle sample cells.
Figure 76:
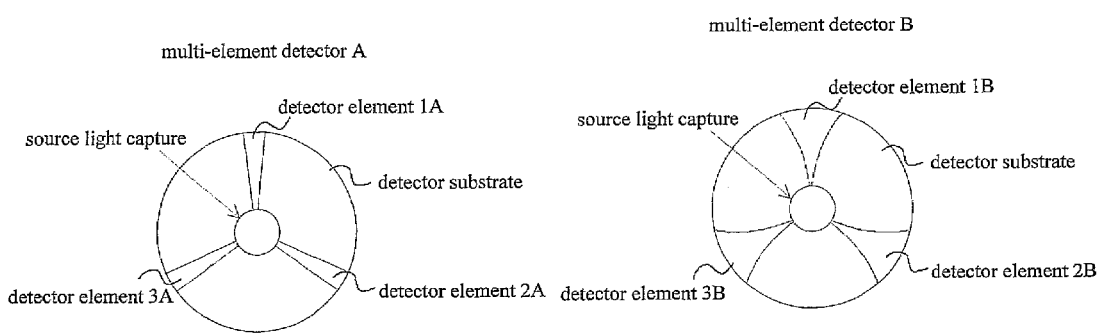
FIG. 76 provides a diagram showing detector elements for measuring the shape of a particle, according to the present invention.
Figure 77:
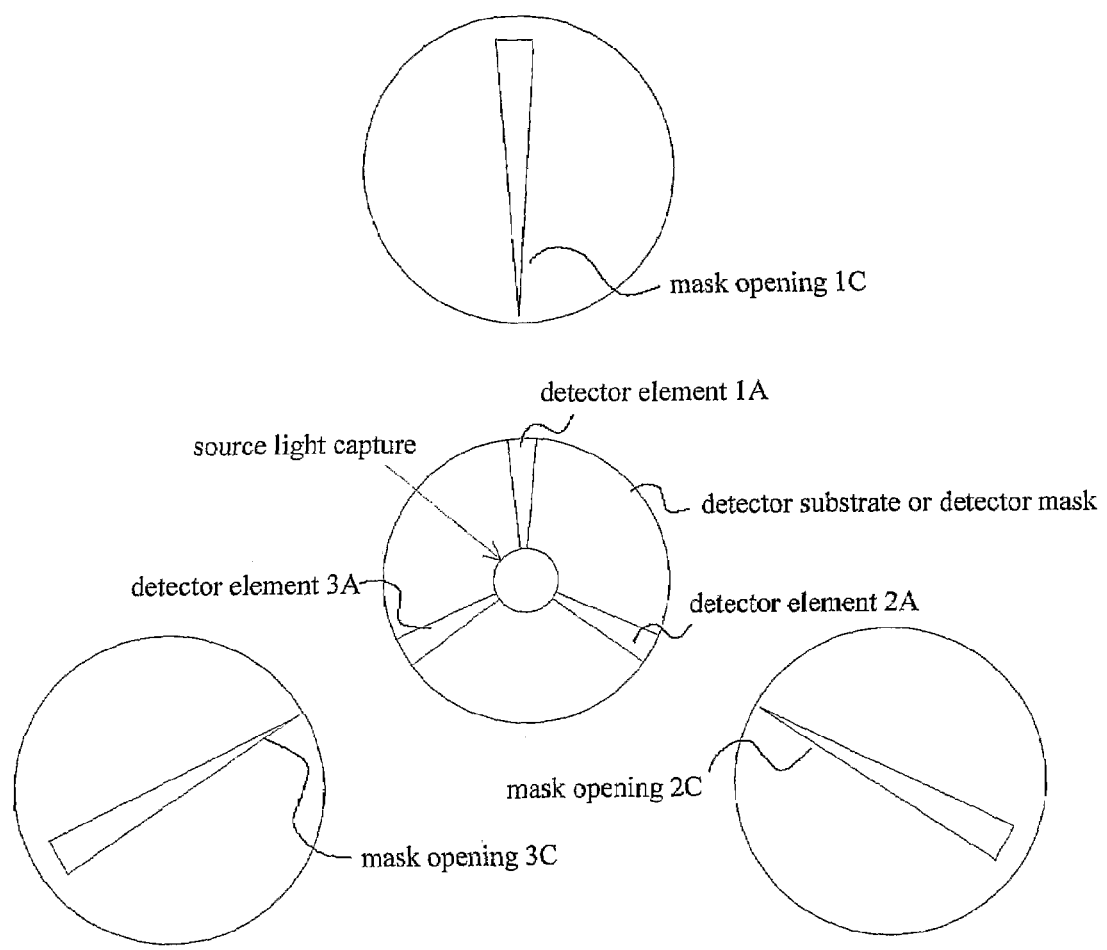
FIG. 77 provides a diagram showing the orientation of detector elements for the optical system of FIG. 74, when measuring scattered light in three ranges of optical scattering planes.

FIGS. 74 through 77 show particle shape measuring systems which combine the concepts of FIGS. 29 through 31, and FIGS. 42 through 45. FIG. 74 shows one system in the first scattering plane of multiple scattering planes. A three scattering plane system is shown, but as mentioned before, any number of scattering planes may be needed to describe the shape of more complicated particles. The lens 4 and lens 5 systems use multiple detector elements to measure scatter in each of the scattering planes on one detector array/lens assembly. The lens 7 and lens 8 systems are repeated in each of the scattering planes to measure the high angle scattered light. These detection systems are aligned as shown in FIG. 77, so that each scattering plane element on multi-element detector A and multi-element detector B measures in the same scattering plane as the corresponding lens 7/lens 8 aperture openings. The configurations of the multi-element detectors are shown in FIG. 76. This concept combines the two concepts described earlier in FIGS. 29-31 and FIGS. 42-45. There is one lens 4/lens5 system with both lens 4 and lens 5 (through beamsplitter 1) centered on the optical axis of the source to measure low angle scatter. Each detector element, shown in FIG. 76, is aligned to view the same scattering plane as the corresponding element on the other multi-element detector, but all three scattering planes are measured by the same multi-element detector. The three Lens7/lens8 systems, which measure the higher angle scatter, each have only one aperture (instead of 3 elements for each of lens4 or lens5) for each lens with shapes like those in FIG. 76 (1C, 2C, 3C apertures have the same (or similar) shape as the detector elements in multi-element detector A and 1D, 2D, 3D have shapes similar to those in multi-element detector B). As before, the ratios of the corresponding detectors C to D and the ratio of each element on the multi-element detector A to the corresponding element on multi-element detector B, provide the particle dimension parameter for the corresponding scattering plane. These parameters are then combined using a lookup table, search algorithm, or regression algorithm to solve for the particle shape. As before, to solve for the dimensions of a rectangular particle with arbitrary orientation, parameters in 3 scattering planes must be measured. The optimal separation of these planes in the plane of FIG. 77 is approximately 120 degrees, with one of the planes being parallel to the flow direction (because many particles will align with the flow direction). The search algorithm will take an initial guess at the width, length, and orientation angle, and then calculate the three parameters for that guess and then compare those parameters to the measured ones to generate a change in the width, length, and orientation for the next guess and then go through the same loop again. As this loop is repeated, the change in the width, length, and orientation diminishes as the algorithm approaches the true width, length, and orientation of the particle. Algorithms such as Newton's method, global optimization, or Levenburg Marquardt could be used. The three dimension parameters could also be replaced by the full set of 12 detector signal values (6 for detectors A and B and 6 for detector sets C and D) for input to these search or optimization algorithms. This would be the case for 3 scattering planes. For particles with more complicated shapes, measurements in more scattering planes would be needed to solve for the shape parameters and the arbitrary orientation, but the same methods would be used to search for the solution. The corresponding elements in detector C and D and in detector A and B could also be detector segments which view different ranges of scattering angle instead of different angular weightings (as shown in FIG. 76) of the same range of scattering angles. However, the use of the use of different angular weightings may provide larger size range because when the particles become very large, very little light may fall on the higher angle detectors and the ratio of high to low angle signals will become multi-valued. The ratio of 2 detectors with different angular weightings (FIG. 76) will have a smooth monotonic size dependence over a large size range.

FIG. 75 shows the use of spherical window shape on the sample cell to avoid focal shift of the focused source spot and of the focal viewing spot of the collection optics as the refractive index of the dispersing fluid is changed. The center of curvature for each surface on each spherical window is at the beam focal position in the sample cell. The bottom portion of FIG. 75 shows a spherical cell with an inlet tube, which ends just above the focal spot of the source beam. This cell is placed into a flow loop as shown in FIG. 13, where the pump pulls the dispersion from the outlet and returns dispersion to the inlet. In this way, homogeneous dispersion passes through the source beam directly from the inlet. Regions far from the inlet, in the spherical cell, may have inhomogeneous particle dispersion, which may not be representative of the entire particle sample. Also when the flow loop is drained, this orientation of the spherical cell will drain completely without leaving residual particles to contaminate the next particle sample.

Figure 78:
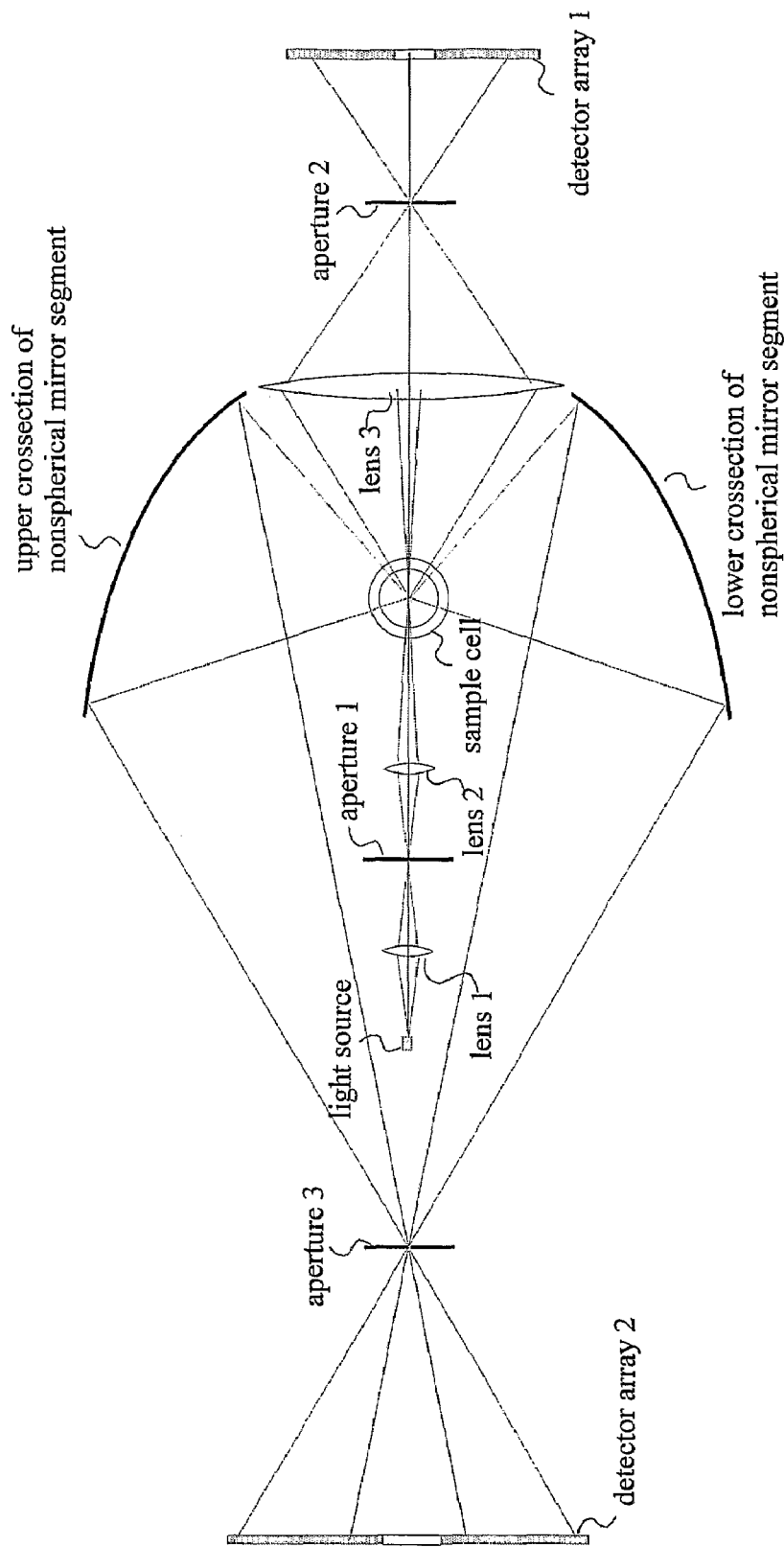
FIG. 78 provides a schematic diagram of an optical system, which measures low angle scatter with a lens, and high angle scattering with a perforated concave mirror, according to the present invention.
Figure 79:
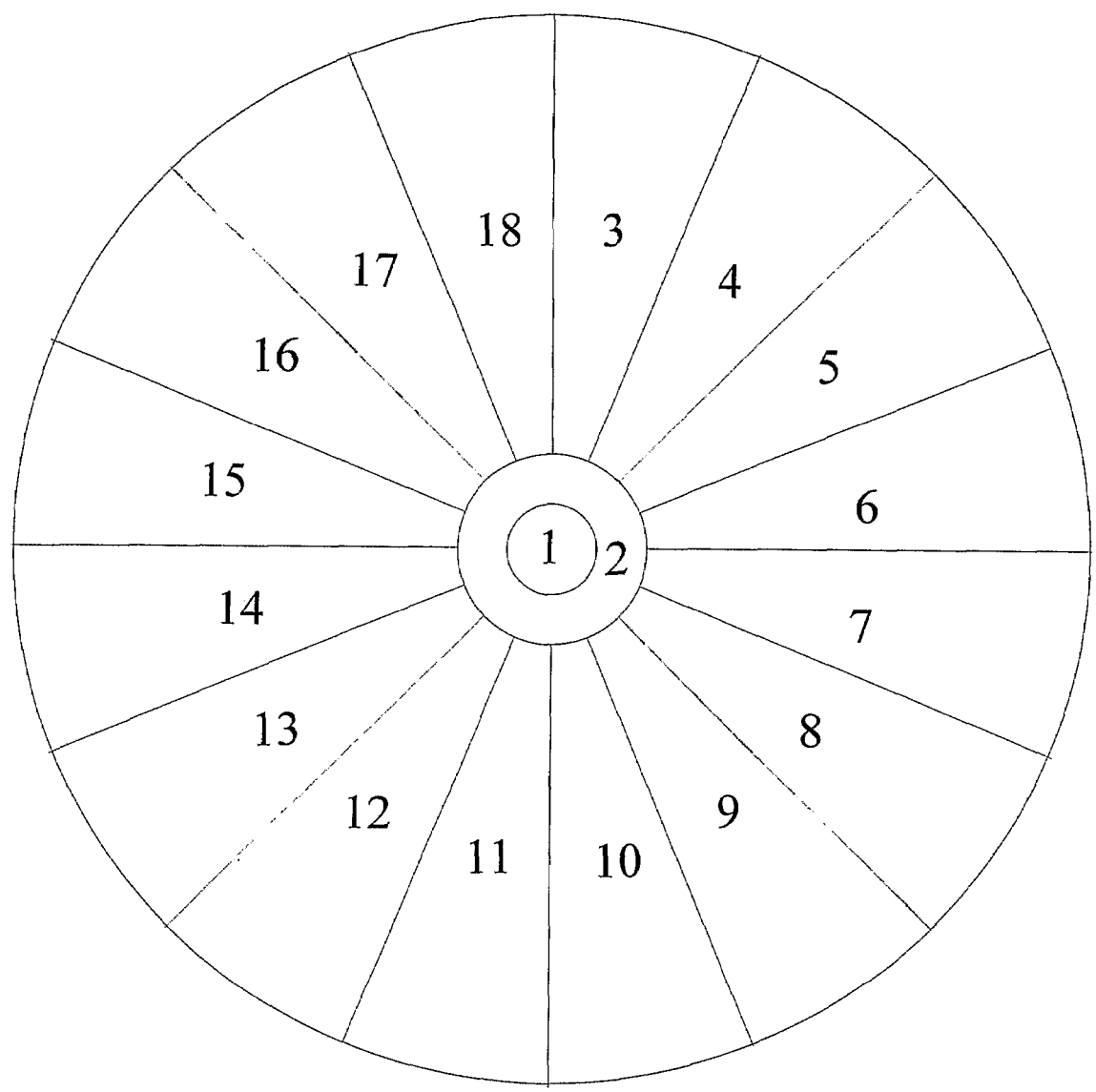
FIG. 79 provides a diagram showing an array of detector elements or optical elements which measure scattered light in multiple ranges of scatter planes and scattering angles, according to the present invention.

Another concept for measuring the shape and size of small particles is shown in FIG. 78. This system consists of two scatter collection subsystems: the first subsystem using lens 3 and detector array 1 and the second subsystem using a segment of a nonspherical mirror and detector array 2. Detector array 1 measures scattered light at low scattering angles and detector 2 measures light scattered at high scattering angles. The light source is spatially filtered by aperture 1 and lens 1. The spatially filtered beam is then focused, by lens 2, into a spherical sample cell (see FIG. 75) which contains the flowing particle dispersion. If the source beam already has appropriately attenuated components at higher divergence angles, then Lens 1 and aperture 1 can be eliminated and lens 2 can focus the source directly into the sample cell. The sample cell should have spherical shaped windows (also see FIG. 75) to minimize the focal shift of the light beam focal spot, due to changes in the refractive index of the dispersant and to reduce Fresnel reflections. If this focal shift or Fresnel reflections are not a problem, planar windows can be used on the sample cell as shown previously. The scattered light from the particles is focused through aperture 2 by lens 3. Aperture 2 is in the image plane of the focal spot of the source inside of the sample cell. As shown previously in FIGS. 43 and 45, aperture 2 will restrict the size of the scattering interaction volume which can be seen by detector array 1 so that the probability of detecting more than one particle in the scattering interaction volume is small. The light passing through aperture 2 is detected by a detector array, as shown in FIG. 79, for example. The detector array contains 18 separate detector elements (numbered 1 through 18 in FIG. 79). Element 1 measures the approximate optical flux of the unscattered light. Element 2 measures the low angle scatter for all scattering planes. Elements 3 through 18 measure the scattered light in 8 different scattering planes (2 detection sides per scattering plane for a total of 16 detectors). For example, detector element 4 and detector element 12 measure the positive and negative scattering angular ranges for a single scattering plane. Actually, each scattering plane is the sum of scattering over a small range of scattering planes, around the center scattering plane for that wedge segment. Sometimes the positive and negative angular ranges will be the same, if the intensity is uniform across the particle and if the crossection of the particle in the scattering plane has rotational symmetry about an axis perpendicular to the scattering plane. Then only detectors 3 through 10 (half of the detector array) would be needed to cover all of the scattering planes. This source uniformity could be insured by using an appropriate attenuation profile across the beam at aperture 1 or diffractive beam shaper as discussed previously. If the intensity uniformity of the source focused spot or particle crossectional symmetry cannot be insured, the positive and negative sides of each scattering plane should be measured separately as shown in FIG. 79. The scattering angle range for detector 1 is limited by the size of lens 3. Typically, a single lens can measure up to scattering angles of approximately 60 degrees. The nonspherical mirror segment collects light scattered at higher angles and focuses this light through aperture 3, which is also in an image plane of the source focal spot in the sample cell. The shape of the nonspherical mirror is designed to minimize the aberrations between the source focal plane in the sample cell and aperture 3. For example, the nonspherical mirror could be a segment of an ellipsoid of revolution, where the source focus in the sample cell and aperture 3 are each located at different foci of the ellipsoid. This aperture 3 defines a restricted scattering volume as shown previously in FIGS. 43 and 45. The light passing through the aperture is projected onto a second detector array, which is similar to that shown in FIG. 79. However, elements 1 and 2 will not be needed for detector array 2 because they are only effective at low scattering angles, where the scattered intensity does not change significantly for various scattering planes. Detector arrays 1 and 2 are oriented so that the bisector of element 3 is parallel to the particle flow direction. Then each element on detector array 2 will provide the scattered light signal at higher scattering angles for the same scattering plane of the corresponding detector element in detector array 1. For each scattering plane, the signals from elements 1 and 2, the 2 elements in that scattering plane from detector array 1, and the 2 elements in that scattering plane from detector array 2 will determine the "effective dimension" in that plane for that particle. Since these calculated "effective dimensions" are not totally independent of each other, they must be calculated from a set of simultaneous equations, one equation from each scattering plane. However, the advantage using many scattering planes is that the directions of the minimum and maximum dimension can be found quickly by comparing the ratio of the high and low angle scattering for each scattering plane. Fewer scattering planes would require much more computation time to solve for the dimensions of a randomly oriented particle, using iterative inversion of the equations. However, when many scattering planes are measured, the major and minor axes, and orientation, of the randomly oriented particle can be found quickly by inspection of flux ratios (see later in FIG. 89). One of the scattering planes should be parallel to the flow of the particles, because the major or minor axis of each particle is more likely to be parallel to the flow direction, particularly in accelerating flow which may occur from a crossectional area change in the sample cell. This crossectional area change may be designed into the flow path to provide the flow acceleration and particle orientation parallel to one of the measured scattering planes.

Figure 80:
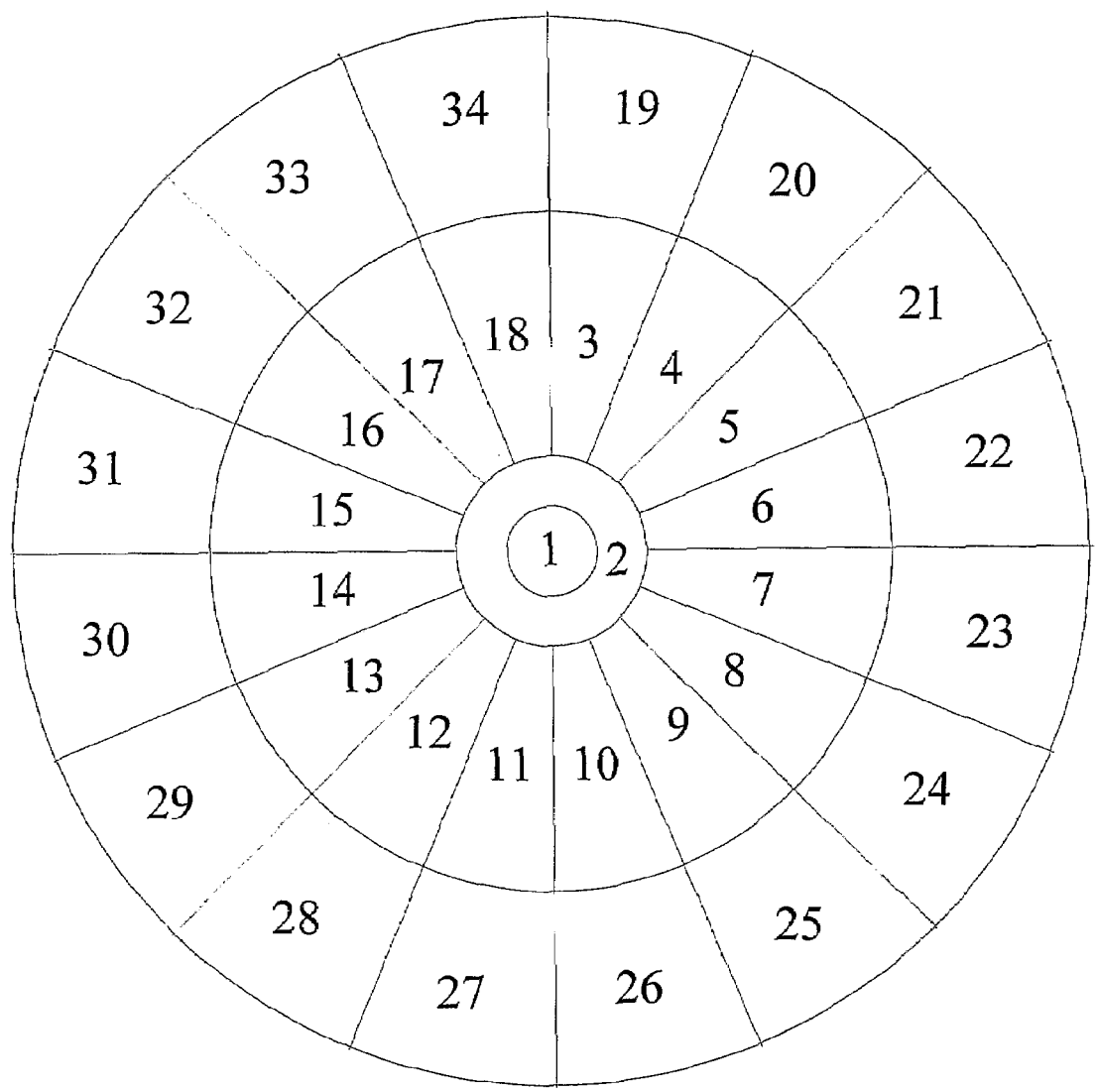
FIG. 80 provides a diagram showing an array of detector elements or optical elements which measure scattered light in multiple ranges of scatter planes and scattering angles, where each group of scattering planes is further divided into ranges of scattering angle, according to the present invention.

In order to increase the range of dimensions which can be measured, more scattering angular ranges must be measured. For example, FIG. 80 shows a detector array which measures two scattering angle ranges for each of the positive and negative scattering sides of each scattering plane. For example, elements 4 and 20 are low and high angle ranges for the positive scattering side and elements 12 and 28 are low and high angle ranges for the negative scattering side of the same scattering plane. These types of detector arrays are easily fabricated in custom silicon photodetector arrays. When very small particles are measured, silicon photodetector arrays may not have sufficient signal to noise to detect the very small scattering intensities. In this case, photomultipliers or avalanche photodiodes may be used, but at much greater expense for manufacture of custom arrays. One solution to this problem is to replace the custom detector array with an array of diffractive, Fresnel, or binary lenses and rout the light from each element of the diffractive optic array to a separate element of a commercially available (inexpensive) linear or 2-dimensional detector array, which could be made of PMT elements. However, it is claimed that any diffractive optic array could be replaced by a detector array with elements of the same shape, if that option is affordable. Arrays of conventional curved surface lenses, diffractive lenses, Fresnel lenses, or binary lenses are all included in the terms optic array or diffractive optic array used in this disclosure. The diffractive optic array would consist of a separate diffractive lens structure covering the aperture of each detector element shape in FIG. 79 or 80. Each diffractive lens would have a separate optical axis. Therefore, each diffractive lens element (or segment) would focus the scattered light captured by the aperture shape of that lens element to a separate point behind the lens array. FIG. 81 shows a lens array, where each detection element section contains a lens with a different optical axis. This idea will work for any types of lens arrays: spherical, nonspherical, diffractive, binary, and Fresnel lenses. FIG. 81 shows a front view of the diffractive or binary lens array, where the curved lines inside each detection element segment represent the diffractive optic structure, whose center is the optical axis of that lens element. The optical axis, of the element corresponding to detector element 1 in FIG. 80, is approximately in the center of that element. The optical axis, of the element corresponding to detector element 2 in FIG. 80, is located off of center of the array to shift the optical axis away from that of element 1.

Figure 82:
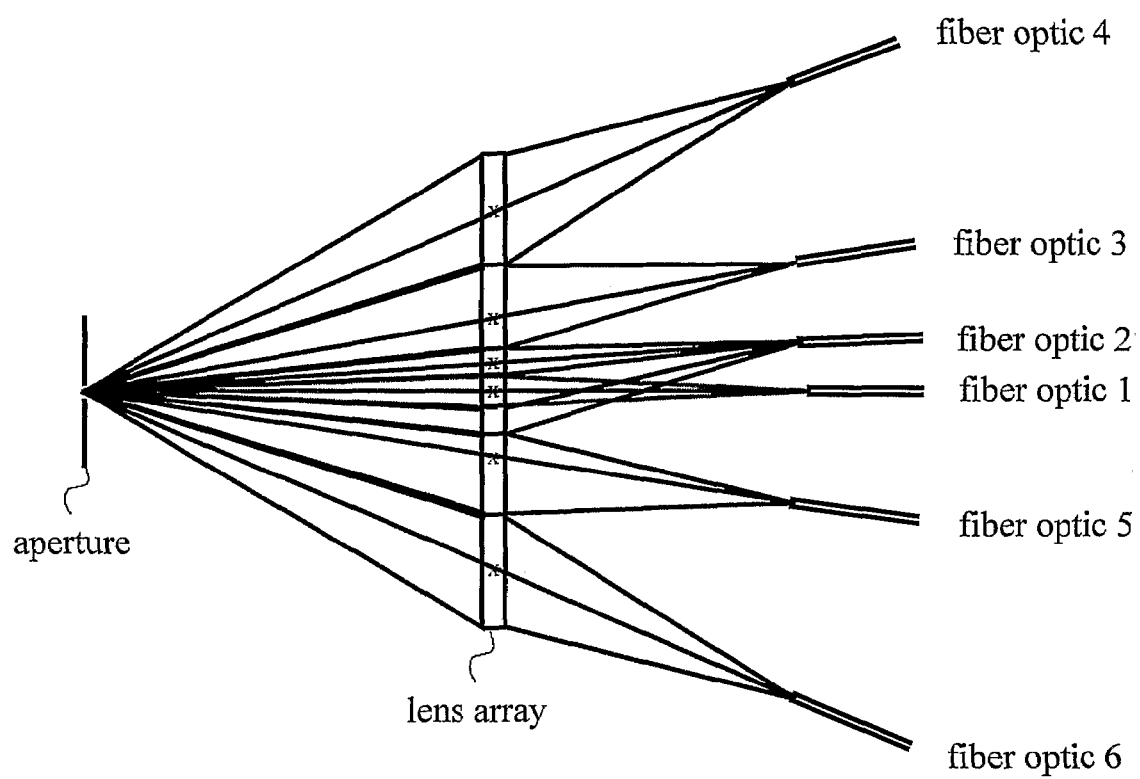
FIG. 82 provides an optical schematic diagram of the diffractive optic of FIG. 81, as used to separate and distribute scattered light among a group of fiber optics.

To demonstrate this concept, consider the elements with optical axes marked with "x", in the front view (FIG. 81) and side view (FIG. 82) of FIG. 81, and the corresponding element numbers in FIG. 80. FIG. 82 shows the paths for light rays which pass through aperture 2 in FIG. 78. The aperture in FIG. 82 could be aperture 2 or aperture 3 in FIG. 78. The lens element for detection element 1 collects the light from the unscattered light beam and focuses that light into fiber optic 1, as shown in FIG. 82. The annular lens element for detection element 2 collects the scattered light at the lower scattering angles and focuses that light into fiber optic 2, as shown in FIG. 82. All of the light from the annular segment of element 2 is focused to one fiber optic, because that annular section is an annular section of one lens element with an optical axis which is shifted from the center of the lens array. FIG. 82 also shows the scattered light focused by other lens elements in the same scattering plane into fiber optics 3, 4, 5, and 6. Each lens element has a separate optical axis so that light passing through aperture 2 (FIG. 78) will be focused into a separate fiber optic for each lens array element, which are shaped to collect the scattered light over the appropriate range of scattering angles for each scattering plane. Each lens element focuses the light from that element into a separate fiber optic, which carries that light to a separate element of a detector array, which may be any type of detector array, including 2 dimensional array or linear arrays. Each fiber optic might also carry light to separate detectors, which are not in an array. Therefore, the detector array does not need to have the shapes of the lens elements so that commercially available (non-custom) detector arrays can be used. And also the detector elements can be much smaller than the lens elements, providing much lower noise and lower cost. The cost of fabricating the custom lens array is much less than the cost of fabricating a custom photomultiplier detector array or silicon detector array. Spherical lens arrays can be molded into plastic or glass. And diffractive lens arrays can be molded or patterned (lithography) into nearly planar plastic or glass plates. The choice of positions for the optical axis for each element should be optimized to reduce optical aberrations. In some cases, the optical axis may lie outside of the lens element. Also, the optical axes could be arranged so that the focused array of spots conforms to the configuration of a 2 dimensional detector array so that the spots can be focused directly onto the detector array, eliminating the fiber optics. This could also be done with linear arrays by creating a linear array of optical axes in the lens array.

The same technique can be used for aperture 3 by replacing detector array 2 (see FIG. 78) with a lens array whose elements are coupled to a separate detector array through fiber optics (or directly coupled to the detector array, without fiber optics, as described above). In this case, elements 1 and 2 may not be needed, because the scattered light distribution from the non-spherical mirror segment has a hole in the center where low scattered light is not captured. The high angle scattering should be separated into different scattering planes due to the high degree of asymmetry in the scattering pattern at higher scattering angles, so the scattered light in annular segments would not be useful.

This lens array idea is most effective for large numbers of detection elements. For smaller numbers of elements, each element could have a separate wedge prism behind it to divert the light to a lens which would focus it onto a particular fiber optic or detector element. But still the point is to eliminate the need for a custom detector array, to reduce the detector element size to reduce noise, and to allow use of highly sensitive detectors such as photomultipliers, which have limited customization.

Quadrant detectors are commercially available for most detector types, including silicon photodiodes and photomultipliers. FIG. 83 shows a method to use two quadrant detectors to measure scattered light from 8 adjacent scattering planes by using a mask which is positioned on top of the quadrant detector. The first quadrant detector replaces each of the detector arrays in FIG. 78. The second quadrant detector captures scattered light at the same distance from the aperture 1 (or aperture 2) as the first quadrant detector by diverting a portion of the beam with a beam splitter placed on front of the first quadrant detector. Each mask is designed and each quadrant detector is oriented as shown in FIG. 83, so that all 8 scattering planes are measured by the two quadrant detectors. In this way, two inexpensive quadrant detectors can measure the equivalent scattering planes measured by one expensive custom 8 element custom detector array. Typically, the central portion of the mask is designed to block the unscattered light from the source beam and to define a minimum scattering angle for each detector element. The detection concepts described in FIGS. 79, 80, 81, 82, and 83 can also be used in the other particle shape measuring optical systems, which were described previously in this disclosure.

Figure 84:
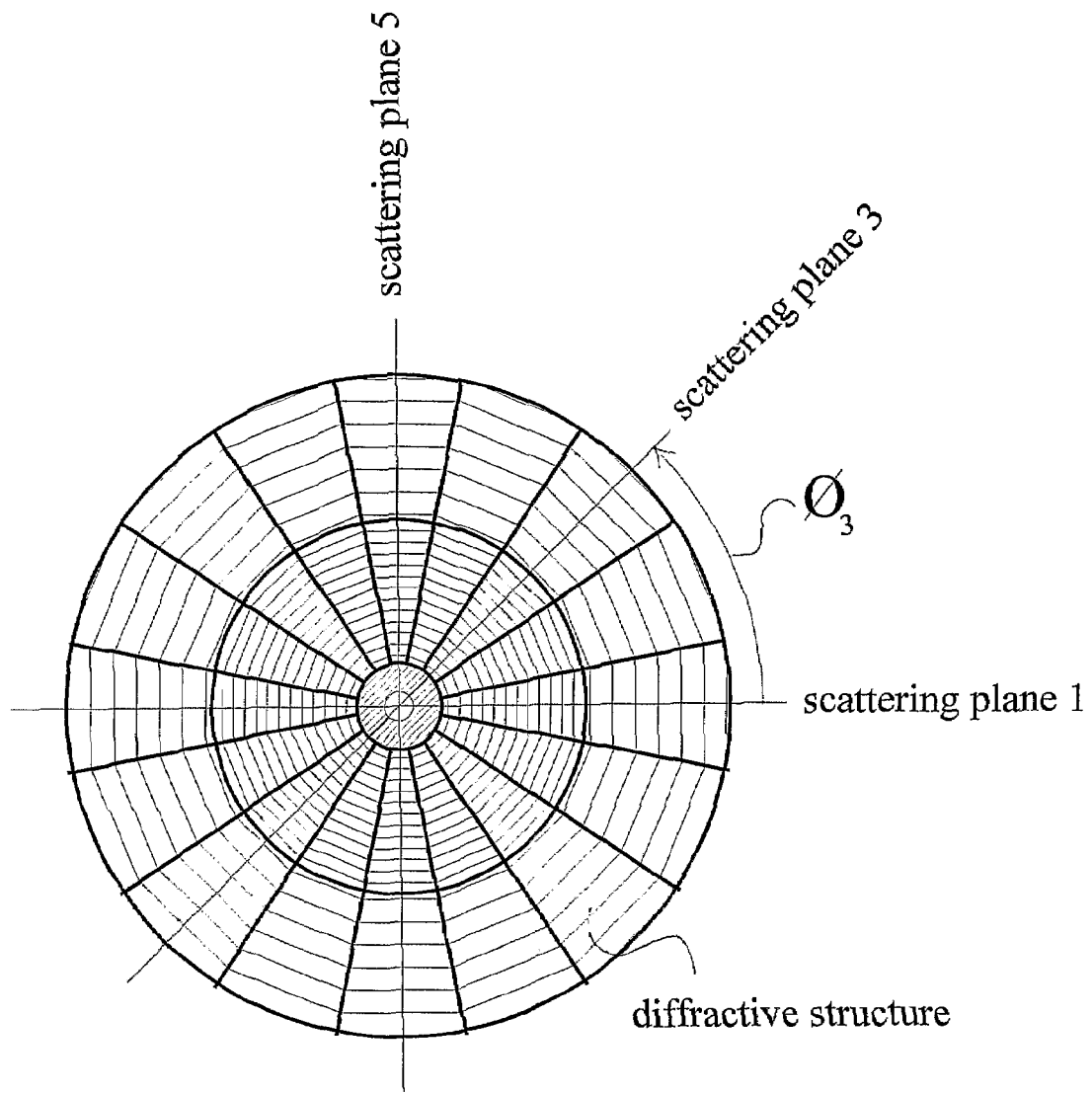
FIG. 84 provides a diagram of a diffractive optic, where different segments consist of linear diffractive gratings, the diagram showing three different center scattering planes, wherein each center scatter plane is the center of a wedge which collects scattered light from a range of scattering planes, according to the present invention.
Figure 85:
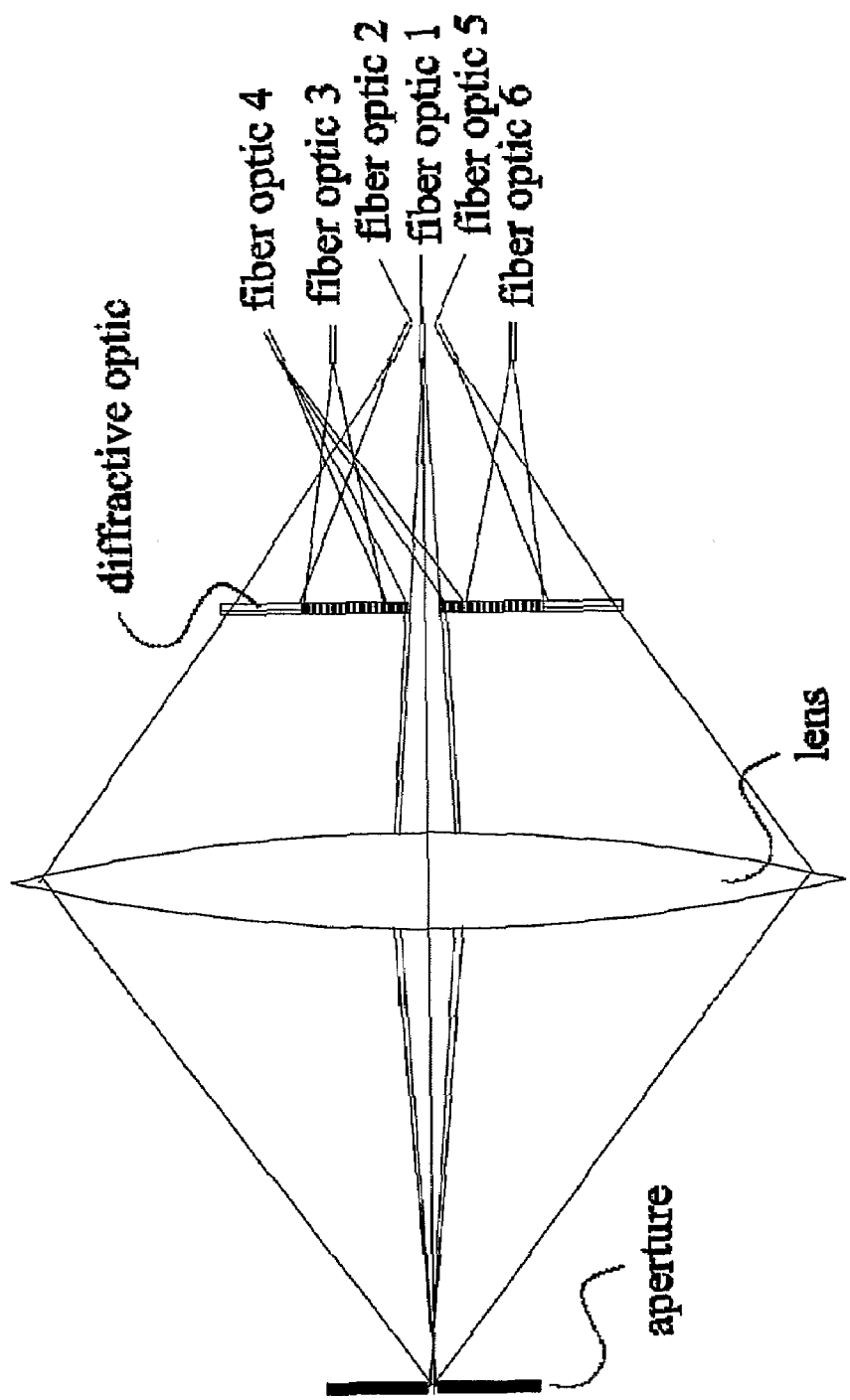
FIG. 85 provides an optical schematic diagram of a hybrid diffractive/conventional lens system, which utilizes diffractive optics as shown in FIG. 84.

FIG. 84 shows a diffractive optic, where different segments consist of linear diffractive gratings which are designed to diffract nearly all of the light into one diffraction order. This diffractive optic is used in a hybrid diffractive/conventional lens system as shown in FIG. 85. The diffractive optic is normal to the optical axis of the optical system. The aperture in FIG. 85 is the same as aperture 2 in FIG. 78. And this design can also be used with aperture 3 in FIG. 78, without the need for the central hole and annular ring segment, because aperture 3 passes only high angle scatter. Consider the case with aperture 2 in FIG. 78. The scattered light is collected by the lens in FIG. 85. The diffractive optic (as shown in FIG. 84) in the back focal plane of the lens, diffracts the light incident on each segment of the diffractive optic into various directions. When the aperture hole is small and only single particles are measured, the diffractive optic does not need to be placed in the back focal plane of the lens, but the diffractive lens array must be scaled to match the marginal rays of the lens in the plane in which it resides. The light from each segment is nominally focused to the image plane of the aperture. However, the light from each segment is focused to a different position on that plane, because the linear grating structure in each segment is oriented in a different direction from the grating structures in other segments. Each wedge segment of the diffractive optic is split into 2 sections, each with a different grating line spacing and diffraction angle. These 2 wedge shaped segments collect scattered light in 2 different angular ranges in each of various scattering planes. For example, scattering planes 1, 3, and 5 are shown in FIG. 84. In addition, there is central hole and a surrounding annular region. The central hole passes the unscattered light beam and the surrounding annular region collects scattered light at very low scattering angles in all scattering planes. At low scattering angles, the scattered light is not strongly dependent upon scattering plane and this annular segment provides a measure of low angle scattering to be used as a basis for each of the scattering planes. FIG. 85 shows the light rays in one of the scattering planes. FIGS. 84 and 85 show the case where the spatial frequency of the lower scattering angle segments is higher than the spatial frequency of the higher scattering angle segments. Hence the separated beams cross each other after the diffractive optic, because the diffraction angle of the lower scattering angle segments is higher than that for the higher scattering angle segments. This could also be reversed, where the spatial frequencies are higher for the higher scattering angle segments. In this case, the focused beams would still be separated at the plane of the fiber optics, but the beams may not cross each other.

The shape of detector array or optic array elements is not limited to wedge shape. Other shapes such as linear shapes shown in FIG. 33 could be used.

Figure 86:
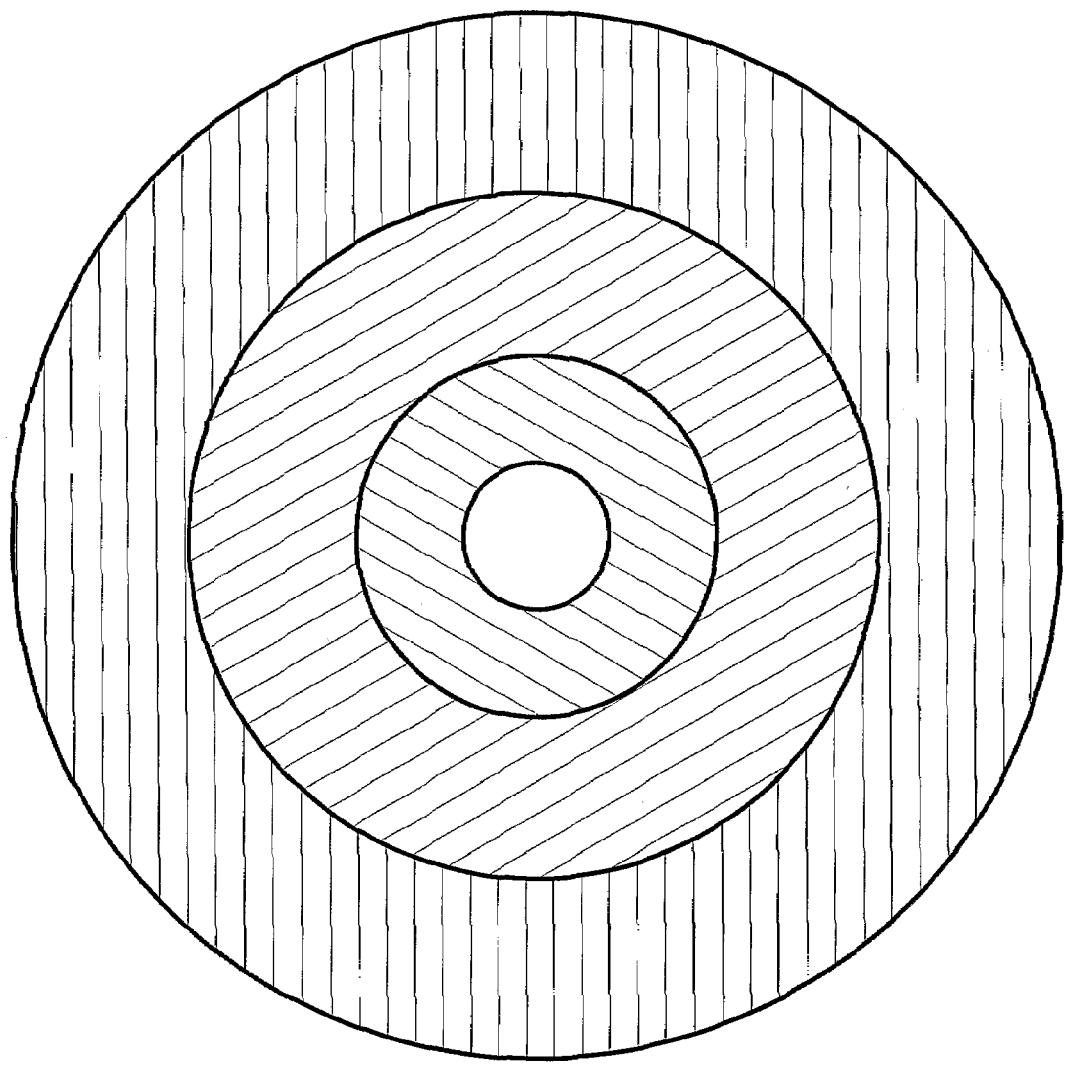
FIG. 86 provides a diagram of an optical element which includes multiple annular regions, each with a different diffractive grating, according to the present invention.

This method can also be used to measure "equivalent particle diameter" without any shape determination. In this case, a diffractive optic as shown in FIG. 86 could be used. This diffractive optic consists of annual rings which define multiple scattering angle ranges. The signals from these annual rings are independent of particle orientation and will only provide "equivalent particle diameter".

When using a photomultiplier (PMT), one must prevent the detector from producing large current levels which will damage the detector. This damage could be avoided by using a feedback loop which reduces the anode voltage of the PMT when the anode current reaches damaging levels. In order to avoid non-linear behavior over the useful range of the detector, the change of anode voltage should be relatively sharp at the current damage threshold level, with very little change below that level. The response time of the feedback loop should be sufficiently short to prevent damage. The feedback signal could also be provided by a premeasuring system as shown in FIGS. 49, 49B, and 51.

Another important point is that any of the static scattering techniques described in this disclosure can be applied to particles which are prepared on a microscope slide, which is scanned through the interaction volume instead of flowing a particle dispersion through the interaction volume. This provides some advantages: the particles are confined to a thin layer reducing the number of coincidence counts and the detection system could integrate scattered light signal for a longer time from smaller particles, to improve signal to noise, by stopping the scan stage or reducing the scan speed when smaller particles are detected (this can also be accomplished by slowing the flow rate in the dispersion case). However, preparing a slide of the particles for analysis, greatly increases the sample preparation time and the potential for sample inhomogeneity. When a cover slip is placed onto the dispersion, the smaller particles are forced farther from their original positions, distorting the homogeneity of the sample.

The scattering signal currents from elements on these detector arrays are digitized to produce scattered signal vs. time for each detector element. The data from each detector element is analyzed to produce a single value from that element per particle. This analysis may involve determining the time of maximum peak of the detection element with largest scatter signal and then using the same time sample for all of the other detection elements. Also the peak can be integrated for all detection elements to produce a single value for each element. Also the methods described previously for pulse analysis can be employed, including the methods (FIG. 28) for eliminating events which are not particles. The final single value for each detector element represents the scattered light flux collected by that element. In the following analysis, the following definitions will be used:

The integral of $F(x)$ between $x=x1$ and $x=x2$ is given by:

$$INT(F(x), x1, x2)$$

The sum of terms of $Fi(x)$ over index i from $i=n$ to $i=m$ is given by:

$$SUM(Fi(x), i=n, i=m)$$

Where $Fi(x)$ is the ith term

Each scattering angle corresponds to a radius, measured from the center of the source beam, in the detection plane. For the case shown in FIG. 78, z is the distance between aperture 2 and detector 1 (or between aperture 3 and detector array 2). Then the relationship between scattering angle $\theta$ and the radius r on the detector is given by:

$$r = Z*\tan(M\theta)$$

where M is the angular magnification of the optical system (lens 3 for detector array 1 and the nonspherical mirror segment for detector array 2). In the case of aperture 3 and detector array 2, the $\theta$ in the above equation is related to the actual scattering angle through a simple equation which describes the angular transformation of the nonspherical mirror segment.

Consider the case of rectangular particles, with dimensions da and db. Then the scattered flux (flux integrated over the pulse, peak flux value of pulse, etc.) collected by the ith detector element can be described by:

$$Fij = INT(I(da, db, \alpha, \emptyset i, r)*Wij(r), r1ij, r2ij)$$

I is the scattered intensity. $\emptyset i$ is the bisecting angle of the intersection of the ith scattering plane with the detector plane in the detector plane, as illustrated in FIG. 84 for the $3^{rd}$ scattering plane. The scattering plane (which contains the scattered ray and the incident light beam) is perpendicular to the detector plane (which is the plane of FIGS. 79, 80, and 83 for example). $Wij(r)$ is the weighting function of scattered light as a function of r for the jth detector aperture, with limits between r1$ij$ and r2$ij$, of the detector for the ith scattering plane.

Let F1 be the flux measured detector element 1 in FIG. 80 and let F2 be the flux measured detector element 2 in FIG. 80. Then the following sets of simultaneous equations can be formed to solve for the dimensions da, db, and random orientation, $\alpha$, of the particle, where Ri is a ratio of two fluxes.

$$Fi = Fij$$

$$Ri = Fij/Fik$$

$$Ri = Fij/F2$$

$$Ri = Fij/F1$$

$$Ri = Fij/Fkj$$

$$Ri = FijA/FijB$$

Recognize that i indicates the ith scattering plane and ij indicates the jth detector in the ith scattering plane. FijA and FijB are the corresponding detector elements from two different detector arrays (A and B), each with a different $Wij(r)$, as shown in detector pairs A and B in FIG. 74, and diffractive optics 1 and 2 in FIG. 87. This equation also holds for more than two detectors (Ri=FijC/FijB, etc.). Also, for all other Ri equations, Wij can be the same or different for the numerator F and the denominator F in the ratio. The above simultaneous equations can be formed from the Fij values measured from each particle. These equations are solved for da, db, and $\alpha$ by using various search, optimization, and regression methods. In most cases, the equations will be non-linear functions of these unknowns, requiring iterative methods for solution. The computation of theoretical values for scattered intensity $I(da, db, \alpha, \emptyset i, r)$, of nonspherical particles, requires long computer time. This is particularly problematic as this computation must be accomplished for each counted particle. Also numerical integration of these functions to produce Fij values during the iterative optimization process requires far too much computer time. This computer time can be reduced by fitting a series of explicitly integratible functions to each of the theoretical $I(da, db, \alpha, \emptyset i, r)$ functions. For example consider the following power series form for the $I(da, db, \alpha, \emptyset i, r)$ and $Wij(r)$ functions:

$$Wij = SUM(Qp(j)*(r^p), p=0, p=pmax)$$

$$Ii = SUM(Cm(da, db, \alpha, \emptyset i)*(r^m), m=0, m=mmax)$$

Where $x^p = x$ to the pth power and $x*y =$ product of x and y.

$$Fij = INT(I(da, db, \alpha, \emptyset i, r)*Wij(r), r1ij, r2ij)$$

$$Fij = INT(SUM(Cm(da, db, \alpha, \emptyset i)*(r^m), m=0, m=mmax)*SUM(Qp(j)*(r^p), p=0, p=pmax), r1ij, r2ij)$$

$$Fij = SUM(Bq(da, db, \alpha, \emptyset i)*(r2ij^{(q+1)})/(q+1)), q=0, q=pmax+mmax)-SUM(Bq(da, db, \alpha, \emptyset i)*(r1ij^{(q+1)})/(q+1)), q=0, q=pmax+mmax)$$

Then the previously listed sets of simultaneous equations can be formed from these equations for Fij. Where Bq are coefficients which are products of values of Cm and Qp, which are all known functions of da, db, $\alpha$, and $\emptyset i$. This concept can easily be extended to other particle types (just assume da and db to be the major and minor axes for an elliptical particle) and particles with more dimensions, such as pentagons, etc. In each case, the model must expand to account for the added dimensions dc, dd, de, etc.

$$Fij=INT(I(da, db, dc, dd, de, \ldots, \emptyset i, r)*Wij(r), r1ij, r2ij)$$

Figure 89:
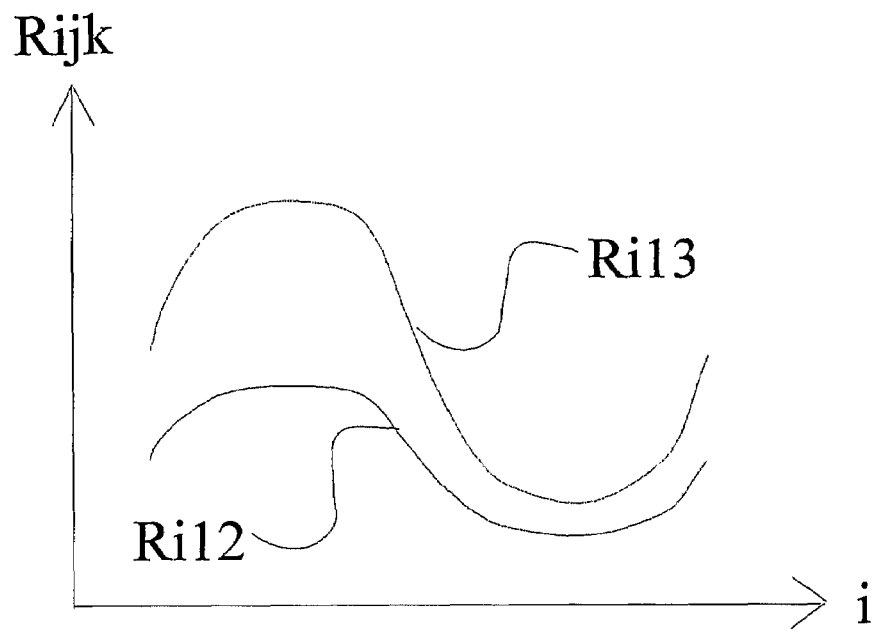
FIG. 89 provides a graph which plots ratios of scatter parameters as a function of center scattering plane orientation, according to the present invention.
Figure 90:
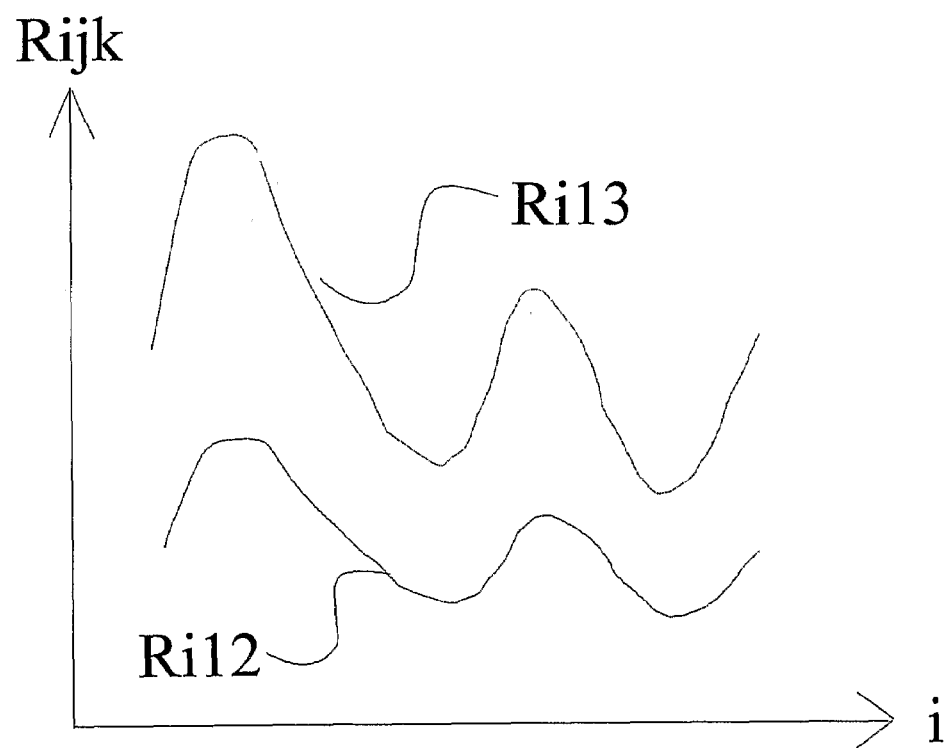
FIG. 90 provides a graph showing plots of ratios of scatter parameters as a function of center scattering plane orientation for a particle with more than two dimensions, according to the present invention.

In order to solve for particle types with larger number of dimensions (i.e. octagons, etc.), sufficient scattering planes and detectors must be used to provide a fully determined set of simultaneous equations. In other words, the number of equations should be greater than or equal to the number unknowns, which include the dimensions, da,db,dc, . . . etc. and the particle orientation, α. However, as indicated before, the solution of these equations can be computationally time consuming. The measurement of scattered light in many scattering planes can reduce the computational time, because the extrema of the dimension function can be found quickly. For example, take the case of the rectangular particle, where da, db, and α could be solved for with only measurements in 3 scattering planes. The solution of these 3 equations may require iterative search and much computer time per particle. However, if scattering is measured in many more scattering planes, the major and minor axes of the rectangle can be determined immediately, eliminating the requirement for determining the particle orientation α or reducing the range of α for the search solution. For example, if we interpolate a plot of Ri vs. Øi (or Rijk vs. i), we will obtain a function (or functions) with a maximum at Ømax and a minimum at Ømin, as shown in FIG. 89. If Ri is the ratio of the high angle flux divided by the low angle flux in the ith scattering plane, then the direction Ømin will provide major axis and the direction Ømax will provide minor axis of the particle; and the R values for those directions will provide the particle dimensions in those directions. This technique can be extended to particles with more dimensions, as shown in FIG. 90, where multiple extrema indicate the Ødirection and effective particle dimension in that direction. Since these dimensions may not be completely independent, this computation may require iterative minimization of the RMS error between Fij (measured) and Fij (theoretical) using various search, optimization, and regression methods. These methods use a first quests to the unknowns (all the dimensions and α) from which the Fij(theoretical) is calculated. Then the difference between Fij (measured) and Fij (theoretical) is used to refine the next guess for the unknowns from which the next Fij (theoretical) is calculated. And this loop is repeated until the fit between all Fij(measured)'s and Fij(theoretical)'s is sufficient, where i=scattering plane index and j=detection array element or lens array element index in a certain scattering plane. This iterative loop is run many times until one of the following RMS errors are minimized.

$$Error=SUM((Fij(\text{measured})-Fij(\text{theoretical}))^2)$$
summed over all $ij$ $$Error=SUM((Rijk(\text{measured})-Rijk(\text{theoretical}))^2)$$
summed over all $ijk$ All of the detector, mask, and diffractive optic configurations shown in this disclosure are only examples. This disclosure claims the measurement of any number of scattering angular ranges in each of any number of scattering planes, as required to determine the shape and size of each particle.

All segmented detector arrays or lens arrays could be replaced by 2-dimensional detector arrays. In this case the inverse 2-dimensional Fourier Transform of the spatial distribution of detector element flux values would produce a direct 2-dimensional function of the particle shape, in the Fraunhofer approximation. The dimensions of the contour plot (perhaps by choosing the 50% contour of the peak contour) of this 2-dimensional inverse Fourier Transform function will provide the outline of the particle directly, for particles which are modeled by the Fraunhofer approximation. However, the size range of this type of array (per number of detector elements) is not as efficient as the wedge shaped scattering plane arrays described previously, because the detector elements in the 2-dimensional array are all the same size. When the particles become large enough to produce scattered light in only the lowest scattering angle detector element, the size determination becomes difficult. This problem could be solved by using a custom array, where low scattering angle elements are smaller than larger scattering angle elements. This progression of element size with increasing scattering angle can also be accomplished with a linear array which follows a lens or diffractive optic with non-linear distortion. The lens or diffractive optic distorts the scattering pattern so that the pattern is spread out near the center and compressed more at higher radii (larger scattering angles) in the pattern. In this way, detector elements closer to the center of the pattern will subtend a smaller scattering angular width than elements farther from the center. This would increase the size range of the detector array and still allow use of standard CCD type linear arrays. However, due to the limited dynamic range of most CCD arrays, a single PMT or other large dynamic range pre-sensor, placed upstream of the CCD array, could provide some indication of scattering signal level before the particle arrives in the view of the CCD array, similar to the systems shown in FIGS. 67 and 68. Then the source power level or CCD electronic gain could be adjusted during the CCD data collection to optimize the signal to noise and fully utilize the range of the analog to digital converter on the CCD.

Figure 87:
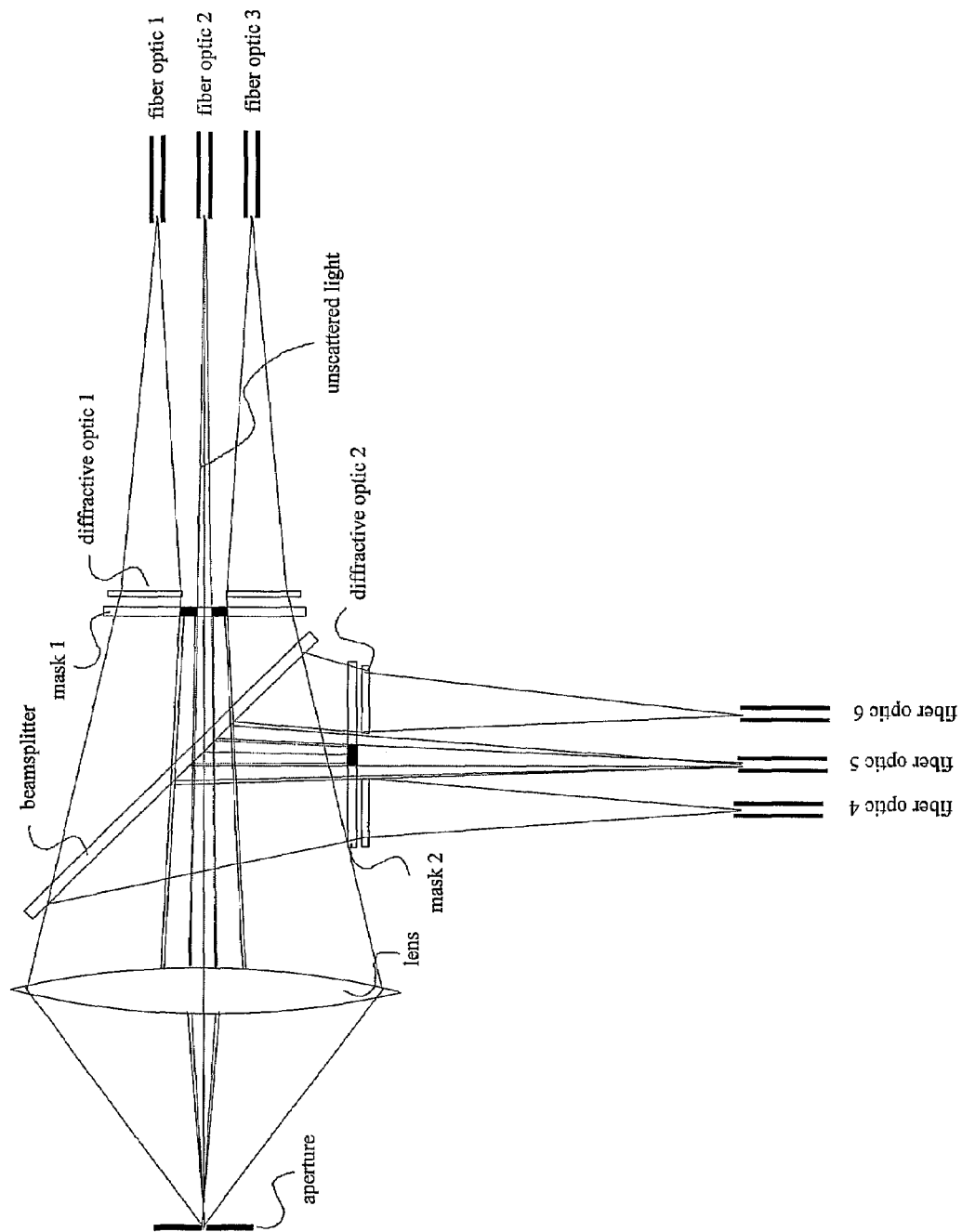
FIG. 87 provides a schematic diagram of an optical system, which utilizes two masks and two optical arrays, or diffractive optics, according to the present invention.
Figure 88:
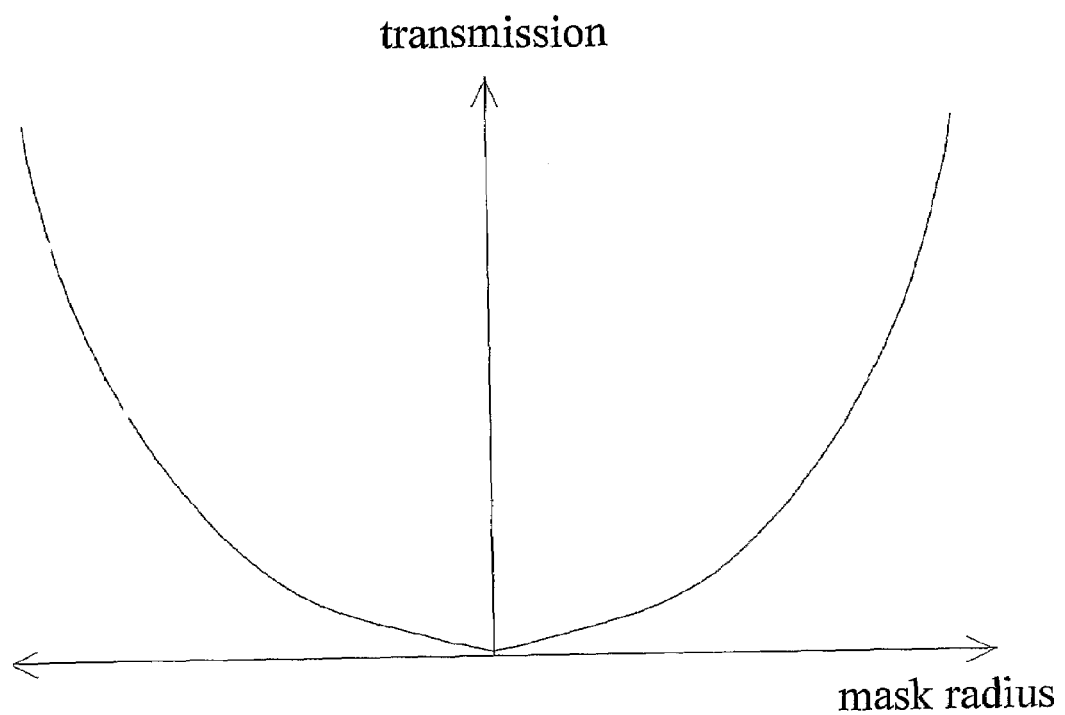
FIG. 88 provides a graph showing an example of a radial transmission function for an optical mask, according to the present invention.

This wider size range can also be obtained by using different weighting functions (Wij) for two different detector elements which view the same range of scattering angle in the same scattering plane, as described previously. As long as the Wij functions are different for the two measurements, the ratio of those scattered flux values will be size dependent over a large range of particle size and will be relatively insensitive to position of the particle in the beam. The Wij function can be implemented in the detector element shape, as shown in FIG. 76, and/or by placing an attenuation mask, which has varying attenuation along the direction of changing scattering angle, over the detector elements of one the arrays or with different Wij functions on each of two or more arrays which see the same scattering angle ranges and scattering planes. This idea can be implemented in the system shown in FIG. 78, using the detection module shown in FIG. 87. The aperture in FIG. 87 could be either aperture 2 or aperture 3 in FIG. 78. In this case, the scattered light (and incident beam when used with aperture 2) is focused by a lens, through a beamsplitter, onto two optical arrays, which are diffractive arrays using conventional lens/diffractive array hybrid as in FIG. 85 (or conventional molded or diffractive optics if no single conventional lens is used). The lens arrays (examples are shown in FIGS. 79, 80, 84, 86) are used to divert the scattered light from different array elements to different positions in the image plane of the beam focus in the cell so that the flux from each element can be collected separately by fiber optics or detectors. The lens array in FIG. 87 is similar to that in FIG. 79, just for illustration, but any of the previous lens arrays could be used in this design. There is a mask on front of each lens array which provides selection of center hole (element 1 in FIG. 78) or the annular ring (element 2 in FIG. 78). This mask also provides light attenuation which varies along the radius (or scattering angle) of the mask, as shown by the transmission function, for example only, in FIG. 88. This transmission function can take many forms, but as long as the radial transmission function of mask 1 is different from the radial transmission function of mask 2, the ratio of flux from corresponding lens elements in diffractive optic 1 and diffractive optic 2 (as captured by the fiber optics or detector elements) will provide dimensional information for the particle in the scattering plane of that element. For example transmission functions for mask 1, T1$ij$, and for mask 2, T2$ij$, could have many cases including:

Case 1: T1$ij$=1 (constant transmission), T2$ij$=r

Case 2: T1$ij$=r, T2$ij$=r^2 where r is the radius along the lens array

Then the effective weighting functions are the product of the transmission functions and the weighting function, Wijs, of the segment or element shape in the detector array or optic array. For wedge shaped segments the shape weighting function is:

$$Wijs=r$$

Hence the effective weighting functions are:

$$W1ij=W1ijs.*T1ij$$

$$W2ij=W2ijs.*T2ij$$

$$R12ij=F1ij/F2ij$$

Where F1$ij$=flux from the jth detector aperture in the ith scattering plane of detector array 1 or optic array 1

Where F2$ij$=flux from the jth detector aperture in the ith scattering plane of detector array 2 or optic array 2

Many combinations of transmission functions will work. This invention disclosure claims the use of any two different W1$ij$ and W2$ij$ functions(using transmission and/or shape weighting functions) and using flux from corresponding array elements, one with W1$ij$ and the other with W2$ij$. Diffractive optic array 1 and diffractive optic array 2 are identical and they are rotated so that each array segment collects scattered light from the same scattering plane as the corresponding element in the other diffractive optic. Then ratio (R12$ij$) of light flux values from these two elements are is used to determine the "effective dimension" of the particle in that scattering plane. However, as described previous, these dimensions are not independent and the full set of simultaneous R12$ij$ equations must be used to solve for the actual dimensions.

In general, we have two cases for measuring 2 dimensional scattering distributions. The detector array can be a set of radial extensions in various scattering planes (as in FIG. 84) or a 2-dimensional array. In first case, we define the array as a function of radius, r, and angle Ø in the detector array or optic array plane, as shown in FIG. 84. In the second case the array is a standard 2-dimensional array (i.e. CCD array) with elements arranged in columns and rows which are defined as a function of x and y. The choice between these cases will be determined from the available computer speed, shape constraints, and particle size range. In order to measure particle shape statistics of a particle sample, an enormous number of particles must be characterized. For example, consider the following case. We are to count particles and characterize them into 25 different dimensional classes. Each class could vary by size or shape. If we want to measure the content of each class to within 5% we need to measure 400 particles per class, if the counting process is Poisson. Therefore we need to measure and characterize 10000 particles. If we want the entire analysis process to take 5 minutes, then we have 30 milliseconds per particle to measure and digitize the scattered light, and solve equations for the shape and dimensions. We could do a full global search for the particle orientation and dimensions using the equations given above. All of the parameters of those equations can be solved from the 2-dimensional scattered intensity distribution in the plane of the detector array or optic array. The theoretical 2-dimensional scattered intensity distribution is calculated using known methods, such as T-matrix and Discrete Dipole Approximation, (see "Light Scattering by Nonspherical Particles", M. Mishchenko, et al.). Then this theoretical intensity distribution is integrated over the areas of each element of detector array or optic array. These values for Fij are calculated for various particle orientations, α, and various particle dimensions. A global search routine would search among these theoretical Fij sets to find the one which best fits to the measured set of Fij. Then the dimensions of that set would be accepted for that particle. While this process will take far longer than 30 milliseconds per particle, it would produce the most accurate determination of particle dimensions and shape. This full search method is claimed by this invention because in some cases, users will be willing to collect data on the optical system computer and then transfer the raw data off-line to a set of parallel processors which continuously crunch data sets 24 hours per day. And also future computers will be capable of doing these computations in the required time. However, for the users, who want their results in real-time (i.e. within 5 minutes) with present personal computers, some of the shortcuts, as described previously, must be employed. In the case of process control, users need results quickly in order to adjust the process parameters in nearly real-time. And also, many times the determined shape and size does not need to be precise because these results only need to correlate to the quality of their product. In general a particle with multiple flat edges will produce a scattering pattern with a radial projection for each edge into a scattering plane which is perpendicular to that edge. So when the ratio data, Rijk, is plotted vs. Øi (or vs. scattering plane) as shown in FIG. 90, one will obtain a maximum in Rijk for each side of a multi-sided particle. So evaluation of Rijk vs. Øi will very quickly determine the orientation of the particles sides and the values of Rijk are then used in a more limited global search routine, which does not have to search over all possible orientations of the particle and over all possible number of particle sides. This will dramatically reduce the search time. Also, the "dimension" of the particle in the direction perpendicular to each side can be determined approximately from Rijk values in the scattering plane which is perpendicular to that side. These values could be used directly to determine "approximate dimensions" of the multisided particle, without a search algorithm, because the approximate dimension can be calculated directly from a theoretical function of Rijk. As the particle model becomes simpler (i.e. rectangle) the orientation and dimensions are calculated immediately by finding the Ømax and Ømin in the Rijk vs. Øi, and then using the Rijk values in those two scattering planes to calculate the dimensions in those scattering planes. If only a few scattering planes are measured, the Rijk function could be interpolated or fit to a theoretical function for the rectangle case, to calculate the exact orientation, which may be between two adjacent scattering planes.

These concepts can be combined with imaging systems to record the image of selected particles after they have passed through the interaction volume. An imaging system could be placed downstream of the interaction volume, with a pulsed light source which is triggered to fire at the correct delay, relative to the scatter pulse time, so that the particle has flowed into the center of the imaging beam during image capture. The pulsed light source has a very short pulse period so that the moving particle has very little motion during the illumination and image capture on a CCD array. The particle is imaged onto the CCD array at high magnification with a lens (microscope objective would be a good choice). In this way, particles which meet certain criteria, can be imaged to determine their morphology.

The alignment of aperture 2 and aperture 3 in FIG. 78, and other related figures, could be accomplished by running a medium concentration sample of sub-micron particles through the sample cell. The concentration is chosen so that a large number of particles are in the interaction volume at the same time so that a constant large scatter signal is seen on the detectors. Then the x, y, and z position of each aperture is adjusted to maximize the scatter signal on the detectors.

Most of the concepts in this disclosure can accommodate aerosol particle samples, by removing the sample cell and by flowing the aerosol through the interaction volume of the incident beam. The effective scattering angles may change due to the change in refractive index of the dispersant.

Figure 93:
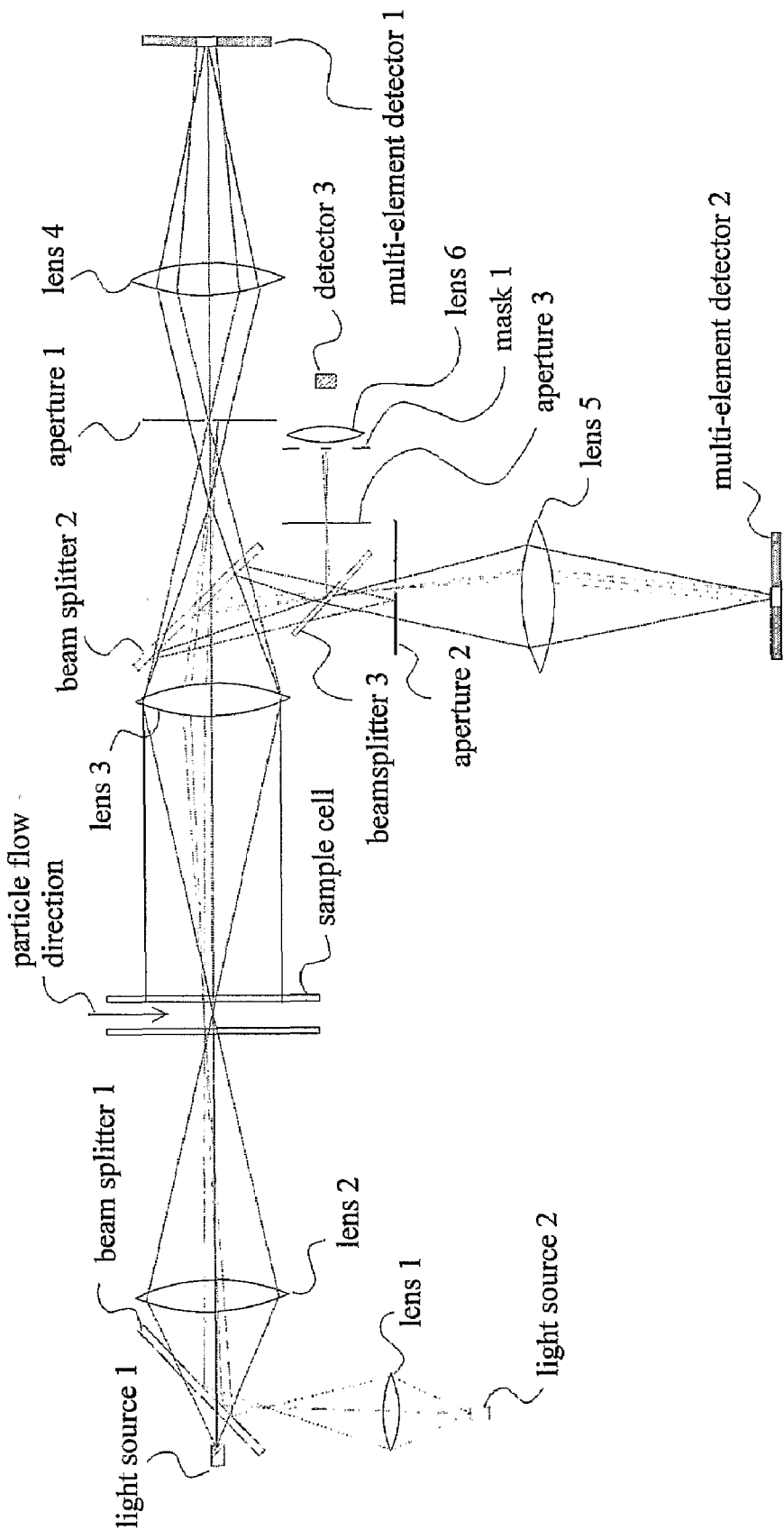
FIG. 93 provides a schematic diagram of an optical system, which provides an upstream scatter detection system to determine the expected scatter signal level for the primary scatter system for each particle, according to the present invention.

In some cases, the dynamic range of detectors will not be sufficient to cover the entire range of scatter signals from the particles. In particular, particles in the Rayleigh scattering range will produce scatter signals proportional to the $6^{th}$ power of the particle diameter. Photomultipliers can also be damaged by large levels of light. FIG. 93 shows an optical system which uses upstream scatter measurement to control the laser power or detection gain (or anode voltage) for a system down stream in particle flow to protect photomultipliers, to maximize the signal to noise, or to avoid detector saturation. Two light sources, light source 1 and light source 2, are combined by beamsplitter 1 and focused into the center of the sample cell to two different locations along the particle flow path. Light source 2 could be magnified to produce a larger spot size in the sample cell for detecting larger particles than the spot from light source 1. However, the other purpose of light source 2 is to detect an oncoming particle before it reaches the focused spot from light source 1. The spot from light source 2 is upstream from the light source 1 spot. The light from both sources and the light scattered from both sources pass through lens 3, which images both light spots to the planes of three apertures, 1, 2 and 3. Apertures 2 and 3, which receive light reflected from beamsplitter 2, block light from the interaction volume of light source 1 but pass light from the interaction volume of light source 2. Likewise, aperture 1, which receives light transmitted by beamsplitter 1, blocks light from the interaction volume of light source 2 but passes light from the interaction volume of light source 1. Therefore multi-element detector 1 sees only light scattered from light source 1; and multi-element detector 2 and detector 3 see only light scattered from light source 2. These multi-element detectors can also be replaced by the optic array systems described previously. Multi-element detector 2 is operated at much lower sensitivity than Multi-element detector 1, which is operated at maximum sensitivity to detect the smallest particles. Whenever a particle, which would saturate and/or damage Multi-element detector 1, passes through light source 2 spot, detector(s) from Multi-element detector 2 or detector 3 will measure the larger amount of scattered light and trigger a circuit to lower the power level of light source 1 or lower the gain (or anode voltage) of Multi-element detector 1 so that Multi-element detector 1 will not be saturated and/or damaged when that same particle passes through the interaction volume for light source 1. The level of adjustment can be variable depending upon the light level measured by Multi-element detector 2 or detector 3. Light source 1 is normally run at maximum power to detect the smallest particles. Light source 1 power is only reduced after a calculated delay time after Multi-element detector 2 detects a potentially damaging or saturating particle scatter signal. After that particle passes through the light source 1 spot, the source 1 power (or gains, anode voltages etc) is reset to maximum. The time delay is calculated from the spacing between the two source spots in the sample cell and the particle flow velocity. The multi-element detector arrays are in the focal plane of lens 4 or lens 5. Notice that the blue light rays indicate that multi-element detector arrays 1 and 2 are effectively, at infinity, in the back focal planes of lenses 4 and 5. These lenses place the detectors at infinity so that the effects of finite pinhole size in apertures 1 and 2 do not cause smearing in the scatter pattern. Typically the pinhole sizes are small enough so that lens 4 and lens 5 are not needed. The advantage of using lens 2 for both sources is not only the cost of manufacture. This design allows the two source spots in the sample cell to be very close to each other, insuring that all particles which flow through the light source 1 spot will have also previously flowed through the light source 2 spot and been detected by multi-element detector 2, even in the event of any flow anomalies in the cell. To provide a large size dynamic range, the sample cell spot size for light source 2 may be much larger than the spot size for light source 1, in order to measure much larger particles. Then many particles which pass through source 1 spot will flow around source 2 spot. In this case, a third system is added using beamsplitter 3 and aperture 3. The pinhole of aperture 3 is smaller than aperture 2 to only pass scatter from the portion of Source 2 spot which is directly above the Source 1 spot. In this way, detector 3 will only see the particles which will eventually pass through the source 1 spot. So detector 3 is used to set the source 1 power level or detector 1 gain (or anode voltage) using the time delay described above. Multi-element detector 2 measures the size of larger particles from a much larger interaction volume as defined by aperture 2. For example, the spot sizes in the sample cell could be 20 microns for light source 1 and 500 microns for light source 2, but aperture 3 would only allow detector 3 to see scatter from a 30 micron portion, of the Source 2 spot, which is directly above the 20 micron spot of Source 1. The 30 micron portion could be slightly larger than the 20 micron spot to accommodate slight flow direction misalignment, because the larger size will only trigger the source 1 power drop more times than needed, but it will guarantee that no particle scatter will saturate and/or damage multi-element detector 1.

Figure 96:
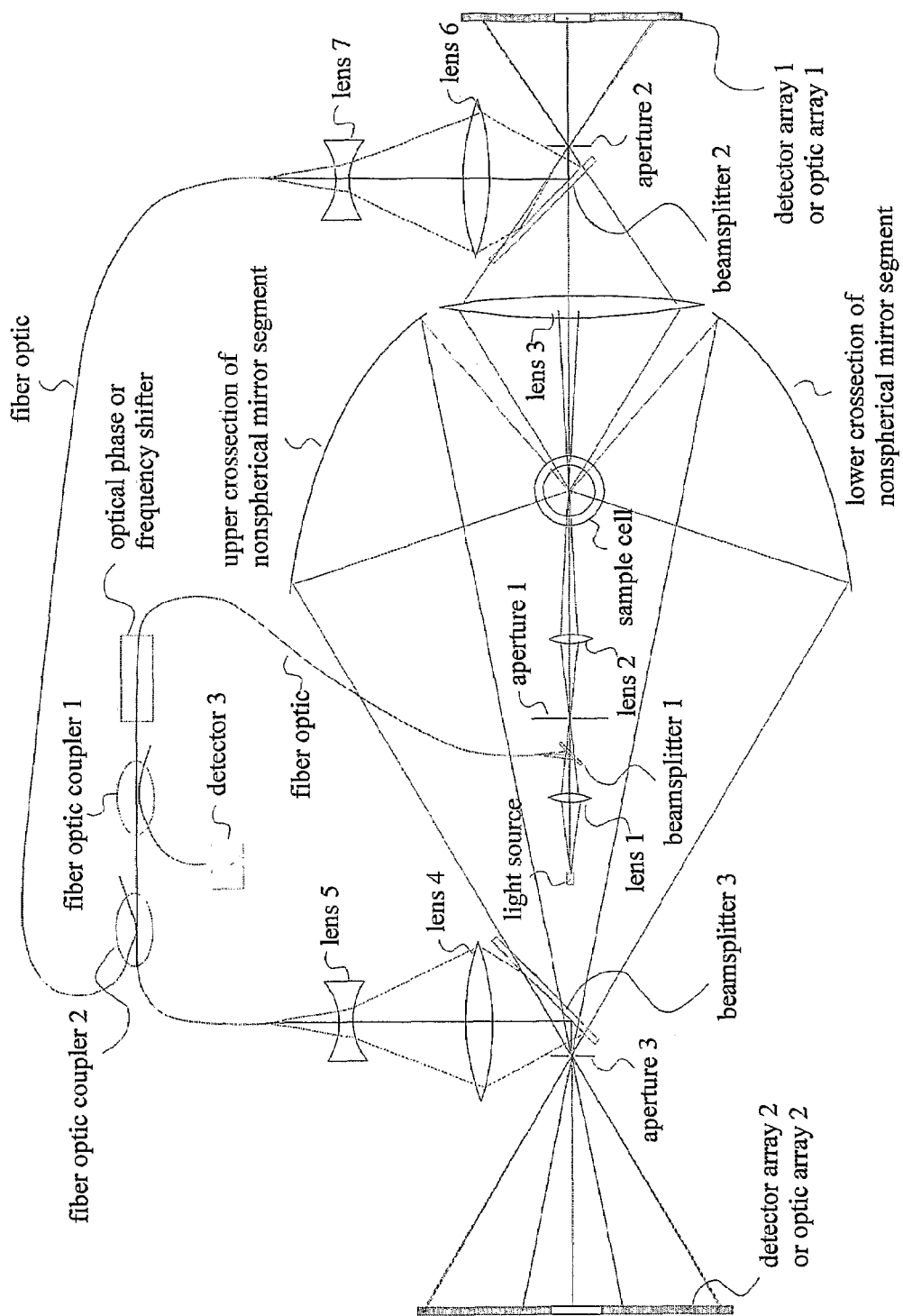
FIG. 96 provides a schematic diagram of a variation of the optical system shown in FIG. 78, which provides heterodyne detection and measures scattered light over multiple scattering angle ranges and in multiple scattering planes.

FIG. 96 shows a variation of the optical system shown in FIG. 78, which provides heterodyne detection and measures scattered light over multiple scattering angle ranges and in multiple scattering planes. Some light is split off from the source light by beamsplitter 1 and focused into a fiber optic. This fiber optic passes through an optional optical phase or frequency shifter to provide an optical frequency shifted local oscillator for the detection of scattered light. This shifter could be an acousto-optic device or moving diffraction grating. The frequency shift can also be provided by a scanned optical phase shifter (moving mirror or piezoelectric fiber stretcher) whose optical phase is ramped by a sawtooth function to produce an effective optical frequency shift during each period of phase ramp. Fiber optic coupler 1 splits off a portion of the light after the phase shifter and passes this light to detector 3 which monitors the fluctuations in the light intensity (I2) which may be due to laser noise or amplitude modulation from the optical frequency or phase shifter. Then the source light is finally split into two fibers by fiber optic coupler 2 to provide local oscillators for both detection systems. The light exiting the one fiber from fiber optic coupler 1 is expanded by negative lens 7 and then focused by lens 6 through aperture 2 (via beamsplitter 2) to be mixed with the scattered light on detector array 1 (or optic array 1). Likewise light, from the other output fiber of fiber optic coupler 2, is expanded by negative lens 5 and then focused by lens 4 through aperture 3 (via beamsplitter 3) to be mixed with the scattered light on detector array 2 (or optic array 2). In this way, heterodyne detection is accomplished with laser noise reduction using the equation and method described previously:

$$Idiff = I1nb - (R/K)*I2nb = \text{Sqrt}(R*(1-R)*S)*Ioc*\cos(F*t+A)$$

Idiff only contains the heterodyne signal. The common mode noise in the local oscillator and the heterodyne signal is removed by this differential measurement (see the previous description of the method). Heterodyne detection provides very high signal to noise, if the laser noise is removed by this equation and method. However, if the heterodyne frequency is only due to Doppler shift of the scattered light from particle motion, then the frequency of the heterodyne beat frequency will depend upon scattering angle and scattering plane (for example, the scattering plane, which is perpendicular to the particle flow, will show zero Doppler frequency shift of the scattered light). The addition of the optical phase or frequency shifter provides a much higher heterodyne frequency which is nearly equal for all scattering angles and scattering planes, allowing heterodyne detection of particle size and shape. The only problem presented by the frequency shifter is that all light that hits the detector, by scatter or reflection, will be frequency shifted. Without the frequency shifter, only scatter from moving particles will contribute to the heterodyne signal at the beat frequency, so background light can be distinguished from particle scatter based upon signal frequency. So when the frequency shifter is used, a background scatter heterodyne signal should be recorded without particles and this background signal should be subtracted from the scatter heterodyne signal with particles present. Addition of an optical frequency shifter also provides a higher beat frequency and phase sensitive detection capability. The signals due to the particle motion and the Doppler effect have random phase for each particle. So the other advantage of the frequency shifter is that the heterodyne signal will have a known phase (same as the frequency shifter), which could allow for phase sensitive detection (lock in amplifier). As shown before, the signals from this system will consist of a sinusoidal signal with an envelope function from a particle's passage through the intensity profile of the source beam. So all of the techniques described previously for processing these signals can be applied to this case.

Also the heterodyne beat frequency will be different for each scattering plane. One method to eliminate this dependence is to design the system to have minimal particle motion induced phase shift by choosing appropriate angles, between the particle motion direction and the beam, and using the optical frequency or phase shifter (FIG. 96) to provide the phase modulation at a high frequency, instead of the phase shift due to particle motion. Then all detector heterodyne signals will have almost the same frequency and phase, with the high signal to noise provided by heterodyne detection. Also the phase modulation signal could be used with phase sensitive detection (lock in amplifier) to detect the heterodyne signal. However, two disadvantages of this system are light reflections and amplitude modulation due to the phase modulator. Without the phase modulator, only scattered light from moving particles will create a heterodyne beat signal. However, with the phase modulator and appropriate angles between the particle motion direction and the beam, all light reaching the detector from scattering or reflections will be at the beat frequency and will be passed by the band pass filter. Also the phase or frequency modulator will produce some small amount of amplitude modulation in the beam, which may completely overwhelm the particle scattering signal, even after it is removed using detector 3 (FIG. 96) and the differential detection described previously. The severity of these problems will be determined by the characteristics of the phase or frequency modulator and the level of light reflections in the optical system.

The system in FIG. 96 could also be designed without fiber optics. Each fiber optic coupler would be replaced by a beamsplitter and the light beams could be routed to lens 5 and lens 7 using mirrors and lenses to create a beam focus at aperture 2 and aperture 3 through beamsplitter 2 and beamsplitter 3, respectively. The negative lenses 5 and 7 may be needed to expand the beam to fill the angular range of light on each detector array or optic array.

Figure 97:
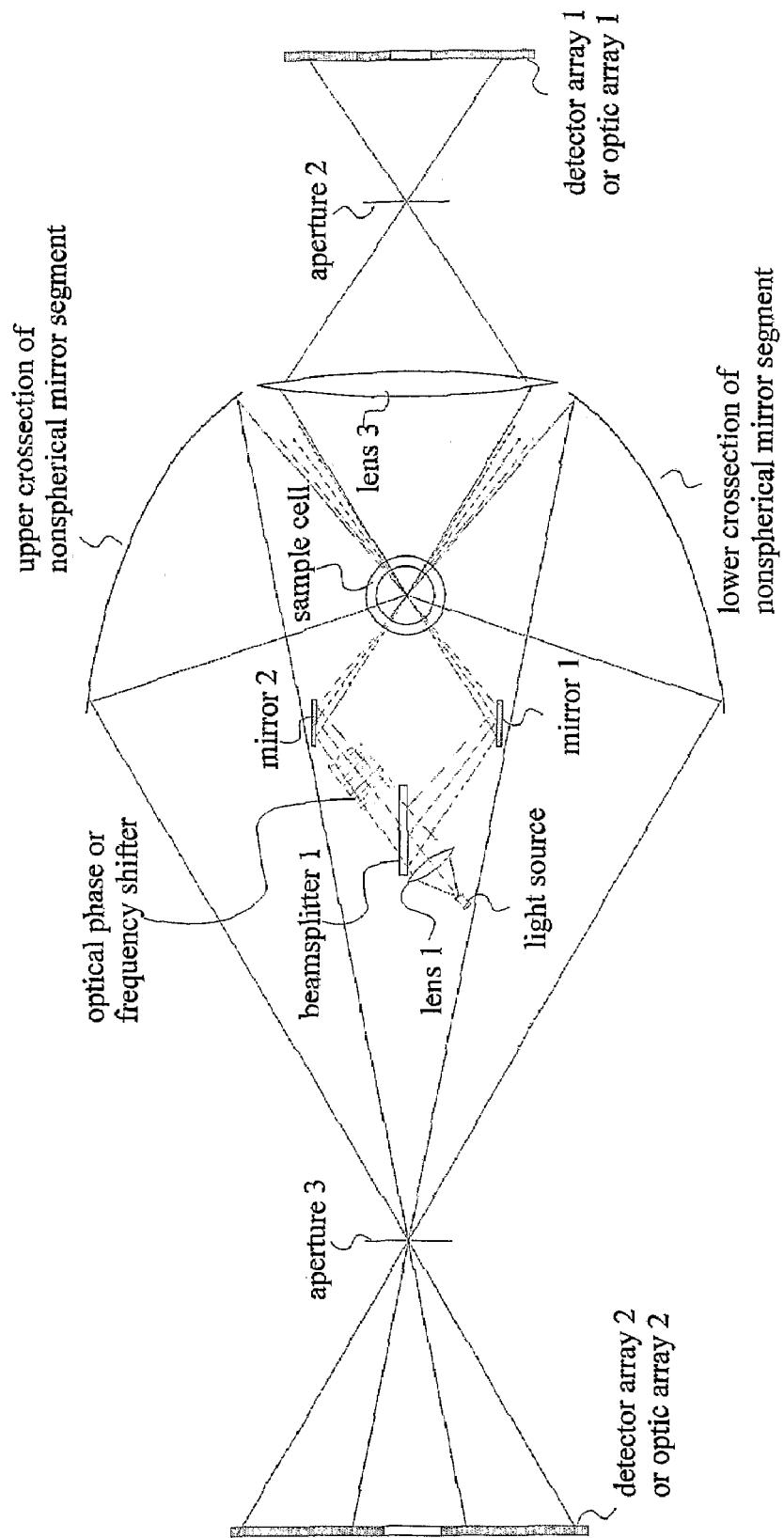
FIG. 97 provides a schematic drawing of a variation of the optical system shown in FIG. 78, which provides an oscillating scatter signal by producing an interference pattern in the interaction volume.

FIG. 97 shows another variation of the optical system shown in FIG. 78. The source beam is split into two beams which cross each other in the interaction volume in the sample cell. The two beams will create a fringe pattern at their intersection, which will modulate the scattered intensity as a particle passes through the intersection, as shown previously in FIG. 18. Lens 1 focuses the source light into the center of the sample cell. However, the light beam is split into two beams by beamsplitter 1. These two beams are reflected by mirror 1 and mirror 2 to cross in the center of the sample cell. One of the beams may pass through an optical frequency shifter to provide a beat signal of known phase and/or higher frequency. The advantage of this method is that only particles passing through the fringe pattern at the intersection of these dual beams will produce signals at the beat frequency. This intersection, and aperture 2 or aperture 3, define a small interaction volume which reduces coincidence particle counts. Addition of an optical frequency shifter provides a higher beat frequency and phase sensitive detection capability. The signals due to the periodicity of the fringe pattern have random phase for each particle. So the other advantage of the frequency shifter is that the heterodyne signal will have a known phase (same as the frequency shifter), which could allow for phase sensitive detection (lock in amplifier). As shown before, the signals from this system will consist of a sinusoidal signal with an envelope function from a particle's passage through the intensity profile of the fringe pattern. So all of the techniques described previously for processing these signals can be applied to this case. In this case, the scattered signal, at each position on the detector array, is the square root of the product of the scattered intensities from each of the crossed light beams. Hence the scattered light intensities, from a particular position on the detector array, in the simultaneous equations shown previously, must be replaced with the square root of the product of the scattered intensities from each of the crossed light beams at that same detector array position.

The method shown in FIG. 97 could also be implemented using the optical system in FIG. 78, by placing a periodic mask in the plane of aperture 1 in FIG. 78. The image of this mask in the sample cell would provide a periodic intensity profile which would modulate the scatter signal from a particle passing through the intensity profile. The mask could have a sinusoidal or square wave transmission profile as shown in a single section of the mask in FIG. 66 (for example). The mask could also be fabricated with a Barker code or other code which has a very sharp autocorrelation function to use correlation between detector signals (also see below). However, in this case the scattering signals are not the square root of the product of scattering signals from two different scattering angles. The signal is only from the actual scattering angles defined before for detector array 1 or detector array 2.

In both FIGS. 96 and 97, the system can be designed to provide beat signals on all detector elements with nearly the same phase and frequency. Hence high level signals can be multiplied times lower level signals to retrieve the lower level signals from noise. This method can also be used with the system shown in FIG. 78, where each particle produces a single pulse. The integral of the product of the largest scatter signal with a smaller signal, which needs to be recovered from the noise, will improve the signal to noise of the integral over the pulse for that smaller signal. This could also be accomplished by only integrating the lower signal while the larger signal is above some threshold, as described previously. This method will also work for signals which are not modulated. The integral of the product of single pulses will also improve the signal to noise of lower level signals when multiplied by higher level signals which have the same pulse shape. This could be accomplished with the following equation which calculates a more accurate estimate to the integral of S2 by using correlation with a higher level signal of the same functional shape (single pulse, amplitude modulated heterodyne signal, etc.):

$$S2I=INT(S1.*S2,t1,t2)/INT(S1,t1,t2)$$

Where S1 is the high level signal and S2 is the low level signal which has high correlation to S1. And t1 and t2 are the start and stop times of the particle scatter pulse. The value of INT(S1.*S2, t1,t2) could be used directly, without normalization, in simultaneous equations, lookup tables, or search models as long as the theoretical model is calculated for INT(S1.*S2, t1,t2).

In both FIGS. 96 and 97, the detector arrays can be replaced by optic arrays as shown in FIGS. 79, 80, 81, 83, 84, and 86, for example. These optic arrays can be configured in a detection system as shown in FIGS. 82, 85, and 87, for example.

All drawings of optical systems in this disclosure are for illustrative purposes and do not necessarily describe the actual size of lens apertures, lens surface shapes, lens designs, lens numerical apertures, and beam divergences. All lens and mirror designs should be optimized for their optical conjugates and design requirements of that optical system using known lens and mirror design methods. The drawings are designed to describe the concept; and so some beam divergences are exaggerated in order to clearly show beam focal planes and image planes within the optical system. If these drawings were made to scale, certain aspects of the invention could not be illustrated. And in particular, the source beam divergence half angle must be smaller than the lowest scattering angle which will be measured from particles in that beam. For low scattering angles (larger particles) the source beam would have a very small divergence angle, which could not be seen on the drawing.

Also in this disclosure, where ever an aperture is used to pass scattered light and that aperture is in an image plane of the scattering particle, a lens can be placed between the detector(s) (or optic array) and that aperture to reduce smearing of the scattering pattern due to the finite size of the aperture. The detectors could be placed in the back focal plane of said lens, where each point in the focal plane corresponds to the same scattering angle from any point in the interaction volume. The detector(s) (or optic array) would be placed in the back focal plane of said lens to effectively place the detector at infinity, where the angular smearing is negligible, as shown and discussed in FIG. 24.

Also in this document, any use of the term "scattering angle" will refer to a range of scattering angles about some mean scattering angle. The angular range is chosen to optimize the performance of the measurement in each case. For example the use of the terms "low scattering angle" or "high scattering angle" refer to two different ranges of scattering angles, because each detector measures scattered light over a certain range of scattering angles Note that all optic arrays described in this disclosure can be constructed from segments of conventional spherical and aspherical lenses, diffractive optics, binary optics, and Fresnel lenses.

Ensemble particle size measuring systems gather data from a large group of particles and then invert the scattering information from the large particle group to determine the particle size distribution. This scatter data usually consists of a scatter signal vs. time (dynamic scattering) or scatter signal vs. scattering angle (static scattering). The data is collected in data sets, which are then combined into a single larger data record for processing and inversion to produce the particle size distribution. Inversion techniques such as deconvolution and search routines have been used. The data set for dynamic light scattering consists of a digital record of the detector signal over a certain time, perhaps 1 second. The power spectra or autocorrelation functions of the data sets are usually combined to produce the combined input to the inversion algorithm for dynamic light scattering to invert the power spectrum or autocorrelation function into a particle size distribution. Also the data sets can be combined by concatenation, or by windowing and concatenation, to produce longer data sets prior to power spectrum estimation or autocorrelation. Then these power spectra or autocorrelation functions are averaged (the values at each frequency or delay are averaged over the data sets) to produce a single function for inversion to particle size. Likewise for angular scattering, the angular scatter signals from multiple detectors are integrated over a short interval. These angular scattering data sets are combined by simply averaging data values at each scattering angle over multiple data sets.

Since the inverse problem for these systems is usually ill-conditioned, detecting small amounts of large particles mixed in a sample of smaller particles may be difficult because all of the particle signals from the particle sample are inverted as one signal set. If the signal, from only a few larger particles, is mixed with the signals from all of the other smaller particles, the total large particle scatter signal may be less than 0.01 percent of the total and be lost in the inversion process. However, in the single short data set which contained the larger particle's scattered light, the larger particle scatter may make up 50% to 90% of the total signal. The larger particle will easily be detected during inversion of these individual data sets.

Users of these systems usually want to detect small numbers of large particles in a much larger number of smaller particles, because these larger particles cause problems in the use of the particle sample. For example, in lens polishing slurries, only a few larger particles can damage the optical surface during the polishing process. In most cases these larger particles represent a very small fraction of the sample on a number basis. Therefore, if many signal sets (a digitized signal vs. time for dynamic scattering or digitized signal vs. scattering angle for static scattering) are collected, only a few sets will include any scattered signals from larger particles. An algorithm could sort out all of the data sets which contain signals from larger particles and invert them separately, in groups, to produce multiple size distributions, which are then weighted by their total signal time and then combined to form the total particle size distribution. The data sets may also be sorted into groups of similar characteristics, and then each group is inverted separately to produce multiple size distributions, which are then weighted by their total signal time and then summed over each size channel to form the total particle size distribution. In this way, the larger particles are found easily and the smaller particle data sets are not distorted by scatter signals from the larger particles.

This technique works better when many short pieces of data are analyzed separately, because then the best discrimination and detection of particles is obtained. However, this also requires much pre-inversion analysis of a large number of data sets. The key is that these data sets can be categorized with very little analysis. In the case of angular light scattering, comparison of signal values from a few scattering angles from each signal set is sufficient to determine which signal sets include signals from larger particles or have specific characteristics. In the case of dynamic light scattering, the spectral power in certain frequency bands, as measured by fast Fourier transform of the data set or by analog electronic bandpass filters could be used to categorize data sets. Consider a dynamic scattering system where the scattering signal from the detector (in heterodyne or homodyne mode) is digitized by an analog to digital converter for presentation to a computer inversion algorithm. In addition, the signal is connected to multiple analog filters and RMS circuits, which are sequentially sampled by the analog to digital converter to append each digitized data set with values of total power in certain appropriate frequency bands which provide optimal discrimination for larger particles. The use of analog filters may shorten the characterization process when compared to the computation of the Fourier transform. These frequency band power values are then used to sort the data sets into groups of similar characteristics. Since larger particles will usually produce a large signal pulse, both signal amplitude and/or frequency characteristics can be used to sort the data sets. The total data from each formed group is then processed and inverted separately to produce an individual particle size distribution. These particle size distributions are summed together after each distribution is weighted by the total time of the data collected for the corresponding group.

The use of analog filters is only critical when the computer speed is not sufficient to calculate the power spectrum of each data set. Otherwise the power spectra could be calculated from each data set first, and then the power values in appropriate frequency bands, as determined from the computed power spectrum, could be used to sort the spectra into groups before the total data from each group is then processed and inverted separately to produce an individual particle size distribution. For example the ratio of the power in two different frequency bands can indicate the presence of large particles. These particle size distributions are summed together after each distribution is weighted by the total time of the data collected for the corresponding group. This process could also be accomplished using the autocorrelation function instead of the power spectrum of the scatter signal. Then the frequency would be replaced by time delay of the autocorrelation function and different bands of time delay would be analyzed to sort the data sets before creating data groups.

In angular scattering, a group of detectors measure scattered light from the particles over a different angular range for each detector. These detector signals are integrated over a certain measurement interval and then the integrals are sampled by multiplexer and an analog to digital converter. In this case, the angular scattering values at appropriate angles, which show optimal discrimination for larger particles, could be used to sort the angular scattering data sets into groups before the total data from each group is then processed and inverted separately to produce an individual particle size distribution for that group. These resulting particle size distributions are summed together after each distribution is weighted by the total time of the data collected for the corresponding group.

These sorting techniques can also be used to eliminate certain data sets from any data set group which is inverted to produce the particle size distribution. For example, in dynamic scattering, larger particles may occasionally pass through the interaction volume of the optical system and produce a large signal with non-Brownian characteristics which would distort the results for the data set group to which this defective data set would be added. Large particles, which are outside of the instrument size range, may also cause errors in the inverted size distribution for smaller particles when their data sets are combined. Therefore, such defective data sets should be rejected and not added to any group. This method would also be useful in conventional dynamic light scattering systems, where multiple groups are not used, to remove bad data sets from the final grouped data which is inverted. By breaking the entire data record into small segments and sorting each segment, the bad data segments can be found and discarded prior to combination of the data power spectra or autocorrelation functions and final data inversion. This method would also be useful in static angular scattering to eliminate data sets from particles which are outside of the instrument size range.

In some cases, a large number of categories for sorted groups are appropriate to obtain optimal separation and characterization of the particle sample. The number of categories is only limited by the cumulated inversion time for all of the sorted groups. The total inversion time may become too long for a large number of groups, because a separate inversion must be done for each group. However, after the information is sorted, abbreviated inversion techniques may be used because the high accuracy of size distribution tails would not be required to obtain high accuracy in the final combined particle size distribution. In many cases, only two groups are necessary to separate out the largest particles or to eliminate defective data sets.

This disclosure claims sorting of data sets for any characteristics of interest (not only large particles) and for any applications where large data sets can be broken up into smaller segments and sorted prior to individual analysis or inversion of each individual set. Then the resulting distributions are combined to create the final result. This includes applications outside of particle size measurement.

Another application is Zeta potential measurement. Low scattering angles are desirable in measurement of mobility of particles to reduce the Doppler broadening due to Brownian motion. However, large particles scatter much more at small angles than small particles do; and so the scatter from any debris in the sample will swamp the Doppler signal from the motion of the smaller charged particles in the electric field. This inventor has disclosed methods of measuring Dynamic light scattering from small interaction volumes created by restricting the size of the illuminating beam and the effective viewing volume. When only scattered light from a very small sample volume is measured, the scatter from large dust particles will be very intermittent, due to their small count per unit volume. So the techniques outlined above can be used to eliminate the portions of the signal vs. time record which contain large signal bursts due to passage of a large particle.

In this way, Zeta potential measurements can be made at low scattering angles without the scattering interference from dust contaminants.

In optical systems which need to count very small particles, light sources with shorter wavelengths may be preferred due to the higher scattering efficiencies (or scattering crosssections) at shorter wavelengths.

Figure 100:
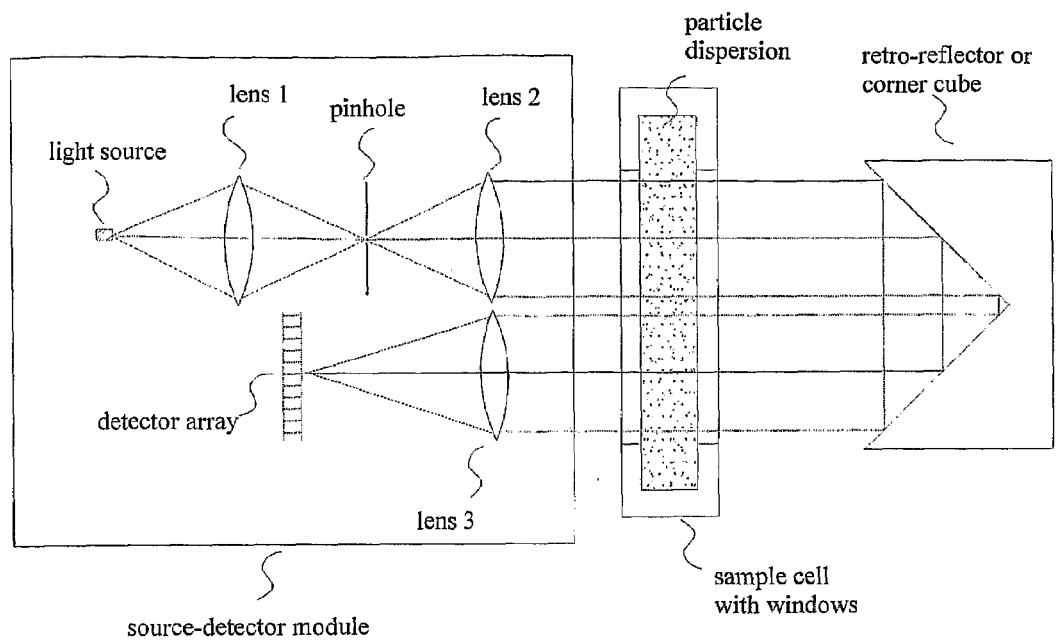
FIG. 100 provides a schematic diagram of an optical system which measures angular scattering distribution from a particle dispersion in a sample cell, wherein optical alignment is maintained by a retro-reflector, according to the present invention.

The alignment of angular scattering systems can drift due to drift of the source beam position or changes in the wedge between the sample cell windows. FIG. 100 shows an optical system which measures angular scattering distribution from a particle dispersion in a sample cell. The angular scattering distribution is used to determine the size distribution of the particles. If the optical wedge between the sample cell windows changes or if the dispersant refractive index is changed, the system will go out of alignment due to refraction in the optical wedge. The laser focus spot will move to another position on the detector array, saturating detector elements which should be measuring scattered light only. This invention uses a retroreflector and a source-detector module to provide stable alignment against the drift sources described above. Lens 1, pinhole, and lens 2 form a spatial filter. The light beam from this spatial filter passes through the sample cell and dispersion. The beam and scattered light are then retroreflected back through the same sample cell, where more scatter occurs on the second pass. All of the scattered light is collected by lens 3, which focuses it onto a detector array in the back focal plane of lens 3. As long as the components are rigidly mounted to a common base in the source-detector module, the system will maintain alignment after initial alignment at the factory. After initial alignment, this system will maintain alignment over a large range of beam alignment drift, dispersant refractive index change, or sample cell wedge drift. If the sample cell drift or dispersant refractive index drift are not problems, the optics can be arranged so that the beam between lens 2 and the retroreflector does not pass through the sample cell, while the beam does pass through the sample cell between the retroreflector and lens 3.

It will be understood that the embodiments of the present invention system and method are merely exemplary and that a person skilled in the art can make many modifications to the embodiments using functionally equivalent components. All such modifications, variations and alternate embodiments are intended to be included within the scope of the present invention as set forth by the claims.

What is claimed is:

1. A method for improving accuracy of particle parameter distributions, the particle parameter distributions being obtained by directing light onto particles and observing light scattered from the particles so as to observe special events, the method comprising the steps of:
   a) selecting an integration time which is sufficiently short such that each special event creates a large characteristic change of integrated scatter signal parameters, when observed by a detector,
   b) deriving data sets corresponding to particles, by integrating signals obtained from a plurality of detectors, using the integration time selected in step (a),
   c) sorting the data sets obtained in step (b) into groups with similar characteristics,
   d) rejecting groups with undesirable characteristics, while accepting other groups for further analysis,
   e) calculating a particle parameter distribution from an average of said data sets, from each accepted group, to obtain a separate parameter distribution for each accepted group, and
   f) combining the individual particle parameter distributions from said groups to produce a final particle parameter distribution.

2. The method of claim 1, further comprising selecting said special events from the group consisting of rare particles, large particles, and scatter signal defects.

3. Apparatus for improving accuracy of particle parameter distributions, the particle parameter distributions being obtained by directing light onto particles and observing light scattered from the particles so as to observe special events, the apparatus comprising:
   a) means for selecting an integration time which is sufficiently short such that each special event creates a large characteristic change of integrated scatter signal parameters, when observed by a detector,
   b) means for deriving data sets corresponding to particles, by integrating signals obtained from a plurality of detectors, using the integration time selected in the selecting means,
   c) means for sorting the data sets, obtained from the deriving means, into groups with similar characteristics,
   d) means for rejecting groups with undesirable characteristics while accepting other groups for further analysis,
   e) means for calculating a particle parameter distribution from an average of said data sets, from each accepted group, to obtain a separate parameter distribution for each accepted group, and
   f) means for combining the individual particle parameter distributions from said groups to produce a final particle parameter distribution.

4. The apparatus of claim 3, wherein said special events are selected from the group consisting of rare particles, large particles, and scatter signal defects.

5. A method for improving accuracy of particle parameter distributions, the particle parameter distributions being obtained by directing light onto particles and observing light scattered from the particles so as to observe special events, the method comprising the steps of:
   a) selecting a data collection period which is sufficiently short such that each special event creates a large characteristic change in a function created in step (c) below, when observed by a detector,
   b) deriving data sets corresponding to particles, by digital sampling of signals obtained from at least one detector, using the data collection period selected in step (a),
   c) creating a function of each data set,
   d) sorting the data sets obtained in step (b) into groups with similar characteristics for said function,
   e) rejecting groups with undesirable characteristics, while accepting other groups for further analysis,
   f) calculating a particle parameter distribution from an average of said functions of said data sets, from each accepted group, to obtain a separate parameter distribution for each accepted group, and
   g) combining the individual particle parameter distributions from said groups to produce a final particle parameter distribution.

6. The method of claim 5, further comprising selecting said special events from the group consisting of rare particles, large particles, and scatter signal defects.

7. Apparatus for improving accuracy of particle parameter distributions, the particle parameter distributions being obtained by directing light onto particles and observing light scattered from the particles so as to observe special events, the apparatus comprising:
   a) means for selecting a data collection period which is sufficiently short such that each special event creates a large characteristic change in a function created by a creating means, below, when observed by a detector, b) means for deriving data sets corresponding to particles, by digital sampling of signals obtained from at least one detector, using the data collection period established by the selecting means, c) means for creating a function, of each of said data sets, d) means for sorting the data sets, obtained from the deriving means, into groups with similar characteristics for said function, e) means for rejecting groups with undesirable characteristics, while accepting other groups for further analysis, f) means for calculating a particle parameter distribution from an average of functions of said data sets, from each accepted group, to obtain a separate parameter distribution for each accepted group, and g) means for combining the individual particle parameter distributions from said groups to produce a final particle parameter distribution.

8. The apparatus of claim 7, wherein said special events are selected from the group consisting of rare particles, large particles, and scatter signal defects.

* * * * *